US009365868B2

(12) United States Patent
Koepke et al.

(10) Patent No.: US 9,365,868 B2

(45) **Date of Patent: *Jun. 14, 2016**

(54) FERMENTATION PROCESS FOR PRODUCING ISOPROPANOL USING A RECOMBINANT MICROORGANISM

(75) Inventors: Michael Koepke, Auckland (NZ); Sean Simpson, Auckland (NZ); Fungmin Liew, Auckland (NZ); Wendy Chen, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 874 days.

This patent is subject to a terminal disclaimer.

(21) Appl. No.: 13/459,211

(22) Filed: Apr. 29, 2012

(65) Prior Publication Data

US 2012/0252083 A1 Oct. 4, 2012

Related U.S. Application Data

(63) Continuation-in-part of application No. 13/403,972, filed on Feb. 23, 2012.

(60) Provisional application No. 61/446,832, filed on Feb. 25, 2011.

(51) Int. Cl.

| | |
|---|---|
| *C12P 7/04* | (2006.01) |
| *C12N 15/00* | (2006.01) |
| *C12N 1/20* | (2006.01) |
| *C12N 9/10* | (2006.01) |
| *C12N 9/88* | (2006.01) |
| *C12N 9/04* | (2006.01) |
| *C07H 21/04* | (2006.01) |
| *C12N 15/74* | (2006.01) |
| *C12P 7/28* | (2006.01) |

(52) U.S. Cl.

CPC ................ *C12P 7/04* (2013.01); *C12N 9/1029* (2013.01); *C12N 9/13* (2013.01); *C12N 9/88* (2013.01); *C12N 15/74* (2013.01); *C12P 7/28* (2013.01)

(58) Field of Classification Search

CPC .......... C12N 9/1029; C12N 9/13; C12N 9/88; C12N 15/74; C12P 7/04

See application file for complete search history.

(56) References Cited

U.S. PATENT DOCUMENTS

| | | | | |
|---|---|---|---|---|
| 2008/0293125 | A1* | 11/2008 | Subbian et al. | ............ 435/252.3 |
| 2009/0203100 | A1* | 8/2009 | Simpson et al. | .............. 435/161 |
| 2009/0246842 | A1* | 10/2009 | Hawkins et al. | .............. 435/157 |
| 2010/0304453 | A1 | 12/2010 | Trawick et al. | |
| 2012/0101304 | A1 | 4/2012 | Becker et al. | |

FOREIGN PATENT DOCUMENTS

| | | |
|---|---|---|
| WO | WO2009/113878 | 9/2009 |
| WO | 2009131040 A1 | 10/2009 |
| WO | WO2010/121849 | 10/2010 |
| WO | 2011022651 | 2/2011 |

OTHER PUBLICATIONS

UniProKB—Q716S7 & Q716S6. 2004.*

Koepke, M. et al. ‘Clostridium ljungdahlii represents a microbial production platform based on syngas’. Proceedings of the National Academy of Sciences of USA. Jul. 2010, vol. 107, No. 29, pp. 13087-13092.

Ramachandriya, K.D. et al. ‘Reduction of acetone to isopropanol using producer gas fermenting microbes’. Biotechnology and Bioengineering. Oct. 2011, vol. 108, No. 10, pp. 2330-2338.

Schiel-Bengelsdorf, B. et al. ‘Pathway engineering and synthetic biology using acetogens’. FEBS Letters. Jul. 2012, vol. 586, No. 15, pp. 2191-2198.

Office Action in Chinese Patent Application No. 2012800204563, dated Jul. 29, 2014.

Lazar, E et al., Mol Cell Biol, 8/3:1247-1252, Mar. 1988.

Hill, Ma and Preiss J., Biochem Biophys Res Comm, 244/2:573-577, Mar. 17, 1998.

Canadian Patent Application 2,825,267 Examination Report, May 26, 2015.

European Search Report for Patent Application 12749472.2, European Patent Office, Feb. 4, 2016.

Durre, New insights and novel developments in clostridial acetone/butanol/isopropanol fermentation, Appl Microbiol. Biotechnol, 49: 639-648, 1998.

Japanese Office Action for Patent Application 2013-555385, Japanese Patent Office, Mar. 31, 2016.

* cited by examiner

*Primary Examiner* — Yong Pak

(74) *Attorney, Agent, or Firm* — Andrea E. Schoen

(57) ABSTRACT

The invention provides, inter alia, methods for the production of acetone, isopropanol and/or precursors of acetone and/or isopropanol by microbial fermentation of substrates comprising CO, genetically modified microorganisms of use in such methods, nucleic acids suitable for preparation of genetically modified microorganisms, a novel alcohol dehydrogenase and nucleic acids encoding same.

14 Claims, 64 Drawing Sheets

MKGFAMLGINKLGWIEKKNPVPGPYDAIVHPLAVSPCTSDIHTVFEGALGNRENMILGHEAVGEIAEVGSEVKDFKVG
DRVIVPCTTPDWRSLEVQAGFQQHSNGMLAGWKFSNFKDGVFADYFHVNDADMNLAILPDEIPLESAVMMTDMM
TTGFHGAELADIKMGSSVVVIGIGAVGLMGIAGSKLRGAGRIIGVGSRPVCVETAKFYGATDIVNYKNGDIVEQIMDLT
HGKGVDRVIMAGGGAETLAQAVTMVKPGGVISNINYHGSGDTLPIPRVQWGCGMAHKTIRGGLCPGGRLRMEMLR
DLVLYKRVDLSKLVTHVFDGAENIEKALLLMKNKPKDLIKSVVTF*

FIG 14

ATGAAAGGTTTTGCAATGTTAGGTATTAACAAATTAGGATGGATTGAAAAGAAAAACCCAGTGCCAGGTCCTTAT
GATGCGATTGTACATCCTCTAGCTGTATCCCCATGTACATCAGATATACATACGGTTTTTGAAGGAGCACTTGGTAA
TAGGGAAAATATGATTTTAGGCCATGAAGCTGTAGGTGAAATAGCCGAAGTTGGCAGCGAAGTTAAAGATTTTAA
AGTTGGCGATAGAGTTATCGTACCATGCACAACACCTGACTGGAGATCTTTAGAAGTCCAAGCTGGTTTTCAGCAG
CATTCAAACGGTATGCTTGCAGGATGGAAGTTTTCCAATTTTAAAGACGGTGTATTTGCAGATTACTTTCATGTAAA
CGATGCAGATATGAATCTTGCCATACTCCCAGATGAAATACCTTTAGAAAGTGCAGTTATGATGACAGACATGATG
ACTACTGGTTTTCATGGAGCAGAACTTGCAGACATAAAAATGGGCTCCAGCGTTGTAGTAATTGGTATAGGAGCT
GTTGGATTAATGGGAATAGCCGGTTCCAAACTTCGAGGAGCAGGCAGAATTATCGGTGTTGGAAGCAGACCTGTT
TGTGTTGAAACAGCTAAATTTTATGGAGCAACTGATATTGTAAATTATAAAAATGGTGATATAGTTGAACAAATCA
TGGACTTAACTCATGGTAAAGGTGTAGACCGTGTAATCATGGCAGGCGGTGGTGCTGAAACACTAGCACAAGCAG
TAACTATGGTTAAACCTGGCGGCGTAATTTCTAACATCAACTACCATGGAAGCGGTGATACTTTACCAATACCTCGT
GTTCAATGGGGCTGCGGCATGGCTCACAAAACTATAAGAGGAGGATTATGCCCCGGCGGACGTCTTAGAATGGA
AATGCTAAGAGATCTTGTTCTATATAAACGTGTTGATTTGAGTAAACTTGTTACTCATGTATTTGATGGTGCAGAAA
ATATTGAAAAGGCCCTTTTGCTTATGAAAAATAAGCCAAAAGATTTAATTAAATCAGTAGTTACATTCTAA

FIG 15

ATGAAAGGTTTTGCAATGTTAGGTATTAACAAATTAGGATGGATTGAAAAGAAAAACCCAGTGCCAGGTCCTTAT
GATGCGATTGTACATCCTCTAGCTGTATCCCCATGTACATCAGATATACATACGGTTTTTGAAGGAGCACTTGGTAA
TAGGGAAAATATGATTTTAGGCCATGAAGCTGTAGGTGAAATAGCCGAAGTTGGCAGCGAAGTTAAAGATTTTAA
AGTTGGCGATAGAGTTATCGTACCATGCACAACACCTGACTGGAGATCTTTAGAAGTCCAAGCTGGTTTTCAGCAG
CATTCAAACGGTATGCTTGCAGGATGGAAGTTTTCCAATTTTAAAGATGGTGTATTTGCAGATTACTTTCATGTAAA
CGATGCAGATATGAATCTTGCCATACTCCCAGATGAAATACCTTTAGAAAGTGCAGTTATGATGACAGACATGATG
ACTACTGGTTTTCATGGAGCAGAACTTGCAGACATAAAAATGGGCTCCAGCGTTGTAGTAATTGGTATAGGAGCT
GTTGGATTAATGGGAATAGCCGGTTCCAAACTTCGAGGAGCAGGCAGAATTATCGGTGTTGGAAGCAGACCTGTT
TGTGTTGAAACAGCTAAATTTTATGGAGCAACTGATATTGTAAATTATAAAAATGGTGATATAGTTGAACAAATCA
TGGACTTAACTCATGGTAAAGGTGTAGACCGTGTAATCATGGCAGGCGGTGGTGCTGAAACACTAGCACAAGCAG
TAACTATGGTTAAACCTGGCGGCGTAATTTCTAACATCAACTACCATGGAAGCGGTGATACTTTACCAATACCTCGT
GTTCAATGGGGCTGCGGCATGGCTCACAAAACTATAAGAGGAGGATTATGCCCCGGCGGACGTCTTAGAATGGA
AATGCTAAGAGATCTTGTTCTATATAAACGTGTTGATTTGAGTAAACTTGTTACTCATGTATTTGATGGTGCAGAAA
ATATTGAAAAGGCCCTTTTGCTTATGAAAAATAAGCCAAAAGATTTAATTAAATCAGTAGTTACATTCTAA

FIG 16

ATGAAAGGTTTTGCAATGTTAGGTATTAACAAGTTAGGATGGATTGAAAAGAAAAACCCAGTACCAGGTCCTTAT
GATGCGATTGTACATCCTCTAGCTGTATCCCCATGTACATCAGATATACATACGGTTTTTGAAGGAGCACTTGGTAA
TAGGGAAAATATGATTTTAGGTCACGAAGCTGTAGGTGAAATAGCTGAAGTTGGCAGTGAAGTTAAAGATTTTAA
AGTTGGCGATAGAGTTATCGTACCATGCACAACACCTGACTGGAGATCCTTAGAAGTCCAAGCTGGTTTTCAACAG
CATTCAAACGGTATGCTTGCAGGATGGAAGTTTTCCAATTTTAAAGACGGTGTATTTGCAGATTACTTTCATGTAAA
CGATGCAGATATGAATCTTGCAATACTTCCAGATGAAATACCTTTAGAAAGTGCAGTTATGATGACAGACATGATG
ACTACTGGTTTTCATGGGGCAGAACTTGCTGACATAAAAATGGGTTCCAGTGTTGTCGTAATTGGTATAGGAGCTG
TTGGATTAATGGGAATAGCCGGTTCCAAACTTCGAGGAGCAGGTAGAATTATCGGTGTTGGAAGCAGACCCGTTT
GTGTTGAAACAGCTAAATTTTATGGAGCAACTGATATTGTAAATTATAAAAATGGTGATATAGTTGAACAAATAAT
GGACTTAACTCATGGTAAAGGTGTAGACCGTGTAATCATGGCAGGCGGTGGTGCTGAAACACTAGCACAAGCAGT
AACTATGGTTAAACCTGGCGGCGTAATTTCTAACATCAACTACCATGGAAGCGGTGATACTTTGCCAATACCTCGT
GTTCAATGGGGCTGCGGCATGGCTCACAAAACTATAAGAGGAGGGTTATGTCCCGGCGGACGTCTTAGAATGGA
AATGCTAAGAGACCTTGTTCTATATAAACGTGTTGATTTGAGCAAACTTGTTACTCATGTATTTGATGGTGCAGAAA
ATATTGAAAAGGCCCTTTTGCTTATGAAAAATAAGCCAAAAGATTTAATTAAATCAGTAGTTACATTCTAA

FIG 17

ATGAAAGAAGTTGTAATAGCTAGTGCAGTAAGAACAGCGATTGGATCTTATGGAAAGTCTCTTAAGGATGTACCA
GCAGTAGATTTAGGAGCTACAGCTATAAAGGAAGCAGTTAAAAAAGCAGGAATAAAACCAGAGGATGTTAATGA
AGTCATTTTAGGAAATGTTCTTCAAGCAGGTTTAGGACAGAATCCAGCAAGACAGGCATCTTTTAAAGCAGGATTA
CCAGTTGAAATTCCAGCTATGACTATTAATAAGGTTTGTGGTTCAGGACTTAGAACAGTTAGCTTAGCAGCACAAA
TTATAAAAGCAGGAGATGCTGACGTAATAATAGCAGGTGGTATGGAAAATATGTCTAGAGCTCCTTACTTAGCGA
ATAACGCTAGATGGGGATATAGAATGGGAAACGCTAAATTTGTTGATGAAATGATCACTGACGGATTGTGGGATG
CATTTAATGATTACCACATGGGAATAACAGCAGAAAACATAGCTGAGAGATGGAACATTTCAAGAGAAGAACAAG
ATGAGTTTGCTCTTGCATCACAAAAAAAAGCTGAAGAAGCTATAAAATCAGGTCAATTTAAAGATGAAATAGTTCC
TGTAGTAATTAAAGGCAGAAAGGGAGAAACTGTAGTTGATACAGATGAGCACCCTAGATTTGGATCAACTATAGA
AGGACTTGCAAAATTAAAACCTGCCTTCAAAAAAGATGGAACAGTTACAGCTGGTAATGCATCAGGATTAAATGA
CTGTGCAGCAGTACTTGTAATCATGAGTGCAGAAAAAGCTAAAGAGCTTGGAGTAAAACCACTTGCTAAGATAGT
TTCTTATGGTTCAGCAGGAGTTGACCCAGCAATAATGGGATATGGACCTTTCTATGCAACAAAAGCAGCTATTGAA
AAAGCAGGTTGGACAGTTGATGAATTAGATTTAATAGAATCAAATGAAGCTTTTGCAGCTCAAAGTTTAGCAGTAG
CAAAAGATTTAAAATTTGATATGAATAAAGTAAATGTAAATGGAGGAGCTATTGCCCTTGGTCATCCAATTGGAGC
ATCAGGTGCAAGAATACTCGTTACTCTTGTACACGCAATGCAAAAAAGAGATGCAAAAAAAGGCTTAGCAACTTTA
TGTATAGGTGGCGGACAAGGAACAGCAATATTGCTAGAAAAGTGCTAG

FIG 18

ATGAATAAATTAGTAAAATTAACAGATTTAAAGCGCATTTTCAAAGATGGCATGACAATTATGGTTGGGGGTTTTT
TAGATTGTGGAACTCCTGAAAATATTATAGATATGCTAGTTGATTTAAATATAAAAAATCTGACTATTATAAGCAAT
GATACAGCTTTTCCTAATAAAGGAATAGGAAAACTTATTGTAAATGGTCAAGTTTCTAAAGTAATTGCTTCACATAT
TGGAACTAATCCTGAAACTGGAAAAAAAATGAGCTCTGGAGAACTTAAAGTTGAGCTTTCCCCACAAGGAACACT
GATTGAAAGAATTCGTGCAGCTGGATCTGGACTCGGAGGTGTATTAACTCCAACTGGACTTGGAACTATCGTTGA
AGAAGGTAAGAAAAAAGTTACTATCGATGGCAAAGAATATCTATTAGAACTTCCTTTATCTGCTGATGTTTCATTAA
TAAAAGGTAGCATTGTAGATGAATTTGGAAATACCTTCTATAGGGCTGCTACTAAAAATTTCAATCCATATATGGC
AATGGCTGCAAAAACAGTTATAGTTGAAGCAGAAAATTTAGTTAAATGTGAAGATTTAAAAAGAGATGCCATAAT
GACTCCTGGCGTATTAGTAGATTATATCGTTAAGGAGGCGGCTTAA

FIG 19

TTGATTGTAGATAAAGTTTTAGCAAAAGAGATAATTGCCAAAAGAGTTGCAAAAGAACTAAAAAAAGACCAACTC
GTAAACCTTGGAATAGGACTTCCAACTTTAGTAGCAAATTATGTACCAAAAGAAATGAACATTACTTTTGAATCAG
AAAATGGCATGGTTGGTATGGCACAAATGGCATCATCAGGTGAAAATGACCCAGATATAATAAATGCTGGCGGG
GAATATGTAACATTATTACCTCAAGGTTCATTTTTTGATAGTTCAATGTCTTTCGCACTAATACGAGGAGGACATGT
TGATGTTGCTGTTCTTGGTGCTCTAGAAGTTGATGAAAAAGGTAATTTAGCTAACTGGATTGTTCCAAATAAAATT
GTCCCAGGTATGGGTGGCGCTATGGATTTAGCAATAGGCGCAAAAAAAATAATAGTGGCAATGCAACATACAGG
AAAAAGTAAACCTAAAATCGTTAAAAAATGTACTCTCCCACTTACTGCTAAGGCTCAAGTGGATTTAATTGTCACAG
AACTTTGTGTAATTGATGTAACAAATGACGGCTTACTTTTAAAAGAAATTCATAAAGATACAACTATTGATGAAATT
AAATTTTTAACAGATGCAGATTTAATTATTCCAGATAACTTAAAGATTATGGATATATGA

FIG 20

ATGTTAGAAAGTGAAGTATCTAAACAAATTACAACTCCACTTGCTGCTCCAGCGTTTCCTAGAGGACCATATAGGT
TTCACAATAGAGAATATCTAAACATTATTTATCGAACTGATTTAGATGCTCTTCGAAAAATAGTACCAGAGCCACTT
GAATTAGATAGAGCATATGTTAGATTTGAAATGATGGCTATGCCTGATACAACCGGACTAGGCTCATATACAGAAT
GTGGTCAAGCTATTCCAGTAAAATATAATGGTGTTAAGGGTGACTACTTGCATATGATGTATCTAGATAATGAACC
TGCTATTGCTGTTGGAAGAGAAAGTAGCGCTTATCCAAAAAAGCTTGGCTATCCAAAGCTATTTGTTGATTCAGAT
ACTTTAGTTGGGACACTTAAATATGGTACATTACCAGTAGCTACTGCAACAATGGGATATAAGCACGAGCCTCTAG
ATCTTAAAGAAGCCTATGCTCAAATTGCAAGACCCAATTTTATGCTAAAAATCATTCAAGGTTACGATGGTAAGCC
AAGAATTTGTGAACTAATATGTGCAGAAAATACTGATATAACTATTCACGGTGCTTGGACTGGAAGTGCACGTCTA
CAATTATTTAGCCATGCACTAGCTCCTCTTGCTGATTTACCTGTATTAGAGATTGTATCAGCATCTCATATCCTCACA
GATTTAACTCTTGGAACACCTAAGGTTGTACATGATTATCTTTCAGTAAAATAA

FIG 21

AGATAGTCATAATAGTTCCAGAATAGTTCAATTTAGAAATTAGACTAAACTTCAAAATGTTTGTTAAATATATACCA
AACTAGTATAGATATTTTTTAAATACTGGACTTAAACAGTAGTAATTTGCCTAAAAAATTTTTTCAATTTTTTTTAAA
AAATCCTTTTCAAGTTGTACATTGTTATGGTAATATGTAATTGAAGAAGTTATGTAGTAATATTGTAAACGTTTCTT
GATTTTTTTACATCCATGTAGTGCTTAAAAAACCAAAATATGTCACATGCAATTGTATATTTCAAATAACAATATTTA
TTTTCTCGTTAAATTCACAAATAATTTATTAATAATATCAATAACCAAGATTATACTTAAATGGATGTTTATTTTTTAA
CACTTTTATAGTAAATATATTTATTTTATGTAGTAAAAAGGTTATAATTATAATTGTATTTATTACAATTAATTAAAAT
AAAAAATAGGGTTTTAGGTAAAATTAAGTTATTTTAAGAAGTAATTACAATAAAAATTGAAGTTATTTCTTTAAGGA
GGGAATTATTAAA

FIG 22

MFPCNAYIEYGDKNMNSFIEDVEQIYNFIKKNIDVEEKMHFIETYKQKSNMKKEISFSEEYYKQKIMNGKNGVVYTPPE
MAAFMVKNLINVNDVIGNPFIKIIDPSCGSGNLICKCFLYLNRIFIKNIEVINSKNNLNLKLEDISYHIVRNNLFGFDIDETAI
KVLKIDLFLISNQFSEKNFQVKDFLVENIDRKYDVFIGNPPYIGHKSVDSSYSYVLRKIYGSIYRDKGDISYCFFQKSLKCLKE
GGKLVFVTSRYFCESCSGKELRKFLIENTSIYKIIDFYGIRPFKRVGIDPMIIFLVRTKNWNNNIEIIRPNKIEKNEKNKFLDSL
FLDKSEKCKKFSISQKSINNDGWVFVDEVEKNIIDKIKEKSKFILKDICHSCQGIITGCDRAFIVDRDIINSRKIELRLIKPWIKS
SHIRKNEVIKGEKFIIYSNLIENETECPNAIKYIEQYKKRLMERRECKKGTRKWYELQWGRKPEIFEEKKIVFPYKSCDNRFA
LDKGSYFSADIYSLVLKKNVPFTYEILLNILNSPLYEFYFKTFAKKLGENLYEYYPNNLMKLCIPSIDFGGENNIEKKLYDFFGL
TDKEIEIVEKIKDNC*

FIG 23

ATGTTTCCGTGCAATGCCTATATCGAATATGGTGATAAAAATATGAACAGCTTTATCGAAGATGTGGAACAGATCT
ACAACTTCATTAAAAAGAACATTGATGTGGAAGAAAAGATGCATTTCATTGAAACCTATAAACAGAAAAGCAACAT
GAAGAAAGAGATTAGCTTTAGCGAAGAATACTATAAACAGAAGATTATGAACGGCAAAAATGGCGTTGTGTACAC
CCCGCCGGAAATGGCGGCCTTTATGGTTAAAAATCTGATCAACGTTAACGATGTTATTGGCAATCCGTTTATTAAA
ATCATTGACCCGAGCTGCGGTAGCGGCAATCTGATTTGCAAATGTTTTCTGTATCTGAATCGCATCTTTATTAAGAA
CATTGAGGTGATTAACAGCAAAAATAACCTGAATCTGAAACTGGAAGACATCAGCTACCACATCGTTCGCAACAAT
CTGTTTGGCTTCGATATTGACGAAACCGCGATCAAAGTGCTGAAAATTGATCTGTTTCTGATCAGCAACCAATTTAG
CGAGAAAAATTTCCAGGTTAAAGACTTTCTGGTGGAAAATATTGATCGCAAATATGACGTGTTCATTGGTAATCCG
CCGTATATCGGTCACAAAAGCGTGGACAGCAGCTACAGCTACGTGCTGCGCAAAATCTACGGCAGCATCTACCGC
GACAAAGGCGATATCAGCTATTGTTTCTTTCAGAAGAGCCTGAAATGTCTGAAGGAAGGTGGCAAACTGGTGTTT
GTGACCAGCCGCTACTTCTGCGAGAGCTGCAGCGGTAAAGAACTGCGTAAATTCCTGATCGAAAACACGAGCATT
TACAAGATCATTGATTTTTACGGCATCCGCCCGTTCAAACGCGTGGGTATCGATCCGATGATTATTTTTCTGGTTCG
TACGAAGAACTGGAACAATAACATTGAAATTATTCGCCCGAACAAGATTGAAAAGAACGAAAAGAACAAATTCCT
GGATAGCCTGTTCCTGGACAAAAGCGAAAAGTGTAAAAAGTTTAGCATTAGCCAGAAAAGCATTAATAACGATGG
CTGGGTTTTCGTGGACGAAGTGGAGAAAAACATTATCGACAAAATCAAAGAGAAAAGCAAGTTCATTCTGAAAGA
TATTTGCCATAGCTGTCAAGGCATTATCACCGGTTGTGATCGCGCCTTTATTGTGGACCGTGATATCATCAATAGCC
GTAAGATCGAACTGCGTCTGATTAAACCGTGGATTAAAAGCAGCCATATCCGTAAGAATGAAGTTATTAAGGGCG
AAAAATTCATCATCTATAGCAACCTGATTGAGAATGAAACCGAGTGTCCGAATGCGATTAAATATATCGAACAGTA
CAAGAAACGTCTGATGGAGCGCCGCGAATGCAAAAAGGGCACGCGTAAGTGGTATGAACTGCAATGGGGCCGTA
AACCGGAAATCTTCGAAGAAAAGAAAATTGTTTTCCCGTATAAAAGCTGTGACAATCGTTTTGCACTGGATAAGGG
TAGCTATTTTAGCGCAGACATTTATAGCCTGGTTCTGAAGAAAAATGTGCCGTTCACCTATGAGATCCTGCTGAATA
TCCTGAATAGCCCGCTGTACGAGTTTTACTTTAAGACCTTCGCGAAAAAGCTGGGCGAGAATCTGTACGAGTACTA
TCCGAACAACCTGATGAAGCTGTGCATCCCGAGCATCGATTTCGGCGGTGAGAACAATATTGAGAAAAAGCTGTA
TGATTTCTTTGGTCTGACGGATAAAGAAATTGAGATTGTGGAGAAGATCAAAGATAACTGCTAA

FIG 24

MKGFAMLGINKLGWIEKERPVAGSYDAIVRPLAVSPCTSDIHTVFEGALGDRKNMILGHEAVGEVVEVGSEVKDFKPG
DRVIVPCTTPDWRSLEVQAGFQQHSNGMLAGWKFSNFKDGVFGEYFHVNDADMNLAILPKDMPLENAVMITDMM
TTGFHGAELADIQMGSSVVVIGIGAVGLMGIAGAKLRGAGRIIGVGSRPICVEAAKFYGATDILNYKNGHIVDQVMKLT
NGKGVDRVIMAGGGSETLSQAVSMVKPGGIISNINYHGSGDALLIPRVEWGCGMAHKTIKGGLCPGGRLRAEMLRD
MVVYNRVDLSKLVTHVYHGFDHIEEALLLMKDKPKDLIKAVVIL

FIG 25

ATGAAAGGTTTTGCAATGCTAGGTATTAATAAGTTAGGATGGATCGAAAAAGAAAGGCCAGTTGCGGGTTCATAT
GATGCTATTGTACGCCCATTAGCAGTATCTCCGTGTACATCAGATATACATACTGTTTTTGAGGGAGCTCTTGGAGA
TAGGAAGAATATGATTTTAGGGCATGAAGCTGTAGGTGAAGTTGTTGAAGTAGGAAGTGAAGTGAAGGATTTTA
AACCTGGTGACAGAGTTATAGTTCCTTGTACAACTCCAGATTGGAGATCTTTGGAAGTTCAAGCTGGTTTTCAACA
GCACTCAAACGGTATGCTCGCAGGATGGAAATTTTCAAATTTCAAGGATGGAGTTTTTGGTGAATATTTTCATGTA
AATGATGCGGATATGAATCTTGCGATTCTACCTAAAGACATGCCATTAGAAAATGCTGTTATGATAACAGATATGA
TGACTACTGGATTTCATGGAGCAGAACTTGCAGATATTCAAATGGGTTCAAGTGTTGTGGTAATTGGCATTGGAGC
TGTTGGCTTAATGGGAATAGCAGGTGCTAAATTACGTGGAGCAGGTAGAATAATTGGAGTGGGGAGCAGGCCGA
TTTGTGTTGAGGCTGCAAAATTTTATGGAGCAACAGATATTCTAAATTATAAAAATGGTCATATAGTTGATCAAGTT
ATGAAATTAACGAATGGAAAAGGCGTTGACCGCGTAATTATGGCAGGCGGTGGTTCTGAAACATTATCCCAAGCA
GTATCTATGGTTAAACCAGGAGGAATAATTTCTAATATAAATTATCATGGAAGTGGAGATGCTTTACTAATACCAC
GTGTAGAATGGGGATGTGGAATGGCTCACAAGACTATAAAAGGAGGTCTTTGTCCTGGGGGACGTTTGAGAGCA
GAAATGTTAAGAGATATGGTAGTATATAATCGTGTTGATCTAAGTAAATTAGTTACACATGTATATCATGGATTTG
ATCACATAGAAGAAGCACTGTTATTAATGAAAGACAAGCCAAAAGACTTAATTAAAGCAGTAGTTATATTATAA

FIG 26

MKGFAMLSIGKVGWIEKEKPAPGPFDAIVRPLAVAPCTSDIHTVFEGAIGERHNMILGHEAVGEVVEVGSEVKDFKPG
DRVVVPAITPDWRTSEVQRGYHQHSGGMLAGWKFSNVKDGVFGEFFHVNDADMNLAHLPKEIPLEAAVMIPDMM
TTGFHGAELADIELGATVAVLGIGPVGLMAVAGAKLRGAGRIIAVGSRPVCVDAAKYYGATDIVNYKDGPIESQIMNLT
EGKGVDAAIIAGGNADIMATAVKIVKPGGTIANVNYFGEGEVLPVPRLEWGCGMAHKTIKGGLCPGGRLRMERLIDLV
FYKRVDPSKLVTHVFRGFDNIEKAFMLMKDKPKDLIKPVVILA

FIG 27

ATGAAAGGTTTTGCAATGCTAGGTATTAATAAGTTAGGATGGATCGAAAAAGAAAGGCCAGTTGCGGGTTCATAT
GATGCTATTGTACGCCCATTAGCAGTATCTCCGTGTACATCAGATATACATACTGTTTTTGAGGGAGCTCTTGGAGA
TAGGAAGAATATGATTTTAGGGCATGAAGCTGTAGGTGAAGTTGTTGAAGTAGGAAGTGAAGTGAAGGATTTTA
AACCTGGTGACAGAGTTATAGTTCCTTGTACAACTCCAGATTGGAGATCTTTGGAAGTTCAAGCTGGTTTTCAACA
GCACTCAAACGGTATGCTCGCAGGATGGAAATTTTCAAATTTCAAGGATGGAGTTTTTGGTGAATATTTTCATGTA
AATGATGCGGATATGAATCTTGCGATTCTACCTAAAGACATGCCATTAGAAAATGCTGTTATGATAACAGATATGA
TGACTACTGGATTTCATGGAGCAGAACTTGCAGATATTCAAATGGGTTCAAGTGTTGTGGTAATTGGCATTGGAGC
TGTTGGCTTAATGGGAATAGCAGGTGCTAAATTACGTGGAGCAGGTAGAATAATTGGAGTGGGGAGCAGGCCGA
TTTGTGTTGAGGCTGCAAAATTTTATGGAGCAACAGATATTCTAAATTATAAAAATGGTCATATAGTTGATCAAGTT
ATGAAATTAACGAATGGAAAAGGCGTTGACCGCGTAATTATGGCAGGCGGTGGTTCTGAAACATTATCCCAAGCA
GTATCTATGGTTAAACCAGGAGGAATAATTTCTAATATAAATTATCATGGAAGTGGAGATGCTTTACTAATACCAC
GTGTAGAATGGGGATGTGGAATGGCTCACAAGACTATAAAAGGAGGTCTTTGTCCTGGGGGACGTTTGAGAGCA
GAAATGTTAAGAGATATGGTAGTATATAATCGTGTTGATCTAAGTAAATTAGTTACACATGTATATCATGGATTTG
ATCACATAGAAGAAGCACTGTTATTAATGAAAGACAAGCCAAAAGACTTAATTAAAGCAGTAGTTATATTATAA

FIG 28

MKEVVIASAVRTAIGSYGKSLKDVPAVDLGATAIKEAVKKAGIKPEDVNEVILGNVLQAGLGQNPARQASFKAGLPVEIP
AMTINKVCGSGLRTVSLAAQIIKAGDADVIIAGGMENMSRAPYLANNARWGYRMGNAKFVDEMITDGLWDAFNDY
HMGITAENIAERWNISREEQDEFALASQKKAEEAIKSGQFKDEIVPVVIKGRKGETVVDTDEHPRFGSTIEGLAKLKPAFK
KDGTVTAGNASGLNDCAAVLVIMSAEKAKELGVKPLAKIVSYGSAGVDPAIMGYGPFYATKAAIEKAGWTVDELDLIES
NEAFAAQSLAVAKDLKFDMNKVNVNGGAIALGHPIGASGARILVTLVHAMQKRDAKKGLATLCIGGGQGTAILLEKC*

FIG 29

MNKLVKLTDLKRIFKDGMTIMVGGFLDCGTPENIIDMLVDLNIKNLTIISNDTAFPNKGIGKLIVNGQVSKVIASHIGTNP
ETGKKMSSGELKVELSPQGTLIERIRAAGSGLGGVLTPTGLGTIVEEGKKKVTIDGKEYLLELPLSADVSLIKGSIVDEFGNT
FYRAATKNFNPYMAMAAKTVIVEAENLVKCEDLKRDAIMTPGVLVDYIVKEAA*

FIG 30

LIVDKVLAKEIIAKRVAKELKKDQLVNLGIGLPTLVANYVPKEMNITFESENGMVGMAQMASSGENDPDIINAGGEYVT
LLPQGSFFDSSMSFALIRGGHVDVAVLGALEVDEKGNLANWIVPNKIVPGMGGAMDLAIGAKKIIVAMQHTGKSKPKI
VKKCTLPLTAKAQVDLIVTELCVIDVTNDGLLLKEIHKDTTIDEIKFLTDADLIIPDNLKIMDI*

FIG 31

MLESEVSKQITTPLAAPAFPRGPYRFHNREYLNIIYRTDLDALRKIVPEPLELDRAYVRFEMMAMPDTTGLGSYTECGQA
IPVKYNGVKGDYLHMMYLDNEPAIAVGRESSAYPKKLGYPKLFVDSDTLVGTLKYGTLPVATATMGYKHEPLDLKEAYA
QIARPNFMLKIIQGYDGKPRICELICAENTDITIHGAWTGSARLQLFSHALAPLADLPVLEIVSASHILTDLTLGTPKVVHDY
LSVK*

FIG 32

TGAAAGAAAGATATGGAACAGTCTATAAAGGCTCTCAGAGGCTCATAGACGAAGAAAGTGGAGAAGTCATAGAG
GTAGACAAGTTATACCGTAAACAAACGTCTGGTAACTTCGTAAAGGCATATATAGTGCAATTAATAAGTATGTTAG
ATATGATTGGCGGAAAAAAACTTAAAATCGTTAACTATATCCTAGATAATGTCCACTTAAGTAACAATACAATGAT
AGCTACAACAAGAGAAATAGCAAAAGCTACAGGAACAAGTCTACAAACAGTAATAACAACACTTAAAATCTTAGA
AGAAGGAAATATTATAAAAAGAAAAACTGGAGTATTAATGTTAAACCCTGAACTACTAATGAGAGGCGACGACCA
AAAACAAAAATACCTCTTACTCGAATTTGGGAACTTTGAGCAAGAGGCAAATGAAATAGATTGACCTCCCAATAAC
ACCACGTAGTTATTGGGAGGTCAATCTATGAAATGCGATTAAGGGCCGGCCAGTGGGCAAGTTGAAAAATTCACA
AAAATGTGGTATAATATCTTTGTTCATTAGAGCGATAAACTTGAATTTGAGAGGGAACTTAGATGGTATTTGAAAA
AATTGATAAAAATAGTTGGAACAGAAAAGAGTATTTTGACCACTACTTTGCAAGTGTACCTTGTACCTACAGCATG
ACCGTTAAAGTGGATATCACACAAATAAAGGAAAAGGGAATGAAACTATATCCTGCAATGCTTTATTATATTGCAA
TGATTGTAAACCGCCATTCAGAGTTTAGGACGGCAATCAATCAAGATGGTGAATTGGGGATATATGATGAGATGA
TACCAAGCTATACAATATTTCACAATGATACTGAAACATTTTCCAGCCTTTGGACTGAGTGTAAGTCTGACTTTAAA
TCATTTTTAGCAGATTATGAAAGTGATACGCAACGGTATGGAAACAATCATAGAATGGAAGGAAAGCCAAATGCT
CCGGAAAACATTTTTAATGTATCTATGATACCGTGGTCAACCTTCGATGGCTTTAATCTGAATTTGCAGAAAGGATA
TGATTATTTGATTCCTATTTTTACTATGGGGAAATATTATAAAGAAGATAACAAAATTATACTTCCTTTGGCAATTCA
AGTTCATCACGCAGTATGTGACGGATTTCACATTTGCCGTTTTGTAAACGAATTGCAGGAATTGATAAATAGTTAA
CTTCAGGTTTGTCTGTAACTAAAAACAAGTATTTAAGCAAAAACATCGTAGAAATACGGTGTTTTTTGTTACCCTAA
GTTTAAACTCCTTTTTGATAATCTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTGTGATGCTCGTCAGGGGGGCGGAGCCT
ATGGAAAAACGCCAGCAACGCGGCCTTTTTACGGTTCCTGGCCTTTTGCTGGCCTTTTGCTCACATGTTCTTTCCTG
CGTTATCCCCTGATTCTGTGGATAACCGTATTACCGCCTTTGAGTGAGCTGATACCGCTCGCCGCAGCCGAACGAC
CGAGCGCAGCGAGTCAGTGAGCGAGGAAGCGGAAGAGCGCCCAATACGCAGGGCCCCCTGCAGGATAAAAAAA
TTGTAGATAAATTTTATAAAATAGTTTTATCTACAATTTTTTTATCAGGAAACAGCTATGACCGCGGCCGCAGATAG
TCATAATAGTTCCAGAATAGTTCAATTTAGAAATTAGACTAAACTTCAAAATGTTTGTTAAATATATACCAAACTAG
TATAGATATTTTTTAAATACTGGACTTAAACAGTAGTAATTTGCCTAAAAAATTTTTTCAATTTTTTTTAAAAAATCCT
TTTCAAGTTGTACATTGTTATGGTAATATGTAATTGAAGAAGTTATGTAGTAATATTGTAAACGTTTCTTGATTTTTT
TACATCCATGTAGTGCTTAAAAAACCAAAATATGTCACATGCAATTGTATATTTCAAATAACAATATTTATTTTCTCG
TTAAATTCACAAATAATTTATTAATAATATCAATAACCAAGATTATACTTAAATGGATGTTTATTTTTTAACACTTTTA
TAGTAAATATATTTATTTTATGTAGTAAAAAGGTTATAATTATAATTGTATTTATTACAATTAATTAAAATAAAAAAT
AGGGTTTTAGGTAAAATTAAGTTATTTTAAGAAGTAATTACAATAAAAATTGAAGTTATTTCTTTAAGGAGGGAAT
TATTCATATGAAAGAAGTTGTAATAGCTAGTGCAGTAAGAACAGCGATTGGATCTTATGGAAAGTCTCTTAAGGAT
GTACCAGCAGTAGATTTAGGAGCTACAGCTATAAAGGAAGCAGTTAAAAAAGCAGGAATAAAACCAGAGGATGT
TAATGAAGTCATTTTAGGAAATGTTCTTCAAGCAGGTTTAGGACAGAATCCAGCAAGACAGGCATCTTTTAAAGCA
GGATTACCAGTTGAAATTCCAGCTATGACTATTAATAAGGTTTGTGGTTCAGGACTTAGAACAGTTAGCTTAGCAG
CACAAATTATAAAAGCAGGAGATGCTGACGTAATAATAGCAGGTGGTATGGAAAATATGTCTAGAGCTCCTTACTT
AGCGAATAACGCTAGATGGGGATATAGAATGGGAAACGCTAAATTTGTTGATGAAATGATCACTGACGGATTGTG
GGATGCATTTAATGATTACCACATGGGAATAACAGCAGAAAACATAGCTGAGAGATGGAACATTTCAAGAGAAGA
ACAAGATGAGTTTGCTCTTGCATCACAAAAAAAAGCTGAAGAAGCTATAAAATCAGGTCAATTTAAAGATGAAAT

FIG 33

AGTTCCTGTAGTAATTAAAGGCAGAAAGGGAGAAACTGTAGTTGATACAGATGAGCACCCTAGATTTGGATCAAC
TATAGAAGGACTTGCAAAATTAAAACCTGCCTTCAAAAAAGATGGAACAGTTACAGCTGGTAATGC
ATCAGGATTAAATGACTGTGCAGCAGTACTTGTAATCATGAGTGCAGAAAAAGCTAAAGAGCTTGGAGTAAAACC
ACTTGCTAAGATAGTTTCTTATGGTTCAGCAGGAGTTGACCCAGCAATAATGGGATATGGACCTTTCTATGCAACA
AAAGCAGCTATTGAAAAAGCAGGTTGGACAGTTGATGAATTAGATTTAATAGAATCAAATGAAGCTTTTGCAGCTC
AAAGTTTAGCAGTAGCAAAAGATTTAAAATTTGATATGAATAAAGTAAATGTAAATGGAGGAGCTATTGCCCTTG
GTCATCCAATTGGAGCATCAGGTGCAAGAATACTCGTTACTCTTGTACACGCAATGCAAAAAAGAGATGCAAAAA
AAGGCTTAGCAACTTTATGTATAGGTGGCGGACAAGGAACAGCAATATTGCTAGAAAAGTGCTAGGAATTCGAGC
TCGGTACCAGGGAGATATTAAAATGAATAAATTAGTAAAATTAACAGATTTAAAGCGCATTTTCAAAGATGGCATG
ACAATTATGGTTGGGGGTTTTTTAGATTGTGGAACTCCTGAAAATATTATAGATATGCTAGTTGATTTAAATATAAA
AAATCTGACTATTATAAGCAATGATACAGCTTTTCCTAATAAAGGAATAGGAAAACTTATTGTAAATGGTCAAGTTT
CTAAAGTAATTGCTTCACATATTGGAACTAATCCTGAAACTGGAAAAAAAATGAGCTCTGGAGAACTTAAAGTTGA
GCTTTCCCCACAAGGAACACTGATTGAAAGAATTCGTGCAGCTGGATCTGGACTCGGAGGTGTATTAACTCCAACT
GGACTTGGAACTATCGTTGAAGAAGGTAAGAAAAAAGTTACTATCGATGGCAAAGAATATCTATTAGAACTTCCTT
TATCTGCTGATGTTTCATTAATAAAAGGTAGCATTGTAGATGAATTTGGAAATACCTTCTATAGGGCTGCTACTAAA
AATTTCAATCCATATATGGCAATGGCTGCAAAAACAGTTATAGTTGAAGCAGAAAATTTAGTTAAATGTGAAGATT
TAAAAAGAGATGCCATAATGACTCCTGGCGTATTAGTAGATTATATCGTTAAGGAGGCGGCTTAATTGATTGTAGA
TAAAGTTTTAGCAAAAGAGATAATTGCCAAAAGAGTTGCAAAAGAACTAAAAAAAGACCAACTCGTAAACCTTGG
AATAGGACTTCCAACTTTAGTAGCAAATTATGTACCAAAAGAAATGAACATTACTTTTGAATCAGAAAATGGCATG
GTTGGTATGGCACAAATGGCATCATCAGGTGAAAATGACCCAGATATAATAAATGCTGGCGGGGAATATGTAACA
TTATTACCTCAAGGTTCATTTTTTGATAGTTCAATGTCTTTCGCACTAATACGAGGAGGACATGTTGATGTTGCTGTT
CTTGGTGCTCTAGAAGTTGATGAAAAAGGTAATTTAGCTAACTGGATTGTTCCAAATAAAATTGTCCCAGGTATGG
GTGGCGCTATGGATTTAGCAATAGGCGCAAAAAAAATAATAGTGGCAATGCAACATACAGGAAAAAGTAAACCTA
AAATCGTTAAAAAATGTACTCTCCCACTTACTGCTAAGGCTCAAGTGGATTTAATTGTCACAGAACTTTGTGTAATT
GATGTAACAAATGACGGCTTACTTTTAAAAGAAATTCATAAAGATACAACTATTGATGAAATTAAATTTTTAACAGA
TGCAGATTTAATTATTCCAGATAACTTAAAGATTATGGATATATGAATCATTCTATTTTAAATATATAACTTTAAAAA
TCTTATGTATTAAAAACTAAGAAAAGAGGTTGATTGTTTTATGTTAGAAAGTGAAGTATCTAAACAAATTACAACTC
CACTTGCTGCTCCAGCGTTTCCTAGAGGACCATATAGGTTTCACAATAGAGAATATCTAAACATTATTTATCGAACT
GATTTAGATGCTCTTCGAAAAATAGTACCAGAGCCACTTGAATTAGATAGAGCATATGTTAGATTTGAAATGATGG
CTATGCCTGATACAACCGGACTAGGCTCATATACAGAATGTGGTCAAGCTATTCCAGTAAAATATAATGGTGTTAA
GGGTGACTACTTGCATATGATGTATCTAGATAATGAACCTGCTATTGCTGTTGGAAGAGAAAGTAGCGCTTATCCA
AAAAAGCTTGGCTATCCAAAGCTATTTGTTGATTCAGATACTTTAGTTGGGACACTTAAATATGGTACATTACCAGT
AGCTACTGCAACAATGGGATATAAGCACGAGCCTCTAGATCTTAAAGAAGCCTATGCTCAAATTGCAAGACCCAAT
TTTATGCTAAAAATCATTCAAGGTTACGATGGTAAGCCAAGAATTTGTGAACTAATATGTGCAGAAAATACTGATA
TAACTATTCACGGTGCTTGGACTGGAAGTGCACGTCTACAATTATTTAGCCATGCACTAGCTCCTCTTGCTGATTTA
CCTGTATTAGAGATTGTATCAGCATCTCATATCCTCACAGATTTAACTCTTGGAACACCTAAGGTTGTACATGATTA
TCTTTCAGTAAAATAAAAGCAATATAGAGGATCCTCTAGAGTCGACGTCACGCGTCCATGGAGATCTCGAGGCCTG
CAGACATGCAAGCTTGGCACTGGCCGTCGTTTTACAACGTCGTGACTGGGAAAACCCTGGCGTTACCCAACTTAAT
CGCCTTGCAGCACATCCCCCTTTCGCCAGCTGGCGTAATAGCGAAGAGGCCCGCACCGATCGCCCTTCCCAACAGT
TGCGCAGCCTGAATGGCGAATGGCGCTAGCATAAAAATAAGAAGCCTGCATTTGCAGGCTTCTTATTTTTATGGCG
CGCCGCATTCACTTCTTTTCTATATAAATATGAGCGAAGCGAATAAGCGTCGGAAAAGCAGCAAAAAGTTTCCTTT
TTGCTGTTGGAGCATGGGGGTTCAGGGGGTGCAGTATCTGACGTCAATGCCGAGCGAAAGCGAGCCGAAGGGTA
GCATTTACGTTAGATAACCCCCTGATATGCTCCGACGCTTTATATAGAAAAGAAGATTCAACTAGGTAAAATCTTAA
TATAGGTTGAGATGATAAGGTTTATAAGGAATTTGTTTGTTCTAATTTTTCACTCATTTTGTTCTAATTTCTTTTAACA
AATGTTCTTTTTTTTTTAGAACAGTTATGATATAGTTAGAATAGTTTAAAATAAGGAGTGAGAAAAAG

FIG 33 (continued)

ATGAATAAATTAGTAAAATTAACAGATTTAAAGCGCATTTTCAAAGATGGCATGACAATTATGGTTGGGGGTTTTT
TAGATTGTGGAACTCCTGAAAATATTATAGATATGCTAGTTGATTTAAATATAAAAAATCTGACTATTATAAGCAAT
GATACAGCTTTTCCTAATAAAGGAATAGGAAAACTTATTGTAAATGGTCAAGTTTCTAAAGTAATTGCTTCACATAT
TGGAACTAATCCTGAAACTGGAAAAAAAAATGAGCTCTGGAGAACTTAAAGTTGAGCTTTCCCCACAAGGAACACT
GATTGAAAGAATTCGTGCAGCTGGATCTGGACTCGGAGGTGTATTAACTCCAACTGGACTTGGAACTATCGTTGA
AGAAGGTAAGAAAAAAGTTACTATCGATGGCAAAGAATATCTATTAGAACTTCCTTTATCTGCTGATGTTTCATTAA
TAAAAGGTAGCATTGTAGATGAATTTGGAAATACCTTCTATAGGGCTGCTACTAAAAATTTCAATCCATATATGGC
AATGGCTGCAAAAACAGTTATAGTTGAAGCAGAAAATTTAGTTAAATGTGAAGATTTAAAAAGAGATGCCATAAT
GACTCCTGGCGTATTAGTAGATTATATCGTTAAGGAGGCGGCTTAATTGATTGTAGATAAAGTTTTAGCAAAAGAG
ATAATTGCCAAAAGAGTTGCAAAAGAACTAAAAAAAGACCAACTCGTAAACCTTGGAATAGGACTTCCAACTTTAG
TAGCAAATTATGTACCAAAAGAAATGAACATTACTTTTGAATCAGAAAATGGCATGGTTGGTATGGCACAAATGGC
ATCATCAGGTGAAAATGACCCAGATATAATAAATGCTGGCGGGGAATATGTAACATTATTACCTCAAGGTTCATTT
TTTGATAGTTCAATGTCTTTCGCACTAATACGAGGAGGACATGTTGATGTTGCTGTTCTTGGTGCTCTAGAAGTTGA
TGAAAAAGGTAATTTAGCTAACTGGATTGTTCCAAATAAAATTGTCCCAGGTATGGGTGGCGCTATGGATTTAGCA
ATAGGCGCAAAAAAAATAATAGTGGCAATGCAACATACAGGAAAAAGTAAACCTAAAATCGTTAAAAAATGTACT
CTCCCACTTACTGCTAAGGCTCAAGTGGATTTAATTGTCACAGAACTTTGTGTAATTGATGTAACAAATGACGGCTT
ACTTTTAAAAGAAATTCATAAAGATACAACTATTGATGAAATTAAATTTTTAACAGATGCAGATTTAATTATTCCAG
ATAACTTAAAGATTATGGATATATGAATCATTCTATTTTAAATATATAACTTTAAAAATCTTATGTATTAAAAACTAA
GAAAAGAGGTTGATTGTTTTATGTTAGAAAGTGAAGTATCTAAACAAATTACAACTCCACTTGCTGCTCCAGCGTTT
CCTAGAGGACCATATAGGTTTCACAATAGAGAATATCTAAACATTATTTATCGAACTGATTTAGATGCTCTTCGAAA
AATAGTACCAGAGCCACTTGAATTAGATAGAGCATATGTTAGATTTGAAATGATGGCTATGCCTGATACAACCGGA
CTAGGCTCATATACAGAATGTGGTCAAGCTATTCCAGTAAAATATAATGGTGTTAAGGGTGACTACTTGCATATGA
TGTATCTAGATAATGAACCTGCTATTGCTGTTGGAAGAGAAAGTAGCGCTTATCCAAAAAAGCTTGGCTATCCAAA
GCTATTTGTTGATTCAGATACTTTAGTTGGGACACTTAAATATGGTACATTACCAGTAGCTACTGCAACAATGGGAT
ATAAGCACGAGCCTCTAGATCTTAAAGAAGCCTATGCTCAAATTGCAAGACCCAATTTTATGCTAAAAATCATTCAA
GGTTACGATGGTAAGCCAAGAATTTGTGAACTAATATGTGCAGAAAATACTGATATAACTATTCACGGTGCTTGGA
CTGGAAGTGCACGTCTACAATTATTTAGCCATGCACTAGCTCCTCTTGCTGATTTACCTGTATTAGAGATTGTATCA
GCATCTCATATCCTCACAGATTTAACTCTTGGAACACCTAAGGTTGTACATGATTATCTTTCAGTAAAATAA

FIG 34

ATGAAAGAAAGATATGGAACAGTCTATAAAGGCTCTCAGAGGCTCATAGACGAAGAAAGTGGAGAAGTCATAGA
GGTAGACAAGTTATACCGTAAACAAACGTCTGGTAACTTCGTAAAGGCATATATAGTGCAATTAATAAGTATGTTA
GATATGATTGGCGGAAAAAAACTTAAAATCGTTAACTATATCCTAGATAATGTCCACTTAAGTAACAATACAATGA
TAGCTACAACAAGAGAAATAGCAAAAGCTACAGGAACAAGTCTACAAACAGTAATAACAACACTTAAAATCTTAG
AAGAAGGAAATATTATAAAAAGAAAAACTGGAGTATTAATGTTAAACCCTGAACTACTAATGAGAGGCGACGACC
AAAAACAAAAATACCTCTTACTCGAATTTGGGAACTTTGAGCAAGAGGCAAATGAAATAGATTGACCTCCCAATAA
CACCACGTAGTTATTGGGAGGTCAATCTATGAAATGCGATTAAGGGCCGGCCAGTGGGCAAGTTGAAAAATTCAC
AAAAATGTGGTATAATATCTTTGTTCATTAGAGCGATAAACTTGAATTTGAGAGGGAACTTAGATGGTATTTGAAA
AAATTGATAAAAATAGTTGGAACAGAAAAGAGTATTTTGACCACTACTTTGCAAGTGTACCTTGTACCTACAGCAT
GACCGTTAAAGTGGATATCACACAAATAAAGGAAAAGGGAATGAAACTATATCCTGCAATGCTTTATTATATTGCA
ATGATTGTAAACCGCCATTCAGAGTTTAGGACGGCAATCAATCAAGATGGTGAATTGGGGATATATGATGAGATG
ATACCAAGCTATACAATATTTCACAATGATACTGAAACATTTTCCAGCCTTTGGACTGAGTGTAAGTCTGACTTTAA
ATCATTTTTAGCAGATTATGAAAGTGATACGCAACGGTATGGAAACAATCATAGAATGGAAGGAAAGCCAAATGC
TCCGGAAAACATTTTTAATGTATCTATGATACCGTGGTCAACCTTCGATGGCTTTAATCTGAATTTGCAGAAAGGAT
ATGATTATTTGATTCCTATTTTTACTATGGGGAAATATTATAAAGAAGATAACAAAATTATACTTCCTTTGGCAATTC
AAGTTCATCACGCAGTATGTGACGGATTTCACATTTGCCGTTTTGTAAACGAATTGCAGGAATTGATAAAT

FIG 35

AGTTAACTTCAGGTTTGTCTGTAACTAAAAACAAGTATTTAAGCAAAAACATCGTAGAAATACGGTGTTTTTTGTTA
CCCTAAGTTTAAACTCCTTTTTGATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTTCCGAAGGTAACTGGCTTCAGCAG
AGCGCAGATACCAAATACTGTTCTTCTAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCCACGCTTCCCGAAGGGAGAAA
GGCGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCAGGGGGGC
GGAGCCTATGGAAAAACGCCAGCAACGCGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGAGTGAGCTGATACCGCTCGCCGCAGCCG
AACGACCGAGCGCAGCGAGTCAGTGAGCGAGGAAGCGGAAGAGCGCCCAATACGCAGGGCCCCCTGCAGGATA
AAAAAATTGTAGATAAATTTTATAAAATAGTTTTATCTACAATTTTTTTATCAGGAAACAGCTATGACCGCGGCCGC
AGATAGTCATAATAGTTCCAGAATAGTTCAATTTAGAAATTAGACTAAACTTCAAAATGTTTGTTAAATATATACCA
AACTAGTATAGATATTTTTTAAATACTGGACTTAAACAGTAGTAATTTGCCTAAAAAATTTTTTCAATTTTTTTTAAA
AAATCCTTTTCAAGTTGTACATTGTTATGGTAATATGTAATTGAAGAAGTTATGTAGTAATATTGTAAACGTTTCTT
GATTTTTTTACATCCATGTAGTGCTTAAAAAACCAAAATATGTCACATGCAATTGTATATTTCAAATAACAATATTTA
TTTTCTCGTTAAATTCACAAATAATTTATTAATAATATCAATAACCAAGATTATACTTAAATGGATGTTTATTTTTTAA
CACTTTTATAGTAAATATATTTATTTTATGTAGTAAAAAGGTTATAATTATAATTGTATTTATTACAATTAATTAAAAT
AAAAAATAGGGTTTTAGGTAAAATTAAGTTATTTTAAGAAGTAATTACAATAAAAATTGAAGTTATTTCTTTAAGGA
GGGAATTATTCATATGAAAGAAGTTGTAATAGCTAGTGCAGTAAGAACAGCGATTGGATCTTATGGAAAGTCTCTT
AAGGATGTACCAGCAGTAGATTTAGGAGCTACAGCTATAAAGGAAGCAGTTAAAAAAGCAGGAATAAAACCAGA
GGATGTTAATGAAGTCATTTTAGGAAATGTTCTTCAAGCAGGTTTAGGACAGAATCCAGCAAGACAGGCATCTTTT
AAAGCAGGATTACCAGTTGAAATTCCAGCTATGACTATTAATAAGGTTTGTGGTTCAGGACTTAGAACAGTTAGCT
TAGCAGCACAAATTATAAAAGCAGGAGATGCTGACGTAATAATAGCAGGTGGTATGGAAAATATGTCTAGAGCTC
CTTACTTAGCGAATAACGCTAGATGGGGATATAGAATGGGAAACGCTAAATTTGTTGATGAAATGATCACTGACG
GATTGTGGGATGCATTTAATGATTACCACATGGGAATAACAGCAGAAAACATAGCTGAGAGATGGAACATTTCAA
GAGAAGAACAAGATGAGTTTGCTCTTGCATCACAAAAAAAAGCTGAAGAAGCTATAAAATCAGGTCAATTTAAAG
ATGAAATAGTTCCTGTAGTAATTAAAGGCAGAAAGGGAGAAACTGTAGTTGATACAGATGAGCACCCTAGATTTG
GATCAACTATAGAAGGACTTGCAAAATTAAAACCTGCCTTCAAAAAAGATGGAACAGTTACAGCTGGTAATGCATC
AGGATTAAATGACTGTGCAGCAGTACTTGTAATCATGAGTGCAGAAAAAGCTAAAGAGCTTGGAGTAAAACCACT
TGCTAAGATAGTTTCTTATGGTTCAGCAGGAGTTGACCCAGCAATAATGGGATATGGACCTTTCTATGCAACAAAA
GCAGCTATTGAAAAAGCAGGTTGGACAGTTGATGAATTAGATTTAATAGAATCAAATGAAGCTTTTGCAGCTCAAA
GTTTAGCAGTAGCAAAAGATTTAAAATTTGATATGAATAAAGTAAATGTAAATGGAGGAGCTATTGCCCTTGGTCA
TCCAATTGGAGCATCAGGTGCAAGAATACTCGTTACTCTTGTACACGCAATGCAAAAAAGAGATGCAAAAAAAGG
CTTAGCAACTTTATGTATAGGTGGCGGACAAGGAACAGCAATATTGCTAGAAAAGTGCTAGGAATTCGAGCTCGG
TACCAGGGAGATATTAAAATGAATAAATTAGTAAAATTAACAGATTTAAAGCGCATTTTCAAAGATGGCATGACAA
TTATGGTTGGGGGTTTTTTAGATTGTGGAACTCCTGAAAATATTATAGATATGCTAGTTGATTTAAATATAAAAAAT
CTGACTATTATAAGCAATGATACAGCTTTTCCTAATAAAGGAATAGGAAAACTTATTGTAAATGGTCAAGTTTCTAA
AGTAATTGCTTCACATATTGGAACTAATCCTGAAACTGGAAAAAAAATGAGCTCTGGAGAACTTAAAGTTGAGCTT
TCCCCACAAGGAACACTGATTGAAAGAATTCGTGCAGCTGGATCTGGACTCGGAGGTGTATTAACTCCAACTGGA
CTTGGAACTATCGTTGAAGAAGGTAAGAAAAAAGTTACTATCGATGGCAAAGAATATCTATTAGAACTTCCTTTAT
CTGCTGATGTTTCATTAATAAAAGGTAGCATTGTAGATGAATTTGGAAATACCTTCTATAGGGCTGCTACTAAAAAT
TTCAATCCATATATGGCAATGGCTGCAAAAACAGTTATAGTTGAAGCAGAAAATTTAGTTAAATGTGAAGATTTAA
AAAGAGATGCCATAATGACTCCTGGCGTATTAGTAGATTATATCGTTAAGGAGGCGGCTTAATTGATTGTAGATAA
AGTTTTAGCAAAAGAGATAATTGCCAAAAGAGTTGCAAAAGAACTAAAAAAAGACCAACTCGTAAAC

FIG 35 (continued)

CTTGGAATAGGACTTCCAACTTTAGTAGCAAATTATGTACCAAAAGAAATGAACATTACTTTTGAATCAGAAAATG
GCATGGTTGGTATGGCACAAATGGCATCATCAGGTGAAAATGACCCAGATATAATAAATGCTGGCGGGGAATATG
TAACATTATTACCTCAAGGTTCATTTTTTGATAGTTCAATGTCTTTCGCACTAATACGAGGAGGACATGTTGATGTT
GCTGTTCTTGGTGCTCTAGAAGTTGATGAAAAAGGTAATTTAGCTAACTGGATTGTTCCAAATAAAATTGTCCCAG
GTATGGGTGGCGCTATGGATTTAGCAATAGGCGCAAAAAAAATAATAGTGGCAATGCAACATACAGGAAAAAGT
AAACCTAAAATCGTTAAAAAATGTACTCTCCCACTTACTGCTAAGGCTCAAGTGGATTTAATTGTCACAGAACTTTG
TGTAATTGATGTAACAAATGACGGCTTACTTTTAAAAGAAATTCATAAAGATACAACTATTGATGAAATTAAATTTT
TAACAGATGCAGATTTAATTATTCCAGATAACTTAAAGATTATGGATATATGAATCATTCTATTTTAAATATATAACT
TTAAAAATCTTATGTATTAAAAACTAAGAAAAGAGGTTGATTGTTTTATGTTAGAAAGTGAAGTATCTAAACAAATT
ACAACTCCACTTGCTGCTCCAGCGTTTCCTAGAGGACCATATAGGTTTCACAATAGAGAATATCTAAACATTATTTA
TCGAACTGATTTAGATGCTCTTCGAAAAATAGTACCAGAGCCACTTGAATTAGATAGAGCATATGTTAGATTTGAA
ATGATGGCTATGCCTGATACAACCGGACTAGGCTCATATACAGAATGTGGTCAAGCTATTCCAGTAAAATATAATG
GTGTTAAGGGTGACTACTTGCATATGATGTATCTAGATAATGAACCTGCTATTGCTGTTGGAAGAGAAAGTAGCGC
TTATCCAAAAAAGCTTGGCTATCCAAAGCTATTTGTTGATTCAGATACTTTAGTTGGGACACTTAAATATGGTACAT
TACCAGTAGCTACTGCAACAATGGGATATAAGCACGAGCCTCTAGATCTTAAAGAAGCCTATGCTCAAATTGCAAG
ACCCAATTTTATGCTAAAAATCATTCAAGGTTACGATGGTAAGCCAAGAATTTGTGAACTAATATGTGCAGAAAAT
ACTGATATAACTATTCACGGTGCTTGGACTGGAAGTGCACGTCTACAATTATTTAGCCATGCACTAGCTCCTCTTGC
TGATTTACCTGTATTAGAGATTGTATCAGCATCTCATATCCTCACAGATTTAACTCTTGGAACACCTAAGGTTGTAC
ATGATTATCTTTCAGTAAAATAAAAGCAATATAGAGGATCCTCTAGAGTCGACTTAGGAGGTTCTATTATGAAAGG
TTTTGCAATGTTAGGTATTAACAAATTAGGATGGATTGAAAAGAAAAACCCAGTGCCAGGTCCTTATGATGCGATT
GTACATCCTCTAGCTGTATCCCCATGTACATCAGATATACATACGGTTTTTGAAGGAGCACTTGGTAATAGGGAAA
ATATGATTTTAGGCCATGAAGCTGTAGGTGAAATAGCCGAAGTTGGCAGCGAAGTTAAAGATTTTAAAGTTGGCG
ATAGAGTTATCGTACCATGCACAACACCTGACTGGAGATCTTTAGAAGTCCAAGCTGGTTTTCAGCAGCATTCAAA
CGGTATGCTTGCAGGATGGAAGTTTTCCAATTTTAAAGATGGTGTATTTGCAGATTACTTTCATGTAAACGATGCA
GATATGAATCTTGCCATACTCCCAGATGAAATACCTTTAGAAAGTGCAGTTATGATGACAGACATGATGACTACTG
GTTTTCATGGAGCAGAACTTGCAGACATAAAAATGGGCTCCAGCGTTGTAGTAATTGGTATAGGAGCTGTTGGAT
TAATGGGAATAGCCGGTTCCAAACTTCGAGGAGCAGGCAGAATTATCGGTGTTGGAAGCAGACCTGTTTGTGTTG
AAACAGCTAAATTTTATGGAGCAACTGATATTGTAAATTATAAAAATGGTGATATAGTTGAACAAATCATGGACTT
AACTCATGGTAAAGGTGTAGACCGTGTAATCATGGCAGGCGGTGGTGCTGAAACACTAGCACAAGCAGTAACTAT
GGTTAAACCTGGCGGCGTAATTTCTAACATCAACTACCATGGAAGCGGTGATACTTTACCAATACCTCGTGTTCAAT
GGGGCTGCGGCATGGCTCACAAAACTATAAGAGGAGGATTATGCCCCGGCGGACGTCTTAGAATGGAAATGCTA
AGAGATCTTGTTCTATATAAACGTGTTGATTTGAGTAAACTTGTTACTCATGTATTTGATGGTGCAGAAAATATTGA
AAAGGCCCTTTTGCTTATGAAAAATAAGCCAAAAGATTTAATTAAATCAGTAGTTACATTCTAAAAATTCATATAAA
AAAACTGTCGCATTAAAAAAATGTCTCGAGGCCTGCAGACATGCAAGCTTGGCACTGGCCGTCGTTTTACAACGTC
GTGACTGGGAAAACCCTGGCGTTACCCAACTTAATCGCCTTGCAGCACATCCCCCTTTCGCCAGCTGGCGTAATAG
CGAAGAGGCCCGCACCGATCGCCCTTCCCAACAGTTGCGCAGCCTGAATGGCGAATGGCGCTAGCATAAAAATAA
GAAGCCTGCATTTGCAGGCTTCTTATTTTTATGGCGCGCCGCATTCACTTCTTTTCTATATAAATATGAGCGAAGCG
AATAAGCGTCGGAAAAGCAGCAAAAAGTTTCCTTTTTGCTGTTGGAGCATGGGGGTTCAGGGGGTGCAGTATCTG
ACGTCAATGCCGAGCGAAAGCGAGCCGAAGGGTAGCATTTACGTTAGATAACCCCCTGATATGCTCCGACGCTTT
ATATAGAAAAGAAGATTCAACTAGGTAAAATCTTAATATAGGTTGAGATGATAAGGTTTATAAGGAATTTGTTTGT
TCTAATTTTTCACTCATTTTGTTCTAATTTCTTTTAACAAATGTTCTTTTTTTTTTAGAACAGTTATGATATAGTTAGAA
TAGTTTAAAATAAGGAGTGAGAAAAAG

FIG 35 (continued)

GTTTGCCACCTGACGTCTAAGAAAAGGAATATTCAGCAATTTGCCCGTGCCGAAGAAAGGCCCACCCGTGAAGGT
GAGCCAGTGAGTTGATTGCTACGTAATTAGTTAGTTAGCCCTTAGTGACTCGTAATACGACTCACTATAGGGCTCG
AGGCGGCCGCGCAACGCAATTAATGTGAGTTAGCTCACTCATTAGGCACCCCAGGCTTTACACTTTATGCTTCCGG
CTCGTATGTTGTGTGGAATTGTGAGCGGATAACAATTTCACACAGGAAACACATATGTTTCCGTGCAATGCCTATA
TCGAATATGGTGATAAAAATATGAACAGCTTTATCGAAGATGTGGAACAGATCTACAACTTCATTAAAAAGAACAT
TGATGTGGAAGAAAAGATGCATTTCATTGAAACCTATAAACAGAAAAGCAACATGAAGAAAGAGATTAGCTTTAG
CGAAGAATACTATAAACAGAAGATTATGAACGGCAAAAATGGCGTTGTGTACACCCCGCCGGAAATGGCGGCCTT
TATGGTTAAAAATCTGATCAACGTTAACGATGTTATTGGCAATCCGTTTATTAAAATCATTGACCCGAGCTGCGGTA
GCGGCAATCTGATTTGCAAATGTTTTCTGTATCTGAATCGCATCTTTATTAAGAACATTGAGGTGATTAACAGCAAA
AATAACCTGAATCTGAAACTGGAAGACATCAGCTACCACATCGTTCGCAACAATCTGTTTGGCTTCGATATTGACG
AAACCGCGATCAAAGTGCTGAAAATTGATCTGTTTCTGATCAGCAACCAATTTAGCGAGAAAAATTTCCAGGTTAA
AGACTTTCTGGTGGAAAATATTGATCGCAAATATGACGTGTTCATTGGTAATCCGCCGTATATCGGTCACAAAAGC
GTGGACAGCAGCTACAGCTACGTGCTGCGCAAAATCTACGGCAGCATCTACCGCGACAAAGGCGATATCAGCTAT
TGTTTCTTTCAGAAGAGCCTGAAATGTCTGAAGGAAGGTGGCAAACTGGTGTTTGTGACCAGCCGCTACTTCTGCG
AGAGCTGCAGCGGTAAAGAACTGCGTAAATTCCTGATCGAAAACACGAGCATTTACAAGATCATTGATTTTTACGG
CATCCGCCCGTTCAAACGCGTGGGTATCGATCCGATGATTATTTTTCTGGTTCGTACGAAGAACTGGAACAATAAC
ATTGAAATTATTCGCCCGAACAAGATTGAAAAGAACGAAAAGAACAAATTCCTGGATAGCCTGTTCCTGGACAAA
AGCGAAAAGTGTAAAAAGTTTAGCATTAGCCAGAAAAGCATTAATAACGATGGCTGGGTTTTCGTGGACGAAGTG
GAGAAAAACATTATCGACAAAATCAAAGAGAAAAGCAAGTTCATTCTGAAAGATATTTGCCATAGCTGTCAAGGC
ATTATCACCGGTTGTGATCGCGCCTTTATTGTGGACCGTGATATCATCAATAGCCGTAAGATCGAACTGCGTCTGAT
TAAACCGTGGATTAAAAGCAGCCATATCCGTAAGAATGAAGTTATTAAGGGCGAAAAATTCATCATCTATAGCAAC
CTGATTGAGAATGAAACCGAGTGTCCGAATGCGATTAAATATATCGAACAGTACAAGAAACGTCTGATGGAGCGC
CGCGAATGCAAAAAGGGCACGCGTAAGTGGTATGAACTGCAATGGGGCCGTAAACCGGAAATCTTCGAAGAAAA
GAAAATTGTTTTCCCGTATAAAAGCTGTGACAATCGTTTTGCACTGGATAAGGGTAGCTATTTTAGCGCAGACATTT
ATAGCCTGGTTCTGAAGAAAAATGTGCCGTTCACCTATGAGATCCTGCTGAATATCCTGAATAGCCCGCTGTACGA
GTTTTACTTTAAGACCTTCGCGAAAAAGCTGGGCGAGAATCTGTACGAGTACTATCCGAACAACCTGATGAAGCTG
TGCATCCCGAGCATCGATTTCGGCGGTGAGAACAATATTGAGAAAAAGCTGTATGATTTCTTTGGTCTGACGGATA
AAGAAATTGAGATTGTGGAGAAGATCAAAGATAACTGCTAAGAATTCGATATCACCCGGGAACTAGTCTGCAGCC
CTTTAGTGAGGGTTAATTGGAGTCACTAAGGGTTAGTTAGTTAGATTAGCAGAAAGTCAAAAGCCTCCGACCGGA
GGCTTTTGACTAAAACTTCCCTTGGGGTTATCATTGGGGCTCACTCAAAGGCGGTAATCAGATAAAAAAAATCCTT
AGCTTTCGCTAAGGATGATTTCTGCTAGAGATGGAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACACGACGGGGAGTCAGGCAACTATGGA
TGAACGAAATAGACAGATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATCCTTTTTGATAATCTCATG
ACCAAAATCCCTTAACGTGAGTTTTCGTTCCACTGAGCGTCAGACCCCTTAATAAGATGATCTTCTTGAGATCGTTT
TGGTCTGCGCGTAATCTCTTGCTCTGAAAACGAAAAAACCGCCTTGCAGGGCGGTTTTTCGAAGGTTCTCTGAGCT
ACCAACTCTTTGAACCGAGGTAACTGGCTTGGAGGAGCGCAGTCACCAAAACTTGTCCTTTCAGTTTAGCCTTAAC
CGGCGCATGACTTCAAGACTAACTCCTCTAAATCAATTACCAGTGGCTGCTGCCAGTGGTGCTTTTGCATGTCTTTC
CGGGTTGGACTCAAGACGATAGTTACCGGATAAGGCGCAGCGGTCGGACTGAACGGGGGGTTCGTGCATACAGT
CCAGCTTGGAGCGAACTGCCTACCCGGAACTGAGTGTCAGGCGTGGAATGAGACAAACGCGGCCATAACAGCGG
AATGACACCGGTAAACCGAAAGGCAGGAACAGGAGAGCGCACGAGGGAGCCGCCAGGGGAAACGCCTGGTATC
TTTATAGTCCTGTCGGGTTTCGCCACCACTGATTTGAGCGTCAGATTTCGTGATGCTTGTCAGGGGGGCGGAGCCT
ATGGAAAAACGGCTTTGCCGCGGCCCTCTCACTTCCCTGTTAAGTATCTTCCTGGCATCTTCCAGGAAATCTCCGCC
CCGTTCGTAAGCCATTTCCGCTCGCCGCAGTCGAACGACCGAGCGTAGCGAGTCAGTGAGCGAGGAAGCGGAAT
ATATCCTGTATCACATATTCTGCTGACGCACCGGTGCAGCCTTTTTTCTCCTGCCACATGAAGCACTTCACTGACACC
CTCATCAGTGCCAACATAGTAAGCCAGTATACACTCCGCTAGCGCTGAGGTCTGCCTCGTGAAG

FIG 36

AAGGTGTTGCTGACTCATACCAGGCCTGAATCGCCCCATCATCCAGCCAGAAAGTGAGGGAGCCACGGTTGATGA
GAGCTTTGTTGTAGGTGGACCAGTTGGTGATTTTGAACTTTTGCTTTGCCACGGAACGGTCTGCGTTGTCGGGAAG
ATGCGTGATCTGATCCTTCAACTCAGCAAAAGTTCGATTTATTCAACAAAGCCACGTTGTGTCTCAAAATCTCTGAT
GTTACATTGCACAAGATAAAAATATATCATCATGAACAATAAAACTGTCTGCTTACATAAACAGTAATACAAGGGG
TGTTTACTAGAGGTTGATCGGGCACGTAAGAGGTTCCAACTTTCACCATAATGAAATAAGATCACTACCGGGCGTA
TTTTTTGAGTTATCGAGATTTTCAGGAGCTAAGGAAGCTAAAATGGAGAAAAAAATCACGGGATATACCACCGTTG
ATATATCCCAATGGCATCGTAAAGAACATTTTGAGGCATTTCAGTCAGTTGCTCAATGTACCTATAACCAGACCGTT
CAGCTGGATATTACGGCCTTTTTAAAGACCGTAAAGAAAAATAAGCACAAGTTTTATCCGGCCTTTATTCACATTCT
TGCCCGCCTGATGAACGCTCACCCGGAGTTTCGTATGGCCATGAAAGACGGTGAGCTGGTGATCTGGGATAGTGT
TCACCCTTGTTACACCGTTTTCCATGAGCAAACTGAAACGTTTTCGTCCCTCTGGAGTGAATACCACGACGATTTCC
GGCAGTTTCTCCACATATATTCGCAAGATGTGGCGTGTTACGGTGAAAACCTGGCCTATTTCCCTAAAGGGTTTATT
GAGAATATGTTTTTTGTCTCAGCCAATCCCTGGGTGAGTTTCACCAGTTTTGATTTAAACGTGGCCAATATGGACAA
CTTCTTCGCCCCCGTTTTCACGATGGGCAAATATTATACGCAAGGCGACAAGGTGCTGATGCCGCTGGCGATCCAG
GTTCATCATGCCGTTTGTGATGGCTTCCATGTCGGCCGCATGCTTAATGAATTACAACAGTACTGTGATGAGTGGC
AGGGCGGGGCGTAATAATACTAGCTCCGGCAAAAAAACGGGCAAGGTGTCACCACCCTGCCCTTTTTCTTTAAAA
CCGAAAAGATTACTTCGC

FIG 36 (continued)

GCGGCCGCGCAACGCAATTAATGTGAGTTAGCTCACTCATTAGGCACCCCAGGCTTTACACTTTATGCTTCCGGCTC
GTATGTTGTGTGGAATTGTGAGCGGATAACAATTTCACACAGGAAACACAT

FIG 37

TTATAAGAAATCCTAAGGAATATGATGTAATGAGTAAAGCTATAAATCCTTATGGAGATGGCAAGGCAGCTTATA
GAATAACAGAAGCTATTTTACAATATTTTGATTTAGCAAAAGGTACATATAGTGAGTTTAAATCAAATTAAAAAGTT
ATAATTTTCAATTTTCATTCTTTTTAAAGGAGATTAGCATACATTTTATCATAATTATACAGACAATATAGTAATATA
TGATGTTAAAATATCAATATATGGTTAAAAATCTGTATATTTTTTCCCATTTTAATTATTTGTACTATAATATTACACT
GAGTGTATTGTATATTTAAAAAATATTTGGTACAATTAGTTAGTTAAATAAATTCTAAATTGTAAATTATCAGAATC
CTTATTAAGGAAATACATAGATTTAAGGAGAAATCATAAAAAGGTGTAATATAAACTGGCTAAAATTGAGCAAAA
ATTGAGCAATTAAGACTTTTTGATTGTATCTTTTTATATATTTAAGGTATATAATCTTATTTATATTGGGGGAACTTG
ATGAATAAACATATTCTAGAC

FIG 38

TAATTTTTTGTGTCAATAATTTTTGTTATATTATTTTAATTAAATTTTTCACATGTATAATTAAAAGTAAGATAGATAT
TCTAATGTACTTACTTAGGTAGAAAAACATGTATACAAAATTAAAAAACTATTATAACACATAGTATCAATATTGAA
GGTAATACTGTTCAATATCGATACAGATAAAAAAATATATAATACAGAAGAAAAAATTATAAATTTGTGGTATAAT
ATAAAGTATAGTAATTTAAGTTTAAACCTCGTGAAAACGCTAACAAATAATAGGAGGTGTATTAT

FIG 39

ATAGTATAACTTTAAAAAACTGTCTTAAAAAGTTGTTATATAAAAAATGTTGACAATTAAACAGCTATTTAGTGCAA
AACAACCATAAAAATTTAAAAAATACCATAAATTACTTGAAAAATAGTTGATAATAATGTAGAGTTATAAACAAAG
GTGAAAAGCATTACTTGTATTCTTTTTTATATATTATTATAAATTAAAATGAAGCTGTATTAGAAAAAATACACACCT
GTAATATAAAATTTTAAATTAATTTTTAATTTTTTCAAAATGTATTTTACATGTTTAGAATTTTGATGTATATTAAAAT
AGTAGAATACATAAGATACTTAATTTAATTAAAGATAGTTAAGTACTTTTCAATGTGCTTTTTTAGATGTTTAATACA
AATCTTTAATTGTAAAAGAAATGCTGTACTATTTACTGTACTAGTGACGGGATTAAACTGTATTAATTATAAATAAA
AAATAAGTACAGTTGTTTAAAATTATATTTTGTATTAAATCTAATAGTACGATGTAAGTTATTTTATACTATTGCTAG
TTTAATAAAAAGATTTAATTATATACTTGAAAAGGAGAGGAATTTTTATGCGTAAA

FIG 40

FIG 43
XhoI (7,311)
7,500
7,922
rep
500
catP
1,000
1,500
ColE1
2,000
P
2,500
thlA
3,000
3,500
4,000
ctfA
4,500
5,000
ctfB
5,500
adc
6,000
SalI (6,197)
6,500
novel adh
7,000
pMTL85147-thlA-ctfAB-adc-adh(C...
7,922 bp

AGATAGTCATAATAGTTCCAGAATAGTTTAATTTAGCATTTGGATTAAATTCCCATATGTTTGTTAAATATATACCAA
ACTAGTATAGATATTTTTAAAATACTGTACTTAAACAGTAGTAATTTACGTAAAAAAATTTTTTGATTTTTTTAAAAA
AGTCCTTTTCAAGTTGTACATTATTATGGTAATATGTAATTGAAGAAGTTGTGTAGTAATATTGTAAACGTTTCTTA
ATTTATTTTCATCCATGTAGTGCTTAAAAAACCAAAATATGTCACACGCAATTGCATATTTCAAACAATAATATTTAT
TTTCTCGTTAAATTCACAAATAATTTATTAATAATATCAATAACCAAGATTATACTTAAATGGATGTTTATTTTTTAAC
ATTTTTTATAGTAAATATATTTATTTTATGTAGTAAAAAGGTTATAATTATAATTGTATTTATTACAATTAATTAAAAT
AAAAAAATAGGGTTTTAGGTAAAATTAAGTTATTTTAAGAAGTAATTACAACAAAAATTGAAGTTATTTCTTTAAG
GAGGGAATTATTAAA

FIG 44

AGATAGTCATAATAGTTCCAGAATAGTTTAATTTTGAAATTGGAGTAAACTTCCAAATGTTTGTTAAATATATACCA
AACTAGTATAGATATTTTTTAAATACTAGACTTAAACAGTAGAAATTTGCCTAAAAAATTTTTTAGTTTTTTAAAAAA
ATCCTTTTCAAGTTGTACGTTATTATGGTAATATGTAATTGAAGAAGTTATGTAATAATATTGTAAACGTTTCTTAAT
TTTTTTACATCCATGTAATGCTTAAAAGACCAAAATATGTCACATGTAATTGTATATTTCACATAATAATATTTATTTT
CTTATTAAATTCACAAATAATTTATTAATAATATCAATAACCAAGATTATACTTAAATGGATGTTTATTTTTTAACATT
TTTTATGGTAAATATATTTATTTTATGTAGTAAAAAGGTTATAATTATAATTGTATTTATTACAATTAATTAAAATAA
AAAATAGGGTTTTAGGTAAAATTAAGTTATTTTAAGAAGTAATTACAACAAAAATTGAAGTTATTTCTTTAAGGAG
GGAATTATTAAA

FIG 45

TTATAAGAAATCCTAAGGAATATGATGTAATGAGTAAAGCTATAAATCCTTATGGAGATGGCAAGGCAGCTTATA
GAATAACAGAAGCTATTTTACAATATTTTGATTTAGCAAAAGGTACATATAGTGAGTTTAAATCAAATTAAAAAGTT
ATAATTTTCAATTTTCATTCTTTTTAAAGGAGATTAGCATACATTTTATCATAATTATACAGACAATATAGTAATATA
TGATGTTAAAATATCAATATATGGTTAAAAATCTGTATATTTTTTCCCATTTTAATTATTTGTACTATAATATTACACT
GAGTGTATTGTATATTTAAAAAATATTTGGTACAATTAGTTAGTTAAATAAATTCTAAATTGTAAATTATCAGAATC
CTTATTAAGGAAATACATAGATTTAAGGAGAAATCATAAAAAGGTGTAATATAAACTGGCTAAAATTGAGCAAAA
ATTGAGCAATTAAGACTTTTTGATTGTATCTTTTTATATATTTAAGGTATATAATCTTATTTATATTGGGGGAAC

FIG 46

TTATAAGAAATCCTAAGGAATATGATGTAATGAGTAAAGCTATAAATCCTTATGGAGATGGCAAGGCAGCTTATA
GAATAACAGAAGCTATTTTACAATATTTTGATTTAGCAAAAGGTACATATAGTGAGTTTAAATCAAATTAAAAAGTT
ATAATTTTGAATTTTCATTCTTTTTAAAGGAGATTAGCATACATTTTATCATAATTATACAGACAATATAGTAATATA
TGATGTTAAAATATCAATATATGGTTAAAAAACTGTATATTTTTTCCCATTTTAATTATTTGTACTATAATATTACACT
GAGTGTATTGTATATTTAAAAAATATTTGGTACAATTAGTTAGTTAAATAAATTCTAAATTATAAATTATCAGAAAC
CTTATTAAGGAAATACATAGATTTAGGGAGAAATAATAAAAAGGTGTAATATAAACTGGCTAAAGTTGAGTAATT
AAGACTTTTAGGTTGTATCTTTTTATATATTTAAGGTATATAATCTTAGTTATATAGGGGGAACTTGATGAATAAAC
ATATTCTAGAC

FIG 47

TAATTTTTTGTGTCAATAATTTTTGTTATATTATTTTAATTAAATTTTTCACATGTATAATTAAAAGTAAGATAGATAT
TCTAATGTACTTACTTAGGTAGAAAAACATGTATACAAAATTAAAAAACTATTATAACACATAGTATCAATATTGAA
GGTAATACTGTTCAATATCGATACAGATAAAAAAAATATATAATACAGAAGAAAAAATTATAAATTTGTGGTATAA
TATAAAGTATAGTAATTTAAGTTTAAACCTCGTGAAAACGCTAACAAATAATAGGAGGTGTATTAT

FIG 48

TAATTTTTTATATCAATAATTTTTATTATATTATTTTAATTAAATTTTTCACATGTATAATTAAAAGTAAGATAGAGAT
AGTTAGGATATTTTAGTGCATTTATTTAGATAAAAAATATGTATACAAGATTAGAAAAAAATTATAACACATAATAG
TTGCATTGAAGGTAATACTGTTCAATATCGATACAGATAAAAAAATTTATAATACAGAAGAAAAAAATATAAATTT
GTGGTATAATATAAAATATAATAATTTAGATTTACACCCCGTGAAAACGCTAACAAATAAATAGGGAG

FIG 49

ATAGTATAACTTTAAAAAACTGTCTTAAAAAGTTGTTATATAAAAAATGTTGACAATTAAACAGCTATTTAGTGCAA
AACAACCATAAAAATTTAAAAAATACCATAAATTACTTGAAAAATAGTTGATAATAATGTAGAGTTATAAACAAAG
GTGAAAAGCATTACTTGTATTCTTTTTTATATATTATTATAAATTAAAATGAAGCTGTATTAGAAAAAATACACACCT
GTAATATAAAATTTTAAATTAATTTTTAATTTTTTCAAAATGTATTTTACATGTTTAGAATTTTGATGTATATTAAAAT
AGTAGAATACATAAGATACTTAATTTAATTAAAGATAGTTAAGTACTTTTCAATGTGCTTTTTTAGATGTTTAATACA
AATCTTTAATTGTAAAAGAAATGCTGTACTATTTACTGTACTAGTGACGGGATTAAACTGTATTAATTATAAATAAA
AAATAAGTACAGTTGTTTAAAATTATATTTTGTATTAAATCTAATAGTACGATGTAAGTTATTTTATACTATTGCTAG
TTTAATAAAAAGATTTAATTATATACTTGAAAAGGAGAGGAATTTTT

FIG 50

ATAGAATAACTTAAAAAAACTGTCTTAAAAAGCTGTTATATAAAAAAATGTTAACAATTAAACAGCTATTTAGTGCA
AAACAACCATAAAAATTTAAAAAATACCATAAATTACTTGAAAAATAGTAGAGAATAATGTAGAGTTATAAACGAA
GGTGAAAAGCATTACTTGTATTCCTTTTTACAGACTATTATAAATTAAGATAAAGCTGTATTAGGAAAAATGCACAC
CTGTAATATAAGGTTTTAAATTAATTTTTAATTTTCCCAAAATGTATTTTACATGTTTAGAATTTTGATGTATATTAAA
ATAGTAGAATACATAAGATACTTAATTTAATAAAGATAGTTAAGTACTTTTCAATGTACTTTTTTAGATATTTAATAC
AAGTTTTTAATTGTAAAAAAATGCTGTGCTATTTACTGTACTAATGGTAGTACTATATCTGTATTAATTGTATGTAAA
AAGTAAGTATAGTTATTTAAGATTATGTTTTGTATTAAATCTAAATAGTACAATGTAGGTTATGTTATACTATTGCTA
GTTTAATAAAAAGATTTAATTATATACTTGAAAAGGAGAGGAATTTTTATGCGTAAA

FIG 51

SEQ ID NO: 72
ATGTATACAGTAGGAGATTACCTATTAGACCGATTACACGAGTTAGGAATTGAAGAAATTTTTGGAGTCCCTGGAG
ACTATAACTTACAATTTTTAGATCAAATTATTTCCCACAAGGATATGAAATGGGTCGGAAATGCTAATGAATTAAAT
GCTTCATATATGGCTGATGGCTATGCTCGTACTAAAAAAGCTGCCGCATTTCTTACAACCTTTGGAGTAGGTGAATT
GAGTGCAGTTAATGGATTAGCAGGAAGTTACGCCGAAAATTTACCAGTAGTAGAAATAGTGGGATCACCTACATC
AAAAGTTCAAAATGAAGGAAAATTTGTTCATCATACGCTGGCTGACGGTGATTTTAAACACTTTATGAAAATGCAC
GAACCTGTTACAGCAGCTCGAACTTTACTGACAGCAGAAAATGCAACCGTTGAAATTGACCGAGTACTTTCTGCAC
TATTAAAAGAAAGAAAACCTGTCTATATCAACTTACCAGTTGATGTTGCTGCTGCAAAAGCAGAGAAACCCTCACT
CCCTTTGAAAAAGGAAAACTCAACTTCAAATACAAGTGACCAAGAAATTTTGAACAAAATTCAAGAAAGCTTGAAA
AATGCCAAAAAACCAATCGTGATTACAGGACATGAAATAATTAGTTTTGGCTTAGAAAAAACAGTCACTCAATTTA
TTTCAAAGACAAAACTACCTATTACGACATTAAACTTTGGTAAAAGTTCAGTTGATGAAGCCCTCCCTTCATTTTTA
GGAATCTATAATGGTACACTCTCAGAGCCTAATCTTAAAGAATTCGTGGAATCAGCCGACTTCATCTTGATGCTTG
GAGTTAAACTCACAGACTCTTCAACAGGAGCCTTCACTCATCATTTAAATGAAAATAAAATGATTTCACTGAATATA
GATGAAGGAAAAATATTTAACGAAAGAATCCAAAATTTTGATTTTGAATCCCTCATCTCCTCTCTCTTAGACCTAAG
CGAAATAGAATACAAAGGAAAATATATCGATAAAAAGCAAGAAGACTTTGTTCCATCAAATGCGCTTTTATCACAA
GACCGCCTATGGCAAGCAGTTGAAAACCTAACTCAAAGCAATGAAACAATCGTTGCTGAACAAGGGACATCATTC
TTTGGCGCTTCATCAATTTTCTTAAAATCAAAGAGTCATTTTATTGGTCAACCCTTATGGGGATCAATTGGATATAC
ATTCCCAGCAGCATTAGGAAGCCAAATTGCAGATAAAGAAAGCAGACACCTTTTATTTATTGGTGATGGTTCACTT
CAACTTACAGTGCAAGAATTAGGATTAGCAATCAGAGAAAAAATTAATCCAATTTGCTTTATTATCAATAATGATG
GTTATACAGTCGAAAGAGAAATTCATGGACCAAATCAAAGCTACAATGATATTCCAATGTGGAATTACTCAAAATT
ACCAGAATCGTTTGGAGCAACAGAAGATCGAGTAGTCTCAAAAATCGTTAGAACTGAAAATGAATTTGTGTCTGTC
ATGAAAGAAGCTCAAGCAGATCCAAATAGAATGTACTGGATTGAGTTAATTTTGGCAAAAGAAGGTGCACCAAAA
GTACTGAAAAAAATGGGCAAACTATTTGCTGAACAAAATAAATCATAA

SEQ ID NO: 73
MYTVGDYLLDRLHELGIEEIFGVPGDYNLQFLDQIISHKDMKWVGNANELNASYMADGYARTKKAAAFLTTFGVGELS
AVNGLAGSYAENLPVVEIVGSPTSKVQNEGKFVHHTLADGDFKHFMKMHEPVTAARTLLTAENATVEIDRVLSALLKER
KPVYINLPVDVAAAKAEKPSLPLKKENSTSNTSDQEILNKIQESLKNAKKPIVITGHEIISFGLEKTVTQFISKTKLPITTLNFG
KSSVDEALPSFLGIYNGTLSEPNLKEFVESADFILMLGVKLTDSSTGAFTHHLNENKMISLNIDEGKIFNERIQNFDFESLIS
SLLDLSEIEYKGKYIDKKQEDFVPSNALLSQDRLWQAVENLTQSNETIVAEQGTSFFGASSIFLKSKSHFIGQPLWGSIGYT
FPAALGSQIADKESRHLLFIGDGSLQLTVQELGLAIREKINPICFIINNDGYTVEREIHGPNQSYNDIPMWNYSKLPESFGA
TEDRVVSKIVRTENEFVSVMKEAQADPNRMYWIELILAKEGAPKVLKKMGKLFAEQNKS*

FIG 54

SEQ ID NO: 74
ATGTCTATTCCAGAAACTCAAAAAGCCATTATCTTCTACGAATCCAACGGCAAGTTGGAGCATAAGGATATCCCAG
TTCCAAAGCCAAAGCCCAACGAATTGTTAATCAACGTCAAGTACTCTGGTGTCTGCCACACCGATTTGCACGCTTG
GCATGGTGACTGGCCATTGCCAACTAAGTTACCATTAGTTGGTGGTCACGAAGGTGCCGGTGTCGTTGTCGGCAT
GGGTGAAAACGTTAAGGGCTGGAAGATCGGTGACTACGCCGGTATCAAATGGTTGAACGGTTCTTGTATGGCCTG
TGAATACTGTGAATTGGGTAACGAATCCAACTGTCCTCACGCTGACTTGTCTGGTTACACCCACGACGGTTCTTTCC
AAGAATACGCTACCGCTGACGCTGTTCAAGCCGCTCACATTCCTCAAGGTACTGACTTGGCTGAAGTCGCGCCAAT
CTTGTGTGCTGGTATCACCGTATACAAGGCTTTGAAGTCTGCCAACTTGAGAGCAGGCCACTGGGCGGCCATTTCT
GGTGCTGCTGGTGGTCTAGGTTCTTTGGCTGTTCAATATGCTAAGGCGATGGGTTACAGAGTCTTAGGTATTGATG
GTGGTCCAGGAAAGGAAGAATTGTTTACCTCGCTCGGTGGTGAAGTATTCATCGACTTCACCAAAGAGAAGGACA
TTGTTAGCGCAGTCGTTAAGGCTACCAACGGCGGTGCCCACGGTATCATCAATGTTTCCGTTTCCGAAGCCGCTAT
CGAAGCTTCTACCAGATACTGTAGGGCGAACGGTACTGTTGTCTTGGTTGGTTTGCCAGCCGGTGCAAAGTGCTCC
TCTGATGTCTTCAACCACGTT
GTCAAGTCTATCTCCATTGTCGGCTCTTACGTGGGGAACAGAGCTGATACCAGAGAAGCCTTAGATTTCTTTGCCA
GAGGTCTAGTCAAGTCTCCAATAAAGGTAGTTGGCTTATCCAGTTTACCAGAAATTTACGAAAAGATGGAGAAGG
GCCAAATTGCTGGTAGATACGTTGTTGACACTTCTAAATAA

SEQ ID NO: 75
MSIPETQKAIIFYESNGKLEHKDIPVPKPKPNELLINVKYSGVCHTDLHAWHGDWPLPTKLPLVGGHEGAGVVVGMGE
NVKGWKIGDYAGIKWLNGSCMACEYCELGNESNCPHADLSGYTHDGSFQEYATADAVQAAHIPQGTDLAEVAPILCA
GITVYKALKSANLRAGHWAAISGAAGGLGSLAVQYAKAMGYRVLGIDGGPGKEELFTSLGGEVFIDFTKEKDIVSAVVK
ATNGGAHGIINVSVSEAAIEASTRYCRANGTVVLVGLPAGAKCSSDVFNHVVKSISIVGSYVGNRADTREALDFFARGLV
KSPIKVVGLSSLPEIYEKMEKGQIAGRYVVDTSK*

SEQ ID NO: 76
CATATGTATACAGTAGGAGATTACCTATTAGACCGATTACACGAGTTAGGAATTGAAGAAATTTTTGGAGTCCCTG
GAGACTATAACTTACAATTTTTAGATCAAATTATTTCCCACAAGGATATGAAATGGGTCGGAAATGCTAATGAATT
AAATGCTTCATATATGGCTGATGGCTATGCTCGTACTAAAAAAGCTGCCGCATTTCTTACAACCTTTGGAGTAGGT
GAATTGAGTGCAGTTAATGGATTAGCAGGAAGTTACGCCGAAAATTTACCAGTAGTAGAAATAGTGGGATCACCT
ACATCAAAAGTTCAAAATGAAGGAAAATTTGTTCATCATACGCTGGCTGACGGTGATTTTAAACACTTTATGAAAA
TGCACGAACCTGTTACAGCAGCTCGAACTTTACTGACAGCAGAAAATGCAACCGTTGAAATTGACCGAGTACTTTC
TGCACTATTAAAAGAAAGAAAACCTGTCTATATCAACTTACCAGTTGATGTTGCTGCTGCAAAAGCAGAGAAACCC
TCACTCCCTTTGAAAAAGGAAAACTCAACTTCAAATACAAGTGACCAAGAAATTTTGAACAAAATTCAAGAAAGCT
TGAAAAATGCCAAAAAACCAATCGTGATTACAGGACATGAAATAATTAGTTTTGGCTTAGAAAAAACAGTCACTCA
ATTTATTTCAAAGACAAAACTACCTATTACGACATTAAACTTTGGTAAAAGTTCAGTTGATGAAGCCCTCCCTTCATT
TTTAGGAATCTATAATGGTACACTCTCAGAGCCTAATCTTAAAGAATTCGTGGAATCAGCCGACTTCATCTTGATGC
TTGGAGTTAAACTCACAGACTCTTCAACAGGAGCCTTCACTCATCATTTAAATGAAAATAAAATGATTTCACTGAAT
ATAGATGAAGGAAAAATATTTAACGAAAGAATCCAAAATTTTGATTTTGAATCCCTCATCTCCTCTCTCTTAGACCT
AAGCGAAATAGAATACAAAGGAAAATATATCGATAAAAAGCAAGAAGACTTTGTTCCATCAAATGCGCTTTTATCA
CAAGACCGCCTATGGCAAGCAGTTGAAAACCTAACTCAAAGCAATGAAACAATCGTTGCTGAACAAGGGACATCA
TTCTTTGGCGCTTCATCAATTTTCTTAAAATCAAAGAGTCATTTTATTGGTCAACCCTTATGGGGATCAATTGGATAT
ACATTCCCAGCAGCATTAGGAAGCCAAATTGCAGATAAAGAAAGCAGACACCTTTTATTTATTGGTGATGGTTCAC
TTCAACTTACAGTGCAAGAATTAGGATTAGCAATCAGAGAAAAAATTAATCCAATTTGCTTTATTATCAATAATGAT
GGTTATACAGTCGAAAGAGAAATTCATGGACCAAATCAAAGCTACAATGATATTCCAATGTGGAATTACTCAAAAT
TACCAGAATCGTTTGGAGCAACAGAAGATCGAGTAGTCTCAAAAATCGTTAGAACTGAAAATGAATTTGTGTCTGT
CATGAAAGAAGCTCAAGCAGATCCAAATAGAATGTACTGGATTGAGTTAATTTTGGCAAAAGAAGGTGCACCAAA
AGTACTGAAAAAAATGGGCAAACTATTTGCTGAACAAAATAAATCATAA

FIG 55

SEQ ID NO: 77
ATGTCTATTCCAGAAACTCAAAAAGCCATTATCTTCTACGAATCCAACGGCAAGTTGGAGCATAAGGATATCCCAG
TTCCAAAGCCAAAGCCCAACGAATTGTTAATCAACGTCAAGTACTCTGGTGTCTGCCACACCGATTTGCACGCTTG
GCATGGTGACTGGCCATTGCCAACTAAGTTACCATTAGTTGGTGGTCACGAAGGTGCCGGTGTCGTTGTCGGCAT
GGGTGAAAACGTTAAGGGCTGGAAGATCGGTGACTACGCCGGTATCAAATGGTTGAACGGTTCTTGTATGGCCTG
TGAATACTGTGAATTGGGTAACGAATCCAACTGTCCTCACGCTGACTTGTCTGGTTACACCCACGACGGTTCTTTCC
AAGAATACGCTACCGCTGACGCTGTTCAAGCCGCTCACATTCCTCAAGGTACTGACTTGGCTGAAGTCGCGCCAAT
CTTGTGTGCTGGTATCACCGTATACAAGGCTTTGAAGTCTGCCAACTTGAGAGCAGGCCACTGGGCGGCCATTTCT
GGTGCTGCTGGTGGTCTAGGTTCTTTGGCTGTTCAATATGCTAAGGCGATGGGTTACAGAGTCTTAGGTATTGATG
GTGGTCCAGGAAAGGAAGAATTGTTTACCTCGCTCGGTGGTGAAGTATTCATCGACTTCACCAAAGAGAAGGACA
TTGTTAGCGCAGTCGTTAAGGCTACCAACGGCGGTGCCCACGGTATCATCAATGTTTCCGTTTCCGAAGCCGCTAT
CGAAGCTTCTACCAGATACTGTAGGGCGAACGGTACTGTTGTCTTGGTTGGTTTGCCAGCCGGTGCAAAGTGCTCC
TCTGATGTCTTCAACCACGTTGTCAAGTCTATCTCCATTGTCGGCTCTTACGTGGGGAACAGAGCTGATACCAGAG
AAGCCTTAGATTTCTTTGCCAGAGGTCTAGTCAAGTCTCCAATAAAGGTAGTTGGCTTATCCAGTTTACCAGAAATT
TACGAAAAGATGGAGAAGGGCCAAATTGCTGGTAGATACGTTGTTGACACTTCTAAATAA

SEQ ID NO: 78
CATATGTATACAGTAGGAGATTACCTATTAGACCGATTACACGAGTTAGGAATTGAAGAAATTTTTGGAGTCCCTG
GAGACTATAACTTACAATTTTTAGATCAAATTATTTCCCACAAGGATATGAAATGGGTCGGAAATGCTAATGAATT
AAATGCTTCATATATGGCTGATGGCTATGCTCGTACTAAAAAAGCTGCCGCATTTCTTACAACCTTTGGAGTAGGT
GAATTGAGTGCAGTTAATGGATTAGCAGGAAGTTACGCCGAAAATTTACCAGTAGTAGAAATAGTGGGATCACCT
ACATCAAAAGTTCAAAATGAAGGAAAATTTGTTCATCATACGCTGGCTGACGGTGATTTTAAACACTTTATGAAAA
TGCACGAACCTGTTACAGCAGCTCGAACTTTACTGACAGCAGAAAATGCAACCGTTGAAATTGACCGAGTACTTTC
TGCACTATTAAAAGAAAGAAAACCTGTCTATATCAACTTACCAGTTGATGTTGCTGCTGCAAAAGCAGAGAAACCC
TCACTCCCTTTGAAAAAGGAAAACTCAACTTCAAATACAAGTGACCAAGAAATTTTGAACAAAATTCAAGAAAGCT
TGAAAAATGCCAAAAAACCAATCGTGATTACAGGACATGAAATAATTAGTTTTGGCTTAGAAAAAACAGTCACTCA
ATTTATTTCAAAGACAAAACTACCTATTACGACATTAAACTTTGGTAAAAGTTCAGTTGATGAAGCCCTCCCTTCATT
TTTAGGAATCTATAATGGTACACTCTCAGAGCCTAATCTTAAAGAATTCGTGGAATCAGCCGACTTCATCTTGATGC
TTGGAGTTAAACTCACAGACTCTTCAACAGGAGCCTTCACTCATCATTTAAATGAAAATAAAATGATTTCACTGAAT
ATAGATGAAGGAAAAATATTTAACGAAAGAATCCAAAATTTTGATTTTGAATCCCTCATCTCCTCTCTCTTAGACCT
AAGCGAAATAGAATACAAAGGAAAATATATCGATAAAAAGCAAGAAGACTTTGTTCCATCAAATGCGCTTTTATCA
CAAGACCGCCTATGGCAAGCAGTTGAAAACCTAACTCAAAGCAATGAAACAATCGTTGCTGAACAAGGGACATCA
TTCTTTGGCGCTTCATCAATTTTCTTAAAATCAAAGAGTCATTTTATTGGTCAACCCTTATGGGGATCAATTGGATAT
ACATTCCCAGCAGCATTAGGAAGCCAAATTGCAGATAAAGAAAGCAGACACCTTTTATTTATTGGTGATGGTTCAC
TTCAACTTACAGTGCAAGAATTAGGATTAGCAATCAGAGAAAAAATTAATCCAATTTGCTTTATTATCAATAATGAT
GGTTATACAGTCGAAAGAGAAATTCATGGACCAAATCAAAGCTACAATGATATTCCAATGTGGAATTACTCAAAAT
TACCAGAATCGTTTGGAGCAACAGAAGATCGAGTAGTCTCAAAAATCGTTAGAACTGAAAATGAATTTGTGTCTGT
CATGAAAGAAGCTCAAGCAGATCCAAATAGAATGTACTGGATTGAGTTAATTTTGGCAAAAGAAGGTGCACCAAA
AGTACTGAAAAAAATGGGCAAACTATTTGCTGAACAAAATAAATCATAAGAATTCAAAAAAAAAAAAAAAAAAAA
AAAAAAAAAAAAAAAATGTCTATTCCAGAAACTCAAAAAGCCATTATCTTCTACGAATCCAACGGCAAGTTGGAGC
ATAAGGATATCCCAGTTCCAAAGCCAAAGCCCAACGAATTGTTAATCAACGTCAAGTACTCTGGTGTCTGCCACAC
CGATTTGCACGCTTGGCATGGTGACTGGCCATTGCCAACTAAGTTACCATTAGTTGGTGGTCACGAAGGTGCCGGT
GTCGTTGTCGGCATGGGTGAAAACGTTAAGGGCTGGAAGATCGGTGACTACGCCGGTATCAAATGGTTGAACGG
TTCTTGTATGGCCTGTGAATACTGTGAATTGGGTAACGAATCCAACTGTCCTCACGCTGACTTGTCTGGTTACACCC
ACGACGGTTCTTTCCAAGAATACGCTACCGCTGACGCT
GTTCAAGCCGCTCACATTCCTCAAGGTACTGACTTGGCTGAAGTCGCGCCAATCTTGTGTGCTGGTATCACCGTATA
CAAGGCTTTGAAGTCTGCCAACTTGAGAGCAGGCCACTGGGCGGCCATTTCTGGTGCTGCTGGTGGTCTAGGTTC
TTTGGCTGTTCAATATGCTAAGGCGATGGGTTACAGAGTCTTAGGTATTGATGGTGGTCCAGGAAAGGAAGAATT
GTTTACCTCGCTCGGTGGTGAAGTATTCATCGACTTCACCAAAGAGAAGGACATTGTTAGCGCAGTCGTTAAGGCT
ACCAACGGCGGTGCCCACGGTATCATCAATGTTTCCGTTTCCGAAGCCGCTATCGAAGCTTCTACCAGATACTGTA
GGGCGAACGGTACTGTTGTCTTGGTTGGTTTGCCAGCCGGTGCAAAGTGCTCCTCTGATGTCTTCAACCACGTTGT
CAAGTCTATCTCCATTGTCGGCTCTTACGTGGGGAACAGAGCTGATACCAGAGAAGCCTTAGATTTCTTTGCCAGA
GGTCTAGTCAAGTCTCCAATAAAGGTAGTTGGCTTATCCAGTTTACCAGAAATTTACGAAAAGATGGAGAAGGGC
CAAATTGCTGGTAGATACGTTGTTGACACTTCTAAATAAGGTACC

FIG 56

SEQ ID NO: 79
AATATGATATTTATGTCCATTGTGAAAGGGATTATATTCAACTATTATTCCAGTTACGTTCATAGAAATTTTCCTTTC
TAAAATATTTTATTCCATGTCAAGAACTCTGTTTATTTCATTAAAGAACTATAAGTACAAAGTATAAGGCATTTGAA
AAAATAGGCTAGTATATTGATTGATTATTTATTTTAAAATGCCTAAGTGAAATATATACATATTATAACAATAAAAT
AAGTATTAGTGTAGGATTTTTAAATAGAGTATCTATTTTCAGATTAAATTTTTGATTATTTGATTTAC
ATTATATAATATTGAGTAAAGTATTGACTAGCAAAATTTTTTGATACTTTAATTTGTGAAATTTCTTATCAAAAGTTA
TATTTTTGAATAATTTTTATTGAAAAATACAACTAAAAAGGATTATAGTATAAGTGTGTGTAATTTTGTGTTAAATTT
AAAGGGAGGAAATGAACATGAAA

SEQ ID NO: 82
AAACTCCTTTTTGATAATCTCATGACCAAAATCCCTTAACGTGAGTTTTCGTTCCACTGAGCGTCAGACCCCGTAGA
AAAGATCAAAGGATCTTCTTGAGATCCTTTTTTTCTGCGCGTAATCTGCTGCTTGCAAACAAAAAAACCACCGCTAC
CAGCGGTGGTTTGTTTGCCGGATCAAGAGCTACCAACTCTTTTTCCGAAGGTAACTGGCTTCAGCAGAGCGCAGAT
ACCAAATACTGTTCTTCTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGGGGGGCGGAGCCTATGG
AAAAACGCCAGCAACGCGGCCTTTTTACGGTTCCTGGCCTTTTGCTGGCCTTTTGCTCACATGTTCTTTCCTGCGTTA
TCCCCTGATTCTGTGGATAACCGTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAGGGCCCCCTGCAGGATAAAAAAATTGTA
GATAAATTTTATAAAATAGTTTTATCTACAATTTTTTTATCAGGAAACAGCTATGACCGCGGCCGCAATATGATATT
TATGTCCATTGTGAAAGGGATTATATTCAACTATTATTCCAGTTACGTTCATAGAAATTTTCCTTTCTAAAATATTTT
ATTCCATGTCAAGAACTCTGTTTATTTCATTAAAGAACTATAAGTACAAAGTATAAGGCATTTGAAAAAATAGGCTA
GTATATTGATTGATTATTTATTTTAAAATGCCTAAGTGAAATATATACATATTATAACAATAAAATAAGTATTAGTGT
AGGATTTTTAAATAGAGTATCTATTTTCAGATTAAATTTTTGATTATTTGATTTACATTATATAATATTGAGTAAAGT
ATTGACTAGCAAAATTTTTTGATACTTTAATTTGTGAAATTTCTTATCAAAAGTTATATTTTTGAATAATTTTTATTGA
AAAATACAACTAAAAAGGATTATAGTATAAGTGTGTGTAATTTTGTGTTAAATTTAAAGGGAGGAAATGAACATG
AAACATATGGTGACCATGATTACGAATTCGAGCTCGGTACCCGGGGATCCTCTAGAGTCGACGTCACGCGTCCAT
GGAGATCTCGAGGCCTGCAGACATGCAAGCTTGGCACTGGCCGTCGTTTTACAACGTCGTGACTGGGAAAACCCT
GGCGTTACCCAACTTAATCGCCTTGCAGCACATCCCCCTTTCGCCAGCTGGCGTAATAGCGAAGAGGCCCGCACCG
ATCGCCCTTCCCAACAGTTGCGCAGCCTGAATGGCGAATGGCGCTAGCATAAAAATAAGAAGCCTGCATTTGCAG
GCTTCTTATTTTTATGGCGCGCCGCATTCACTTCT

FIG 57

TTTCTATATAAATATGAGCGAAGCGAATAAGCGTCGGAAAAGCAGCAAAAAGTTTCCTTTTTGCTGTTGGAGCATG
GGGGTTCAGGGGGTGCAGTATCTGACGTCAATGCCGAGCGAAAGCGAGCCGAAGGGTAGCATTTACGTTAGATA
ACCCCCTGATATGCTCCGACGCTTTATATAGAAAAGAAGATTCAACTAGGTAAAATCTTAATATAGGTTGAGATGA
TAAGGTTTATAAGGAATTTGTTTGTTCTAATTTTTCACTCATTTTGTTCTAATTTCTTTTAACAAATGTTCTTTTTTTTT
TAGAACAGTTATGATATAGTTAGAATAGTTTAAAATAAGGAGTGAGAAAAAGATGAAAGAAAGATATGGAACAG
TCTATAAAGGCTCTCAGAGGCTCATAGACGAAGAAAGTGGAGAAGTCATAGAGGTAGACAAGTTATACCGTAAAC
AAACGTCTGGTAACTTCGTAAAGGCATATATAGTGCAATTAATAAGTATGTTAGATATGATTGGCGGAAAAAAACT
TAAAATCGTTAACTATATCCTAGATAATGTCCACTTAAGTAACAATACAATGATAGCTACAACAAGAGAAATAGCA
AAAGCTACAGGAACAAGTCTACAAACAGTAATAACAACACTTAAAATCTTAGAAGAAGGAAATATTATAAAAAGA
AAAACTGGAGTATTAATGTTAAACCCTGAACTACTAATGAGAGGCGACGACCAAAAACAAAAATACCTCTTACTCG
AATTTGGGAACTTTGAGCAAGAGGCAAATGAAATAGATTGACCTCCCAATAACACCACGTAGTTATTGGGAGGTC
AATCTATGAAATGCGATTAAGGGCCGGCCGAAGCAAACTTAAGAGTGTGTTGATAGTGCAGTATCTTAAAATTTTG
TATAATAGGAATTGAAGTTAAATTAGATGCTAAAAATTTGTAATTAAGAAGGAGTGATTACATGAACAAAAATATA
AAATATTCTCAAAACTTTTTAACGAGTGAAAAAGTACTCAACCAAATAATAAAACAATTGAATTTAAAAGAAACCG
ATACCGTTTACGAAATTGGAACAGGTAAAGGGCATTTAACGACGAAACTGGCTAAAATAAGTAAACAGGTAACGT
CTATTGAATTAGACAGTCATCTATTCAACTTATCGTCAGAAAAATTAAAACTGAATACTCGTGTCACTTTAATTCACC
AAGATATTCTACAGTTTCAATTCCCTAACAAACAGAGGTATAAAATTGTTGGGAGTATTCCTTACCATTTAAGCACA
CAAATTATTAAAAAAGTGGTTTTTGAAAGCCATGCGTCTGACATCTATCTGATTGTTGAAGAAGGATTCTACAAGC
GTACCTTGGATATTCACCGAACACTAGGGTTGCTCTTGCACACTCAAGTCTCGATTCAGCAATTGCTTAAGCTGCCA
GCGGAATGCTTTCATCCTAAACCAAAAGTAAACAGTGTCTTAATAAAACTTACCCGCCATACCACAGATGTTCCAG
ATAAATATTGGAAGCTATATACGTACTTTGTTTCAAAATGGGTCAATCGAGAATATCGTCAACTGTTTACTAAAAAT
CAGTTTCATCAAGCAATGAAACACGCCAAAGTAAACAATTTAAGTACCGTTACTTATGAGCAAGTATTGTCTATTTT
TAATAGTTATCTATTATTTAACGGGAGGAAATAATTCTATGAGTCGCTTTTGTAAATTTGGAAAGTTACACGTTACT
AAAGGGAATGTGTTT

FIG 57 (continued)

SEQ ID NO: 83
AAACTCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACT
GTTCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCG
TCAGGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAAC
CGTATTACCGCCTTTGAGTGAGCTGATACCGCTCGCCGCAGCCGAACGACCGAGCGCAGC
GAGTCAGTGAGCGAGGAAGCGGAAGAGCGCCCAATACGCAGGGCCCCCTGCAGGATAAAA
AAATTGTAGATAAATTTTATAAAATAGTTTTATCTACAATTTTTTTATCAGGAAACAGCT
ATGACCGCGGCCGCAATATGATATTTATGTCCATTGTGAAAGGGATTATATTCAACTATT
ATTCCAGTTACGTTCATAGAAATTTTCCTTTCTAAAATATTTTATTCCATGTCAAGAACT
CTGTTTATTTCATTAAAGAACTATAAGTACAAAGTATAAGGCATTTGAAAAAATAGGCTA
GTATATTGATTGATTATTTATTTTAAAATGCCTAAGTGAAATATATACATATTATAACAA
TAAAATAAGTATTAGTGTAGGATTTTTAAATAGAGTATCTATTTTCAGATTAAATTTTTG
ATTATTTGATTTACATTATATAATATTGAGTAAAGTATTGACTAGCAAAATTTTTTGATA
CTTTAATTTGTGAAATTTCTTATCAAAAGTTATATTTTTGAATAATTTTTATTGAAAAAT
ACAACTAAAAAGGATTATAGTATAAGTGTGTGTAATTTTGTGTTAAATTTAAAGGGAGGA
AATGAACATGAAACATATGTATACAGTTGGTGATTATTTACTTGATAGATTACATGAACT
TGGAATAGAAGAAATTTTTGGTGTACCAGGTGATTACAATCTTCAATTCTTAGATCAAAT
AATATCACATAAGGATATGAAATGGGTTGGTAATGCTAATGAATTAAATGCATCATATAT
GGCAGACGGATATGCAAGAACTAAAAAGGCAGCAGCATTTCTTACTACATTTGGTGTTGG
TGAATTAAGTGCAGTAAATGGATTAGCTGGAAGTTACGCAGAAAACTTACCAGTTGTTGA
AATAGTTGGATCTCCTACTAGTAAAGTACAAAATGAAGGTAAATTTGTACATCACACTCT
TGCAGATGGTGATTTTAAGCATTTTATGAAAATGCATGAACCTGTTACAGCTGCAAGAAC
ACTTCTTACAGCTGAAAACGCTACTGTAGAAATTGATAGAGTTTTATCTGCTTTACTTAA
AGAAAGAAAGCCAGTATATATTAACCTTCCAGTAGATGTAGCAGCAGCAAAAGCTGAGAA
ACCTTCATTACCACTTAAAAAGGAAAATTCAACATCAAATACATCTGATCAAGAGATATT
AAATAAAATTCAGGAAAGTCTTAAAAATGCAAAGAAACCTATAGTAATAACTGGACATGA
AATAATTAGTTTTGGATTAGAAAAGACAGTTACACAGTTTATAAGTAAAACTAAGCTTCC
AATTACAACTTTAAATTTTGGAAAGAGTTCAGTAGATGAGGCACTTCCATCATTCTTAGG
AATTTATAATGGAACATTATCTGAACCTAATCTTAAAGAATTTGTAGAGAGTGCTGATTT
TATATTAATGTTAGGTGTAAAACTTACTGATAGTAGTACTGGTGCATTTACTCATCATCT
TAACGAAAATAAGATGATATCATTAAATATAGACGAAGGTAAAATATTCAATGAAAGAAT
ACAGAACTTTGATTTTGAATCACTTATATCATCATTACTTGATTTATCAGAGATAGAATA
CAAAGGAAAATATATAGATAAAAAGCAAGAAGATTTTGTTCCATCTAATGCTCTTCTTTC
TCAAGATAGACTTTGGCAAGCAGTTGAGAATCTTACACAGTCTAATGAAACTATAGTTGC
TGAGCAAGGAACATCATTTTTCGGTGCATCAAGTATATTTTTAAAATCTAAAAGTCACTT
TATTGGACAACCTCTTTGGGGTTCTATTGGATATACTTTTCCAGCAGCTTTAGGAAGTCA
AATAGCTGATAAAGAAAGTAGACATTTATTATTTATTGGTGACGGTTCACTTCAGCTTAC
AGTACAAGAATTAGGATTAGCTATAAGAGAGAAGATAAATCCTATTTGTTTCATAATAAA
CAATGATGGATATACTGTAGAAAGAGAAATTCACGGACCAAATCAGTCATATAATGATAT

FIG 58

TCCAATGTGGAATTATTCAAAGTTACCTGAATCTTTCGGTGCTACTGAAGATAGAGTAGT
TTCTAAAATTGTTAGAACAGAGAACGAATTTGTATCTGTTATGAAAGAAGCTCAGGCTGA
CCCTAATAGAATGTATTGGATTGAATTAATTTTAGCAAAAGAAGGTGCTCCTAAAGTACT
TAAGAAAATGGGAAAATTATTTGCAGAACAAAATAAGTCATAAGAATTCCCATAATAAAG
AAAGAATTTTAAATAAAGGAGGAACAAAGATGAGTATACCAGAAACACAAAAAGCAATTA
TATTTTATGAGTCAAATGGAAAATTAGAGCATAAAGATATACCTGTACCAAAACCAAAAC
CAAACGAACTTCTTATAAATGTTAAGTATTCTGGTGTTTGTCATACTGATCTTCATGCAT
GGCATGGTGATTGGCCTCTTCCAACTAAATTACCTCTTGTAGGTGGTCATGAAGGTGCTG
GTGTAGTTGTAGGTATGGGTGAAAATGTTAAAGGTTGGAAAATAGGTGATTATGCTGGAA
TTAAATGGCTTAATGGATCTTGTATGGCATGCGAGTATTGTGAATTAGGAAATGAAAGTA
ATTGTCCACATGCTGACTTAAGTGGTTATACTCATGATGGATCTTTTCAAGAATATGCTA
CTGCAGATGCAGTTCAGGCTGCACACATTCCACAGGGAACTGATCTTGCTGAAGTAGCTC
CTATATTATGCGCTGGAATTACAGTATACAAAGCATTAAAAAGTGCTAATCTTAGAGCAG
GACACTGGGCAGCTATAAGTGGTGCTGCAGGTGGTTTAGGATCTTTAGCAGTTCAATATG
CTAAAGCTATGGGATATAGAGTATTAGGAATAGACGGTGGTCCAGGAAAAGAAGAGTTAT
TTACATCATTAGGTGGTGAAGTTTTTATAGATTTCACAAAGGAAAAAGATATTGTTTCAG
CTGTAGTAAAGGCAACTAATGGTGGTGCACACGGAATTATAAATGTTTCAGTATCTGAAG
CAGCAATAGAAGCAAGTACTAGATATTGTAGAGCAAACGGAACAGTAGTTTTAGTTGGAC
TTCCAGCTGGTGCAAAGTGTTCATCTGACGTATTTAACCATGTAGTAAAGAGTATTTCAA
TAGTTGGATCTTACGTAGGTAATAGAGCTGATACAAGAGAAGCTTTAGATTTCTTTGCAA
GAGGTTTAGTTAAGAGTCCTATAAAAGTAGTAGGACTTTCATCACTTCCTGAAATTTATG
AAAAGATGGAAAAGGGACAAATAGCTGGTAGATATGTTGTAGATACAAGTAAATAAGGTA
CCCGGGGATCCTCTAGAGTCGACGTCACGCGTCCATGGAGATCTCGAGGCCTGCAGACAT
GCAAGCTTGGCACTGGCCGTCGTTTTACAACGTCGTGACTGGGAAAACCCTGGCGTTACC
CAACTTAATCGCCTTGCAGCACATCCCCCTTTCGCCAGCTGGCGTAATAGCGAAGAGGCC
CGCACCGATCGCCCTTCCCAACAGTTGCGCAGCCTGAATGGCGAATGGCGCTAGCATAAA
AATAAGAAGCCTGCATTTGCAGGCTTCTTATTTTTATGGCGCGCCGCATTCACTTCTTTT
CTATATAAATATGAGCGAAGCGAATAAGCGTCGGAAAAGCAGCAAAAAGTTTCCTTTTTG
CTGTTGGAGCATGGGGGTTCAGGGGGTGCAGTATCTGACGTCAATGCCGAGCGAAAGCGA
GCCGAAGGGTAGCATTTACGTTAGATAACCCCCTGATATGCTCCGACGCTTTATATAGAA
AAGAAGATTCAACTAGGTAAAATCTTAATATAGGTTGAGATGATAAGGTTTATAAGGAAT
TTGTTTGTTCTAATTTTTCACTCATTTTGTTCTAATTTCTTTTAACAAATGTTCTTTTTT
TTTTAGAACAGTTATGATATAGTTAGAATAGTTTAAAATAAGGAGTGAGAAAAAGATGAA
AGAAAGATATGGAACAGTCTATAAAGGCTCTCAGAGGCTCATAGACGAAGAAAGTGGAGA
AGTCATAGAGGTAGACAAGTTATACCGTAAACAAACGTCTGGTAACTTCGTAAAGGCATA
TATAGTGCAATTAATAAGTATGTTAGATATGATTGGCGGAAAAAAACTTAAAATCGTTAA
CTATATCCTAGATAATGTCCACTTAAGTAACAATACAATGATAGCTACAACAAGAGAAAT
AGCAAAAGCTACAGGAACAAGTCTACAAACAGTAATAACAACACTTAAAATCTTAGAAGA
AGGAAATATTATAAAAAGAAAAACTGGAGTATTAATGTTAAACCCTGAACTACTAATGAG
AGGCGACGACCAAAAACAAAAATACCTCTTACTCGAATTTGGGAACTTTGAGCAAGAGGC
AAATGAAATAGATTGACCTCCCAATAACACCACGTAGTTATTGGGAGGTCAATCTATGAA
ATGCGATTAAGGGCCGGCCGAAGCAAACTTAAGAGTGTGTTGATAGTGCAGTATCTTAAA
ATTTTGTATAATAGGAATTGAAGTTAAATTAGATGCTAAAAATTTGTAATTAAGAAGGAG
TGATTACATGAACAAAAATATAAAATATTCTCAAAACTTTTTAACGAGTGAAAAAGTACT
CAACCAAATAATAAAACAATTGAATTTAAAAGAAACCGATACCGTTTACGAAATTGGAAC
AGGTAAAGGGCATTTAACGACGAAACTGGCTAAAATAAGTAAACAGGTAACGTCTATTGA
ATTAGACAGTCATCTATTCAACTTATCGTCAGAAAAATTAAAACTGAATACTCGTGTCAC
TTTAATTCACCAAGATATTCTACAGTTTCAATTCCCTAACAAACAGAGGTATAAAATTGT

FIG 58 (continued)

TGGGAGTATTCCTTACCATTTAAGCACACAAATTATTAAAAAAGTGGTTTTTGAAAGCCA
TGCGTCTGACATCTATCTGATTGTTGAAGAAGGATTCTACAAGCGTACCTTGGATATTCA
CCGAACACTAGGGTTGCTCTTGCACACTCAAGTCTCGATTCAGCAATTGCTTAAGCTGCC
AGCGGAATGCTTTCATCCTAAACCAAAAGTAAACAGTGTCTTAATAAAACTTACCCGCCA
TACCACAGATGTTCCAGATAAATATTGGAAGCTATATACGTACTTTGTTTCAAAATGGGT
CAATCGAGAATATCGTCAACTGTTTACTAAAAATCAGTTTCATCAAGCAATGAAACACGC
CAAAGTAAACAATTTAAGTACCGTTACTTATGAGCAAGTATTGTCTATTTTTAATAGTTA
TCTATTATTTAACGGGAGGAAATAATTCTATGAGTCGCTTTTGTAAATTTGGAAAGTTAC
ACGTTACTAAAGGGAATGTGTTT

FIG 58 (continued)

SEQ ID NO: 84
AAACTCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACT
GTTCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCG
TCAGGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAAC
CGTATTACCGCCTTTGAGTGAGCTGATACCGCTCGCCGCAGCCGAACGACCGAGCGCAGC
GAGTCAGTGAGCGAGGAAGCGGAAGAGCGCCCAATACGCAGGGCCCCCTGCAGGATAAAA
AAATTGTAGATAAATTTTATAAAATAGTTTTATCTACAATTTTTTTATCAGGAAACAGCT
ATGACCGCGGCCGCAATATGATATTTATGTCCATTGTGAAAGGGATTATATTCAACTATT
ATTCCAGTTACGTTCATAGAAATTTTCCTTTCTAAAATATTTTATTCCATGTCAAGAACT
CTGTTTATTTCATTAAAGAACTATAAGTACAAAGTATAAGGCATTTGAAAAAATAGGCTA
GTATATTGATTGATTATTTATTTTAAAATGCCTAAGTGAAATATATACATATTATAACAA
TAAAATAAGTATTAGTGTAGGATTTTTAAATAGAGTATCTATTTTCAGATTAAATTTTTG
ATTATTTGATTTACATTATATAATATTGAGTAAAGTATTGACTAGCAAAATTTTTTGATA
CTTTAATTTGTGAAATTTCTTATCAAAAGTTATATTTTTGAATAATTTTTATTGAAAAAT
ACAACTAAAAAGGATTATAGTATAAGTGTGTGTAATTTTGTGTTAAATTTAAAGGGAGGA
AATGAACATGAAACATATGTATACAGTTGGTGATTATTTACTTGATAGATTACATGAACT
TGGAATAGAAGAAATTTTTGGTGTACCAGGTGATTACAATCTTCAATTCTTAGATCAAAT
AATATCACATAAGGATATGAAATGGGTTGGTAATGCTAATGAATTAAATGCATCATATAT
GGCAGACGGATATGCAAGAACTAAAAAGGCAGCAGCATTTCTTACTACATTTGGTGTTGG
TGAATTAAGTGCAGTAAATGGATTAGCTGGAAGTTACGCAGAAAACTTACCAGTTGTTGA
AATAGTTGGATCTCCTACTAGTAAAGTACAAAATGAAGGTAAATTTGTACATCACACTCT
TGCAGATGGTGATTTTAAGCATTTTATGAAAATGCATGAACCTGTTACAGCTGCAAGAAC
ACTTCTTACAGCTGAAAACGCTACTGTAGAAATTGATAGAGTTTTATCTGCTTTACTTAA
AGAAAGAAAGCCAGTATATATTAACCTTCCAGTAGATGTAGCAGCAGCAAAAGCTGAGAA
ACCTTCATTACCACTTAAAAAGGAAAATTCAACATCAAATACATCTGATCAAGAGATATT
AAATAAAATTCAGGAAAGTCTTAAAAATGCAAAGAAACCTATAGTAATAACTGGACATGA

FIG 59

AATAATTAGTTTTGGATTAGAAAAGACAGTTACACAGTTTATAAGTAAAACTAAGCTTCC
AATTACAACTTTAAATTTTGGAAAGAGTTCAGTAGATGAGGCACTTCCATCATTCTTAGG
AATTTATAATGGAACATTATCTGAACCTAATCTTAAAGAATTTGTAGAGAGTGCTGATTT
TATATTAATGTTAGGTGTAAAACTTACTGATAGTAGTACTGGTGCATTTACTCATCATCT
TAACGAAAATAAGATGATATCATTAAATATAGACGAAGGTAAAATATTCAATGAAAGAAT
ACAGAACTTTGATTTTGAATCACTTATATCATCATTACTTGATTTATCAGAGATAGAATA
CAAAGGAAAATATATAGATAAAAAGCAAGAAGATTTTGTTCCATCTAATGCTCTTCTTTC
TCAAGATAGACTTTGGCAAGCAGTTGAGAATCTTACACAGTCTAATGAAACTATAGTTGC
TGAGCAAGGAACATCATTTTTCGGTGCATCAAGTATATTTTTAAAATCTAAAAGTCACTT
TATTGGACAACCTCTTTGGGGTTCTATTGGATATACTTTTCCAGCAGCTTTAGGAAGTCA
AATAGCTGATAAAGAAAGTAGACATTTATTATTTATTGGTGACGGTTCACTTCAGCTTAC
AGTACAAGAATTAGGATTAGCTATAAGAGAGAAGATAAATCCTATTTGTTTCATAATAAA
CAATGATGGATATACTGTAGAAAGAGAAATTCACGGACCAAATCAGTCATATAATGATAT
TCCAATGTGGAATTATTCAAAGTTACCTGAATCTTTCGGTGCTACTGAAGATAGAGTAGT
TTCTAAAATTGTTAGAACAGAGAACGAATTTGTATCTGTTATGAAAGAAGCTCAGGCTGA
CCCTAATAGAATGTATTGGATTGAATTAATTTTAGCAAAAGAAGGTGCTCCTAAAGTACT
TAAGAAAATGGGAAAATTATTTGCAGAACAAAATAAGTCATAAGAATTTGTTTGTTCTAA
TTTTTCACTCATTTTGTTCTAATTTCTTTTAACAAATGTTCTTTTTTTTTTAGAACAGTT
ATGATATAGTTAGAATAGTTTAAAATAAGGAGTGAGAAAAAGATGAAAGAAAGATATGGA
ACAGTCTATAAAGGCTCTCAGAGGCTCATAGACGAAGAAAGTGGAGAAGTCATAGAGGTA
GACAAGTTATACCGTAAACAAACGTCTGGTAACTTCGTAAAGGCATATATAGTGCAATTA
ATAAGTATGTTAGATATGATTGGCGGAAAAAAACTTAAAATCGTTAACTATATCCTAGAT
AATGTCCACTTAAGTAACAATACAATGATAGCTACAACAAGAGAAATAGCAAAAGCTACA
GGAACAAGTCTACAAACAGTAATAACAACACTTAAAATCTTAGAAGAAGGAAATATTATA
AAAAGAAAAACTGGAGTATTAATGTTAAACCCTGAACTACTAATGAGAGGCGACGACCAA
AAACAAAAATACCTCTTACTCGAATTTGGGAACTTTGAGCAAGAGGCAAATGAAATAGAT
TGACCTCCCAATAACACCACGTAGTTATTGGGAGGTCAATCTATGAAATGCGATTAAGGG
CCGGCCGAAGCAAACTTAAGAGTGTGTTGATAGTGCAGTATCTTAAAATTTTGTATAATA
GGAATTGAAGTTAAATTAGATGCTAAAAATTTGTAATTAAGAAGGAGTGATTACATGAAC
AAAAATATAAAATATTCTCAAAACTTTTTAACGAGTGAAAAAGTACTCAACCAAATAATA
AAACAATTGAATTTAAAAGAAACCGATACCGTTTACGAAATTGGAACAGGTAAAGGGCAT
TTAACGACGAAACTGGCTAAAATAAGTAAACAGGTAACGTCTATTGAATTAGACAGTCAT
CTATTCAACTTATCGTCAGAAAAATTAAAACTGAATACTCGTGTCACTTTAATTCACCAA
GATATTCTACAGTTTCAATTCCCTAACAAACAGAGGTATAAAATTGTTGGGAGTATTCCT
TACCATTTAAGCACACAAATTATTAAAAAAGTGGTTTTTGAAAGCCATGCGTCTGACATC
TATCTGATTGTTGAAGAAGGATTCTACAAGCGTACCTTGGATATTCACCGAACACTAGGG
TTGCTCTTGCACACTCAAGTCTCGATTCAGCAATTGCTTAAGCTGCCAGCGGAATGCTTT
CATCCTAAACCAAAAGTAAACAGTGTCTTAATAAAACTTACCCGCCATACCACAGATGTT
CCAGATAAATATTGGAAGCTATATACGTACTTTGTTTCAAAATGGGTCAATCGAGAATAT
CGTCAACTGTTTACTAAAAATCAGTTTCATCAAGCAATGAAACACGCCAAAGTAAACAAT
TTAAGTACCGTTACTTATGAGCAAGTATTGTCTATTTTTAATAGTTATCTATTATTTAAC
GGGAGGAAATAATTCTATGAGTCGCTTTTGTAAATTTGGAAAGTTACACGTTACTAAAGG
GAATGTGTTT

FIG 59 (continued)

SEQ ID NO: 95
AAACTCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACT
GTTCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCG
TCAGGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAAC
CGTATTACCGCCTTTGAGTGAGCTGATACCGCTCGCCGCAGCCGAACGACCGAGCGCAGC
GAGTCAGTGAGCGAGGAAGCGGAAGAGCGCCCAATACGCAGGGCCCCCTGCAGGGCCGCA
GATAGTCATAATAGTTCCAGAATAGTTCAATTTAGAAATTAGACTAAACTTCAAAATGTT
TGTTAAATATATACCAAACTAGTATAGATATTTTTTAAATACTGGACTTAAACAGTAGTA
ATTTGCCTAAAAAATTTTTTCAATTTTTTTTAAAAAATCCTTTTCAAGTTGTACATTGTT
ATGGTAATATGTAATTGAAGAAGTTATGTAGTAATATTGTAAACGTTTCTTGATTTTTTT
ACATCCATGTAGTGCTTAAAAAACCAAAATATGTCACATGCAATTGTATATTTCAAATAA
CAATATTTATTTTCTCGTTAAATTCACAAATAATTTATTAATAATATCAATAACCAAGAT
TATACTTAAATGGATGTTTATTTTTTAACACTTTTATAGTAAATATATTTATTTTATGTA
GTAAAAAGGTTATAATTATAATTGTATTTATTACAATTAATTAAAATAAAAAATAGGGTT
TTAGGTAAAATTAAGTTATTTTAAGAAGTAATTACAATAAAAATTGAAGTTATTTCTTTA
AGGAGGGAATTATTCATATGAAAGAAGTTGTAATAGCTAGTGCAGTAAGAACAGCGATTG
GATCTTATGGAAAGTCTCTTAAGGATGTACCAGCAGTAGATTTAGGAGCTACAGCTATAA
AGGAAGCAGTTAAAAAAGCAGGAATAAAACCAGAGGATGTTAATGAAGTCATTTTAGGAA
ATGTTCTTCAAGCAGGTTTAGGACAGAATCCAGCAAGACAGGCATCTTTTAAAGCAGGAT
TACCAGTTGAAATTCCAGCTATGACTATTAATAAGGTTTGTGGTTCAGGACTTAGAACAG
TTAGCTTAGCAGCACAAATTATAAAAGCAGGAGATGCTGACGTAATAATAGCAGGTGGTA
TGGAAAATATGTCTAGAGCTCCTTACTTAGCGAATAACGCTAGATGGGGATATAGAATGG
GAAACGCTAAATTTGTTGATGAAATGATCACTGACGGATTGTGGGATGCATTTAATGATT
ACCACATGGGAATAACAGCAGAAAACATAGCTGAGAGATGGAACATTTCAAGAGAAGAAC
AAGATGAGTTTGCTCTTGCATCACAAAAAAAAGCTGAAGAAGCTATAAAATCAGGTCAAT
TTAAAGATGAAATAGTTCCTGTAGTAATTAAAGGCAGAAAGGGAGAAACTGTAGTTGATA
CAGATGAGCACCCTAGATTTGGATCAACTATAGAAGGACTTGCAAAATTAAAACCTGCCT
TCAAAAAAGATGGAACAGTTACAGCTGGTAATGCATCAGGATTAAATGACTGTGCAGCAG
TACTTGTAATCATGAGTGCAGAAAAAGCTAAAGAGCTTGGAGTAAAACCACTTGCTAAGA
TAGTTTCTTATGGTTCAGCAGGAGTTGACCCAGCAATAATGGGATATGGACCTTTCTATG
CAACAAAAGCAGCTATTGAAAAAGCAGGTTGGACAGTTGATGAATTAGATTTAATAGAAT
CAAATGAAGCTTTTGCAGCTCAAAGTTTAGCAGTAGCAAAAGATTTAAAATTTGATATGA
ATAAAGTAAATGTAAATGGAGGAGCTATTGCCCTTGGTCATCCAATTGGAGCATCAGGTG
CAAGAATACTCGTTACTCTTGTACACGCAATGCAAAAAAGAGATGCAAAAAAAGGCTTAG
CAACTTTATGTATAGGTGGCGGACAAGGAACAGCAATATTGCTAGAAAAGTGCTAGGAAT
TCGAGCTCGGTACCAGGGAGATATTAAAATGAATAAATTAGTAAAATTAACAGATTTAAA
GCGCATTTTCAAAGATGGCATGACAATTATGGTTGGGGGTTTTTTAGATTGTGGAACTCC
TGAAAATATTATAGATATGCTAGTTGATTTAAATATAAAAAATCTGACTATTATAAGCAA
TGATACAGCTTTTCCTAATAAAGGAATAGGAAAACTTATTGTAAATGGTCAAGTTTCTAA

FIG 60

AGTAATTGCTTCACATATTGGAACTAATCCTGAAACTGGAAAAAAAATGAGCTCTGGAGA
ACTTAAAGTTGAGCTTTCCCCACAAGGAACACTGATTGAAAGAATTCGTGCAGCTGGATC
TGGACTCGGAGGTGTATTAACTCCAACTGGACTTGGAACTATCGTTGAAGAAGGTAAGAA
AAAAGTTACTATCGATGGCAAAGAATATCTATTAGAACTTCCTTTATCTGCTGATGTTTC
ATTAATAAAAGGTAGCATTGTAGATGAATTTGGAAATACCTTCTATAGGGCTGCTACTAA
AAATTTCAATCCATATATGGCAATGGCTGCAAAAACAGTTATAGTTGAAGCAGAAAATTT
AGTTAAATGTGAAGATTTAAAAAGAGATGCCATAATGACTCCTGGCGTATTAGTAGATTA
TATCGTTAAGGAGGCGGCTTAATTGATTGTAGATAAAGTTTTAGCAAAAGAGATAATTGC
CAAAAGAGTTGCAAAAGAACTAAAAAAAGACCAACTCGTAAACCTTGGAATAGGACTTCC
AACTTTAGTAGCAAATTATGTACCAAAAGAAATGAACATTACTTTTGAATCAGAAAATGG
CATGGTTGGTATGGCACAAATGGCATCATCAGGTGAAAATGACCCAGATATAATAAATGC
TGGCGGGGAATATGTAACATTATTACCTCAAGGTTCATTTTTTGATAGTTCAATGTCTTT
CGCACTAATACGAGGAGGACATGTTGATGTTGCTGTTCTTGGTGCTCTAGAAGTTGATGA
AAAAGGTAATTTAGCTAACTGGATTGTTCCAAATAAAATTGTCCCAGGTATGGGTGGCGC
TATGGATTTAGCAATAGGCGCAAAAAAAATAATAGTGGCAATGCAACATACAGGAAAAAG
TAAACCTAAAATCGTTAAAAAATGTACTCTCCCACTTACTGCTAAGGCTCAAGTGGATTT
AATTGTCACAGAACTTTGTGTAATTGATGTAACAAATGACGGCTTACTTTTAAAAGAAAT
TCATAAAGATACAACTATTGATGAAATTAAATTTTTAACAGATGCAGATTTAATTATTCC
AGATAACTTAAAGATTATGGATATATGAATCGCGGCCGCAATATGATATTTATGTCCATT
GTGAAAGGGATTATATTCAACTATTATTCCAGTTACGTTCATAGAAATTTTCCTTTCTAA
AATATTTTATTCCATGTCAAGAACTCTGTTTATTTCATTAAAGAACTATAAGTACAAAGT
ATAAGGCATTTGAAAAAATAGGCTAGTATATTGATTGATTATTTATTTTAAAATGCCTAA
GTGAAATATATACATATTATAACAATAAAATAAGTATTAGTGTAGGATTTTTAAATAGAG
TATCTATTTTCAGATTAAATTTTTGATTATTTGATTTACATTATATAATATTGAGTAAAG
TATTGACTAGCAAAATTTTTTGATACTTTAATTTGTGAAATTTCTTATCAAAAGTTATAT
TTTTGAATAATTTTTATTGAAAAATACAACTAAAAAGGATTATAGTATAAGTGTGTGTAA
TTTTGTGTTAAATTTAAAGGGAGGAAATGAACATGAAACATATGTATACAGTTGGTGATT
ATTTACTTGATAGATTACATGAACTTGGAATAGAAGAAATTTTTGGTGTACCAGGTGATT
ACAATCTTCAATTCTTAGATCAAATAATATCACATAAGGATATGAAATGGGTTGGTAATG
CTAATGAATTAAATGCATCATATATGGCAGACGGATATGCAAGAACTAAAAAGGCAGCAG
CATTTCTTACTACATTTGGTGTTGGTGAATTAAGTGCAGTAAATGGATTAGCTGGAAGTT
ACGCAGAAAACTTACCAGTTGTTGAAATAGTTGGATCTCCTACTAGTAAAGTACAAAATG
AAGGTAAATTTGTACATCACACTCTTGCAGATGGTGATTTTAAGCATTTTATGAAAATGC
ATGAACCTGTTACAGCTGCAAGAACACTTCTTACAGCTGAAAACGCTACTGTAGAAATTG
ATAGAGTTTTATCTGCTTTACTTAAAGAAAGAAAGCCAGTATATATTAACCTTCCAGTAG
ATGTAGCAGCAGCAAAAGCTGAGAAACCTTCATTACCACTTAAAAAGGAAAATTCAACAT
CAAATACATCTGATCAAGAGATATTAAATAAAATTCAGGAAAGTCTTAAAAATGCAAAGA
AACCTATAGTAATAACTGGACATGAAATAATTAGTTTTGGATTAGAAAAGACAGTTACAC
AGTTTATAAGTAAAACTAAGCTTCCAATTACAACTTTAAATTTTGGAAAGAGTTCAGTAG
ATGAGGCACTTCCATCATTCTTAGGAATTTATAATGGAACATTATCTGAACCTAATCTTA
AAGAATTTGTAGAGAGTGCTGATTTTATATTAATGTTAGGTGTAAAACTTACTGATAGTA
GTACTGGTGCATTTACTCATCATCTTAACGAAAATAAGATGATATCATTAAATATAGACG
AAGGTAAAATATTCAATGAAAGAATACAGAACTTTGATTTTGAATCACTTATATCATCAT
TACTTGATTTATCAGAGATAGAATACAAAGGAAAATATATAGATAAAAAGCAAGAAGATT
TTGTTCCATCTAATGCTCTTCTTTCTCAAGATAGACTTTGGCAAGCAGTTGAGAATCTTA
CACAGTCTAATGAAACTATAGTTGCTGAGCAAGGAACATCATTTTTCGGTGCATCAAGTA
TATTTTTAAAATCTAAAAGTCACTTTATTGGACAACCTCTTTGGGGTTCTATTGGATATA
CTTTTCCAGCAGCTTTAGGAAGTCAAATAGCTGATAAAGAAAGTAGACATTTATTATTTA

FIG 60 (continued)

TTGGTGACGGTTCACTTCAGCTTACAGTACAAGAATTAGGATTAGCTATAAGAGAGAAGA
TAAATCCTATTTGTTTCATAATAAACAATGATGGATATACTGTAGAAAGAGAAATTCACG
GACCAAATCAGTCATATAATGATATTCCAATGTGGAATTATTCAAAGTTACCTGAATCTT
TCGGTGCTACTGAAGATAGAGTAGTTTCTAAAATTGTTAGAACAGAGAACGAATTTGTAT
CTGTTATGAAAGAAGCTCAGGCTGACCCTAATAGAATGTATTGGATTGAATTAATTTTAG
CAAAAGAAGGTGCTCCTAAAGTACTTAAGAAAATGGGAAAATTATTTGCAGAACAAAATA
AGTCATAAGAATTTGTTTGTTCTAATTTTTCACTCATTTTGTTCTAATTTCTTTTAACAA
ATGTTCTTTTTTTTTTAGAACAGTTATGATATAGTTAGAATAGTTTAAAATAAGGAGTGA
GAAAAAGATGAAAGAAAGATATGGAACAGTCTATAAAGGCTCTCAGAGGCTCATAGACGA
AGAAAGTGGAGAAGTCATAGAGGTAGACAAGTTATACCGTAAACAAACGTCTGGTAACTT
CGTAAAGGCATATATAGTGCAATTAATAAGTATGTTAGATATGATTGGCGGAAAAAAACT
TAAAATCGTTAACTATATCCTAGATAATGTCCACTTAAGTAACAATACAATGATAGCTAC
AACAAGAGAAATAGCAAAAGCTACAGGAACAAGTCTACAAACAGTAATAACAACACTTAA
AATCTTAGAAGAAGGAAATATTATAAAAAGAAAAACTGGAGTATTAATGTTAAACCCTGA
ACTACTAATGAGAGGCGACGACCAAAAACAAAAATACCTCTTACTCGAATTTGGGAACTT
TGAGCAAGAGGCAAATGAAATAGATTGACCTCCCAATAACACCACGTAGTTATTGGGAGG
TCAATCTATGAAATGCGATTAAGGGCCGGCCGAAGCAAACTTAAGAGTGTGTTGATAGTG
CAGTATCTTAAAATTTTGTATAATAGGAATTGAAGTTAAATTAGATGCTAAAAATTTGTA
ATTAAGAAGGAGTGATTACATGAACAAAAATATAAAATATTCTCAAAACTTTTTAACGAG
TGAAAAAGTACTCAACCAAATAATAAAACAATTGAATTTAAAAGAAACCGATACCGTTTA
CGAAATTGGAACAGGTAAAGGGCATTTAACGACGAAACTGGCTAAAATAAGTAAACAGGT
AACGTCTATTGAATTAGACAGTCATCTATTCAACTTATCGTCAGAAAAATTAAAACTGAA
TACTCGTGTCACTTTAATTCACCAAGATATTCTACAGTTTCAATTCCCTAACAAACAGAG
GTATAAAATTGTTGGGAGTATTCCTTACCATTTAAGCACACAAATTATTAAAAAAGTGGT
TTTTGAAAGCCATGCGTCTGACATCTATCTGATTGTTGAAGAAGGATTCTACAAGCGTAC
CTTGGATATTCACCGAACACTAGGGTTGCTCTTGCACACTCAAGTCTCGATTCAGCAATT
GCTTAAGCTGCCAGCGGAATGCTTTCATCCTAAACCAAAAGTAAACAGTGTCTTAATAAA
ACTTACCCGCCATACCACAGATGTTCCAGATAAATATTGGAAGCTATATACGTACTTTGT
TTCAAAATGGGTCAATCGAGAATATCGTCAACTGTTTACTAAAAATCAGTTTCATCAAGC
AATGAAACACGCCAAAGTAAACAATTTAAGTACCGTTACTTATGAGCAAGTATTGTCTAT
TTTTAATAGTTATCTATTATTTAACGGGAGGAAATAATTCTATGAGTCGCTTTTGTAAAT
TTGGAAAGTTACACGTTACTAAAGGGAATGTGTTT

FIG 60 (continued)

SEQ ID NO: 98
CCAGTGGGCAAGTTGAAAAATTCACAAAAATGTGGTATAATATCTTTGTTCATTAGAGCG
ATAAACTTGAATTTGAGAGGGAACTTAGATGGTATTTGAAAAAATTGATAAAAATAGTTG
GAACAGAAAAGAGTATTTTGACCACTACTTTGCAAGTGTACCTTGTACCTACAGCATGAC
CGTTAAAGTGGATATCACACAAATAAAGGAAAAGGGAATGAAACTATATCCTGCAATGCT
TTATTATATTGCAATGATTGTAAACCGCCATTCAGAGTTTAGGACGGCAATCAATCAAGA
TGGTGAATTGGGGATATATGATGAGATGATACCAAGCTATACAATATTTCACAATGATAC
TGAAACATTTTCCAGCCTTTGGACTGAGTGTAAGTCTGACTTTAAATCATTTTTAGCAGA
TTATGAAAGTGATACGCAACGGTATGGAAACAATCATAGAATGGAAGGAAAGCCAAATGC
TCCGGAAAACATTTTTAATGTATCTATGATACCGTGGTCAACCTTCGATGGCTTTAATCT
GAATTTGCAGAAAGGATATGATTATTTGATTCCTATTTTTACTATGGGGAAATATTATAA
AGAAGATAACAAAATTATACTTCCTTTGGCAATTCAAGTTCATCACGCAGTATGTGACGG
ATTTCACATTTGCCGTTTTGTAAACGAATTGCAGGAATTGATAAATAGTTAACTTCAGGT
TTGTCTGTAACTAAAAACAAGTATTTAAGCAAAAACATCGTAGAAATACGGTGTTTTTTG
TTACCCTAAGTTTAAACTCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGTTTG
TTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGA
TAAGTCGTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGA
CAGGTATCCGGTAAGCGGCAGGGTCGGAACAGGAGAGCGCACGAGGGAGCTTCCAGGGGG
AAACGCCTGGTATCTTTATAGTCCTGTCGGGTTTCGCCACCTCTGACTTGAGCGTCGATT
TTTGTGATGCTCGTCAGGGGGGCGGAGCCTATGGAAAAACGCCAGCAACGCGGCCTTTTT
ACGGTTCCTGGCCTTTTGCTGGCCTTTTGCTCACATGTTCTTTCCTGCGTTATCCCCTGA
TTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCCAATACGCAGGGCCCC
CTGCAGGATAAAAAAATTGTAGATAAATTTTATAAAATAGTTTTATCTACAATTTTTTTA
TCAGGAAACAGCTATGACCGCGGCCGCAGATAGTCATAATAGTTCCAGAATAGTTCAATT
TAGAAATTAGACTAAACTTCAAAATGTTTGTTAAATATATACCAAACTAGTATAGATATT
TTTTAAATACTGGACTTAAACAGTAGTAATTTGCCTAAAAAAATTTTTTCAATTTTTTTTA
AAAAATCCTTTTCAAGTTGTACATTGTTATGGTAATATGTAATTGAAGAAGTTATGTAGT
AATATTGTAAACGTTTCTTGATTTTTTTACATCCATGTAGTGCTTAAAAAACCAAAATAT
GTCACATGCAATTGTATATTTCAAATAACAATATTTATTTTCTCGTTAAATTCACAAATA
ATTTATTAATAATATCAATAACCAAGATTATACTTAAATGGATGTTTATTTTTTAACACT
TTTATAGTAAATATATTTATTTTATGTAGTAAAAAGGTTATAATTATAATTGTATTTATT
ACAATTAATTAAAATAAAAAATAGGGTTTTAGGTAAAATTAAGTTATTTTAAGAAGTAAT
TACAATAAAAATTGAAGTTATTTCTTTAAGGAGGGAATTATTCATATGAAAGAAGTTGTA
ATAGCTAGTGCAGTAAGAACAGCGATTGGATCTTATGGAAAGTCTCTTAAGGATGTACCA
GCAGTAGATTTAGGAGCTACAGCTATAAAGGAAGCAGTTAAAAAAGCAGGAATAAAACCA
GAGGATGTTAATGAAGTCATTTTAGGAAATGTTCTTCAAGCAGGTTTAGGACAGAATCCA
GCAAGACAGGCATCTTTTAAAGCAGGATTACCAGTTGAAATTCCAGCTATGACTATTAAT
AAGGTTTGTGGTTCAGGACTTAGAACAGTTAGCTTAGCAGCACAAATTATAAAAGCAGGA
GATGCTGACGTAATAATAGCAGGTGGTATGGAAAATATGTCTAGAGCTCCTTACTTAGCG
AATAACGCTAGATGGGGATATAGAATGGGAAACGCTAAATTTGTTGATGAAATGATCACT
GACGGATTGTGGGATGCATTTAATGATTACCACATGGGAATAACAGCAGAAAACATAGCT
GAGAGATGGAACATTTCAAGAGAAGAACAAGATGAGTTTGCTCTTGCATCACAAAAAAAA
GCTGAAGAAGCTATAAAATCAGGTCAATTTAAAGATGAAATAGTTCCTGTAGTAATTAAA
GGCAGAAAGGGAGAAACTGTAGTTGATACAGATGAGCACCCTAGATTTGGATCAACTATA
GAAGGACTTGCAAAATTAAAACCTGCCTTCAAAAAAGATGGAACAGTTACAGCTGGTAAT

FIG 61

GCATCAGGATTAAATGACTGTGCAGCAGTACTTGTAATCATGAGTGCAGAAAAAGCTAAA
GAGCTTGGAGTAAAACCACTTGCTAAGATAGTTTCTTATGGTTCAGCAGGAGTTGACCCA
GCAATAATGGGATATGGACCTTTCTATGCAACAAAAGCAGCTATTGAAAAAGCAGGTTGG
ACAGTTGATGAATTAGATTTAATAGAATCAAATGAAGCTTTTGCAGCTCAAAGTTTAGCA
GTAGCAAAAGATTTAAAATTTGATATGAATAAAGTAAATGTAAATGGAGGAGCTATTGCC
CTTGGTCATCCAATTGGAGCATCAGGTGCAAGAATACTCGTTACTCTTGTACACGCAATG
CAAAAAAGAGATGCAAAAAAAGGCTTAGCAACTTTATGTATAGGTGGCGGACAAGGAACA
GCAATATTGCTAGAAAAGTGCTAGGAATTCGAGCTCGGTACCAGGGAGATATTAAAATGA
ATAAATTAGTAAAATTAACAGATTTAAAGCGCATTTTCAAAGATGGCATGACAATTATGG
TTGGGGGTTTTTTAGATTGTGGAACTCCTGAAAATATTATAGATATGCTAGTTGATTTAA
ATATAAAAAATCTGACTATTATAAGCAATGATACAGCTTTTCCTAATAAAGGAATAGGAA
AACTTATTGTAAATGGTCAAGTTTCTAAAGTAATTGCTTCACATATTGGAACTAATCCTG
AAACTGGAAAAAAAATGAGCTCTGGAGAACTTAAAGTTGAGCTTTCCCCACAAGGAACAC
TGATTGAAAGAATTCGTGCAGCTGGATCTGGACTCGGAGGTGTATTAACTCCAACTGGAC
TTGGAACTATCGTTGAAGAAGGTAAGAAAAAAGTTACTATCGATGGCAAAGAATATCTAT
TAGAACTTCCTTTATCTGCTGATGTTTCATTAATAAAAGGTAGCATTGTAGATGAATTTG
GAAATACCTTCTATAGGGCTGCTACTAAAAATTTCAATCCATATATGGCAATGGCTGCAA
AAACAGTTATAGTTGAAGCAGAAAATTTAGTTAAATGTGAAGATTTAAAAAGAGATGCCA
TAATGACTCCTGGCGTATTAGTAGATTATATCGTTAAGGAGGCGGCTTAATTGATTGTAG
ATAAAGTTTTAGCAAAAGAGATAATTGCCAAAAGAGTTGCAAAAGAACTAAAAAAAGACC
AACTCGTAAACCTTGGAATAGGACTTCCAACTTTAGTAGCAAATTATGTACCAAAAGAAA
TGAACATTACTTTTGAATCAGAAAATGGCATGGTTGGTATGGCACAAATGGCATCATCAG
GTGAAAATGACCCAGATATAATAAATGCTGGCGGGGAATATGTAACATTATTACCTCAAG
GTTCATTTTTTGATAGTTCAATGTCTTTCGCACTAATACGAGGAGGACATGTTGATGTTG
CTGTTCTTGGTGCTCTAGAAGTTGATGAAAAAGGTAATTTAGCTAACTGGATTGTTCCAA
ATAAAATTGTCCCAGGTATGGGTGGCGCTATGGATTTAGCAATAGGCGCAAAAAAAATAA
TAGTGGCAATGCAACATACAGGAAAAAGTAAACCTAAAATCGTTAAAAAATGTACTCTCC
CACTTACTGCTAAGGCTCAAGTGGATTTAATTGTCACAGAACTTTGTGTAATTGATGTAA
CAAATGACGGCTTACTTTTAAAAGAAATTCATAAAGATACAACTATTGATGAAATTAAAT
TTTTAACAGATGCAGATTTAATTATTCCAGATAACTTAAAGATTATGGATATATGAATCA
TTCTATTTTAAATATATAACTTTAAAAATCTTATGTATTAAAAACTAAGAAAAGAGGTTG
ATTGTTTTATGTTAGAAAGTGAAGTATCTAAACAAATTACAACTCCACTTGCTGCTCCAG
CGTTTCCTAGAGGACCATATAGGTTTCACAATAGAGAATATCTAAACATTATTTATCGAA
CTGATTTAGATGCTCTTCGAAAAATAGTACCAGAGCCACTTGAATTAGATAGAGCATATG
TTAGATTTGAAATGATGGCTATGCCTGATACAACCGGACTAGGCTCATATACAGAATGTG
GTCAAGCTATTCCAGTAAAATATAATGGTGTTAAGGGTGACTACTTGCATATGATGTATC
TAGATAATGAACCTGCTATTGCTGTTGGAAGAGAAAGTAGCGCTTATCCAAAAAAGCTTG
GCTATCCAAAGCTATTTGTTGATTCAGATACTTTAGTTGGGACACTTAAATATGGTACAT
TACCAGTAGCTACTGCAACAATGGGATATAAGCACGAGCCTCTAGATCTTAAAGAAGCCT
ATGCTCAAATTGCAAGACCCAATTTTATGCTAAAAATCATTCAAGGTTACGATGGTAAGC
CAAGAATTTGTGAACTAATATGTGCAGAAAATACTGATATAACTATTCACGGTGCTTGGA
CTGGAAGTGCACGTCTACAATTATTTAGCCATGCACTAGCTCCTCTTGCTGATTTACCTG
TATTAGAGATTGTATCAGCATCTCATATCCTCACAGATTTAACTCTTGGAACACCTAAGG
TTGTACATGATTATCTTTCAGTAAAATAAAAGCAATATAGAGGATCCAGGAGGAACAAAG
ATGAGTATACCAGAAACACAAAAAGCAATTATATTTTATGAGTCAAATGGAAAATTAGAG
CATAAAGATATACCTGTACCAAAACCAAAACCAAACGAACTTCTTATAAATGTTAAGTAT
TCTGGTGTTTGTCATACTGATCTTCATGCATGGCATGGTGATTGGCCTCTTCCAACTAAA

FIG 61 (continued)

```
TTACCTCTTGTAGGTGGTCATGAAGGTGCTGGTGTAGTTGTAGGTATGGGTGAAAATGTT
AAAGGTTGGAAAATAGGTGATTATGCTGGAATTAAATGGCTTAATGGATCTTGTATGGCA
TGCGAGTATTGTGAATTAGGAAATGAAAGTAATTGTCCACATGCTGACTTAAGTGGTTAT
ACTCATGATGGATCTTTTCAAGAATATGCTACTGCAGATGCAGTTCAGGCTGCACACATT
CCACAGGGAACTGATCTTGCTGAAGTAGCTCCTATATTATGCGCTGGAATTACAGTATAC
AAAGCATTAAAAAGTGCTAATCTTAGAGCAGGACACTGGGCAGCTATAAGTGGTGCTGCA
GGTGGTTTAGGATCTTTAGCAGTTCAATATGCTAAAGCTATGGGATATAGAGTATTAGGA
ATAGACGGTGGTCCAGGAAAAGAAGAGTTATTTACATCATTAGGTGGTGAAGTTTTTATA
GATTTCACAAAGGAAAAAGATATTGTTTCAGCTGTAGTAAAGGCAACTAATGGTGGTGCA
CACGGAATTATAAATGTTTCAGTATCTGAAGCAGCAATAGAAGCAAGTACTAGATATTGT
AGAGCAAACGGAACAGTAGTTTTAGTTGGACTTCCAGCTGGTGCAAAGTGTTCATCTGAC
GTATTTAACCATGTAGTAAAGAGTATTTCAATAGTTGGATCTTACGTAGGTAATAGAGCT
GATACAAGAGAAGCTTTAGATTTCTTTGCAAGAGGTTTAGTTAAGAGTCCTATAAAAGTA
GTAGGACTTTCATCACTTCCTGAAATTTATGAAAAGATGGAAAAGGGACAAATAGCTGGT
AGATATGTTGTAGATACAAGTAAATAAGGCCATGGAGATCTCGAGGCCTGCAGACATGCA
AGCTTGGCACTGGCCGTCGTTTTACAACGTCGTGACTGGGAAAACCCTGGCGTTACCCAA
CTTAATCGCCTTGCAGCACATCCCCCTTTCGCCAGCTGGCGTAATAGCGAAGAGGCCCGC
ACCGATCGCCCTTCCCAACAGTTGCGCAGCCTGAATGGCGAATGGCGCTAGCATAAAAAT
AAGAAGCCTGCATTTGCAGGCTTCTTATTTTTATGGCGCGCCGCCATTATTTTTTTGAAC
AATTGACAATTCATTTCTTATTTTTTATTAAGTGATAGTCAAAAGGCATAACAGTGCTGA
ATAGAAAGAAATTTACAGAAAAGAAAATTATAGAATTTAGTATGATTAATTATACTCATT
TATGAATGTTTAATTGAATACAAAAAAAAATACTTGTTATGTATTCAATTACGGGTTAAA
ATATAGACAAGTTGAAAAATTTAATAAAAAAATAAGTCCTCAGCTCTTATATATTAAGCT
ACCAACTTAGTATATAAGCCAAAACTTAAATGTGCTACCAACACATCAAGCCGTTAGAGA
ACTCTATCTATAGCAATATTTCAAATGTACCGACATACAAGAGAAACATTAACTATATAT
ATTCAATTTATGAGATTATCTTAACAGATATAAATGTAAATTGCAATAAGTAAGATTTAG
AAGTTTATAGCCTTTGTGTATTGGAAGCAGTACGCAAAGGCTTTTTTATTTGATAAAAAT
TAGAAGTATATTTATTTTTTCATAATTAATTTATGAAAATGAAAGGGGGTGAGCAAAGTG
ACAGAGGAAAGCAGTATCTTATCAAATAACAAGGTATTAGCAATATCATTATTGACTTTA
GCAGTAAACATTATGACTTTTATAGTGCTTGTAGCTAAGTAGTACGAAAGGGGGAGCTTT
AAAAAGCTCCTTGGAATACATAGAATTCATAAATTAATTTATGAAAAGAAGGGCGTATAT
GAAAACTTGTAAAAATTGCAAAGAGTTTATTAAAGATACTGAAATATGCAAAATACATTC
GTTGATGATTCATGATAAAACAGTAGCAACCTATTGCAGTAAATACAATGAGTCAAGATG
TTTACATAAAGGGAAAGTCCAATGTATTAATTGTTCAAAGATGAACCGATATGGATGGTG
TGCCATAAAAATGAGATGTTTTACAGAGGAAGAACAGAAAAAAGAACGTACATGCATTAA
ATATTATGCAAGGAGCTTTAAAAAAGCTCATGTAAAGAAGAGTAAAAAGAAAAAATAATT
TATTTATTAATTTAATATTGAGAGTGCCGACACAGTATGCACTAAAAAATATATCTGTGG
TGTAGTGAGCCGATACAAAAGGATAGTCACTCGCATTTTCATAATACATCTTATGTTATG
ATTATGTGTCGGTGGGACTTCACGACGAAAACCCACAATAAAAAAAGAGTTCGGGGTAGG
GTTAAGCATAGTTGAGGCAACTAAACAATCAAGCTAGGATATGCAGTAGCAGACCGTAAG
GTCGTTGTTTAGGTGTGTTGTAATACATACGCTATTAAGATGTAAAAATACGGATACCAA
TGAAGGGAAAAGTATAATTTTTGGATGTAGTTTGTTTGTTCATCTATGGGCAAACTACGT
CCAAAGCCGTTTCCAAATCTGCTAAAAAGTATATCCTTTCTAAAATCAAAGTCAAGTATG
AAATCATAAATAAAGTTTAATTTTGAAGTTATTATGATATTATGTTTTTCTATTAAAATA
AATTAAGTATATAGAATAGTTTAATAATAGTATATACTTAATGTGATAAGTGTCTGACAG
TGTCACAGAAAGGATGATTGTTATGGATTATAAGCGGCCGG
```

FIG 61 (continued)

SEQ ID NO: 101
CCAGTGGGCAAGTTGAAAAATTCACAAAAATGTGGTATAATATCTTTGTTCATTAGAGCG
ATAAACTTGAATTTGAGAGGGAACTTAGATGGTATTTGAAAAAATTGATAAAAATAGTTG
GAACAGAAAAGAGTATTTTGACCACTACTTTGCAAGTGTACCTTGTACCTACAGCATGAC
CGTTAAAGTGGATATCACACAAATAAAGGAAAAGGGAATGAAACTATATCCTGCAATGCT
TTATTATATTGCAATGATTGTAAACCGCCATTCAGAGTTTAGGACGGCAATCAATCAAGA
TGGTGAATTGGGGATATATGATGAGATGATACCAAGCTATACAATATTTCACAATGATAC
TGAAACATTTTCCAGCCTTTGGACTGAGTGTAAGTCTGACTTTAAATCATTTTTAGCAGA
TTATGAAAGTGATACGCAACGGTATGGAAACAATCATAGAATGGAAGGAAAGCCAAATGC
TCCGGAAAACATTTTTAATGTATCTATGATACCGTGGTCAACCTTCGATGGCTTTAATCT
GAATTTGCAGAAAGGATATGATTATTTGATTCCTATTTTTACTATGGGGAAATATTATAA
AGAAGATAACAAAATTATACTTCCTTTGGCAATTCAAGTTCATCACGCAGTATGTGACGG
ATTTCACATTTGCCGTTTTGTAAACGAATTGCAGGAATTGATAAATAGTTAACTTCAGGT
TTGTCTGTAACTAAAAACAAGTATTTAAGCAAAAACATCGTAGAAATACGGTGTTTTTTG
TTACCCTAAGTTTAAACTCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGTTTG
TTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGA
TAAGTCGTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGA
CAGGTATCCGGTAAGCGGCAGGGTCGGAACAGGAGAGCGCACGAGGGAGCTTCCAGGGGG
AAACGCCTGGTATCTTTATAGTCCTGTCGGGTTTCGCCACCTCTGACTTGAGCGTCGATT
TTTGTGATGCTCGTCAGGGGGGCGGAGCCTATGGAAAAACGCCAGCAACGCGGCCTTTTT
ACGGTTCCTGGCCTTTTGCTGGCCTTTTGCTCACATGTTCTTTCCTGCGTTATCCCCTGA
TTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCCAATACGCAGGGCCCC
CTGCAGGATAAAAAAATTGTAGATAAATTTTATAAAATAGTTTTATCTACAATTTTTTTA
TCAGGAAACAGCTATGACCGCGGCCGCAGATAGTCATAATAGTTCCAGAATAGTTCAATT
TAGAAATTAGACTAAACTTCAAAATGTTTGTTAAATATATACCAAACTAGTATAGATATT
TTTTAAATACTGGACTTAAACAGTAGTAATTTGCCTAAAAAATTTTTTCAATTTTTTTTA
AAAAATCCTTTTCAAGTTGTACATTGTTATGGTAATATGTAATTGAAGAAGTTATGTAGT
AATATTGTAAACGTTTCTTGATTTTTTTACATCCATGTAGTGCTTAAAAAACCAAAATAT
GTCACATGCAATTGTATATTTCAAATAACAATATTTATTTTCTCGTTAAATTCACAAATA
ATTTATTAATAATATCAATAACCAAGATTATACTTAAATGGATGTTTATTTTTTAACACT
TTTATAGTAAATATATTTATTTTATGTAGTAAAAAGGTTATAATTATAATTGTATTTATT
ACAATTAATTAAAATAAAAAATAGGGTTTTAGGTAAAATTAAGTTATTTTAAGAAGTAAT
TACAATAAAAATTGAAGTTATTTCTTTAAGGAGGGAATTATTCATATGAAAGAAGTTGTA
ATAGCTAGTGCAGTAAGAACAGCGATTGGATCTTATGGAAAGTCTCTTAAGGATGTACCA
GCAGTAGATTTAGGAGCTACAGCTATAAAGGAAGCAGTTAAAAAAGCAGGAATAAAACCA
GAGGATGTTAATGAAGTCATTTTAGGAAATGTTCTTCAAGCAGGTTTAGGACAGAATCCA
GCAAGACAGGCATCTTTTAAAGCAGGATTACCAGTTGAAATTCCAGCTATGACTATTAAT
AAGGTTTGTGGTTCAGGACTTAGAACAGTTAGCTTAGCAGCACAAATTATAAAAGCAGGA
GATGCTGACGTAATAATAGCAGGTGGTATGGAAAATATGTCTAGAGCTCCTTACTTAGCG

FIG 62

AATAACGCTAGATGGGGATATAGAATGGGAAACGCTAAATTTGTTGATGAAATGATCACT
GACGGATTGTGGGATGCATTTAATGATTACCACATGGGAATAACAGCAGAAAACATAGCT
GAGAGATGGAACATTTCAAGAGAAGAACAAGATGAGTTTGCTCTTGCATCACAAAAAAAA
GCTGAAGAAGCTATAAAATCAGGTCAATTTAAAGATGAAATAGTTCCTGTAGTAATTAAA
GGCAGAAAGGGAGAAACTGTAGTTGATACAGATGAGCACCCTAGATTTGGATCAACTATA
GAAGGACTTGCAAAATTAAAACCTGCCTTCAAAAAAGATGGAACAGTTACAGCTGGTAAT
GCATCAGGATTAAATGACTGTGCAGCAGTACTTGTAATCATGAGTGCAGAAAAAGCTAAA
GAGCTTGGAGTAAAACCACTTGCTAAGATAGTTTCTTATGGTTCAGCAGGAGTTGACCCA
GCAATAATGGGATATGGACCTTTCTATGCAACAAAAGCAGCTATTGAAAAAGCAGGTTGG
ACAGTTGATGAATTAGATTTAATAGAATCAAATGAAGCTTTTGCAGCTCAAAGTTTAGCA
GTAGCAAAAGATTTAAAATTTGATATGAATAAAGTAAATGTAAATGGAGGAGCTATTGCC
CTTGGTCATCCAATTGGAGCATCAGGTGCAAGAATACTCGTTACTCTTGTACACGCAATG
CAAAAAAGAGATGCAAAAAAAGGCTTAGCAACTTTATGTATAGGTGGCGGACAAGGAACA
GCAATATTGCTAGAAAAGTGCTAGGAATTCGAGCTCGGTACCAGGGAGATATTAAAATGA
ATAAATTAGTAAAATTAACAGATTTAAAGCGCATTTTCAAAGATGGCATGACAATTATGG
TTGGGGGTTTTTTAGATTGTGGAACTCCTGAAAATATTATAGATATGCTAGTTGATTTAA
ATATAAAAAATCTGACTATTATAAGCAATGATACAGCTTTTCCTAATAAAGGAATAGGAA
AACTTATTGTAAATGGTCAAGTTTCTAAAGTAATTGCTTCACATATTGGAACTAATCCTG
AAACTGGAAAAAAAATGAGCTCTGGAGAACTTAAAGTTGAGCTTTCCCCACAAGGAACAC
TGATTGAAAGAATTCGTGCAGCTGGATCTGGACTCGGAGGTGTATTAACTCCAACTGGAC
TTGGAACTATCGTTGAAGAAGGTAAGAAAAAAGTTACTATCGATGGCAAAGAATATCTAT
TAGAACTTCCTTTATCTGCTGATGTTTCATTAATAAAAGGTAGCATTGTAGATGAATTTG
GAAATACCTTCTATAGGGCTGCTACTAAAAATTTCAATCCATATATGGCAATGGCTGCAA
AAACAGTTATAGTTGAAGCAGAAAATTTAGTTAAATGTGAAGATTTAAAAAGAGATGCCA
TAATGACTCCTGGCGTATTAGTAGATTATATCGTTAAGGAGGCGGCTTAATTGATTGTAG
ATAAAGTTTTAGCAAAAGAGATAATTGCCAAAAGAGTTGCAAAAGAACTAAAAAAAGACC
AACTCGTAAACCTTGGAATAGGACTTCCAACTTTAGTAGCAAATTATGTACCAAAAGAAA
TGAACATTACTTTTGAATCAGAAAATGGCATGGTTGGTATGGCACAAATGGCATCATCAG
GTGAAAATGACCCAGATATAATAAATGCTGGCGGGGAATATGTAACATTATTACCTCAAG
GTTCATTTTTTGATAGTTCAATGTCTTTCGCACTAATACGAGGAGGACATGTTGATGTTG
CTGTTCTTGGTGCTCTAGAAGTTGATGAAAAAGGTAATTTAGCTAACTGGATTGTTCCAA
ATAAAATTGTCCCAGGTATGGGTGGCGCTATGGATTTAGCAATAGGCGCAAAAAAAATAA
TAGTGGCAATGCAACATACAGGAAAAAGTAAACCTAAAATCGTTAAAAAATGTACTCTCC
CACTTACTGCTAAGGCTCAAGTGGATTTAATTGTCACAGAACTTTGTGTAATTGATGTAA
CAAATGACGGCTTACTTTTAAAAGAAATTCATAAAGATACAACTATTGATGAAATTAAAT
TTTTAACAGATGCAGATTTAATTATTCCAGATAACTTAAAGATTATGGATATATGAATCA
TTCTATTTTAAATATATAACTTTAAAAATCTTATGTATTAAAAACTAAGAAAAGAGGTTG
ATTGTTTTATGTTAGAAAGTGAAGTATCTAAACAAATTACAACTCCACTTGCTGCTCCAG
CGTTTCCTAGAGGACCATATAGGTTTCACAATAGAGAATATCTAAACATTATTTATCGAA
CTGATTTAGATGCTCTTCGAAAAATAGTACCAGAGCCACTTGAATTAGATAGAGCATATG
TTAGATTTGAAATGATGGCTATGCCTGATACAACCGGACTAGGCTCATATACAGAATGTG
GTCAAGCTATTCCAGTAAAATATAATGGTGTTAAGGGTGACTACTTGCATATGATGTATC
TAGATAATGAACCTGCTATTGCTGTTGGAAGAGAAAGTAGCGCTTATCCAAAAAAGCTTG
GCTATCCAAAGCTATTTGTTGATTCAGATACTTTAGTTGGGACACTTAAATATGGTACAT
TACCAGTAGCTACTGCAACAATGGGATATAAGCACGAGCCTCTAGATCTTAAAGAAGCCT
ATGCTCAAATTGCAAGACCCAATTTTATGCTAAAAATCATTCAAGGTTACGATGGTAAGC
CAAGAATTTGTGAACTAATATGTGCAGAAAATACTGATATAACTATTCACGGTGCTTGGA

FIG 62 (continued)

CTGGAAGTGCACGTCTACAATTATTTAGCCATGCACTAGCTCCTCTTGCTGATTTACCTG
TATTAGAGATTGTATCAGCATCTCATATCCTCACAGATTTAACTCTTGGAACACCTAAGG
TTGTACATGATTATCTTTCAGTAAAATAAAAGCAATATAGAGGATCCACAGCTATGACCG
CGGCCGCAATATGATATTTATGTCCATTGTGAAAGGGATTATATTCAACTATTATTCCAG
TTACGTTCATAGAAATTTTCCTTTCTAAAATATTTTATTCCATGTCAAGAACTCTGTTTA
TTTCATTAAAGAACTATAAGTACAAAGTATAAGGCATTTGAAAAAATAGGCTAGTATATT
GATTGATTATTTATTTTAAAATGCCTAAGTGAAATATATACATATTATAACAATAAAATA
AGTATTAGTGTAGGATTTTTAAATAGAGTATCTATTTTCAGATTAAATTTTTGATTATTT
GATTTACATTATATAATATTGAGTAAAGTATTGACTAGCAAAATTTTTTGATACTTTAAT
TTGTGAAATTTCTTATCAAAAGTTATATTTTTGAATAATTTTTATTGAAAAATACAACTA
AAAAGGATTATAGTATAAGTGTGTGTAATTTTGTGTTAAATTTAAAGGGAGGAAATGAAC
ATGAAACATATGTATACAGTTGGTGATTATTTACTTGATAGATTACATGAACTTGGAATA
GAAGAAATTTTTGGTGTACCAGGTGATTACAATCTTCAATTCTTAGATCAAATAATATCA
CATAAGGATATGAAATGGGTTGGTAATGCTAATGAATTAAATGCATCATATATGGCAGAC
GGATATGCAAGAACTAAAAAGGCAGCAGCATTTCTTACTACATTTGGTGTTGGTGAATTA
AGTGCAGTAAATGGATTAGCTGGAAGTTACGCAGAAAACTTACCAGTTGTTGAAATAGTT
GGATCTCCTACTAGTAAAGTACAAAATGAAGGTAAATTTGTACATCACACTCTTGCAGAT
GGTGATTTTAAGCATTTTATGAAAATGCATGAACCTGTTACAGCTGCAAGAACACTTCTT
ACAGCTGAAAACGCTACTGTAGAAATTGATAGAGTTTTATCTGCTTTACTTAAAGAAAGA
AAGCCAGTATATATTAACCTTCCAGTAGATGTAGCAGCAGCAAAAGCTGAGAAACCTTCA
TTACCACTTAAAAAGGAAAATTCAACATCAAATACATCTGATCAAGAGATATTAAATAAA
ATTCAGGAAAGTCTTAAAAATGCAAAGAAACCTATAGTAATAACTGGACATGAAATAATT
AGTTTTGGATTAGAAAAGACAGTTACACAGTTTATAAGTAAAACTAAGCTTCCAATTACA
ACTTTAAATTTTGGAAAGAGTTCAGTAGATGAGGCACTTCCATCATTCTTAGGAATTTAT
AATGGAACATTATCTGAACCTAATCTTAAAGAATTTGTAGAGAGTGCTGATTTTATATTA
ATGTTAGGTGTAAAACTTACTGATAGTAGTACTGGTGCATTTACTCATCATCTTAACGAA
AATAAGATGATATCATTAAATATAGACGAAGGTAAAATATTCAATGAAAGAATACAGAAC
TTTGATTTTGAATCACTTATATCATCATTACTTGATTTATCAGAGATAGAATACAAAGGA
AAATATATAGATAAAAAGCAAGAAGATTTTGTTCCATCTAATGCTCTTCTTTCTCAAGAT
AGACTTTGGCAAGCAGTTGAGAATCTTACACAGTCTAATGAAACTATAGTTGCTGAGCAA
GGAACATCATTTTTCGGTGCATCAAGTATATTTTTAAAATCTAAAAGTCACTTTATTGGA
CAACCTCTTTGGGGTTCTATTGGATATACTTTTCCAGCAGCTTTAGGAAGTCAAATAGCT
GATAAAGAAAGTAGACATTTATTATTTATTGGTGACGGTTCACTTCAGCTTACAGTACAA
GAATTAGGATTAGCTATAAGAGAGAAGATAAATCCTATTTGTTTCATAATAAACAATGAT
GGATATACTGTAGAAAGAGAAATTCACGGACCAAATCAGTCATATAATGATATTCCAATG
TGGAATTATTCAAAGTTACCTGAATCTTTCGGTGCTACTGAAGATAGAGTAGTTTCTAAA
ATTGTTAGAACAGAGAACGAATTTGTATCTGTTATGAAAGAAGCTCAGGCTGACCCTAAT
AGAATGTATTGGATTGAATTAATTTTAGCAAAAGAAGGTGCTCCTAAAGTACTTAAGAAA
ATGGGAAAATTATTTGCAGAACAAAATAAGTCATAAGAATTCCCATAATAAAGAAAGAAT
TTTAAATAAAGGAGGAACAAAGATGAGTATACCAGAAACACAAAAAGCAATTATATTTTA
TGAGTCAAATGGAAAATTAGAGCATAAAGATATACCTGTACCAAAACCAAAACCAAACGA
ACTTCTTATAAATGTTAAGTATTCTGGTGTTTGTCATACTGATCTTCATGCATGGCATGG
TGATTGGCCTCTTCCAACTAAATTACCTCTTGTAGGTGGTCATGAAGGTGCTGGTGTAGT
TGTAGGTATGGGTGAAAATGTTAAAGGTTGGAAAATAGGTGATTATGCTGGAATTAAATG
GCTTAATGGATCTTGTATGGCATGCGAGTATTGTGAATTAGGAAATGAAAGTAATTGTCC
ACATGCTGACTTAAGTGGTTATACTCATGATGGATCTTTTCAAGAATATGCTACTGCAGA
TGCAGTTCAGGCTGCACACATTCCACAGGGAACTGATCTTGCTGAAGTAGCTCCTATATT

FIG 62 (continued)

ATGCGCTGGAATTACAGTATACAAAGCATTAAAAAGTGCTAATCTTAGAGCAGGACACTG
GGCAGCTATAAGTGGTGCTGCAGGTGGTTTAGGATCTTTAGCAGTTCAATATGCTAAAGC
TATGGGATATAGAGTATTAGGAATAGACGGTGGTCCAGGAAAAGAAGAGTTATTTACATC
ATTAGGTGGTGAAGTTTTTATAGATTTCACAAAGGAAAAAGATATTGTTTCAGCTGTAGT
AAAGGCAACTAATGGTGGTGCACACGGAATTATAAATGTTTCAGTATCTGAAGCAGCAAT
AGAAGCAAGTACTAGATATTGTAGAGCAAACGGAACAGTAGTTTTAGTTGGACTTCCAGC
TGGTGCAAAGTGTTCATCTGACGTATTTAACCATGTAGTAAAGAGTATTTCAATAGTTGG
ATCTTACGTAGGTAATAGAGCTGATACAAGAGAAGCTTTAGATTTCTTTGCAAGAGGTTT
AGTTAAGAGTCCTATAAAAGTAGTAGGACTTTCATCACTTCCTGAAATTTATGAAAAGAT
GGAAAAGGGACAAATAGCTGGTAGATATGTTGTAGATACAAGTAAATAAGGCCATGGAGA
TCTCGAGGCCTGCAGACATGCAAGCTTGGCACTGGCCGTCGTTTTACAACGTCGTGACTG
GGAAAACCCTGGCGTTACCCAACTTAATCGCCTTGCAGCACATCCCCCTTTCGCCAGCTG
GCGTAATAGCGAAGAGGCCCGCACCGATCGCCCTTCCCAACAGTTGCGCAGCCTGAATGG
CGAATGGCGCTAGCATAAAAATAAGAAGCCTGCATTTGCAGGCTTCTTATTTTTATGGCG
CGCCGCCATTATTTTTTTGAACAATTGACAATTCATTTCTTATTTTTTATTAAGTGATAG
TCAAAAGGCATAACAGTGCTGAATAGAAAGAAATTTACAGAAAAGAAAATTATAGAATTT
AGTATGATTAATTATACTCATTTATGAATGTTTAATTGAATACAAAAAAAAATACTTGTT
ATGTATTCAATTACGGGTTAAAATATAGACAAGTTGAAAAATTTAATAAAAAAATAAGTC
CTCAGCTCTTATATATTAAGCTACCAACTTAGTATATAAGCCAAAACTTAAATGTGCTAC
CAACACATCAAGCCGTTAGAGAACTCTATCTATAGCAATATTTCAAATGTACCGACATAC
AAGAGAAACATTAACTATATATATTCAATTTATGAGATTATCTTAACAGATATAAATGTA
AATTGCAATAAGTAAGATTTAGAAGTTTATAGCCTTTGTGTATTGGAAGCAGTACGCAAA
GGCTTTTTTATTTGATAAAAATTAGAAGTATATTTATTTTTTCATAATTAATTTATGAAA
ATGAAAGGGGGTGAGCAAAGTGACAGAGGAAAGCAGTATCTTATCAAATAACAAGGTATT
AGCAATATCATTATTGACTTTAGCAGTAAACATTATGACTTTTATAGTGCTTGTAGCTAA
GTAGTACGAAAGGGGGAGCTTTAAAAAGCTCCTTGGAATACATAGAATTCATAAATTAAT
TTATGAAAAGAAGGGCGTATATGAAAACTTGTAAAAATTGCAAAGAGTTTATTAAAGATA
CTGAAATATGCAAAATACATTCGTTGATGATTCATGATAAAACAGTAGCAACCTATTGCA
GTAAATACAATGAGTCAAGATGTTTACATAAAGGGAAAGTCCAATGTATTAATTGTTCAA
AGATGAACCGATATGGATGGTGTGCCATAAAAATGAGATGTTTTACAGAGGAAGAACAGA
AAAAAGAACGTACATGCATTAAATATTATGCAAGGAGCTTTAAAAAAGCTCATGTAAAGA
AGAGTAAAAAGAAAAAATAATTTATTTATTAATTTAATATTGAGAGTGCCGACACAGTAT
GCACTAAAAAATATATCTGTGGTGTAGTGAGCCGATACAAAAGGATAGTCACTCGCATTT
TCATAATACATCTTATGTTATGATTATGTGTCGGTGGGACTTCACGACGAAAACCCACAA
TAAAAAAAGAGTTCGGGGTAGGGTTAAGCATAGTTGAGGCAACTAAACAATCAAGCTAGG
ATATGCAGTAGCAGACCGTAAGGTCGTTGTTTAGGTGTGTTGTAATACATACGCTATTAA
GATGTAAAAATACGGATACCAATGAAGGGAAAAGTATAATTTTTGGATGTAGTTTGTTTG
TTCATCTATGGGCAAACTACGTCCAAAGCCGTTTCCAAATCTGCTAAAAAGTATATCCTT
TCTAAAATCAAAGTCAAGTATGAAATCATAAATAAAGTTTAATTTTGAAGTTATTATGAT
ATTATGTTTTTCTATTAAAATAAATTAAGTATATAGAATAGTTTAATAATAGTATATACT
TAATGTGATAAGTGTCTGACAGTGTCACAGAAAGGATGATTGTTATGGATTATAAGCGGC
CGG

FIG 62 (continued)

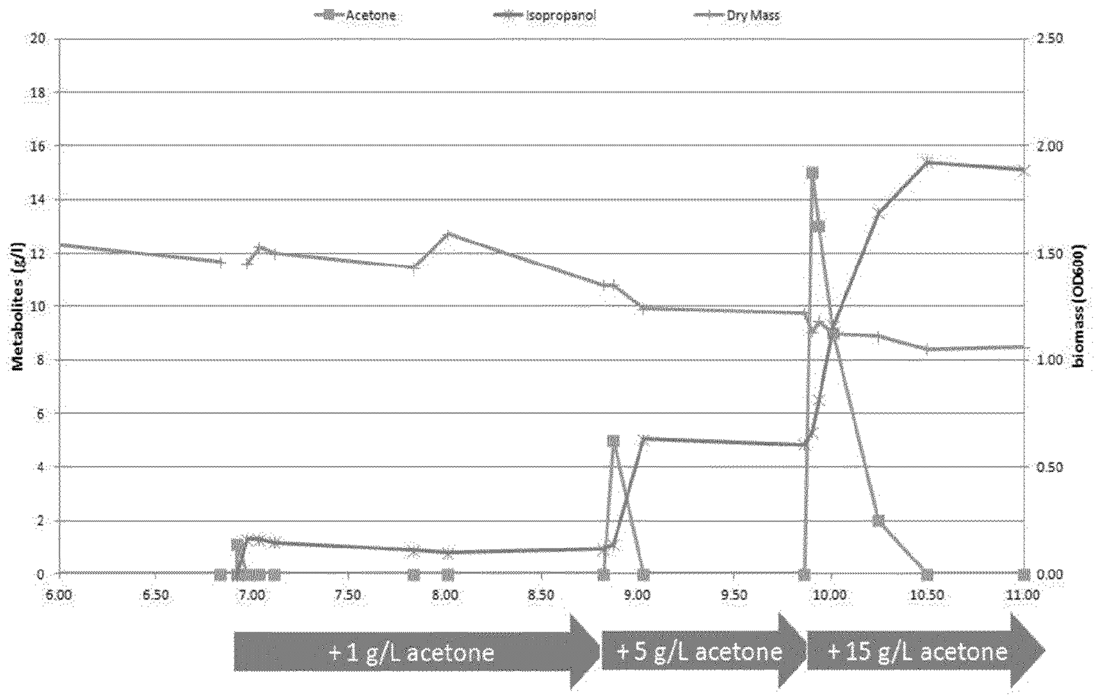
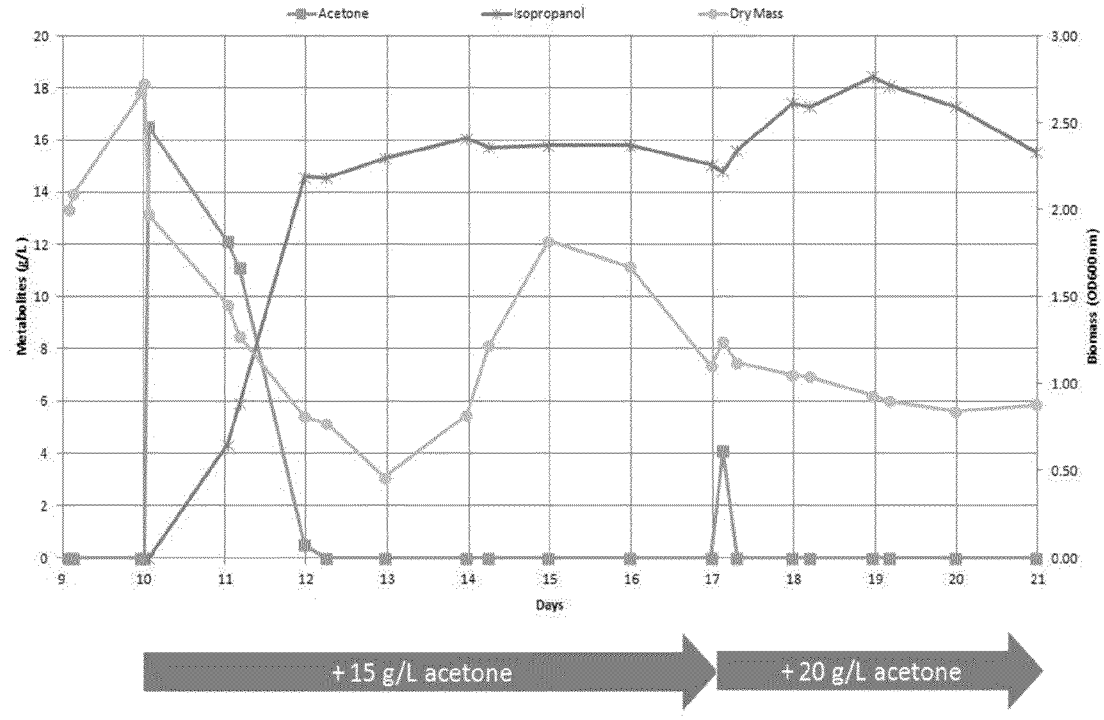
FIG 74

FERMENTATION PROCESS FOR PRODUCING ISOPROPANOL USING A RECOMBINANT MICROORGANISM

CROSS REFERENCE TO RELATED APPLICATION

This is application is a Continuation-In-Part of copending U.S. application Ser. No. 13/403,972 filed on Feb. 23, 2012 which in turn claims the priority of Provisional Application No. 61/446,832 filed on Feb. 25, 2011 all of which are incorporated by reference in their entirety.

FIELD OF THE INVENTION

The present invention relates to methods for the production of acetone, isopropanol and/or a precursor of acetone and/or isopropanol by microbial fermentation of gaseous substrates comprising carbon monoxide using genetically modified micro-organisms.

BACKGROUND OF THE INVENTION

Some microorganisms such as *Clostridium acetobutylicum* or *Clostridium beijerinckii* are known to produce acetone or isopropanol as major by-products during butanol fermentation (ABE or IBE fermentation) [George H A, Johnson J L, Moore W E C, Holdeman L V, Chen J S: Acetone, isopropanol, and butanol production by *Clostridium beijerinckii* (syn. *Clostridium butylicum*) and *Clostridium aurantibutyricum*. *Appl Environ Microbiol* 45: 1160-1163]. However, all these organisms rely on sugar or starch based substrates. Acetogenic organisms such as the closely related microorganisms *Clostridium autoethanogenum, C. ljungdahlii*, and *C. ragsdalei* are able to grow chemoautotrophically on CO or $CO_2/H_2$ containing gases as sole energy and carbon source and synthesize products such as acetate, ethanol, or 2,3-butanediol, but neither acetone nor isopropanol [Munasinghe P C, Khanal S K: Biomass-derived syngas fermentation into biofuels: Opportunities and challenges. *Bioresource Technol* 2010, 5013-22].

Recently, production of isopropanol was reported in a study on *Clostridium ragsdalei* (*Clostridium strain* P11) in a 100-L pilot scale fermentor from switchgrass derived syngas [Kundiyana D K, Huhnke R L, Wilkins M R: Syngas fermentation in a 100-L pilot scale fermentor: Design and process considerations. *J Biosci Bioeng* 2010, 109: 492-498]. However, a related study from the same lab showed that this was due to a contamination in the used syngas since it was passed through a scrubbing mixture containing 20% acetone [Ramachandriya K D: Effect of biomass generated producer gas, methane and physical parameters on producer gas fermentations by *Clostridium* strain P11. Masters thesis, Oklahoma State University 2009]. The authors also noted that the production of isopropanol may be the result of reduction of propionic acid rather than acetone. Experiments carried out by the inventors of the present invention with *Clostridium ragsdalei* (*Clostridium* strain P11) and also *C. autoethanogenum* and *C. ljungdahlii* have never shown the production of acetone, isopropanol, or propionic acid.

The cost of many carbohydrate feed stocks suitable for the production of chemical products such as acetone and isoproanol is influenced by their value as human food or animal feed, and the cultivation of starch or sucrose-producing crops for such production is not economically sustainable in all geographies. Therefore, it is of interest to develop technologies to convert lower cost and/or more abundant carbon resources into useful chemical products such as acetone and isopropanol.

CO is a major free energy-rich by-product of the incomplete combustion of organic materials such as coal or oil and oil derived products. For example, the steel industry in Australia is reported to produce and release into the atmosphere over 500,000 tonnes of CO annually.

It is an object of the invention to overcome one or more of the disadvantages of the prior art, or to at least to provide the public with a useful choice.

SUMMARY OF INVENTION

The invention generally provides, inter alia, methods for the production of acetone, isopropanol and/or precursors of acetone and/or isopropanol by microbial fermentation of gaseous substrates comprising CO, genetically modified microorganisms of use in such methods, nucleic acids suitable for preparation of genetically modified microorganisms and a novel alcohol dehydrogenase and nucleic acids encoding same.

In a first aspect, the invention provides a carboxydotrophic acetogenic recombinant microorganism capable of producing acetone, isopropanol and/or a precursor of acetone and/or isopropanol by fermentation of a substrate comprising CO.

In one particular embodiment, the microorganism is adapted to express at least one enzyme in the isopropanol biosynthesis pathway which are not naturally present in a parental microorganism from which the recombinant microorganism is derived. In another embodiment, the microorganism is adapted to over-express one or more enzymes in the isopropanol biosynthesis pathway which are naturally present in a parental microorganism from which the recombinant microorganism is derived.

In one particular embodiment, the microorganism is adapted to express one or more enzymes in the acetone biosynthesis pathway which are not naturally present in a parental microorganism from which the recombinant microorganism is derived. In another embodiment, the microorganism is adapted to over-express one or more enzymes in the acetone biosynthesis pathway which are naturally present in a parental microorganism from which the recombinant microorganism is derived.

In one particular embodiment, the microorganism is adapted to express one or more enzymes involved in the conversion of acetone to isopropanol which are not naturally present in a parental microorganism from which the recombinant microorganism is derived. In another embodiment, the microorganism is adapted to over-express one or more enzymes involved in the conversion of acetone to isopropanol which are naturally present in a parental microorganism from which the recombinant microorganism is derived.

In one embodiment, the parental microorganism is capable of fermenting a gaseous substrate comprising CO to produce acetone but not of converting acetone to isopropanol and the recombinant microorganism is adapted to express one or more enzymes involved in the conversion of acetone to isopropanol.

In another embodiment, the parental microorganism is capable of converting acetone to isopropanol but is not capable of fermenting a substrate comprising CO to produce acetone and the recombinant microorganism is adapted to express one or more enzymes in the acetone biosynthesis pathway.

In one embodiment, the parental microorganism is not capable of fermenting a substrate comprising CO to produce acetone and isopropanol and the recombinant microorganism is adapted to express one or more enzymes in the acetone biosynthesis pathway and one or more enzymes involved in the conversion of acetone to isopropanol.

In one embodiment the one or more enzymes in the isopropanol and/or acetone biosynthesis pathway are chosen from the group consisting:

Acetyl-Coenzyme A acetyltransferase (Thiolase; ThlA; E.C. 2.3.1.9);

Acetoacetyl-CoA:Acetate Coenzyme A transferase A (CoA transferase; CtfA; EC 2.8.3.9);

Acetoacetyl-CoA:Acetate Coenzyme A transferase B (CoA transferase; CtfB; EC 2.8.3.9);

Acetoacetate decarboxylase (Adc; EC 4.1.1.4);

Alpha-ketoisovalerate decarboxylase (decarboxylase; KivD; EC4.1.1.74); and,

A functionally equivalent variant of any one or more thereof.

In one embodiment, the Acetyl-Coenzyme A acetyltransferase (Thiolase; ThlA) is that derived from *C. acetobutylicum.*

In one embodiment, the enzymes Acetoacetyl-CoA:Acetate Coenzyme A transferase A (CoA transferase; CtfA), Acetoacetyl-CoA:Acetate Coenzyme A transferase B (CoA transferase; CtfB) and Acetoacetate decarboxylase (Adc) are derived from *C. beijerinckii.*

In one embodiment, the Alpha-ketoisovalerate decarboxylase (decarboxylase; KivD) is that derived from *Lactococcus lactis.*

In one embodiment, the one or more enzyme involved in the conversion of acetone to isopropanol are chosen from the group consisting:

Alcohol Dehydrogenase (Adh; EC 1.1.1.2);

Alcohol dehydrogenase (Adh2; EC 1.1.1.1) and,

A functionally equivalent variant thereof.

In one embodiment, the Alcohol Dehydrogenase (Adh) is derived from *C. autoethanogenum, C. ljungdahlii*, and/or *C. ragsdalei*. In one embodiment, the alcohol dehydrogenase has the amino acid sequence of SEQ_ID NO. 1, or it is a functionally equivalent variant thereof. In one embodiment, the functionally equivalent variant has at least approximately 88%, 89%, 90%, 91%, 92%, 93%, 94%, 95%, 96%, 97%, 98% or 99% sequence identity to SEQ_ID NO. 1.

In one embodiment, the Alcohol Dehydrogenase (Adh2) is derived from *S. cerevisiae.*

In one embodiment, the microorganism comprises one or more exogenous nucleic acids adapted to increase expression of one or more nucleic acids native to the parental microorganism and which one or more nucleic acids encode one or more of the enzymes referred to herein before.

In one embodiment, the one or more exogenous nucleic acid adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster or Phosphotransacetylase/Acetate kinase operon promoters. In one embodiment, the promoter has the sequence of SEQ_ID No. 22 or SEQ ID no. 77, or is a functionally equivalent variant thereof.

In one embodiment, the microorganism comprises one or more exogenous nucleic acids encoding and adapted to express one or more of the enzymes referred to herein before. In one embodiment, the microorganisms comprise one or more exogenous nucleic acid encoding and adapted to express at least two of the enzymes. In other embodiments, the microorganism comprises one or more exogenous nucleic acid encoding and adapted to express 3, 4, 5 or 6 of the enzymes.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), and Acetoacetate decarboxylase (Adc; EC 4.1.1.4) or a functionally equivalent variant of any one or more thereof.

In one particular embodiment, the microorganism comprises one or more exogenous nucleic acids encoding Alcohol Dehydrogenase (Adh; EC 1.1.1.2) or a functionally equivalent variant thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), Acetoacetate decarboxylase (Adc; EC 4.1.1.4), and Alcohol Dehydrogenase (Adh; EC 1.1.1.2), or a functionally equivalent variant of any one or more thereof.

In one particular embodiment, the microorganism comprises one or more exogenous nucleic acids encoding each of Alpha-ketoisovalerate decarboxylase (decarboxylase; KivD; EC4.1.1.74), and Alcohol dehydrogenase (Adh2; EC 1.1.1.1), or a functionally equivalent variant of any one or more thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), and Alpha-ketoisovalerate decarboxylase (decarboxylase; KivD; EC4.1.1.74), or a functionally equivalent variant of any one or more thereof.

In one particular embodiment, the microorganism comprises one or more exogenous nucleic acids encoding Alpha-ketoisovalerate decarboxylase (decarboxylase; KivD; EC4.1.1.74), or a functionally equivalent variant thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), Acetoacetate decarboxylase (Adc; EC 4.1.1.4), and Alcohol dehydrogenase (Adh2; EC 1.1.1.1), or a functionally equivalent variant of any one or more thereof.

In another particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), Alpha-ketoisovalerate decarboxylase (decarboxylase; KivD; EC4.1.1.74), and Alcohol dehydrogenase (Adh2; EC 1.1.1.1), or a functionally equivalent variant of any one or more thereof.

In one embodiment, the nucleic acid encoding Acetyl-Coenzyme A acetyltransferase (Thiolase; ThlA) comprises the sequence SEQ_ID NO. 18, or a functionally equivalent variant thereof. In one embodiment, the nucleic acid encoding Acetoacetyl-CoA:Acetate Coenzyme A transferase A (CoA transferase; CtfA) comprises the sequence SEQ_ID NO. 19, or a functionally equivalent variant thereof. In one embodiment, the nucleic acid encoding Acetoacetyl-CoA:Acetate Coenzyme A transferase B (CoA transferase; CtfB) comprises the sequence SEQ_ID NO. 20, or a functionally equivalent variant thereof. In one embodiment, the nucleic acid encoding Acetoacetate decarboxylase (Adc) comprises the sequence SEQ_ID NO. 21, or a functionally equivalent variant thereof. In one embodiment, the nucleic acid encoding Alpha-ketoisovalerate decarboxylase (decarboxylase; KivD) comprises the sequence SEQ_ID NO. 71, or a functionally equivalent variant thereof. In one embodiment, the nucleic acid encoding Alcohol Dehydrogenase (Adh) comprises the sequence SEQ_ID NO. 2, SEQ_ID NO. 3, or SEQ_ID NO. 4, or a functionally equivalent variant of any one thereof. In one embodiment, the functionally equivalent variant of the nucleic acid encoding alcohol dehydrogenase (Adh) has at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4. In one embodiment, the nucleic acid encoding Alcohol dehydrogenase (Adh2) comprises the sequence SEQ_ID NO. 75, or a functionally equivalent variant thereof.

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid. In one particular embodiment, the expression plasmid has the nucleotide sequence SEQ_ID No. 46, 48, 83, 84, 95, 98 or 101.

In one embodiment, the parental microorganism is selected from the group of carboxydotrophic acetogenic bacteria selected from the group comprising *Clostridium autoethanogenum, Clostridium ljungdahlii, Clostridium ragsdalei, Clostridium carboxidivorans, Clostridium drakei, Clostridium scatologenes, Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii*, and *Thermoanaerobacter kiuvi*.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes encoding ThlA, CtfA, CtfB, Adc, KivD, Adh and Adh2. In one particular embodiment, the parental microorganism lacks a gene encoding Adh. In another particular embodiment, the parental microorganism lacks each of the genes encoding ThlA, CtfA, CtfB, and Adc and KivD.

In second aspect, the invention provides an Alcohol Dehydrogenase (Adh) having the amino acid sequence of SEQ_ID NO. 1, or a functionally equivalent variant of any one thereof.

In one particular embodiment, the functionally equivalent variant of the Alcohol Dehydrogenase (Adh) has at least approximately 88%, 89%, 90%, 91%, 92%, 93%, 94%, 95%, 96%, 97%, 98% or 99% sequence identity to SEQ_ID NO. 1.

In a third aspect, the invention provides a nucleic acid encoding Adh of SEQ_ID NO. 1 or a functionally equivalent variant thereof.

In a fourth aspect, the invention provides a nucleic acid having the sequence chosen from the group consisting:

SEQ_ID NO. 2

SEQ_ID NO. 3

SEQ_ID NO. 4; and,

A functionally equivalent variant of any one thereof.

In one particular embodiment, a functionally equivalent variant of SEQ_ID NO. 2, 3 or 4 is a nucleic acid at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4.

In a fifth aspect, the invention provides a nucleic acid capable of hybridising to at least a portion of the nucleic acid SEQ_ID NO. 2, 3 or 4, a nucleic acid complementary to any one thereof, or a functionally equivalent variant of any one thereof.

In a sixth aspect, the invention provides a nucleic acid chosen from the group consisting: SEQ_ID NO. 5; SEQ_ID NO. 6; SEQ_ID NO. 7; SEQ_ID NO. 8; SEQ_ID NO. 9; SEQ_ID NO. 10; SEQ_ID NO. 11; SEQ_ID NO. 12; SEQ_ID NO. 13; SEQ_ID NO. 14; SEQ_ID NO. 15; SEQ_ID NO. 16; SEQ_ID NO. 17; SEQ_ID NO. 18; SEQ_ID NO. 23; SEQ_ID NO. 24; SEQ_ID NO. 25; SEQ_ID NO. 26; SEQ_ID NO. 27; SEQ_ID NO. 28; SEQ_ID NO. 29; SEQ_ID NO. 30; SEQ_ID NO. 31; SEQ_ID NO. 32; SEQ_ID NO. 33; SEQ_ID NO. 64; SEQ_ID NO. 65; SEQ_ID NO. 66; SEQ_ID NO. 67; SEQ_ID NO. 68; SEQ_ID NO. 69; SEQ_ID NO. 70; SEQ_ID NO. 71; SEQ_ID NO. 85; SEQ_ID NO. 86; SEQ_ID NO. 87; SEQ_ID NO. 88; SEQ_ID NO. 89; SEQ_ID NO. 90; SEQ_ID NO. 91; SEQ_ID NO. 92; SEQ_ID NO. 93; SEQ_ID NO. 94; SEQ_ID NO. 96; SEQ_ID NO. 97; SEQ_ID NO. 99; SEQ_ID NO. 100.

In a seventh aspect, the invention provides a nucleic acid encoding one or more enzymes which when expressed in a microorganism allows the microorganism to produce acetone, isopropanol and/or a precursor of acetone and/or isopropanol by fermentation of substrate comprising CO.

In one embodiment, the nucleic acid encodes two or more enzymes which when expressed in a microorganism allows the microorganism to produce acetone, isopropanol and/or a precursor of acetone and/or isopropanol by fermentation of substrate comprising CO.

In one embodiment, the nucleic acids of the invention encode 3, 4, 5 or 6 such enzymes.

In one embodiment, the enzymes are chosen from Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), Alpha-ketoisovalerate decarboxylase (decarboxylase; KivD), Alcohol dehydrogenase (Adh2), Alcohol Dehydrogenase (Adh) and a functionally equivalent variant of any one or more thereof.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), and Acetoacetate decarboxylase (Adc) or a functionally equivalent variant of any one or more thereof, in any order.

In one embodiment, the nucleic acid comprises nucleic acid sequences encoding Alcohol Dehydrogenase (Adh) or a functionally equivalent variant thereof.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), and Alcohol Dehydrogenase (Adh) or a functionally equivalent variant of any one or more thereof, in any order.

In one embodiment, the nucleic acid comprises nucleic acid sequences encoding each of Alpha-ketoisovalerate decarboxylase (decarboxylase; KivD), Alcohol dehydrogenase (Adh2), or a functionally equivalent variant of any one or more thereof, in any order.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Alpha-ketoisovalerate decarboxylase (decarboxylase; KivD), or a functionally equivalent variant of any one or more thereof, in any order.

In one embodiment, the nucleic acid comprises nucleic acid sequences encoding each of Alpha-ketoisovalerate decarboxylase (decarboxylase; KivD), or a functionally equivalent variant of any one or more thereof, in any order.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), Alcohol dehydrogenase (Adh2), or a functionally equivalent variant of any one or more thereof, in any order.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), Alpha-ketoisovalerate decarboxylase (decarboxylase; KivD), Alcohol dehydrogenase (Adh2), or a functionally equivalent variant of any one or more thereof, in any order.

In one embodiment, the nucleic acid encodes Acetyl-Coenzyme A acetyltransferase (Thiolase; ThlA) having the sequence of SEQ_ID NO. 42 or a functionally equivalent variant thereof.

In one embodiment, the nucleic acid encodes Acetoacetyl-CoA:Acetate Coenzyme A transferase A (CoA transferase; CtfA) having the sequence of SEQ_ID NO. 43 or a functionally equivalent variant thereof.

In one embodiment, the nucleic acid encodes Acetoacetyl-CoA:Acetate Coenzyme A transferase B (CoA transferase; CtfB) having the sequence of SEQ_ID NO 43 and SEQ_ID NO 44, or a functionally equivalent variant thereof.

In one embodiment, the nucleic acid encodes Acetoacetate decarboxylase (Adc) having the sequence of SEQ ID No. 45, or a functionally equivalent variant thereof.

In one embodiment, the nucleic acid encodes Alcohol Dehydrogenase (Adh) having the sequence of SEQ_ID NO 38 and SEQ_ID NO 40. In one particular embodiment, the nucleic acid encodes Alcohol Dehydrogenase (Adh) having the sequence of SEQ_ID NO. 1, or a functionally equivalent variant thereof. In one particular embodiment, the functionally equivalent variant of Alcohol Dehydrogenase (Adh) has at least approximately 88%, 89%, 90%, 91%, 92%, 93%, 94%, 95%, 96%, 97%, 98% or 99% sequence identity to SEQ_ID NO. 1.

In one embodiment, the nucleic acid encodes Alpha-ketoisovalerate decarboxylase (decarboxylase; KivD) having the sequence of SEQ ID No. 73, or a functionally equivalent variant thereof.

In one embodiment, the nucleic acid encodes Alcohol dehydrogenase (Adh2) having the sequence of SEQ ID No. 75, or a functionally equivalent variant thereof.

In one embodiment, the nucleic acid sequence encoding Acetyl-Coenzyme A acetyltransferase (Thiolase; ThlA) comprises SEQ_ID NO. 18, or is a functionally equivalent variant thereof.

In one embodiment, the nucleic acid sequence encoding Acetoacetyl-CoA:Acetate Coenzyme A transferase A (CoA transferase; CtfA) comprises SEQ_ID NO. 19, or is a functionally equivalent variant thereof.

In one embodiment, the nucleic acid sequence encoding Acetoacetyl-CoA:Acetate Coenzyme A transferase B (CoA transferase; CtfB) comprises SEQ_ID NO. 20, or is a functionally equivalent variant thereof.

In one embodiment, the nucleic acid sequence encoding Acetoacetate decarboxylase (Adc) comprises SEQ_ID NO. 21, or is a functionally equivalent variant thereof.

In one embodiment, the nucleic acid sequence encoding Alcohol Dehydrogenase (Adh) comprises SEQ_ID NO. 39 or 41. In one particular embodiment, the nucleic acid sequence encoding Alcohol Dehydrogenase (Adh) comprises SEQ_ID NO. 2, SEQ_ID NO. 3, or SEQ_ID NO. 4, or is a functionally equivalent variant of any one thereof. In one embodiment, the functionally equivalent variant of SEQ_ID NO. 2, SEQ_ID NO. 3, or SEQ_ID NO. 4 has at least approximately 83%, 84%, 85%, 86%, 88%, 89%, 90%, 91%, 92%, 93%, 94%, 95%, 96%, 97%, 98% or 99% sequence identity to SEQ_ID NO. 2, 3 or 4.

In one embodiment, the nucleic acid sequence encoding Alpha-ketoisovalerate decarboxylase (decarboxylase; KivD) comprises SEQ_ID NO. 72 or 76, or is a functionally equivalent variant thereof.

In one embodiment, the nucleic acid sequence encoding Alcohol dehydrogenase (Adh2) comprises SEQ_ID NO. 74 or 77, or is a functionally equivalent variant thereof.

In one embodiment, the nucleic acids of the invention further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum*. In one particular embodiment, the promoter has the sequence of SEQ_ID NO. 22, SEQ_ID NO. 79, or is a functionally equivalent variant thereof.

In an eighth aspect, the invention provides a nucleic acid construct or vector comprising one or more nucleic acid of the seventh aspect.

In one particular embodiment, the nucleic acid construct or vector is an expression construct or vector. In one particular embodiment, the expression construct or vector is a plasmid. In one particular embodiment, the expression plasmid has the nucleotide sequence SEQ_ID No. 46, 47, 48, 83, 84, 95, 98 or 101.

In a ninth aspect, the invention provides host organisms comprising any one or more of the nucleic acids of the seventh aspect or vectors or constructs of the eighth aspect.

In a tenth aspect, the invention provides a composition comprising an expression constructor vector as referred to in the eighth aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In an eleventh aspect, the invention provides a method of producing a recombinant microorganism of the invention comprising:

a) introduction into a shuttle microorganism of (i) an expression construct/vector of the eighth aspect of the invention and (ii) a methylation construct/vector comprising a methyltransferase gene;

b) expression of the methyltransferase gene;

c) isolation of one or more constructs/vectors from the shuttle microorganism; and, d) introduction of at least the expression construct/vector into a destination microorganism.

In one embodiment, both the methyltransferase gene of step B is expressed consitutively. In another embodiment, expression of the methyltransferase gene of step B is induced.

In one embodiment, both the methylation construct/vector and the expression construct/vector are isolated in step C. In another embodiment, only the expression construct/vector is isolated in step C.

In one embodiment, only the expression construct/vector is introduced into the destination microorganism. In another embodiment, both the expression construct/vector and the methylation construct/vector are introduced into the destination microorganism.

In a related aspect, the invention provides a method of producing a recombinant microorganism of the invention comprising:

a. methylation of an expression construct/vector of the eighth aspect of the invention in vitro by a methyltransferase;

b. introduction of the expression construct/vector into a destination microorganism.

In a further related aspect, the invention provides a method of producing a recombinant microorganism of the invention comprising:

a. introduction into the genome of a shuttle microorganism of a methyltransferase gene b. introduction of an expression construct/vector of the eighth aspect of the invention into the shuttle microorganism c. isolation of one or more constructs/vectors from the shuttle microorganism; and, d. introduction of at least the expression construct/vector into a destination microorganism.

In a twelfth aspect, the invention provides a method for the production of acetone, isopropanol, and/or a precursor of acetone and/or isopropanol by microbial fermentation comprising fermenting a substrate comprising CO using a recombinant microorganism of the first aspect of the invention.

In one embodiment the method comprises the steps of:

(a) providing a gaseous substrate comprising CO to a bioreactor containing a culture of one or more microorganism of the first aspect of the invention; and (b) anaerobically fermenting the culture in the bioreactor to produce acetone, isopropanol, and/or a precursor of acetone and/or isopropanol.

In one embodiment the method comprises the steps of:

(a) capturing CO-containing gas produced as a result of the industrial process, before the gas is released into the atmosphere;

(b) the anaerobic fermentation of the CO-containing gas to produce acetone, isopropanol, and/or a precursor acetone and/or isopropanol by a culture comprising at least one microorganism of the first aspect of the invention.

In particular embodiments of the method aspects, the microorganism is maintained in an aqueous culture medium.

In particular embodiments of the method aspects, the fermentation of the substrate takes place in a bioreactor.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering one or more of acetone, isopropanol, and/or a precursor of acetone and/or isopropanol from the fermentation broth, the fermentation broth.

In another aspect, the invention provides one or more of acetone, isopropanol, and a precursor of acetone and/or isopropanol when produced by the method of the sixth aspect.

In another aspect, the invention provides a method for the production of a microorganism of the first aspect of the invention comprising transforming a carboxydotrophic acetogenic parental microorganism with one or more exogenous nucleic acid such that the microorganism is capable of producing acetone, isopropanol and/or a precursor of acetone and/or isopropanol by fermentation of a substrate comprising CO, wherein the parental microorganism is not capable of producing acetone, isopropanol and/or a precursor thereof by fermentation of a substrate comprising CO.

In one particular embodiment, a parental microorganism is transformed with one or more exogenous nucleic acid adapted to express one or more enzymes in the isopropanol biosynthesis pathway which are not naturally present in the parental microorganism. In another embodiment, a parental microorganism is transformed with one or more nucleic acid adapted to over-express one or more enzymes in the isopropanol biosynthesis pathway which are naturally present in the parental microorganism.

In one particular embodiment, a parental microorganism is transformed with one or more exogenous nucleic acids adapted to express one or more enzymes in the acetone biosynthesis pathway which are not naturally present in the parental microorganism. In another embodiment, a parental microorganism is transformed with one or more exogenous nucleic acids adapted to over-express one or more enzymes in the acetone biosynthesis pathway which are naturally present in the parental microorganism.

In one particular embodiment, a partental microorganism is transformed with one or more nucleic acid adapted to express one or more enzymes involved in the conversion of acetone to isopropanol which are not naturally present in the parental microorganism. In another embodiment, a parental microorganism is transformed with one or more nucleic acids adapted to over-express one or more enzymes involved in the conversion of acetone to isopropanol which are naturally present in the parental microorganism.

In certain embodiments, the one or more enzymes are as herein before described.

In another aspect, the invention provides a recombinant microorganism capable of producing acetone and comprising one or more exogenous nucleic acid encoding one or more enzyme adapted to convert acetoactate to acetone, wherein the recombinant microorganism is derived from a parental microorganism which is capable of producing acetolactate but not acetone. In one embodiment, one or more enzyme comprises KivD or a functionally equivalent variant thereof.

In another aspect, the invention provides a recombinant microorganism capable of producing acetone and comprising one or more exogenous nucleic acid encoding each of the enzymes thlA, ctfA, ctfB and kivD or a functionally equivalent variant of any one or more thereof, wherein the recombinant microorganism is derived from a parental microorganism which is not capable of producing acetolactate, acetoacetyl-CoA and acetone.

In another aspect, the invention provides a recombinant microorganism capable of producing acetone and comprising one or more exogenous nucleic acid encoding each of the enzymes ctfA, ctfB and kivD or a functionally equivalent variant of any one or more thereof, wherein the recombinant microorganism is derived from a parental microorganism which is not capable of producing acetolactate and acetone.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which:

FIG. 14 shows SEQ_ID NO 1: Amino acid sequence of novel alcohol dehydrogenase from *C. autoethanogeum, C. ljungdahlii* and *C. ragsdalei.*

FIG. 15 shows SEQ_ID NO 2: Nucleic acid sequence of novel alcohol dehydrogenase gene from *C. autoethanogeum.*

FIG. 16 shows SEQ_ID NO 3: Nucleic acid sequence of novel alcohol dehydrogenase gene from *C. ljungdahlii.*

FIG. 17 shows SEQ_ID NO 4: Nucleic acid sequence of novel alcohol dehydrogenase gene from *C. ragsdalei.*

FIG. 18 shows SEQ_ID NO 18: Nucleic acid sequence of Thiolase gene (thlA) from *C. acetobutylicum* ATCC824.

FIG. 19 shows SEQ_ID NO 19: Nucleic acid sequence of Acetoacetyl-CoA:acetate Coenzyme A transferase A (ctfA) gene from *C. beijerinckii* NCIMB8052.

FIG. 20 shows SEQ_ID NO 20: Nucleic acid sequence of Acetoacetyl-CoA:acetate Coenzyme A transferase B (ctfB) gene from *C. beijerinckii* NCIMB8052.

FIG. 21 shows SEQ_ID NO 21: Nucleic acid sequence of Acetoacetate decarboxylase (adc) gene from *C. beijerinckii* NCIMB8052.

FIG. 22 shows SEQ_ID NO 22: Nucleic acid sequence of Wood-Ljungdahl cluster promoter ($P_{WL}$) from *C. autoethanogenum.*

FIG. 23 shows SEQ_ID NO 34: Amino acid sequence of designed Type II methyltransferase gene.

FIG. 24 shows SEQ_ID NO 35: Nucleic acid sequence of designed Type II methyltransferase gene.

FIG. 25 shows SEQ_ID NO 38: Amino acid sequence of NADP-dependent alcohol dehydrogenase from *Clostridium beijerinckii* NRRL B-593.

FIG. 26 shows SEQ_ID NO 39: Nucleic acid sequence of NADP-dependent alcohol dehydrogenase from *Clostridium beijerinckii* NRRL B-593.

FIG. 27 shows SEQ_ID NO 40: Amino acid sequence of NADP-dependent alcohol dehydrogenase from *Thermoanaerobacter brockii* ATCC 53556.

FIG. 28 shows SEQ_ID NO 41: Nucleic acid sequence of alcohol dehydrogenase from *Thermoanaerobacter brockii.*

FIG. 29 shows SEQ_ID NO 42: Amino acid sequence of Thiolase ThlA from *C. acetobutylicum* ATCC824.

FIG. 30 shows SEQ_ID NO 43: Amino acid sequence of Acetoacetyl-CoA:acetate Coenzyme A transferase A CtfA from *C. beijerinckii* NCIMB8052.

FIG. 31 shows SEQ_ID NO 44: Amino acid sequence of Acetoacetyl-CoA:acetate Coenzyme A transferase A CtfB from *C. beijerinckii* NCIMB8052.

FIG. 32 shows SEQ_ID NO 45: Amino acid sequence of Acetoacetate decarboxylase Adc from *C. beijerinckii* NCIMB8052.

FIG. 33 shows SEQ_ID NO 46: Nucleic acid sequence of expression plasmid containing novel alcohol dehydrogenase pMTL85147-thlA-ctfAB-adc.

FIG. 34 shows SEQ_ID NO 47: Nucleic acid sequence of Acetoacetyl-CoA:acetate Coenzyme A transferase A (ctfA), acetoacetyl-CoA:acetate Coenzyme A transferase B (ctfB), and acetoacetate decarboxylase (adc) operon of *C. beijerinckii.*

FIG. 35 shows SEQ_ID NO 48: Nucleic acid sequence of expression plasmid containing novel alcohol dehydrogenase pMTL85147-thlA-ctfAB-adc-adh.

FIG. 36 shows SEQ_ID NO 49: Nucleic acid sequence of designed methylation plasmid.

FIG. 37 shows SEQ_ID NO 50: Nucleic acid sequence of lac promoter.

FIG. 38 shows SEQ_ID NO 51: Nucleic acid sequence of *Clostridium autoethanogenum* $F_1F_O$ ATPase operon promoter region.

FIG. 39 shows SEQ_ID NO 52: Nucleic acid sequence of *Clostridium autoethanogenum* Rnf complex operon promoter region.

FIG. 40 shows SEQ_ID NO 53: Nucleic acid sequence of *Clostridium autoethanogenum* Pyruvate:ferredoxin oxidoreductase promoter region.

FIG. 44 shows SEQ_ID NO 56: Nucleic acid sequence of Wood-Ljungdahl cluster promoter ($P_{WL}$) from *C. ljungdahlii.*

FIG. 45 shows SEQ_ID NO 57: Nucleic acid sequence of Wood-Ljungdahl cluster promoter ($P_{WL}$) from *C. ragsdalei.*

FIG. 46 shows SEQ_ID NO 58: Nucleic acid sequence of *Clostridium ljungdahlii* $F_1F_O$ ATPase operon promoter region.

FIG. 47 shows SEQ_ID NO 59: Nucleic acid sequence of *Clostridium ragsdalei* $F_1F_O$ ATPase operon promoter region.

FIG. 48 shows SEQ_ID NO 60: Nucleic acid sequence of *Clostridium ljungdahlii* Rnf complex operon promoter region.

FIG. 49 shows SEQ_ID NO 61: Nucleic acid sequence of *Clostridium ragsdalei* Rnf complex operon promoter region.

FIG. 50 shows SEQ_ID NO 62: Nucleic acid sequence of *Clostridium ljungdahlii* Pyruvate:ferredoxin oxidoreductase promoter region.

FIG. 51 shows SEQ_ID NO 63: Nucleic acid sequence of *Clostridium ragsdalei* Pyruvate:ferredoxin oxidoreductase promoter region.

FIG. 54 shows SEQ_ID No. 73: Amino acid sequence of alpha-ketoisovalerate decarboxylase KivD from *Lactococcus* lactis KF147 and SEQ_ID No. 72 Nucleic acid sequence of Alpha-ketoacid decarboxylase (kivd).

FIG. 55 shows Seq. ID No. 76: Codon optimized sequence of Alpha-ketoacid decarboxylase (kivd), SEQ_ID No. 75: Amino acid sequence of alcohol dehydrogenase Adh2 from *Saccharomyces cerevisiae* and SEQ_ID No. 74 Nucleic acid sequence of Alcohol dehydrogenase (adh2)

FIG. 56 shows Seq. ID No. 78: Synthetic operon of codon optimized Alpha-ketoacid decarboxylase (kivd) and Alcohol dehydrogenase (Adh2) including spacer sequence with ribosomal binding site, flanked by NdeI and KpnI and Seq. ID No. 77: Codon optimized sequence of Alcohol dehydrogenase (Adh2).

FIG. 57 shows SEQ_ID No. 82: Nucleic acid sequence of *E. coli-Clostridium* shuttle vector pMTL 85245 and SEQ_ID No. 79: Nucleic acid sequence of Phosphotransacetylase Acetate kinase promoter from *C. autoethanogenum,*

FIG. 58 shows SEQ_ID No. 83: Nucleic acid sequence of expression plasmid pMTL85245-kivd-adh2

FIG. 59 shows SEQ_ID No. 84 Nucleic acid sequence of expression plasmid pMTL85245-kivd FIG. 60 shows SEQ_ID No. 93: Nucleic acid sequence of expression plasmid pMTL85245-P-thl-ctfAB-P-kivd FIG. 61 shows SEQ_ID No. 98 Nucleic acid sequence of expression plasmid pMTL83147-thlA-ctfAB-adc-adh2.

FIG. 62 shows SEQ_ID No. 101 Nucleic acid sequence of expression plasmid pMTL83147-thlA-ctfAB-adc-P-kivd-adh2.

FIG. 74 shows complete conversion of acetone to isopropanol at high concentrations and rates when fed into a stable continuous culture of *C. autoethanogenum* DSM23693 with CO-containing steel mill gas as substrate.

DETAILED DESCRIPTION OF THE INVENTION

Figure 1:
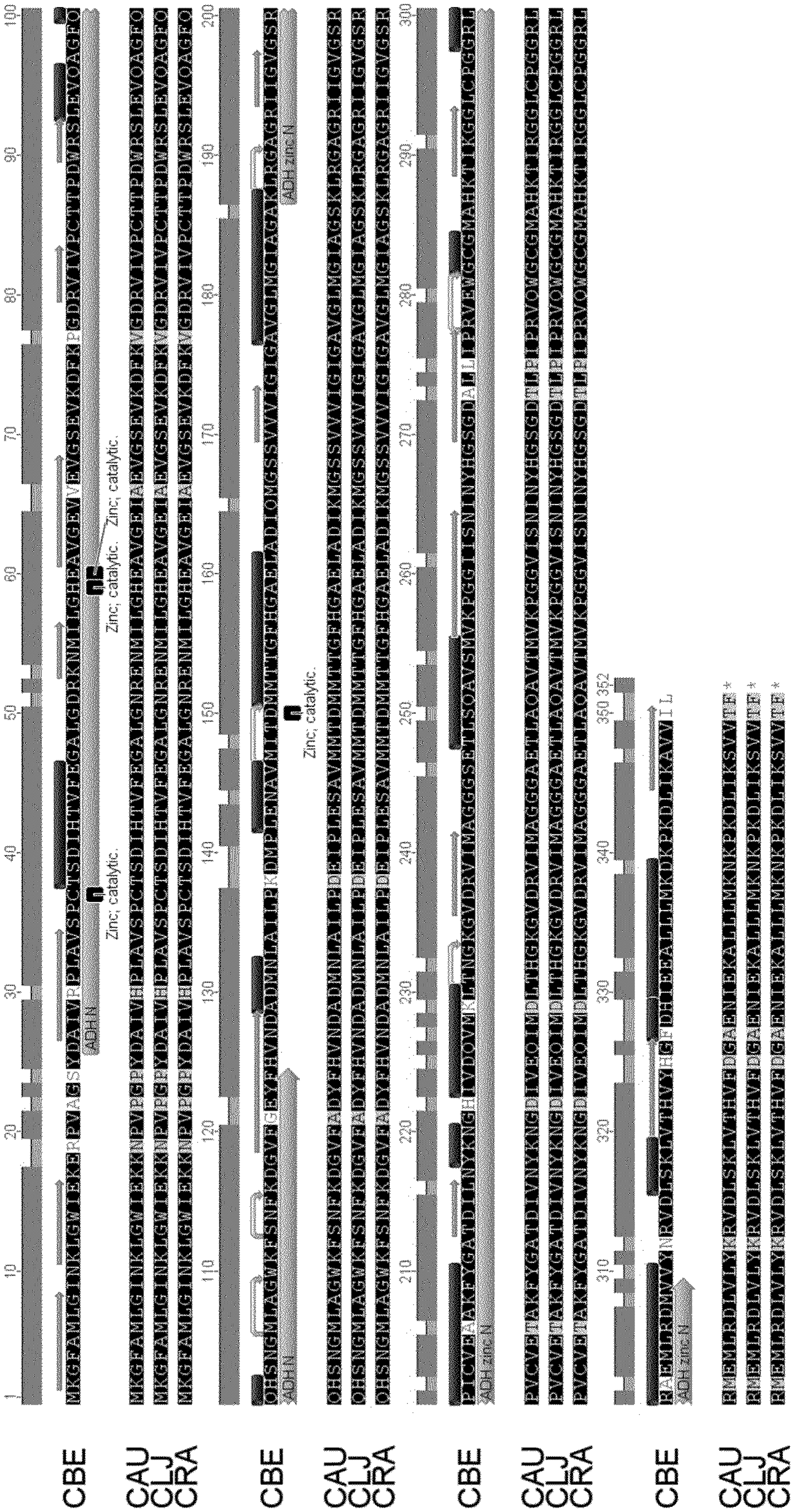
FIG. 1 shows amino acid alignment of novel alcohol dehydrogenase of *C. autoethanogenum* (CAU)(SEQ ID NO: 1), *C. ljungdahlii* (CLJ)(SEQ ID NO: 1), and *C. ragsdalei* (CRA) (SEQ ID NO: 1) with the secondary alcohol dehydrogenase of *C. beijerinckii* strain NRRL-B593 (SEQ ID NO: 38).

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The production of acetone and/or isopropanol by microbial fermentation of gaseous substrates comprising CO has not previously been reported. The inventors of the present invention have now demonstrated (inter alia), through genetic modification, the production of acetone and isopropanol in species of carboxydotrophic acetogenic bacteria capable of using CO as a carbon and energy source. The inventors have also surprisingly been able to demonstrate the natural enzymatic conversion of acetone to isopropanol in presence of CO-containing gases by closely related carboxydotrophic acetogenic species *C. autoethanogenum, C. ljungdahlii*, and *C. ragsdalei*. A novel alcohol dehydrogenase was identified, which was shown to be expressed constitutively at a high level during a normal fermentation run with *C. autoethanogenum* and is able to convert acetone to isopropanol at high concentrations and ratios. The inventors have also found two genes that surprisingly confer activity towards acetone and isopropanol in *C. autoethanogenum*. These genes, an alpha-ketoacid decarboxylase (Kivd) from *Lactococcus lactis* and an alcohol dehydrogenase (Adh2) from *Saccharomyces cerevisiae* haven't been reported to confer activity towards acetone or isopropanol or any of it's precursors, rather converting amino acid precursors into branched chain alcohols. The inventors demonstrated production of acetone and isopropanol from CO in *C. autoethanogenum* using several different gene and enzyme combinations.

Accordingly, the invention provides, for example, methods for the production of acetone, isopropanol and/or precursors of acetone and/or isopropanol by microbial fermentation of substrates comprising CO, genetically modified microorganisms of use in such methods, nucleic acids suitable for preparation of genetically modified microorganisms and novel alcohol dehydrogenases and nucleic acids encoding same.

As referred to herein, a "fermentation broth" is a culture medium comprising at least a nutrient media and bacterial cells.

As referred to herein, a shuttle microorganism is a microorganism in which a methyltransferase enzyme is expressed and is distinct from the destination microorganism.

As referred to herein, a destination microorganism is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated acetone and/or isopropanol concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium acetobutylicum, Clostridium beijerinckii, C. saccharobutylicum* and *C. saccharoperbutylacetonicum*, details of which are publicly available on websites such as Genbank or NCBI. In the case of genes derived from *Sacchromyces cerevisiae* and *Lactococcus lactics*, homologous genes may be found, for example, in *Staphylococcus epidermidis* (for example, NP_765765.1, EGG67352.1, ZP_04826144.1, ZP_04797999.1), *Bacillus cereus* (for example, ZP_04273468.1, ZP_04317620.1) and *Bacillus thuringiensis* (for example, YP_003664720.1). The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods outlined in Wiesenborn et al [Thiolase from *Clostridium acetobutylicum* ATCC 824 and Its Role in the Synthesis of Acids and Solvents. *Appl Environ Microbiol.* 1988, 54: 2717-2722], Wiesenborn et al [Coenzyme A transferase from *Clostridium acetobutylicum* ATCC 824 and its role in the uptake of acids. *Appl Environ Microbiol.* 1989, 55:323-9.], Peterson and Bennet [Purification of acetoacetate decarboxylase from *Clostridium acetobutylicum* ATCC 824 and cloning of the acetoacetate decarboxylase gene in *Escherichia coli. Appl Environ Microbiol.* 1990 56: 3491-3498], Ismail et al. [Purification and characterization of a primary-secondary alcohol dehydrogenase from two strains of *Clostridium beijerinckii. J Bacteriol* 1993, 175: 5097-5105], de la Plaza et al [Biochemical and molecular characterization of a-ketoisovalerate decarboxylase, an enzyme involved in the formation of aldehydes from amino acids by *Lactococcus lactis*. FEMS Microbiol Lett. 2004 238: 367-374] or Khorkin et al [NADP-dependent bacterial alcohol dehydrogenases: crystal structure, cofactor-binding and cofactor specificity of the ADHs of *Clostridium beijerinckii* and *Thermoanaerobacter brockii. J Mol Biol.* 1998, 22: 278(5): 967-981] may be used to assess enzyme activity.

"Over-express", "over expression" and like terms and phrases when used in relation to the invention should be taken broadly to include any increase in expression of one or more protein as compared to the expression level of the protein of a parental microorganism under the same conditions. It should not be taken to mean that the protein is expressed at any particular level.

A "parental microorganism" is a microorganism used to generate a recombinant microorganism of the invention. The parental microorganism may be one that occurs in nature (ie a wild type microorganism) or one that has been previously modified but which does not express or over-express one or more of the enzymes the subject of the present invention. Accordingly, the recombinant microorganisms of the invention have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

Figure 4:
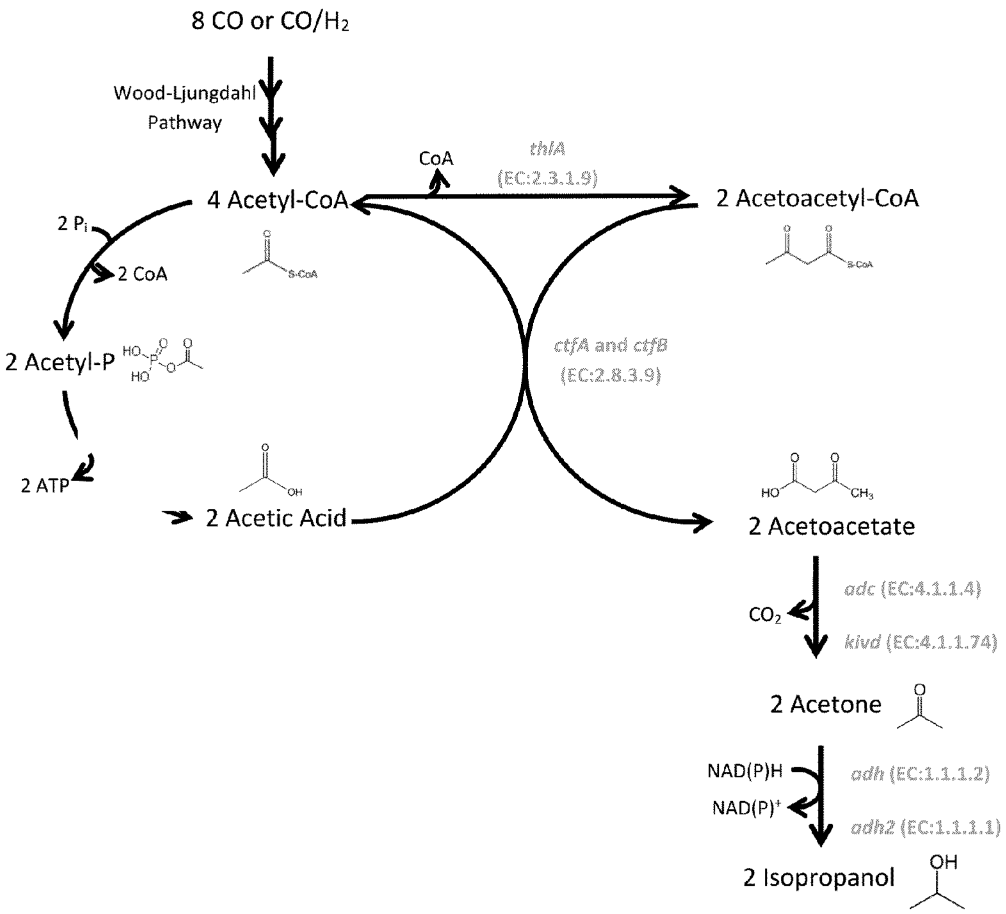
FIG. 4 shows the pathway for production of acetone and isopropanol from CO or $CO/H_2$ containing gases in engineered *C. autoethanogenum* and *C. ljungdahlii* carrying plasmid pMTL85147-thlA-ctfA-ctfB-adc.

The "isopropanol biosynthesis pathway" is the enzymatic pathway allowing for metabolism of CO or $CO/H_2$ to isopropanol, as outlined, for example, in FIG. 4.

The "acetone biosynthesis pathway" is the enzymatic pathway allowing for metabolism of CO or $CO/H_2$ to acetone, as outlined, for example, in FIG. 4.

A "precursor" of acetone includes Acetyl-CoA, Acetoacetyl-CoA, Acetoacetate, Acetyl-Phosphate and Acetic Acid.

A "precursor" of isopropanol includes Acetyl-CoA, Acetoacetyl-CoA, Acetoacetate, Acetone, Acetyl-Phosphate and Acetic Acid.

Reference to "alcohol dehydrogenases" should be taken to include alcohol dehydrogenases which are capable of catalysing the conversion of ketones (such as acetone) to secondary alcohols (such as isopropanol), or vice versa. Such alcohol dehydrogenases include secondary alcohol dehydrogenases and primary alcohol dehydrogenases. A "secondary alcohol dehydrogenase" is one which can convert ketones (such as acetone) to secondary alcohols (such as isopropanol), or vice versa. A "primary alcohol dehydrogenase" is one which can convert aldehydes to primary alcohols, or vice versa; however, a number of primary alcohol dehydrogenases are also capable of catalysing the conversion of ketones to secondary alcohols, or vice versa. These alcohol dehydrogenases may also be referred to as "primary-secondary alcohol dehydrogenases".

As discussed herein before, the invention provides a recombinant microorganism capable of producing acetone, isopropanol and/or a precursor of acetone and/or isopropanol by fermentation of a substrate comprising CO.

In one particular embodiment, the microorganism is adapted to express one or more enzymes in the isopropanol biosynthesis pathway which are not naturally present in the parental microorganism. In another embodiment, the microorganism is adapted to over-express one or more enzymes in the isopropanol biosynthesis pathway which are naturally present in the parental microorganism.

In one particular embodiment, the microorganism is adapted to express one or more enzymes in the acetone biosynthesis pathway which are not naturally present in the parental microorganism. In another embodiment, the microorganism is adapted to over-express one or more enzymes in the acetone biosynthesis pathway which are naturally present in the parental microorganism.

In one particular embodiment, the microorganism is adapted to express one or more enzymes involved in the conversion of acetone to isopropanol which are not naturally present in the parental microorganism. In another embodiment, the microorganism is adapted to over-express one or more enzymes involved in the conversion of acetone to isopropanol which are naturally present in the parental microorganism.

In one embodiment, the parental microorganism is capable of fermenting a substrate comprising CO to produce acetone but not of converting acetone to isopropanol and the recombinant microorganism is adapted to express one or more enzymes involved in the conversion of acetone to isopropanol.

In another embodiment, the parental microorganism is capable of converting acetone to isopropanol but is not capable of fermenting a substrate comprising CO to produce acetone and the recombinant microorganism is adapted to express one or more enzymes in the acetone biosynthesis pathway.

In one embodiment, the parental microorganism is not capable of fermenting a substrate comprising CO to produce acetone and isopropanol and the recombinant microorganism is adapted to express one or more enzymes in the acetone biosynthesis pathway and one or more enzymes involved in the conversion of acetone to isopropanol.

The microorganism may be adapted to express or over-express the one or more enzymes by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not naturally present within the parental microorganism.

In certain embodiments, the parental microorganism may be transformed to provide a combination of increased or over-expression of one or more genes native to the parental microorganism and introduction of one or more genes not native to the parental microorganism. For example, one or more genes encoding an enzyme in the acetone biosynthesis pathway may be native to the parental microorganism but it may not include one or more gene encoding an enzyme involved in the conversion of acetone to isopropanol, or vice versa. The microorganism could be engineered to over-express the one or more native genes encoding an enzyme in the acetone biosynthesis pathway and to introduce a gene encoding an enzyme involved in conversion of acetone to isopropanol, or vice versa. Similarly, the microorganism could be engineered to over-express one or more enzymes in the acetone biosynthesis pathway (and/or the conversion of acetone to isopropanol) and to introduce one or more genes encoding an enzyme involved in the same pathway. Skilled persons will appreciate various other combinations of use in the invention.

In one embodiment the one or more enzymes in the acetone biosynthesis pathway are chosen from the group consisting:

Acetyl-Coenzyme A acetyltransferase (Thiolase; ThlA; E.C. 2.3.1.9);

Acetoacetyl-CoA:Acetate Coenzyme A transferase A (CoA transferase; CtfA; EC 2.8.3.9);

Acetoacetyl-CoA:Acetate Coenzyme A transferase B (CoA transferase; CtfB; EC 2.8.3.9);

Acetoacetate decarboxylase (Adc; EC 4.1.1.4);

Alpha-ketoisovalerate decarboxylase (decarboxylase; KivD; EC4.1.1.74); and,

A functionally equivalent variant of any one or more thereof.

By way of example only, sequence information for each of the peptides in provided in table 6 or table 18 herein after.

The enzymes used in the microorganisms of the invention may be derived from any appropriate source, including different genera and species of bacteria, or other organisms. However, in one embodiment, the Acetyl-Coenzyme A acetyltransferase (Thiolase; ThlA) is that derived from *C. acetobutylicum*. In one embodiment, the Acetyl-Coenzyme A acetyltransferase has the amino acid sequence exemplified in table 6 herein after, or it is a functionally equivalent variant thereof.

In one embodiment, the enzymes Acetoacetyl-CoA:Acetate Coenzyme A transferase A (CoA transferase; CtfA), Acetoacetyl-CoA:Acetate Coenzyme A transferase B (CoA transferase; CtfB) and Acetoacetate decarboxylase (Adc) are derived from *C. Beijerinckii*.

In one embodiment, the enzymes alpha-ketoisovalerate decarboxylase (decarboxylase; KivD) is that derived from *L. lactis*.

In one embodiment, each enzyme has the amino acid sequence exemplified in table 6 or 18 herein after, or it is a functionally equivalent variant thereof.

In one embodiment, the one or more enzyme involved in the conversion of acetone to isopropanol are chosen from the group consisting:

Alcohol Dehydrogenase (Adh; EC 1.1.1.2);

Alcohol dehydrogenase (Adh2; EC 1.1.1.1); and,

A functionally equivalent variant thereof.

Again, the alcohol dehydrogenase enzyme used in the invention may be derived from any appropriate source, including different genera and species of bacteria (for example, the species of bacteria exemplified in table 13 herein after. However, in one particular embodiment, the Alcohol Dehydrogenase (Adh) is derived from *C. autoethanogenum*, *C. ljungdahlii*, and/or *C. ragsdalei*. In one embodiment, the alcohol dehydrogenase has the amino acid sequence of SEQ_ID NO. 1 or it is a functionally equivalent variant thereof. In one embodiment, the functionally equivalent variant has at least approximately 88%, 89%, 90%, 91%, 92%, 93%, 94%, 95%, 96%, 97%, 98% or 99% sequence identity to SEQ_ID NO. 1.

In one embodiment, the Alcohol Dehydrogenase (Adh2) is derived from *S. cerevisiae*.

In one embodiment, the microorganism comprises one or more exogenous nucleic acids adapted to increase expression of one or more nucleic acids native to the parental microorganism and which one or more nucleic acids encode one or more of the enzymes referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or Phosphotransacetylase/Acetate kinase operon promoters. In one embodiment, the promoter has the sequence of SEQ_ID No. 22 or 77, or is a functionally equivalent variant thereof. In another embodiment, a Wood-Ljungdahl cluster promoter ($P_{WL}$) (SEQ ID No. 56 or 57), the promoter region of $F_1F_O$-ATPase operon (SEQ_ID NO 51, 58 or 59), Rnf complex operon promoter region (SEQ_ID NO 52, 60 or 61), or Pyruvate:ferredoxin oxidoreductase (SEQ_ID NO 53, 62 or 63) promoter region could be used. It will be appreciated by those of skill in the art that other promoters which can direct expression, preferably a high level of expression under appropriate fermentation conditions, would be effective as alternatives to the exemplified embodiments.

In one embodiment, the microorganism comprises one or more exogenous nucleic acids encoding and adapted to express one or more of the enzymes referred to herein before. In one embodiment, the microorganisms comprise one or more exogenous nucleic acid encoding and adapted to express at least two of the enzymes. In other embodiments, the microorganism comprises one or more exogenous nucleic acid encoding and adapted to express 3, 4, 5, or 6 of the enzymes.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), and Acetoacetate decarboxylase (Adc; EC 4.1.1.4) or a functionally equivalent variant of any one or more thereof.

In one particular embodiment, the microorganism comprises one or more exogenous nucleic acids encoding Alcohol Dehydrogenase (Adh; EC 1.1.1.2) or a functionally equivalent variant thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), Acetoacetate decarboxylase (Adc; EC 4.1.1.4), and Alcohol Dehydrogenase (Adh; EC 1.1.1.2), or a functionally equivalent variant of any one or more thereof.

In one particular embodiment, the microorganism comprises one or more exogenous nucleic acids encoding each of Alpha-ketoisovalerate decarboxylase (decarboxylase; KivD; EC4.1.1.74), and Alcohol dehydrogenase (Adh2; EC 1.1.1.1), or a functionally equivalent variant of any one or more thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), and Alpha-ketoisovalerate decarboxylase (decarboxylase; KivD; EC4.1.1.74), or a functionally equivalent variant of any one or more thereof.

In one particular embodiment, the microorganism comprises one or more exogenous nucleic acids encoding Alpha-ketoisovalerate decarboxylase (decarboxylase; KivD; EC4.1.1.74), or a functionally equivalent variant of any one or more thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA: Acetate Coenzyme A transferase B (CoA transferase; CtfB; EC 2.8.3.9), Acetoacetate decarboxylase (Adc; EC 4.1.1.4), and Alcohol dehydrogenase (Adh2; EC 1.1.1.1), or a functionally equivalent variant of any one or more thereof.

In another particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), Alpha-ketoisovalerate decarboxylase (decarboxylase; KivD; EC4.1.1.74), and Alcohol dehydrogenase (Adh2; EC 1.1.1.1), or a functionally equivalent variant of any one or more thereof.

In one embodiment, Acetyl-Coenzyme A acetyltransferase (Thiolase; ThlA) is encoded by a nucleic acid comprising SEQ_ID NO. 18, or a functionally equivalent variant thereof. In one embodiment, the Acetoacetyl-CoA:Acetate Coenzyme A transferase A (CoA transferase; CtfA) is encoded by a nucleic acid comprising SEQ_ID NO. 19, or a functionally equivalent variant thereof. In one embodiment, Acetoacetyl-CoA:Acetate Coenzyme A transferase B (CoA transferase; CtfB) is encoded by a nucleic acid comprising SEQ_ID NO. 20, or a functionally equivalent variant thereof. In one embodiment, Acetoacetate decarboxylase (Adc) is encoded by a nucleic acid comprising SEQ_ID NO. 21, or a functionally equivalent variant thereof. In one embodiment, the alpha-ketoisovalerate decarboxylase (decarboxylase; KivD) is encoded by a nucleic acid comprising SEQ_ID NO. 72 or 76, or a functionally equivalent variant of any one thereof. In one embodiment, the Alcohol Dehydrogenase (Adh) is encoded by a nucleic acid comprising SEQ_ID NO. 2, SEQ_ID NO. 3, or SEQ_ID NO. 4, or a functionally equivalent variant of any one thereof. In one embodiment, the Alcohol Dehydrogenase (Adh2) is encoded by a nucleic acid comprising SEQ_ID NO. 74 or 77, or a functionally equivalent variant of any one thereof.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination. In one particular embodiment, the construct encodes each of ThlA, CtfA, CtfB, and Adc and optionally, Adh. In another embodiment, the one or more exogenous nucleic acids is a nucleic acid construct or vector, in one particular embodiment a plasmid, encoding Adh, and optionally ThlA, CtfA, CtfB, and/or Adc. In one particular embodiment, the construct encodes all of ThlA, CtfA, CtfB, Adc and Adh. The vector may also comprise other combinations of nucleic acids encoding alternative enzyme combinations, as is apparent from the description elsewhere in this document. In one particular embodiment, the vector comprises 1, 2, 3 or 4 of the nucleic acid sequences SEQ_ID NO. 19, 20, 21 and 22 or a functionally equivalent variant of any one thereof, in any order. In another embodiment, the vector comprises SEQ_ID_NO. 2, 3 and/or 4, or a functionally equivalent variant of any one thereof, in any order. In one embodiment, the vector comprises 1, 2, 3, or 4 of sequences SEQ_ID NO. 19, 20, 21 and 22 or a functionally equivalent variant of any one thereof and SEQ_ID NO. 2, 3 or 4, or a functionally equivalent variant of any one thereof, in any order.

In another embodiment, the vector comprises one or more of SEQ ID No. 72, 76, 74, 77, alone or in combination with one or more of the nucleic acids represented by SEQ ID No. 19, 20, 21, 22, 2, 3, and 4.

The exogenous nucleic acids may remain extra-chromosomal upon transformation of the parent microorganism or may integrate into the genome of the parent microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. In one embodiment, the promoter has the sequence of SEQ_ID No. 22, SEQ ID No. 77, or is a functionally equivalent variant of any one thereof. In another embodiment, a Wood-Ljungdahl cluster promoter ($P_{WL}$) (SEQ ID No. 56 or 57), the promoter region of $F_1F_O$-ATPase operon (SEQ_ID NO 51, 58 or 59), Rnf complex operon promoter region (SEQ_ID NO 52, 60 or 61), or Pyruvate:ferredoxin oxidoreductase (SEQ_ID NO 53, 62 or 63) promoter region could be used. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid. In one particular embodiment, the expression plasmid has the nucleotide sequence SEQ_ID No. 46, 48, 83, 84, 95, 98, or 101.

In one embodiment, the parental microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium coskatii, Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii*, and *Thermoanaerobacter kiuvi.*

In one particular embodiment, the parental microorganism is selected from the cluster of ethanologenic, acetogenic Clostridia comprising the species *C. autoethanogenum, C. ljungdahlii*, and *C. ragsdalei* and related isolates. These include but are not limited to strains *C. autoethanogenum* JAI-$1^T$ (DSM10061) [Abrini J, Naveau H, Nyns E-J: *Clostridium autoethanogenum*, sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* $PETC^T$ (DSM13528=ATCC 55383) [Tanner R S, Miller L M, Yang D: *Clostridium ljungdahlii* sp. nov., an Acetogenic Species in Clostridial rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. 2002, U.S. Pat. No. 6,368,819], *C. ljungdahlii* 0-52 (ATCC 55989) [Gaddy J L, Clausen E C, Ko C—W: Microbial process for the preparation of acetic acid as well as solvent for its extraction from the fermentation broth. 2002, U.S. Pat. No. 6,368,819], *C. ragsdalei* $P11^T$ (ATCC BAA-622) [Huhnke R L, Lewis R S, Tanner R S: Isolation and Characterization of novel Clostridial Species. International patent 2008, WO 2008/028055], related isolates such as "*C. coskatii*" [Zahn et al—Novel ethanologenic species *Clostridium coskatii* (US Patent Application number US20110229947)], or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel Clostridial Species. International patent 2008, WO 2008/028055].

All species of this cluster have a similar morphology and size (logarithmic growing cells are between 0.5-0.7×3-5 μm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not.

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes encoding ThlA, CtfA, CtfB, Adc, KivD, Adh and Adh2. In one particular embodiment, the parental microorganism lacks a gene encoding Adh. In another particular embodiment, the parental microorganism lacks each of the genes encoding ThlA, CtfA, CtfB, Adc, and KivD.

The inventors have identified a novel Adh protein. Accordingly, the invention provides an Alcohol Dehydrogenase (Adh) having the amino acid sequence of SEQ_ID NO. 1, or a functionally equivalent variant of any one thereof. In one particular embodiment, the functionally equivalent variant of Alcohol Dehydrogenase (Adh) has at least approximately 88%, 89%, 90%, 91%, 92%, 93%, 94%, 95%, 96%, 97%, 98% or 99% sequence identity to SEQ_ID NO. 1.

In addition the invention provides a nucleic acid encoding Adh of SEQ_ID NO. 1 or a functionally equivalent variant thereof. Skilled persons will readily appreciate such nucleic acids, having regard to the amino acid sequence provided herein and the genetic code and the degeneracy therein. However, by way of example, nucleic acids encoding Adh of SEQ_ID NO. 1 include the nucleic acids of SEQ_ID NO. 2, 3 or 4, or functionally equivalent variants thereof. In one particular embodiment, a functionally equivalent variant of SEQ_ID NO. 2, 3 or 4 is a nucleic acid having at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4.

The invention also provides nucleic acids which are capable of hybridising to at least a portion of the nucleic acid SEQ_ID NO. 2, 3 or 4, a nucleic acid complementary to any one thereof, or a functionally equivalent variant of any one thereof. Such nucleic acids will preferably hybridise to the nucleic acid of SEQ_ID NO. 2, 3 or 4, a nucleic acid complementary to any one thereof, or a functionally equivalent variant of any one thereof, under stringent hybridisation conditions. "Stringent hybridisation conditions" means that the nucleic acid is capable of hybridising to a target template under standard hybridisation conditions such as those described in Sambrook et al, Molecular Cloning: A Laboratory Manual (1989), Cold Spring Harbor Laboratory Press, New York, USA. It will be appreciated that the minimal size of such nucleic acids is a size which is capable of forming a stable hybrid between a given nucleic acid and the complementary sequence to which it is designed to hybridise. Accordingly, the size is dependent on the nucleic acid composition and percent homology between the nucleic acid and its complementary sequence, as well as the hybridisation conditions which are utilised (for example, temperature and salt concentrations). In one embodiment, the nucleic acid is at least 10 nucleotides in length, at least 15 nucleotides in length, at least, 20 nucleotides in length, at least 25 nucleotides in length, or at least 30 nucleotides in length.

The inventor's have also identified a number of novel nucleic acids useful as probes and primers, as detailed herein after in the examples section. For example, SEQ_ID NO. 5; SEQ_ID NO. 6; SEQ_ID NO. 7; SEQ_ID NO. 8; SEQ_ID NO. 9; SEQ_ID NO. 10; SEQ_ID NO. 11; SEQ_ID NO. 12; SEQ_ID NO. 13; SEQ_ID NO. 14; SEQ_ID NO. 15; SEQ_ID NO. 16; SEQ_ID NO. 17; SEQ_ID NO. 18; SEQ_ID NO. 23; SEQ_ID NO. 24; SEQ_ID NO. 25; SEQ_ID NO. 26; SEQ_ID NO. 27; SEQ_ID NO. 28; SEQ_ID NO. 29; SEQ_ID NO. 30; SEQ_ID NO. 31; SEQ_ID NO. 32; SEQ_ID NO. 33; SEQ_ID NO. 64; SEQ_ID NO. 65; SEQ_ID NO. 66; SEQ_ID NO. 67; SEQ_ID NO. 68; SEQ_ID NO. 69; SEQ_ID NO. 70; SEQ_ID NO. 71; SEQ_ID NO. 85; SEQ_ID NO. 86; SEQ_ID NO. 87; SEQ_ID NO. 88; SEQ_ID NO. 89; SEQ_ID NO. 90; SEQ_ID NO. 91; SEQ_ID NO. 92; SEQ_ID NO. 93; SEQ_ID NO. 94; SEQ_ID NO. 96; SEQ_ID NO. 97; SEQ_ID NO. 99; SEQ_ID NO. 100.

The invention also provides nucleic acids and nucleic acid constructs of use in generating a recombinant microorganism of the invention.

In one embodiment, the nucleic acids comprises sequences encoding one or more of the enzymes which when expressed in a microorganism allows the microorganism to produce acetone, isopropanol and/or a precursor of acetone and/or isopropanol by fermentation of substrate comprising CO. In one particular embodiment, the invention provides a nucleic acid encoding two or more enzymes which when expressed in a microorganism allows the microorganism to produce acetone, isopropanol and/or a precursor of acetone and/or isopropanol by fermentation of substrate comprising CO. In one embodiment, the nucleic acids of the invention encode 3, 4, 5 or 6 such enzymes.

In one particular embodiment, the enzymes are chosen from Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), ketoisovalerate decarboxylase (decarboxylase; KivD), Alcohol Dehydrogenase (Adh), Alcohol Dehydrogenase (Adh2), and a functionally equivalent variant of any one or more thereof.

In one embodiment, a nucleic acid of the invention comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), and Acetoacetate decarboxylase (Adc) or a functionally equivalent variant of any one or more thereof, in any order In one embodiment, a nucleic acid of the invention comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), and Alcohol Dehydrogenase (Adh) or a functionally equivalent variant of any one or more thereof, in any order.

In one embodiment, a nucleic acid of the invention comprises nucleic acid sequences encoding each of Alpha-ketoisovalerate decarboxylase (decarboxylase; KivD), and Alcohol dehydrogenase (Adh2), or a functionally equivalent variant of any one or more thereof, in any order.

In one embodiment, a nucleic acid of the invention comprises nucleic acids encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), and Alpha-ketoisovalerate decarboxylase (decarboxylase; KivD), or a functionally equivalent variant of any one or more thereof, in any order.

In one embodiment, a nucleic acid of the invention comprises nucleic acids encoding Alpha-ketoisovalerate decarboxylase (decarboxylase; KivD), or a functionally equivalent variant thereof.

In one embodiment, a nucleic acid of the invention comprises nucleic acids encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), and Alcohol dehydrogenase (Adh2), or a functionally equivalent variant of any one or more thereof, in any order.

In another embodiment, a nucleic acid of the invention comprises nucleic acids encoding each of Acetyl-Coenzyme A acetyltransferase (Thiolase; ThlA), Acetoacetyl-CoA:Acetate Coenzyme A transferase A (CoA transferase), Acetoacetyl-CoA:Acetate Coenzyme A transferase B (CoA transferase; CtfB), Acetoacetate decarboxylase (Adc), Alpha-ketoisovalerate decarboxylase (decarboxylase; KivD), and Alcohol dehydrogenase (Adh2), or a functionally equivalent variant of any one or more thereof, in any order.

Exemplary amino acid sequences and nucleic acid sequence encoding each of the above enzymes are provided in GenBank as described elsewhere herein (see, in particular, the examples provided in tables 6 and 18 herein after). However, skilled persons will readily appreciate alternative nucleic acids sequences encoding the enzymes or functionally equivalent variants thereof, having regard to the information contained herein, in GenBank and other databases, and the genetic code.

In one embodiment, Acetyl-Coenzyme A acetyltransferase (Thiolase; ThlA) has the sequence of Seq_ID No. 42 or a functionally equivalent variant thereof. In one embodiment, the Acetoacetyl-CoA:Acetate Coenzyme A transferase A (CoA transferase; CtfA) has the sequence of Seq_ID No. 43, or a functionally equivalent variant thereof. In one embodiment, Acetoacetyl-CoA:Acetate Coenzyme A transferase B (CoA transferase; CtfB) has the sequence of Seq_ID No. 44 or a functionally equivalent variant thereof. In one embodiment, Acetoacetate decarboxylase (Adc) has the sequence of Seq_ID No. 45, or a functionally equivalent variant thereof. In one embodiment, Alpha-ketoisovalerate decarboxylase (decarboxylase; KivD) has the sequence of Seq_ID No. 73, or a functionally equivalent variant thereof. In one embodiment, Alcohol Dehydrogenase (Adh) has the sequence of SEQ_ID NO 38 and SEQ_ID NO 40. In one particular embodiment, the Alcohol Dehydrogenase (Adh) has the sequence of SEQ_ID NO. 1, or a functionally equivalent variant thereof. In one particular embodiment, the functionally equivalent variant of Alcohol Dehydrogenase (Adh) has at least approximately 88%, 89%, 90%, 91%, 92%, 93%, 94%, 95%, 96%, 97%, 98% or 99% sequence identity to SEQ_ID NO. 1. In one embodiment, Alcohol Dehydrogenase (Adh2) has the sequence of SEQ_ID NO 75, or a functionally equivalent variant thereof.

In one embodiment, the nucleic acid sequence encoding Acetyl-Coenzyme A acetyltransferase (Thiolase; ThlA) comprises SEQ_ID NO. 18, or is a functionally equivalent variant thereof. In one embodiment, the nucleic acid sequence encoding Acetoacetyl-CoA:Acetate Coenzyme A transferase A (CoA transferase; CtfA) comprises SEQ_ID NO. 19, or is a functionally equivalent variant thereof. In one embodiment, the nucleic acid sequence encoding Acetoacetyl-CoA:Acetate Coenzyme A transferase B (CoA transferase; CtfB) comprises SEQ_ID NO. 20, or is a functionally equivalent variant thereof. In one embodiment, the nucleic acid sequence encoding Acetoacetate decarboxylase (Adc) comprises SEQ_ID NO. 21, or is a functionally equivalent variant thereof. In one embodiment, the nucleic acid sequence encoding Alpha-ketoisovalerate decarboxylase (decarboxylase; KivD) comprises SEQ_ID NO. 72 or 76, or is a functionally equivalent variant of any one thereof. In one embodiment, the nucleic acid sequence encoding Alcohol Dehydrogenase (Adh2) comprises SEQ_ID NO. 74 or 77, or is a functionally equivalent variant thereof. In one embodiment, the nucleic acid sequence encoding Alcohol Dehydrogenase (Adh) comprises Seq_ID No. 39 or SEQ_ID NO 41, or is a functionally equivalent variant of any one thereof. In one particular embodiment, the nucleic acid sequence encoding Alcohol Dehydrogenase (Adh) comprises SEQ_ID NO. 2, SEQ_ID NO. 3, or SEQ_ID NO. 4, or is a functionally equivalent variant of any one thereof. In one embodiment, the functionally equivalent variant of SEQ_ID NO. 2, SEQ_ID NO. 3, or SEQ_ID NO. 4 has at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kindase promoter is used. In another embodiment a pyruvate:ferredoxin oxidoreductase promoter, an Rnf complex operon promoter or an ATP synthase operon promoter. In one particular embodiment, the promoter is from *C. autoethanogenum*. In one particular embodiment, the promoter has the sequence of SEQ_ID NO. 22, SEQ ID No 79, or is a functionally equivalent variant of any one thereof. In other embodiments, the promoter has the sequence of SEQ ID No. 56, 57, 51, 58, 59, 52, 60, 61, 53, 62 or 63, or is a functionally equivalent variant of any one thereof.

The nucleic acids of the invention may remain extra-chromosomal upon transformation of a parental microorganism or may be adapted for intergration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid. In one particular embodiment, the expression plasmid has the nucleotide sequence SEQ_ID No. 46, 48, 83, 84, 95, 98 or 101.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

The one or more exogenous nucleic acids may be delivered to a parental microorganism as naked nucleic acids or may be formulated with one or more agents to facilitate the tranformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:

introduction into a shuttle microorganism of (i) of an expression construct/vector as described herein and (ii) a methylation construct/vector comprising a methyltransferase gene;

expression of the methyltransferase gene;

isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli, Bacillus subtillis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter (preferably encoded by SEQ_ID NO 50) and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ_ID No. 34, or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ_ID NO 35, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used. In one particular embodiment, the plasmid has the sequence of SEQ_ID NO. 49.

The invention provides a method for the production of one or more desirable products (acetone, isopropanol, and/or or a precursor of acetone and/or isopropanol) by microbial fermentation comprising fermenting a substrate comprising CO using a recombinant microorganism of the invention. The methods of the invention may be used to reduce the total atmospheric carbon emissions from an industrial process.

Preferably, the fermentation comprises the steps of anaerobically fermenting a substrate in a bioreactor to produce the one or more products using a recombinant microorganism of the invention.

In one embodiment the method comprises the steps of:

(a) providing a substrate comprising CO to a bioreactor containing a culture of one or more microorganism of the invention; and (b) anaerobically fermenting the culture in the bioreactor to produce the one or more products.

In one embodiment the method comprises the steps of:

(a) capturing CO-containing gas produced as a result of the industrial process, before the gas is released into the atmosphere;

(b) the anaerobic fermentation of the CO-containing gas to produce the one or more products by a culture containing one or more microorganism of the invention.

In an embodiment of the invention, the gaseous substrate fermented by the microorganism is a gaseous substrate comprising CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, gasification of biomass, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen) which can be produced from various sources. The CO produced from industrial processes is normally flared off to produce $CO_2$ and therefore the invention has particular utility in reducing $CO_2$ greenhouse gas emissions and producing isopropanol and/or acetone. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and fermentation of CO-to-the at least one product to occur, in addition to the CO-containing substrate gas, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce butanol using CO are known in the art. For example, suitable media are described Biebel (2001). In one embodiment of the invention the media is as described in the Examples section herein after.

The fermentation should desirably be carried out under appropriate conditions for the CO-to-the one or more product(s) fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of the one or more products. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-the one or more product(s) conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Acetone, isopropanol, or a mixed stream containing acetone and/or isopropanol and/or one or more other products, may be recovered from the fermentation broth by methods known in the art, such as fractional distillation or evaporation, pervaporation, gas stripping and extractive fermentation, including for example, liquid-liquid extraction.

In certain preferred embodiments of the invention, the one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.

Microorganisms and Growth Conditions

*Acetobacterium woodii* DSM1030, *Clostridium aceticum* DSM1496, *C. autoethanogenum* DSM23693, *C. carboxidivorans* DSM15243, and *C. ljungdahlii* DSM13528 were sourced from DSMZ (The German Collection of Microorganisms and Cell Cultures, Inhoffenstraβe 7 B, 38124 Braunschweig, Germany). *C. autoethanogenum* DSM23693 is a derivate of *C. autoethanogenum* DSM10061.

*C. ragsdalei* ATCC BAA-622 were sourced from the American Type Culture Collection, Manassas, Va. 20108, USA.

*C. acetobutylicum* ATCC824, *C. beijerinckii* NRRL-B593, and *C. beijerinckii* NCIMB8052 were obtained from Prof. David Jones (University of Otago) and can also be obtained from public strain collections DSMZ and ATCC under accession numbers ATCC824/DSM792, DSM6423, and ATCC51743 respectively.

*Escherichia coli* DH5α-T1$^R$ was sourced from Invitrogen, Carlsbad, Calif. 92008, USA and *Escherichia coli* XL1-Blue MRF' Kan and ABLE K from Stratagene (Santa Clara, Calif. 95051-7201, USA). *Escherichia coli* JW3350-2 was sourced from The Coli Genetic Stock Center (CGSC), New Haven, Conn. 06520-8103.

*E. coli* was cultivated under both aerobic and anaerobic conditions, while all other strains were grown strictly anaerobically in a volume of 50 ml liquid media in serum bottles with fructose (heterotrophic growth) or 30 psi CO-containing steel mill gas (collected from New Zealand Steel site in Glenbrook, NZ; composition: 44% CO, 32% $N_2$, 22% $CO_2$, 2% $H_2$) in the headspace (autotrophic growth).

Media was prepared using standard anaerobic techniques [Hungate R E: A roll tube method for cultivation of strict anaerobes, in Norris J R and Ribbons D W (eds.), Methods in Microbiology, vol. 3B. Academic Press, New York, 1969: 117-132; Wolfe R S: Microbial formation of methane. *Adv Microb Physiol* 1971, 6: 107-146] according to formulations are given in Table 2-4. For solid media, 1.2% Bacto agar (BD, Frankton Lakes, N.J. 07417, USA) was added.

All strains were grown at 37° C., except for *A. woodii, C. aceticum*, and *C. ragsdalei* which were grown at 30° C.

TABLE 2

PETC medium (*A. woodii*, pH 8.2; *C. aceticum*, pH 7.4; *C. autoethanogenum*, *C. carboxidivorans*, *C. ljungdahlii*, and *C. ragsdalei*, pH 5.6)

| Media component | Concentration per 1.0 L of media |
|---|---|
| $NH_4Cl$ | 1 g |
| KCl | 0.1 g |
| $MgSO_4•7H_2O$ | 0.2 g |
| NaCl | 0.8 g |
| $KH_2PO_4$ | 0.1 g |

TABLE 2-continued

PETC medium (*A. woodii*, pH 8.2; *C. aceticum*, pH 7.4; *C. autoethanogenum*, *C. carboxidivorans*, *C. ljungdahlii*, and *C. ragsdalei*, pH 5.6)

| | |
|---|---|
| $CaCl_2$ | 0.02 g |
| Trace metal solution (see below) | 10 ml |
| Wolfe's vitamin solution (see below) | 10 ml |
| Yeast Extract (optional) | 1 g |
| Resazurin (2 g/L stock) | 0.5 ml |
| $NaHCO_3$ | 2 g |
| Reducing agent | 0.006-0.008% (v/v) |
| Fructose (for heterotrophic growth) | 5 g |

| Trace metal solution | per L of stock |
|---|---|
| Nitrilotriacetic Acid | 2 g |
| $MnSO_4•H_2O$ | 1 g |
| $Fe(SO_4)_2(NH_4)_2•6H_2O$ | 0.8 g |
| $CoCl_2•6H_2O$ | 0.2 g |
| $ZnSO_4•7H_2O$ | 0.2 mg |
| $CuCl_2•2H_2O$ | 0.02 g |
| $NaMoO_4•2H_2O$ | 0.02 g |
| $Na_2SeO_3$ | 0.02 g |
| $NiCl_2•6H_2O$ | 0.02 g |
| $Na_2WO_4•2H_2O$ | 0.02 g |

| Reducing agent stock | per 100 mL of stock |
|---|---|
| NaOH | 0.9 g |
| Cystein•HCl | 4 g |
| $Na_2S$ | 4 g |

TABLE 3

Reinforced Clostridial Medium RCM (*C. acetobutylicum*, *C. beijerinckii*)

| Media component | Concentration per 1.0 L of media |
|---|---|
| Pancreatic Digest of Casein | 5 g |
| Proteose Peptone No. 3 | 5 g |
| Beef Extract | 10 g |
| Yeast Extract | 3 g |
| Dextrose | 5 g |
| NaCl | 5 g |
| Soluble starch | 1 g |
| Cystein•HCl | 0.5 g |
| Sodium Acetate | 3 g |

TABLE 4

Luria Bertani medium LB (*E. coli*)

| Media component | Concentration per 1.0 L of media |
|---|---|
| Tryptone | 10 g |
| Yeast Extract | 5 g |
| NaCl | 10 g |

TABLE 5

SD-8 minimal media (*E. coli*)

| Media component | Concentration per 1.0 L of media |
|---|---|
| $NH_4Cl$ | 7 g |
| $Na_2HPO_4$ | 7.5 g |
| $K_2SO_4$ | 0.85 g |
| $MgSO_4•7H_2O$ | 0.17 g |
| $KH_2PO_4$ | 7.5 g |

TABLE 5-continued

| SD-8 minimal media (*E. coli*) | |
|---|---|
| Trace metal solution (see below) | 0.8 ml |
| Yeast Extract | 5 g |
| Glucose | 20 g |
| **Trace metal solution** | **per 100 L of stock** |
| $MnSO_4 \cdot H_2O$ | 1 g |
| $FeSO_4 \cdot 7H_2O$ | 4 g |
| $CoCl_2 \cdot 6H_2O$ | 0.4 g |
| $ZnSO_4 \cdot 7H_2O$ | 0.2 g |
| $CuCl_2 \cdot 2H_2O$ | 0.1 g |
| $Na_2MoO_4 \cdot 2H_2O$ | 0.2 g |
| $Al_2(SO_4)_3$ | 2.83 g |
| $H_3BO_4$ | 0.5 g |

Fermentations with *C. autoethanogenum* DSM23693 were carried out in 1.5 L bioreactors at 37° C. and CO-containing steel mill gas as sole energy and carbon source as described below. A defined medium was used containing per litre: MgCl, $CaCl_2$ (0.5 mM), KCl (2 mM), $H_3PO_4$ (5 mM), Fe (100 μM), Ni, Zn (5 μM), Mn, B, W, Mo, Se (2 μM) was prepared for culture growth. The media was transferred into the bioreactor and autoclaved at 121° C. for 45 minutes. After autoclaving, the medium was supplemented with Thiamine, Pantothenate (0.05 mg), Biotin (0.02 mg) and reduced with 3 mM Cysteine-HCl. To achieve anaerobicity the reactor vessel was sparged with nitrogen through a 0.2 μm filter. Prior to inoculation, the gas was switched to CO-containing steel mill gas, feeding continuously to the reactor. The gas flow was initially set at 80 ml/min, increasing to 200 ml/min during mid exponential phase, while the agitation was increased from 200 rpm to 350. $Na_2S$ was dosed into the bioreactor at 0.25 ml/hr. Once the OD600 reached 0.5, the bioreactor was switched to a continuous mode at a rate of 1.0 ml/min (Dilution rate 0.96 $d^{-1}$). Media samples were taken to measure the biomass and metabolites and a headspace analysis of the in- and outflowing gas was performed on regular basis.

Analysis of Metabolites

HPLC analysis of acetone, isopropanol and other metabolites was performed using an Agilent 1100 Series HPLC system equipped with a RID operated at 35° C. (Refractive Index Detector) and an Alltech IOA-2000 Organic acid column (150×6.5 mm, particle size 5 μm) kept at 60° C. Slightly acidified water was used (0.005 M $H_2SO_4$) as mobile phase with a flow rate of 0.7 ml/min. To remove proteins and other cell residues, 400 μl samples were mixed with 100 μl of a 2% (w/v) 5-Sulfosalicylic acid and centrifuged at 14,000×g for 3 min to separate precipitated residues. 10 μl of the supernatant were then injected into the HPLC for analyses.

GC analysis of acetone, isopropanol and other metabolites was performed using an Agilent 6890N headspace GC equipped with a Supelco PDMS 100 1 cm fiber, an Alltech EC-1000 (30 m×0.25 mm×0.25 μm) column, and a flame ionization detector (FID). 5 ml samples were transferred into a Hungate tube, heated to 40° C. in a water bath and exposed to the fiber for exactly 5 min. The injector was kept at 250° C. and helium with a constant flow of 1 ml/min was used as carrier gas. The oven program was 40° C. for 5 min, followed by an increase of 10° C./min up to 200° C. The temperature was then further increased to 220° C. with a rate of 50° C./min followed by a 5 min hold this temperature, before the temperature was decreased to 40° C. with a rate of 50° C./min and a final 1 min hold. The FID was kept at 250° C. with 40 ml/min hydrogen, 450 ml/min air and 15 ml/min nitrogen as make up gas.

Headspace Analysis

Measurements were carried out on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Genetic Modification of *C. autoethanogenum* and *C. ljungdahlii* for Acetone Production Using Clostridial Pathway

*C. autoethanogenum* and *C. ljungdahlii* are naturally not able to produce acetone, therefore the acetone biosynthesis pathway occurring in other Clostridial species was introduced into both organisms (FIG. 4). The first step in the Clostridial acetone biosynthesis pathway from acetyl-CoA to acetoacetyl-CoA is catalysed by a acetyl-Coenzyme A acetyltransferase or thiolase. The conversion of acetoacetyl-CoA to acetone is then catalysed by a specialized set of enzymes acetate/butyrate-acetoacetate CoA-transferase complex and acetoacetate decarboxylase, which can be found in few organisms like *C. acetobutylicum* and *C. beijerinckii* (Table 6).

TABLE 6

Accession numbers of genes and enzymes involved in acetone and isopropanol formation.

| | *C. acetobutylicum* | | *C. beijerinckii* | |
|---|---|---|---|---|
| Description | nucleic acid | amino acid | nucleic acid | Amino acid |
| Thiolase (ThlA) | NC_003030.1; GI: 1119056 | NP_349476.1 | NC_009617; GI: 5294796 | YP_001310706.1 |
| Acetate/Butyrate-acetoacetate CoA-transferase subunit A (CtfA) | NC_001988.2; GI: 1116168 | NP_149326.1 | NC_009617; GI: 5294994 | YP_001310904.1 |
| Acetate/Butyrate-acetoacetate CoA-transferase subunit A CtfB | NC_001988.2; GI: 1116169 | NP_149327.1 | NC_009617; GI: 5294995 | YP_001310905.1 |
| Acetoacetate decarboxylase (Adc) | NC_001988.2; GI: 1116170 | NP_149328.1 | NC_009617; GI: 5294996 | YP_001310906.1 |

Figure 3:
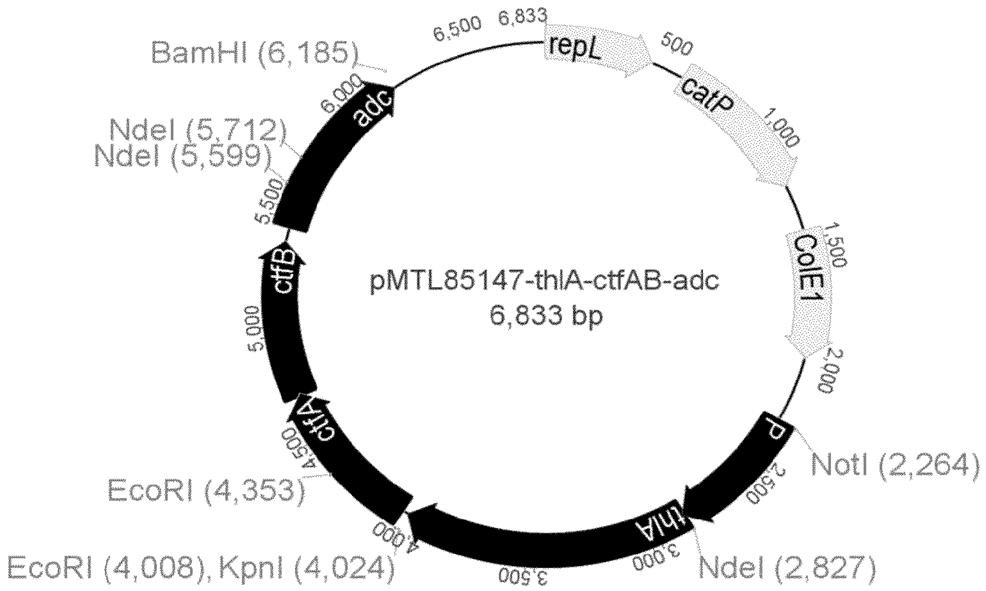
FIG. 3 shows acetone expression plasmid pMTL85147-thlA-ctfA-ctfB-adc.

Whereas the genes of *C. acetobutylicum* encoding the respective enzymes are split into 2 operons, the genes of *C. beijerinckii* form a common operon, which the inventor(s) believe offers an advantage. The genes encoding a thiolase from *C. acetobutylicum* and the operon coding for enzymes acetate/butyrate-acetoacetate CoA-transferase subunit A, acetate/butyrate-acetoacetate CoA-transferase subunit B and acetoacetate decarboxylase were assembled into a synthetic operon under control of a strong, native *C. autoethanogenum* promoter (FIG. 3). This construct was used to genetically engineer both organism for acetone production. In order to create a recombinant strain, a novel methyltransferase was used to methylate the construct, which was then transformed and expressed in *C. autoethanogenum* DSM23693 and *C. ljungdahlii* DSM13528 (described herein after). Production of acetone was shown on different industrial gas streams (steel mill waste gas, syngas).

Construction of Expression Plasmid with Clostridial Acetone Pathway Genes:

Standard Recombinant DNA and molecular cloning techniques were used in this invention [Sambrook J, Fritsch E F, Maniatis T: Molecular Cloning: A laboratory Manual, Cold Spring Harbour Laboratory Press, Cold Spring Harbour, 1989; Ausubel F M, Brent R, Kingston R E, Moore D D, Seidman J G, Smith J A, Struhl K: Current protocols in molecular biology. John Wiley & Sons, Ltd., Hoboken, 1987]. DNA sequences of acetone biosynthetic genes are shown in Table 7. The Wood-Ljungdahl cluster promoter of *C. autoethanogenum* (upstream of CO dehydrogenase gene acsA) was used for expression of target genes (Table 7).

TABLE 7

Sequences used for Clostridial acetone expression plasmid

| Description | Source | SEQ_ID NO. |
|---|---|---|
| Thiolase (thlA) | *Clostridium acetobutylicum* ATCC 824; NC_003030.1; GI: 1119056 | 18 |
| Acetoacetyl-CoA: acetate Coenzyme A transferase A (ctfA), acetoacetyl-CoA: acetate Coenzyme A transferase B (ctfB), and acetoacetate decarboxylase (adc) operon | *Clostridium beijerinckii* NCIMB 8052; NC_009617; region: 4,400,524-4,402,656; including GI: 5294994, GI: 5294995, and GI: 5294996 | 47 |
| Wood-Ljungdahl cluster promoter ($P_{wL}$) | *Clostridium autoethanogenum* DSM10061 | 22 |

Genomic DNA from *Clostridium acetobutylicum* ATCC824, *C. beijerinckii* NCIMB8052 and *C. autoethanogenum* DSM10061 was isolated using a modified method by Bertram and Dürre (Conjugal transfer and expression of streptococcal transposons in *Clostridium acetobutylicum. Arch Microbiol* 1989, 151: 551-557). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 μl lysozyme (~100,000 U) were added and the mixture was incubated at 37° C. for 30 min, followed by addition of 280 μl of a 10% (w/v) SDS solution and another incubation for 10 min. RNA was digested at room temperature by addition of 240 μl of an EDTA solution (0.5 M, pH 8), 20 μl Tris-HCl (1 M, pH 7.5), and 10 μl RNase A. Then, 100 μl Proteinase K (0.5 U) were added and proteolysis took place for 1-3 h at 37° C. Finally, 600 μl of sodium perchlorate (5 M) were added, followed by a phenol-chloroform extraction and an isopropanol precipitation. DNA quantity and quality was inspected spectrophotometrically.

Acetone biosynthetic genes and the Wood-Ljungdahl cluster promoter were amplified by PCR with oligonucleotides in Table 8 using iProof High Fidelity DNA Polymerase (Bio-Rad Labratories, Hercules, Calif. 94547, USA) and the following program: initial denaturation at 98° C. for 30 seconds, followed by 32 cycles of denaturation (98° C. for 10 seconds), annealing (50-62° C. for 30-120 seconds) and elongation (72° C. for 45 seconds), before a final extension step (72° C. for 10 minutes).

TABLE 8

Oligonucleotides used for amplification of acetone biosynthesis genes and promoter region

| Description | Oligonucleotide Name | DNA Sequence (5' to 3') | SEQ_ID NO. |
|---|---|---|---|
| ThlA | ThlA-Cac-NdeI-F | GTTCATATGAAAGAAGTTGTAATAGC | 23 |
| | ThlA-Cac-EcoRI-R | CAAGAATTCCTAGCACTTTTCTAGC | 24 |
| CtfA, CtfB, Adc operon | Ctf-adc-cbei-KpnI-F | CTAGGTACCAGGGAGATATTAAAATG | 25 |
| | Ctf-adc-cbei-BamH1-R | CGTGGATCCTCTATATTGCTTTTATT | 26 |

TABLE 8-continued

Oligonucleotides used for amplification of acetone biosynthesis genes and promoter region

| Description | Oligonucleotide Name | DNA Sequence (5' to 3') | SEQ_ID NO. |
|---|---|---|---|
| $P_{WL}$ | Pwoodlj-NotI-F | AAGCGGCCGCAGATAGTCATAATAG TTCC | 27 |
| | Pwoodlj-NdeI-R | TTCCATATGAATAATTCCCTCCTTAA AGC | 28 |

Figure 5:
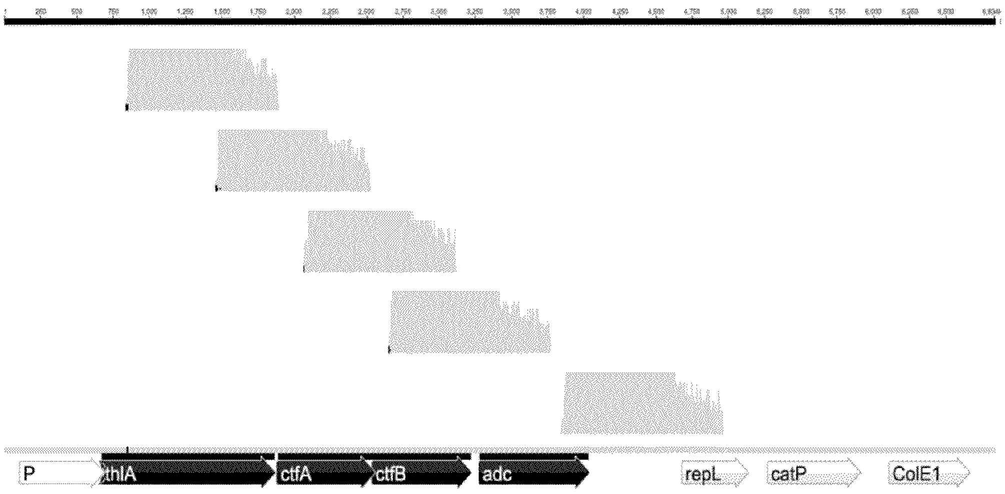
FIG. 5 shows the sequencing results of acetone expression plasmid pMTL85147-thlA-ctfA-ctfB-adc.

The amplified 573 bp promoter region of the Wood-Ljungdahl cluster ($P_{WL}$) was cloned into the *E. coli-Clostridium* shuttle vector pMTL 85141 (FJ797651.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] using NotI and NdeI restriction sites and strain DH5α-$T1^R$. The created plasmid pMTL85147 and the 1,194 bp PCR product of the thiolase gene were both cut with NdeI and EcoRI. A ligation was transformed into *E. coli* XL1-Blue MRF' Kan resulting in plasmid pMTL85147-thlA. Subsequently, the amplified 2,177 bp PCR fragment of the ctfA-ctfB-adc operon from *C. beijerinckii* NCIMB 8052 was cloned into this vector using KpnI and BamHI and *E. coli* ABLE K, creating plasmid pMTL85147-thlA-ctfA-ctfB-adc. The insert of the resulting plasmid pMTL85147-thlA-ctfAB-adc was completely sequenced using oligonucleotides given in Table 9 and results confirmed that the acetone biosynthesis genes and promoter region were free of mutations (FIG. 5).

TABLE 9

Oligonucleotides used for sequencing

| Oligonucleotide Name | DNA Sequence (5' to 3') | SEQ_ID NO. |
|---|---|---|
| Seq-ThlA-CtfAB-Adh 3539-4139 | CAGAGGATGTTAATGAAGTC | 29 |
| Seq-ThlA-CtfAB-Adh 4140-4740 | CTGTGCAGCAGTACTTGT | 30 |
| Seq-ThlA-CtfAB-Adh 4741-5341 | GCAATGATACAGCTT | 31 |
| Seq-ThlA-CtfAB-Adh 5342-5942 | AACCTTGGAATAGGACTTC | 32 |
| Seq-ThlA-CtfAB-Adh 6544-7144 | TGTGAACTAATATGTGCAGA | 33 |
| M13 Forward | GTAAAACGACGGCCAG | 56 |
| M13 Reverse | CAGGAAACAGCTATGAC | 57 |

Acetone Production in *E. coli* with Clostridial Acetone Pathway Genes:

To confirm the functionality of the constructed plasmid, a metabolic profile from a 5 ml overnight culture of *E. coli* ABLE K harbouring plasmid pMTL85147-thlA-ctfA-ctfB-adc were obtained using GC and HPLC, confirming acetone production.

Figure 42A:
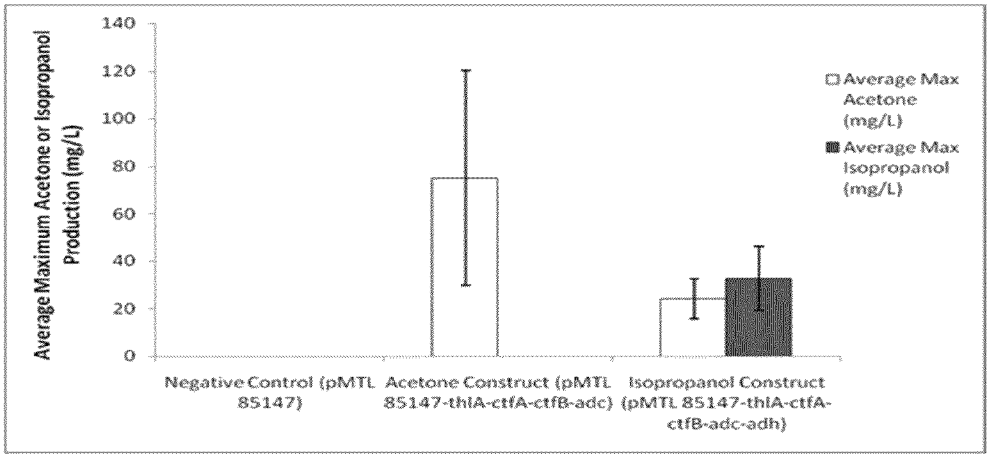
FIG. 42 shows the results of acetone and isopropanol production with *E. coli* XL-1 Blue MRF' Kan carrying control plasmid (pMTL85147), acetone expression plasmid (pMTL85147-thlA-ctfA-ctfB-adc), and acetone expression plasmid including the novel alcohol dehydrogaenase (pMTL85147-thlA-ctfA-ctfB-adc-adh).
Figure 42B:
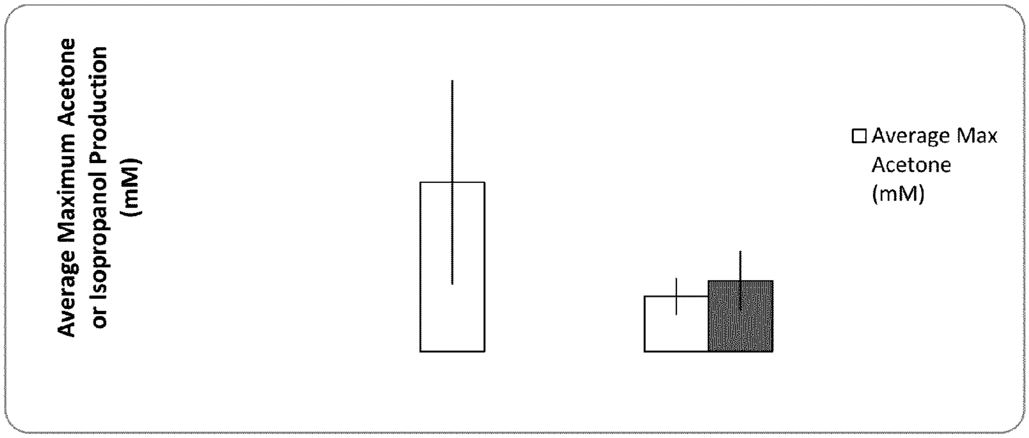

To investigate this further, detailed growth experiments were carried out in triplicates with SD-8 minimal media containing 25 μg/ml chloramphenicol and *E. coli* XL-1 Blue MRF' Kan carrying either plasmid pMTL 85147 (negative control) or expression plasmid pMTL 85147-thlA-ctfA-ctfB-adc (FIG. 42). While no acetone production could be observed in the negative control, an average maximum acetone production of 75.05 mg/L with an average dry biomass of 1.44 g/L was measured for the strain carrying the acetone plasmid.

Figure 6:
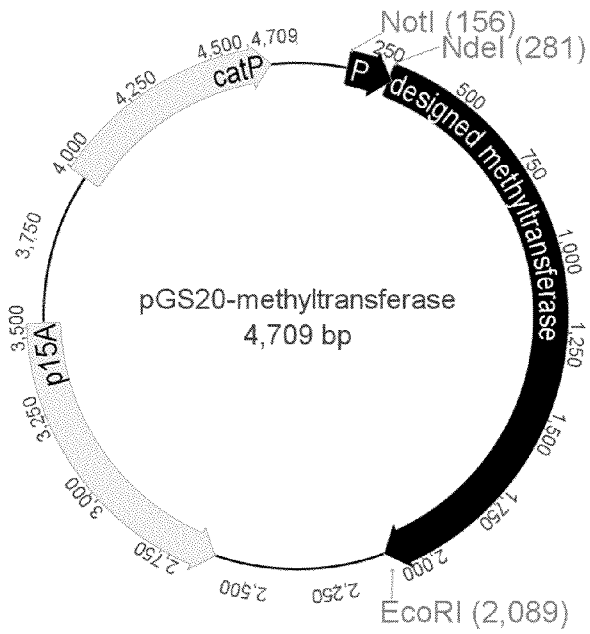
FIG. 6 illustrates the designed methylation plasmid.

Methylation of Expression Plasmid with Clostridial Acetone Pathway Genes:

Methylation of the acetone expression plasmid pMTL85147-thlA-ctfA-ctfB-adc was performed in vivo in *E. coli* using a synthesized hybrid Type II methyltransferase gene (SEQ_ID NO 35) designed from methyltransferase genes from *C. autoethanogenum, C. ragsdalei* and *C. ljungdahlii*. The methyltransferase (SEQ_ID NO 34) was synthesized and fused with an inducible lac promoter in vector pGS20 (ATG:biosynthetics GmbH, Merzhausen, Germany) (FIG. 6; SEQ_ID NO 49).

Both expression plasmid and methylation plasmid were transformed into same cells of restriction negative *E. coli* XL1-Blue MRF' Kan, which is possible due to their compatible Gram-(−) origins of replication (high copy ColE1 in expression plasmid and low copy p15A in methylation plasmid). In vivo methylation was induced by addition of 1 mM IPTG, and methylated plasmids were isolated using QIAGEN Plasmid Midi Kit (QIAGEN GmbH, Hilden, Germany). The resulting mix was used for transformation experiments with *C. autoethanogenum* DSM23693 and *C. ljungdahlii* DSM 13528, but only the abundant (high-copy) expression plasmid has a Gram-(+) replication origin (repL) allowing to replicate in Clostridia.

Transformation of Methylated Acetone Expression Plasmid in *C. autoethanogenum* and *C. ljungdahlii:*

To make competent cells of *C. autoethanogenum* DSM23693 and *C. ljungdahlii* DSM 13528, a 50 ml culture (PETC media (Table 2) with steel mill gas and fructose as carbon source; 37° C.) was subcultured to fresh media for 3 consecutive days. These cells were used to inoculate 50 ml PETC media containing 40 mM DL-threonine at an $OD_{600nm}$ of 0.05. When the culture reached an $OD_{600nm}$ of 0.4, the cells were transferred into an anaerobic chamber and harvested at 4,700×g and 4° C. The culture was twice washed with ice-cold electroporation buffer (270 mM sucrose, 1 mM MgCl2, 7 mM sodium phosphate, pH 7.4) and finally suspended in a volume of 500 μl fresh electroporation buffer. This mixture was transferred into a pre-cooled electroporation cuvette with a 0.4 cm electrode gap containing ~1 μg of the methylated plasmid mix. Since an additional Type I restriction system was identified in the genome of *C. ljungdahlii* compared to *C. autoethanogenum,* 5 μl of a Type I restriction inhibitor (EPICENTRE Biotechnologies, Madison, Wis. 53713, USA) were added to the plasmid mix, which increased the transformation efficiency of *C. ljungdahlii* by 2-10 fold. The cells were mixed with plasmid and restriction inhibitor and immediately pulsed using a Gene pulser Xcell electroporation system (Bio-Rad Labratories, Hercules, Calif. 94547, USA) with the following settings: 2.5 kV, 600Ω, and 25 μF. Time constants were between 3.7-5.1 ms. For regeneration, the culture was transferred in 5 ml special regeneration media (Table 10), which increased recovery of the cells, which was monitored at a wavelength of 600 nm using a Spectronic Helios Epsilon Spectrophotometer (Thermo Fisher Scientific Inc., Waltham Mass. 02454, USA) equipped with a tube holder. Once growth was observed (one doubling) the cells were harvested, suspended in 200 μl fresh media and plated on selective PETC plates with 15 μg/ml thiamphenicol (dissolved in 100% (v/v) dimethylfuran (DMF)) and 30 psi steel mill gas in the headspace. 50-200 colonies were visible after 4-6 days, which were used to inoculate 2 ml PETC media containing 15 μg/ml thiamphenicol (in DMF) and fructose and 30 psi steel mill gas as carbon source. When growth occurred, the culture was up-scaled into 5 ml and later 50 ml PETC media containing each 15 μg/ml thiamphenicol (in DMF) and 30 psi steel mill gas in the headspace as sole carbon source.

TABLE 10

Regeneration media

| Media component | Concentration per 1.0 L of media |
|---|---|
| $NH_4Cl$ | 1 g |
| KCl | 0.1 g |
| $MgSO_4 \cdot 7H_2O$ | 0.2 g |
| $KH_2PO_4$ | 0.2 g |
| $CaCl_2$ | 0.02 g |
| Trace metal solution (see Table 2) | 10 ml |
| Wolfe's vitamin solution (see Table 2) | 10 ml |
| Yeast Extract | 2 g |
| Resazurin (2 g/L stock) | 0.5 ml |
| 2-(N-morpholino)ethanesulfonic acid (MES) | 20 g |
| Reducing agent | 0.006-0.008% (v/v) |
| Fructose | 5 g |
| Sodium acetate | 0.25 g |
| $Fe (SO_4)_2(NH_4)_2 \cdot 6H_2O$ | 0.05 g |
| Nitriolotriacetic Acid | 0.05 g |
| pH 5.7 | Adjusted with NaOH |

Figure 7:
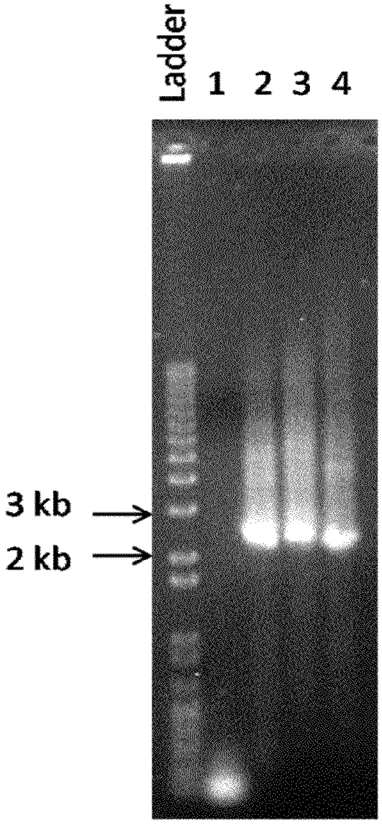
FIG. 7 shows detection of ctfAB-adc (2.2 kb) from PCR of plasmids isolated from transformed *C. autoethanogenum* DSM23693 and *C. ljungdahlii* DSM13528. Ladder=1 KB Plus DNA ladder (Invitrogen); 1=non-template control; 2=plasmid isolated from *C. autoethanogenum;* 3=plasmid isolated from *C. ljungdahlii;* 4=original pMTL85147-thlA-ctfAB-adc (positive control).

Confirmation of Successful Transformation of *C. autoethanogenum* and *C. ljungdahlii* with Acetone Plasmid with Clostridial Acetone Pathway Genes:

To verify the DNA transfer, a plasmid mini prep was performed from 10 ml culture volume using Zyppy plasmid miniprep kit (Zymo Research, Irvine, Calif. 92614, USA). Since the quality of the isolated plasmid wasn't sufficient for a restriction digest due to Clostridial exonuclease activity [Burchhardt G and Dürre P, Isolation and characterization of DNase-deficient mutants of *Clostridium acetobutylicum. Curr Microbiol* 1990, 21: 307-311] with the isolated plasmid as template using primers ctf-adc-cbei-KpnI-F (Seq_ID no 25) and ctf-adc-cbei-BamHI-R (SEQ_ID NO 26) to confirm the presence of the plasmid (FIG. 7). PCR was carried out using iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 135 seconds), before a final extension step (72° C. for 5 minutes).

To confirm the identity of the clones, genomic DNA was isolated using the protocol given above from 50 ml cultures of each *C. autoethanogenum* DSM23693 and *C. ljungdahlii* DSM13528. A PCR was performed against the 16s rRNA gene using oligonucleotides fD1 (SEQ_ID NO 36: CCGAATTCGTCGACAACAGAGTTTGATC-CTGGCTCAG) and rP2 (SEQ_ID NO 37: CCCGGGATC-CAAGCTTACGGCTACCTTGTTACGACTT) [Weisberg W G, Barns S M, Pelletier B A and Lane D J, 16S ribosomal DNA amplification for phylogenetic study. *J Bacteriol* 1990, 173: 697-703] and iNtRON Maximise Premix PCR kit (Intron Bio Technologies, Sangdaewon Joongwon Seognam Kyunggi, Korea) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes).

All sequences obtained had >99.9% identity against the 16s rRNA gene (rrsA) of *C. autoethanogenum* (Y18178, GI:7271109) and respectively *C. ljungdahlii* (CP001666.1; GI:300433347).

Acetone Production from CO and $CO_2/H_2$ with Clostridial Acetone Pathway Genes in *C. autoethanogenum* and *C. jungdahlii:*

Figure 9:
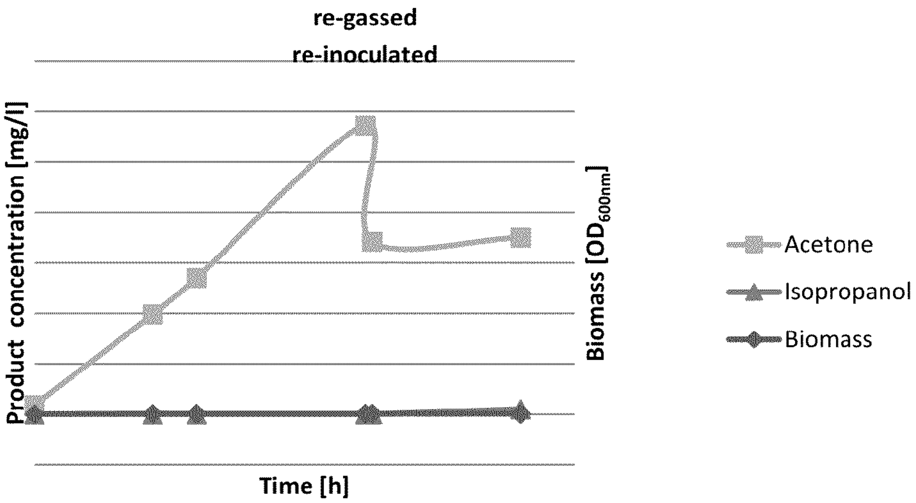
FIG. 9 shows the result of growth experiments with *C. ljungdahlii* DSM13528+pMTL85147-thlA-ctfAB-adc on steel mill gas.
Figure 10:
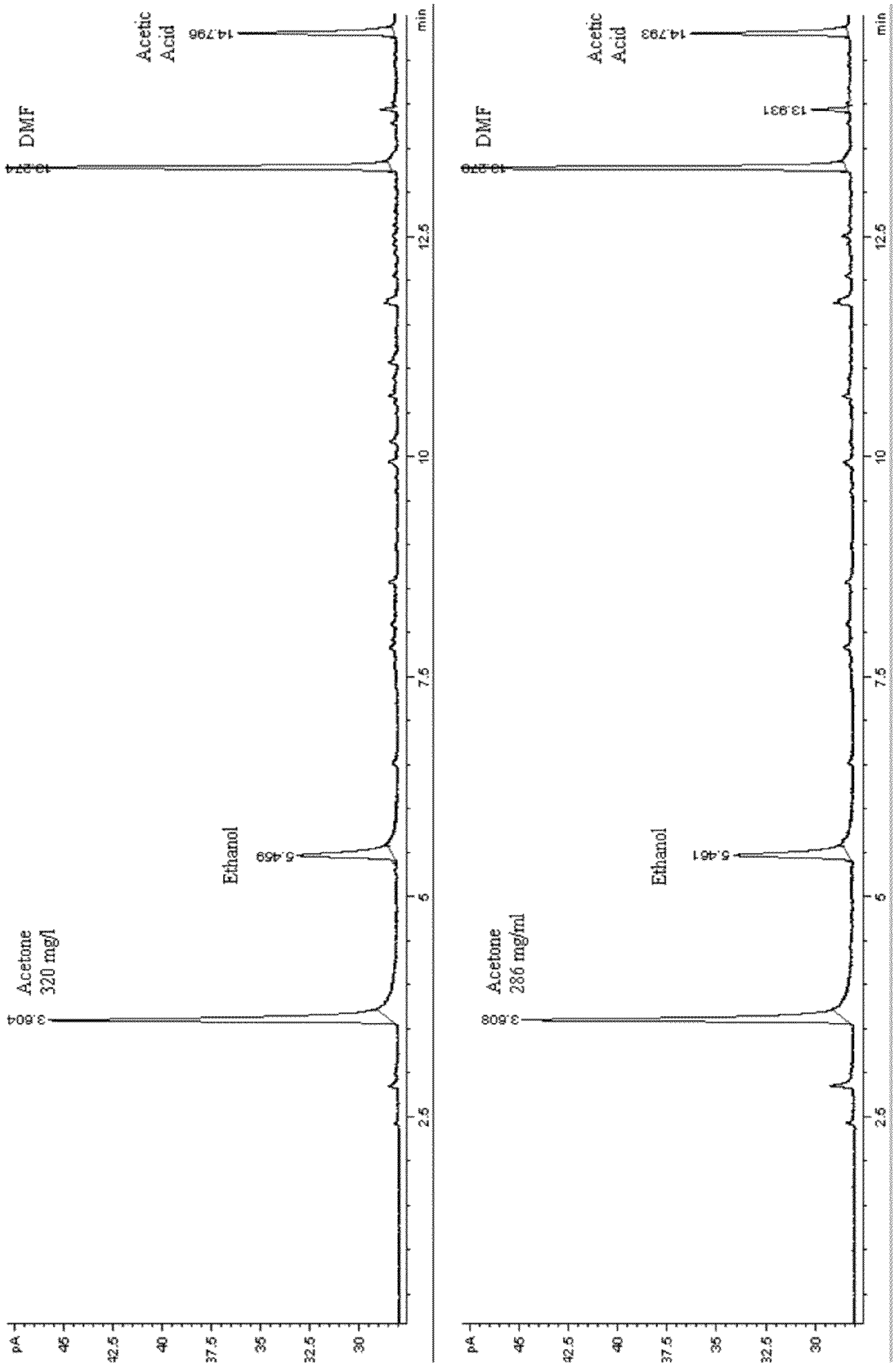
FIG. 10 shows the GC result confirming acetone production with *C. autoethanogenum* DSM13528+pMTL85147-thlA-ctfAB-adc (top) and *C. ljungdahlii* DSM13528+pMTL85147-thlA-ctfAB-adc (bottom) from steel mill gas.
Figure 11:
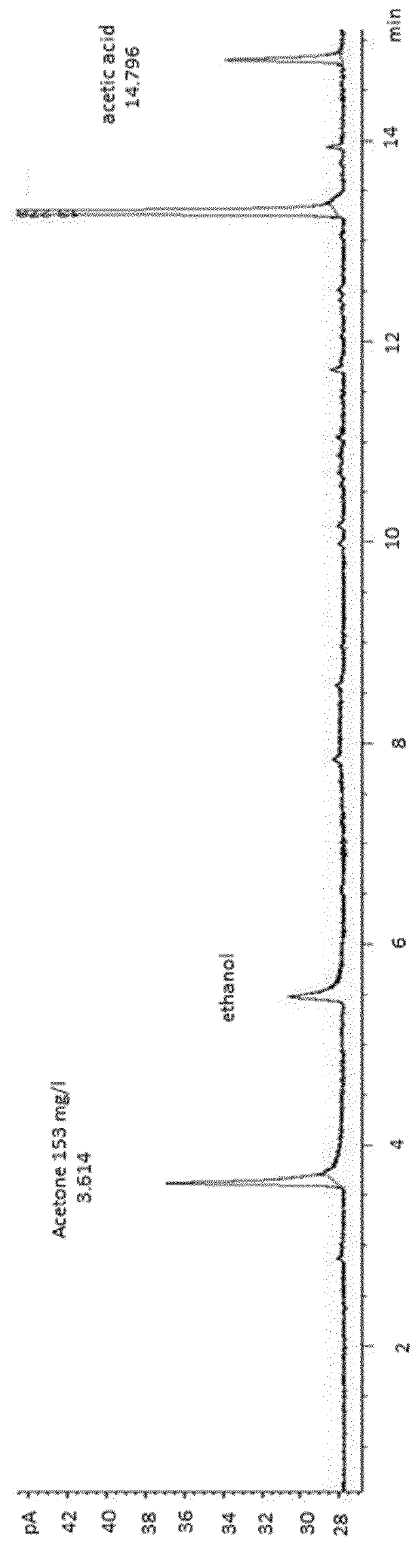
FIG. 11 shows the GC result confirming acetone production with *C. autoethanogenum* DSM23693+pMTL85147-thlA-ctfAB-adc from syngas.

Growth experiments were carried out with transformed *C. autoethanogenum* DSM23693 and *C. ljungdahlii* DSM 13528 carrying plasmid pMTL85147-thlA-ctfAB-adc in 250 ml PETC media (Table 2; without fructose and yeast extract) in 1 l Schott bottles with rubber stoppers and 30 psi steel mill gas (collected from New Zealand Steel site in Glenbrook, NZ; composition: 44% CO, 32% $N_2$, 22% $CO_2$, 2% $H_2$) in the headspace as sole energy and carbon source. Acetone production was confirmed with both strains using HPLC and GC analysis. In Schott bottles acetone concentrations of around 0.3 g/l (6.5 mM) after 48 hours were achieved with both, *C. autoethanogenum* DSM23693 (FIGS. 8 and 10) and *C. ljungdahlii* DSM 13528 (FIGS. 9 and 10). Using appropriate conditions, the produced acetone can then be further converted to isopropanol. Acetone production of 153 mg/ml was also demonstrated on 30 psi biomass syngas (Range Fuels Inc., Broomfield, Colo.; composition: 29% CO, 45% $H_2$, 13% $CH_4$, 12% $CO_2$, 1% $N_2$) as sole energy and carbon source in 50 ml PETC media (Table 2; without fructose and yeast extract) in serum bottles with *C. autoethanogenum* DSM23693 (FIG. 11).

Figure 52:
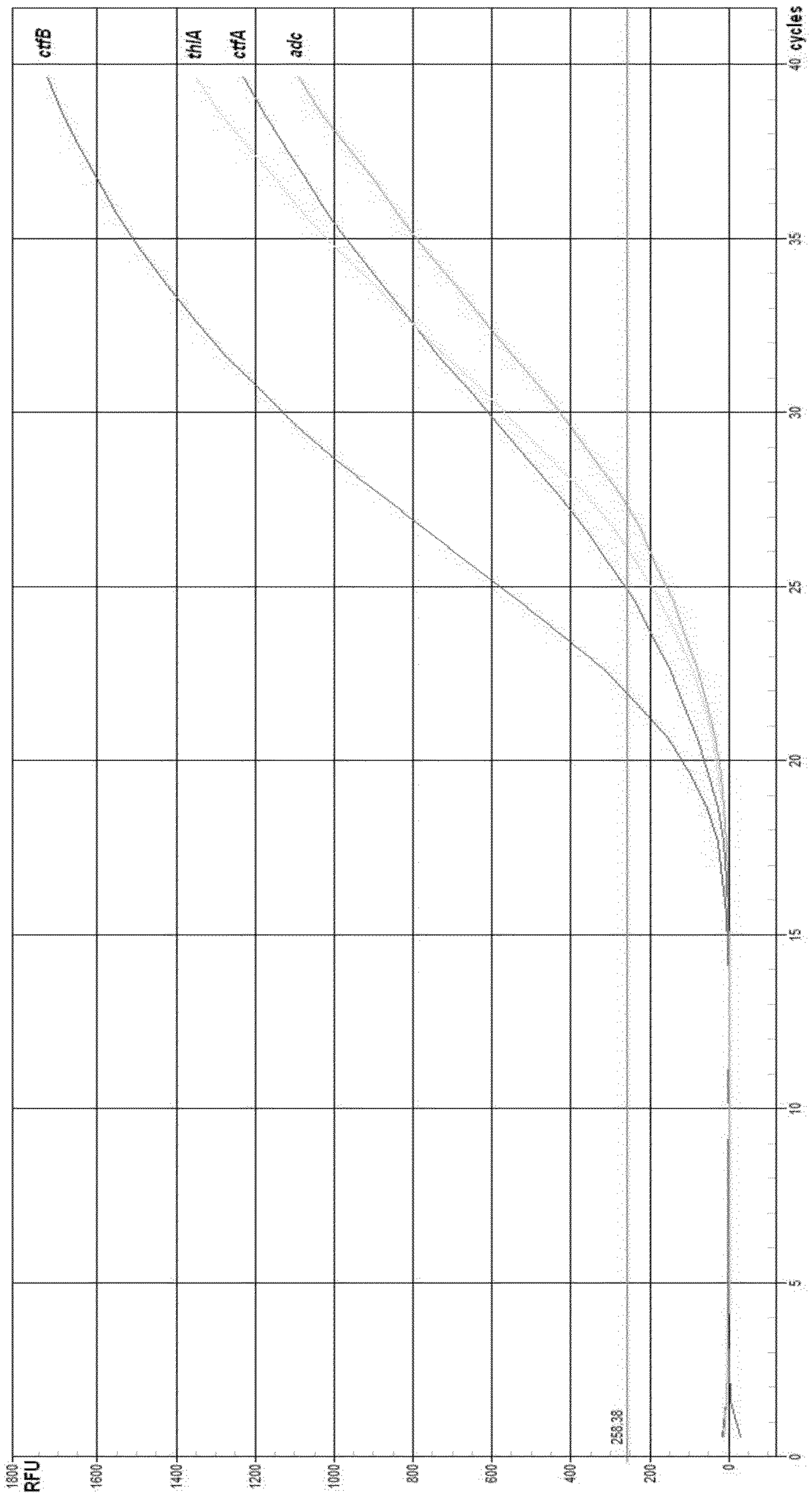
FIG. 52 shows qRT-PCR amplification plot confirming amplification of probes for heterologous genes thlA, ctfA, ctfB, and adc in *Clostridium autoethanogenum* harbouring plasmid pMTL85147-thlA-ctfAB-adc
Figure 53:
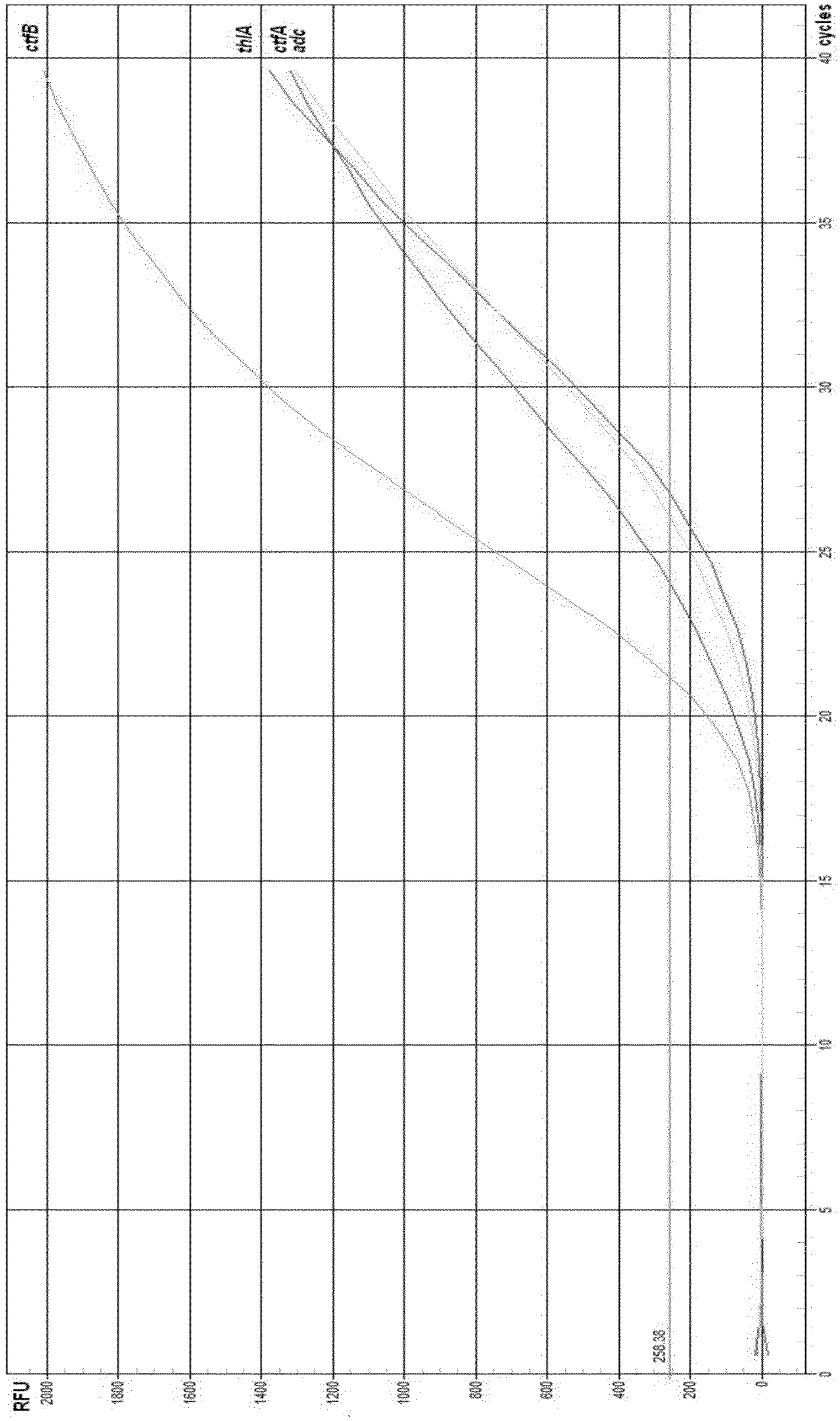
FIG. 53 shows qRT-PCR amplification plot confirming amplification of probes for heterologous genes thlA, ctfA, ctfB, and adc in *Clostridium ljungdahlii* harbouring plasmid pMTL85147-thlA-ctfAB-adc

Expression of Heterologous with Clostridial Acetone Pathway Genes in *C. autoethanogenum:* qRT-PCR experiments were performed to confirm successful expression of introduced genes thlA, ctfA, ctfB, and adc leading to acetone production in *C. autoethanogenum* and *C. ljungdahlii*. Signals for all genes could successfully be detected (FIGS. 52 and 53).

A 50-ml culture of each *C. autoethanogenum* and *C. ljungdahlii* harbouring plasmid pMTL85147-harvested by centrifugation (6,000×g, 5 min, 4° C.), snap frozen in liquid nitrogen and stored at −80° C. until RNA extraction. Total RNA was isolated using PureLink™ RNA Mini Kit (Invitrogen, Carlsbad, Calif., USA) and eluted in 100 µL of RNase-free water. After DNase I treatment (Roche Applied Science, Indianapolis, Ind., USA), the reverse transcription step was then carried out using SuperScript III Reverse Transcriptase Kit (Invitrogen, Carlsbad, Calif., USA). RNA was checked using an Agilent Bioanalyzer 2100 (Agilent Technologies, Santa Clara, Calif., USA), Qubit Fluorometer (Invitrogen, Carlsbad, Calif., USA) and by gel electrophoresis. A non-RT control was performed for every primer pair. All qRT-PCR reactions were performed in duplicates using a MyiQ Single Colour Detection System (Bio-Rad Labratories, Carlsbad, Calif., USA) in a total reaction volume of 15 µL with 25 ng of cDNA template, 67 nM of each primer (Table 17), and 1× iQ SYBR Green Supermix (Bio-Rad Labratories, Carlsbad, Calif., USA). The reaction conditions were 95° C. for 3 min, followed by 40 cycles of 95° C. for 15 s, 55° C. for 15 s and 72° C. for 30 s. For detection of primer dimerisation or other artifacts of amplification, a melting-curve analysis was performed immediately after completion of the qPCR (38 cycles of 58° C. to 95° C. at 1° C./s). Two housekeeping genes (Guanylate kinase and formate tetrahydrofolate ligase) were included for each cDNA sample for normalization. Derivation of relative gene expression was conducted using Relative Expression Software Tool (REST©) 2008 V2.0.7 (38). Dilution series of cDNA spanning 4 log units were used to generate standard curves and the resulting amplification efficiencies to calculate concentration of mRNA.

TABLE 17

Oligonucleotides for qRT-PCR

| Target | Oligonucleotide Name | DNA Sequence (5' to 3') | SEQ_ID NO. |
|---|---|---|---|
| Guanylate kinase (gnk) | GnK-F | TCAGGACCTTCTGGAACTGG | 5 |
| | GnK-R | ACCTCCCCTTTTCTTGGAGA | 6 |
| Formate tetrahydrofolate ligase (FoT4L) | FoT4L-F | CAGGTTTCGGTGCTGACCTA | 7 |
| | FoT4L-F | AACTCCGCCGTTGTATTTCA | 8 |
| Thiolase A | thlA-RT-F | TTGATGAAATGATCACTGACGGATT | 64 |
| | thlA-RT-R | GAAATGTTCCATCTCTCAGCTATGT | 65 |
| | ctfB-RT-F | CTAATACGAGGAGGACATGTTGATG | 66 |
| Acetoacetyl-CoA:Acetate CoA-transferase B | ctfB-RT-R | CACCCATACCTGGGACAATTTTATT | 67 |
| | ctfA-RT-F | GGGCTGCTACTAAAAATTTCAATCC | 68 |
| Acetoacetyl-CoA:Acetate CoA-transferase A | ctfA-RT-R | CAGGAGTCATTATGGCATCTCTTTT | 69 |
| | adc-RT-F | TAGTACCAGAGCCACTTGAATTAGA | 70 |
| Acetoacetate decarboxylase | adc-RT-R | GGAATAGCTTGACCACATTCTGTAT | 71 |

Conversion of Acetone to Isopropanol by *C. autoethanogenum, C. ljungdahlii*, and *C. ragsdalei:*

Acetone can be further converted to isopropanol by action of an alcohol dehydrogenase. However, only few microorganisms such as *C. beijerinckii* NRRL-B593 are described to produce isopropanol, and acetone-to-isopropanol converting enzymes are very rare in nature. So far only two secondary alcohol dehydrogenases have been identified and described to date, from *C. beijerinckii* NRRL-B593 [Ismaiel A A, Zhu C X, Colby G D, Chen J S: Purification and characterization of a primary-secondary alcohol dehydrogenase from two strains of *Clostridium beijerinckii. J Bacteriol* 1993, 175: 5097-5105] (SEQ_ID NO 38-39) and *Thermoanaerobacter brockii* [Peretz M and Burstein Y: Amino acid sequence of alcohol dehydrogenase from the thermophilic bacterium *Thermoanaerobium brockii. Biochemistry.* 1989, 28:6549-6555] (SEQ_ID NO 40-41).

Therefore, a collection of microorganisms—acetogenic bacteria, acetone and isopropanol producing Clostridia and *E. coli*—were tested for their ability to convert acetone to isopropanol (Table 11).

TABLE 11

| Addition of acetone to growing cultures of various microorganisms. | | | | | | |
|---|---|---|---|---|---|---|
| | | | Directly after acetone addition | | End of growth | |
| Organism/Sample | Description | Media | Acetone [g/l] | Isopropanol [g/l] | Acetone [g/l] | Isopropanol [g/l] |
| *Acetobacterium woodii* DSM1030 | Acetogenic species | PETC (pH 8.2) | 10.81 | 0 | 10.83 | 0 |
| *Clostridium aceticum* DSM1496 | | PETC (pH 7.4) | 10.07 | 0 | 10.09 | 0 |
| *C. autoethanogenum* DSM23693 | | PETC (pH 5.9) | 9.25 | 0 | 1.13 | 8.03 |
| *C. carboxidivorans* DSM15243 | | | 10.43 | 0 | 10.34 | 0 |
| *C. ljungdahlii* DSM13528 | | | 10.23 | 0 | 3.73 | 6.54 |
| *C. ragsdalei* ATCC BAA-622 | | | 11.25 | 0 | 9.94 | 1.34 |
| *C. beijerinckii* NRRL-B593 | Isopopanol producing species | RCM | 9.96 | 0 | 7.65 | 2.54 |
| *C. beijerinckii* NCIMB8052 | Acetone producing species | | 10.49 | 0 | 10.59 | 0 |
| *C. acetobutylicum* ATCC824 | | | 10.80 | 0 | 10.91 | 0 |
| *Escherichia coli* DH5 (Invitrogen) | | LB + glucose | 11.67 | 0 | 11.71 | 0 |
| Blank media | Control | PETC | 10.51 | 0 | 10.55 | 0 |

All cultures were inoculated to an $OD_{600nm}$ of 0.1 in 50 ml appropriate media containing a heterotrophic carbon source and 30 psi steel mill gas. The cultures were allowed to double ($OD_{600nm}$=0.2) before acetone was added. A sample was taken and analyzed by HPLC and GC immediately after acetone addition and again at the end of growth (which were followed by measuring the optical density). Results are summarized in Table 11. Blank media was used as negative control.

As expected, isopropanol producing strain *C. beijerinckii* NRRL-B593 [George H A, Johnson J L, Moore W E C, Holdeman L V, Chen J S: Acetone, isopropanol, and butanol production by *Clostridium beijerinckii* (syn. *Clostridium butylicum*) and *Clostridium aurantibutyricum. Appl Environ Microbiol* 45: 1160-1163] had the ability to reduce externally added acetone to isopropanol by action of its alcohol dehydrogenase. A different strain of *C. beijerinckii*, NRCIMB8052, which lacks this enzyme wasn'table to convert acetone to isopropanol, as the acetone producing *C. acetobutylicum* ATCC-824. The same is also true for *E. coli.*

Surprisingly, three carboxydotrophic acetogenic bacteria *C. autoethanogenum, C. ljungdahlii*, and *C. ragsdalei*, which form a subcluster within the Clostridial rRNA Homology Group I, were found to be able to convert acetone to isopropanol as well, while all other acetogenic bacteria tested couldn't utilize acetone (Table 11). Conversion of different amounts of acetone to isopropanol by *C. autoethanogenum* was then tested using different concentrations (Table 12).

TABLE 12

| Conversion of different concentrations of acetone to isopropanol by cultures of *C. autoethanogenum* DSM23693. | | |
|---|---|---|
| Acetone [g/l] added | Acetone [g/l] left at end of growth | Isopropanol [g/l] left at end of growth |
| 0 | 0 | 0 |
| 1.66 | 0.22 | 1.48 |
| 9.25 | 1.13 | 8.03 |
| 26.13 | 17.82 | 8.39 |
| 50.01 | 43.30 | 6.95 |

A reactor study with *C. autoethanogenum* DSM23693 was performed to demonstrate effective conversion of acetone to isopropanol at high rates. The reactor was set-up as described above. Once in continuous mode with stable biomass and metabolite production, acetone was added to both the bioreactor and the feed medium. Acetone was spiked into the reactor to a certain level, which was then obtained by continuous feeding. Initially, 1 g/L acetone was added, once the metabolite concentrations had stabilised, the concentration was increased to 5 g/L, 15 g/l, and in a second experiment to 20 g/L. Even at high concentrations of 20 g/L the culture converted all acetone to isopropanol at high rate demonstrating that the identified primary:secondary alcohol dehydrogenase is highly effective (FIG. 74).

Identification of a Novel Alcohol Dehydrogenase in *C. autoethanogenum, C. ljungdahlii*, and *C. ragsdalei:*

To confirm that the conversion of acetone to isopropanol by *C. autoethanogenum* is driven enzymatically, enzyme assays were carried out with crude extract of *C. autoethanogenum* 23693, *C. beijerinckii* NRRL-B593, and *C. carboxidivorans* DSM15243 according to Ismaiel et al [Ismaiel A A, Zhu C X, Colby G D, Chen J S: Purification and characterization of a primary-secondary alcohol dehydrogenase from two strains of *Clostridium beijerinckii. J Bacteriol* 1993, 175: 5097-5105].

Crude extracts were obtained by sonication and lysozyme treatment (100,000 U/ml) of late exponential cultures. Cell debris was removed by centrifugation and protein concentrations was determined using the Pierce BCA protein assay— reducing agent compatible (Thermo Fisher Scientific Inc., Waltham Mass. 02454, USA). The assay mixture (1 ml) contained 50 mM Tris buffer (pH 7.5), 1 mM dithiothreitol (DTT), and 0.2 mM NAD(P)H. The reaction was started by adding 10 mM of the substrate acetone (from a 10-fold dilution in water) and followed spectrophotometrically with a Spectramax M2 (Molecular Devices, Inc., Sunnyvale, Calif. 94089-1136, USA) at a wavelength of 365 nm. $H_2O$ was used as negative control instead of crude extract and respectively acetone. Enzyme activity could be detected with crude extracts of both *C. beijerinckii* and *C. autoethanogenum* and NADPH (not with NADH), but not with crude extracts of *C. carboxidivorans* DSM15243 or $H_2O$ (with both NADPH and NADH). This demonstrates that the conversion of acetone to isopropanol by *C. autoethanogenum* is driven enzymatically, and as no activity was detected with NADH, the enzyme appears to be NADPH-dependent.

By sequencing and careful analysis, a novel alcohol dehydrogenase gene/enzyme was identified in all three strain, *C. autoethanogenum, C. ljungdahlii*, and *C. ragsdalei* (FIG. 1; SEQ_ID NO. 1-4). The amino acid sequence was found to be identical in all three species and share some homology to the primary-secondary alcohol dehydrogenase of *C. beijerinckii* NRRL-B593 (87%) and *T. brockii* ATCC 53556 (76%) (Table 13). Compared to the well-described secondary alcohol dehydrogenase of *C. beijerinckii* NRRL-B593 [Ismaiel A A, Zhu C X, Colby G D, Chen J S: Purification and characterization of a primary-secondary alcohol dehydrogenase from two strains of *Clostridium beijerinckii. J Bacteriol* 1993, 175: 5097-5105], a total of 49 amino acids exchanges were found. 4 amino acids of the catalytic centre of the protein are conserved, however, other amino acids in the catalytic domain are not (FIG. 1). A motif search predicted the novel alcohol dehydrogenase gene/enzyme to be zinc and NAD(P)H dependent. The respective genes coding for the novel alcohol dehydrogenase was found to be 98% identical within the 3 species *C. autoethanogenum, C. ljungdahlii*, and *C. ragsdalei*, but only 82% identical to the one from *C. beijerinckii* and 72% identical to the one from *T. brockii* (Table 14).

TABLE 13

Comparison of amino acid sequences of novel alcohol dehydrogenase and known secondary alcohol dehydrogenases

| Organism | Description | Seq ID | Accession number | Reference | Score | e-Value | Identity |
|---|---|---|---|---|---|---|---|
| *C. autoethanogenum* | — | SEQ_ID NO. 1 | — | — | 717 bits (1852) | 0 | 351/351 (100%) |
| *C. ljungdahlii* | zinc-containing alcohol dehydrogenase | SEQ_ID NO. 1 | YP_003780646.1 | — | 717 bits (1852) | 0 | 351/351 (100%) |
| *C. ragsdalei* | — | SEQ_ID NO. 1 | — | — | 717 bits (1852) | 0 | 351/351 (100%) |
| *C. beijerinckii* NRRL B-593 | NADP-dependent alcohol dehydrogenase | SEQ_ID NO. 38 | P25984.2 | Ismaiel et al., 1993 | 630 bits (1626) | 7E−179 | 302/351 (87%) |
| *T. brockii* ATCC 53556 | NADP-dependent alcohol dehydrogenase | SEQ_ID NO. 40 | P14941.1 | Peretz and Burstein, 1989 | 557 bits (1436) | 7E−157 | 264/351 (76%) |

TABLE 14

Comparison of nucleic acid sequences of novel alcohol dehydrogenase and known secondary alcohol dehydrogenases

| Organism | Description | Seq ID | Accession number | Reference | Score | e-Value | Identity |
|---|---|---|---|---|---|---|---|
| *C. autoethanogenum* | | SEQ_ID NO. 2 | — | — | 1905 bits (2112) | 0 | 1056/1056 (100%) |
| *C. ljungdahlii* | zinc-containing alcohol dehydrogenase | SEQ_ID NO. 3 | CP001666.1 | — | 1900 bits (2106) | 0 | 1055/1056 (99%) |
| *C. ragsdalei* | | SEQ_ID NO. 4 | — | — | 1803 bits (1998) | 0 | 1033/1056 (98%) |
| *C. beijerinckii* NRRL B-593 | NADP-dependent alcohol dehydrogenase | SEQ_ID NO. 39 | AF157307.2 | — | 558 bits (618) | 0 | 861/1056 (82%) |
| *T. brockii* | alcohol dehydrogenase | SEQ_ID NO. 41 | X64841.1 | — | 562 bits (622) | 3.00E−155 | 757/1053 (72%) |

Expression Studies of the Novel Alcohol Dehydrogenase from *C. autoethanogenum*

To identify, if the gene encoding the novel alcohol dehydrogenase is active during a normal fermentation with *C. autoethanogenum*, as well as identifying potential promoter regions for gene-overexpression, a qRT-PCR study with a over 250 genes was performed.

Samples were taken from a typical 1.5 l fed-batch fermentation run as described above over the whole growth (4 days). The samples were harvested by centrifugation (6,000×g, 5 min, 4° C.) and the cell pellet snap frozen in liquid nitrogen and stored at −80° C. until use. RNA was isolated by thawing the cell pellet on ice and suspending it in 100 μL of lysozyme solution (50,000 U lysozyme, 0.5 μL 10% SDS, 10 mM Tris-HCl, 0.1 mM EDTA; pH 8). After 5 min, 350 μL of lysis buffer (containing 10 μL of 2-mercaptoethanol) was added.

The cell suspension was mechanistically disrupted by passing five times through an 18-21 gauge needle. RNA was then isolated using PureLink™ RNA Mini Kit (Invitrogen, Carlsbad, Calif. 92008, USA) and eluted in 100 µL of RNase-free water. The RNA was checked via PCR and gel electrophoresis and quantified spectrophotometrically, and treated with DNase I (Roche) if necessary. The reverse transcription step was carried out using SuperScript III Reverse Transcriptase Kit (Invitrogen, Carlsbad, Calif. 92008, USA). RT-PCR reactions were performed in MyiQ Single Colour Real-Time PCR Detection System (Bio-Rad Labratories, Hercules, Calif. 94547, USA) in a reaction volume of 15 µL with 25 ng of cDNA template, 67 nM of each primer (Table 15), and 1× iQ SYBR Green Supermix (Bio-Rad Labratories, Hercules, Calif. 94547, USA). Guanylate kinase (GnK) and formate tetrahydrofolate ligase (FoT4L) were used as housekeeping gene and non-template controls were included. The reaction conditions were 95° C. for 3 min, followed by 40 cycles of 95° C. for 15 s, 55° C. for 15 s and 72° C. for 30 s. A melting-curve analysis was performed immediately after completion of the qRT PCR (38 cycles of 58° C. to 95° C. at 1° C./s), for detection of primer dimerisation or other artifacts of amplification. Data on the expression level was computed in the form of threshold cycle ($C_t$) values based on PCR base line subtracted curve fit method as calculated by the Biorad iQ5 2.0 software. The raw $C_t$ values were further analyzed using Relative Expression Software Tool (REST©) 2008 V2.0.7.

Figure 2:
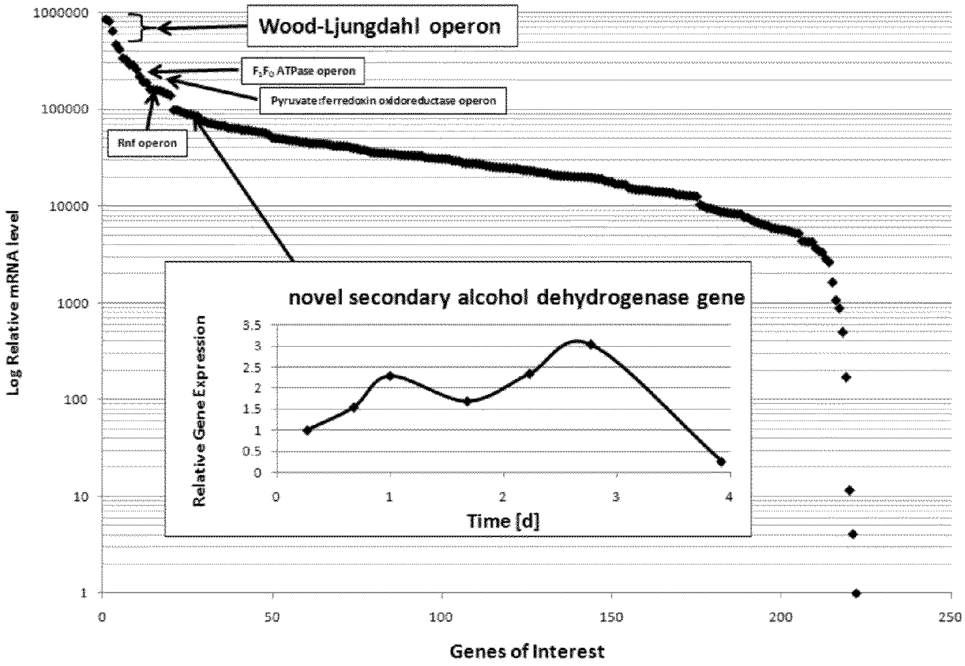
FIG. 2 show expression of novel alcohol dehydrogenase gene of *Clostridium autoethanogenum* DSM23693 during a typical fermentation run, as well as expression of genes controlled by Wood-Ljungdahl operon promoter, $F_1F_O$ ATPase operon promoter, Rnf complex operon promoter, and Pyruvate:ferredoxin oxidoreductase promoter. mRNA levels of more than 200 genes of interest were compared.

10-fold higher than the alcohol dehydrogenase gene (FIG. 2). The respective promoter (SEQ_ID NO 22) region is therefore ideal to over-express genes, such as the genes for acetone biosynthesis enzymes and an alcohol dehydrogenase gene, although in the case of over-expression of an alcohol dehydrogenase gene native to the micro-organisms it may require additional genetic modification to ensure sufficient co-factor availability. This could include, for example, (over-)expression of further genes to increase the NADPH pool such as transhydrogenase, elimination of competing NADPH consuming reactions, or protein engineering to change the co-factor requirement to NADH. Other useful promoter regions identified for gene over-expression include the promoter region of $F_1F_O$-ATPase operon (SEQ_ID NO 51), Rnf complex operon (SEQ_ID NO 52), and Pyruvate:ferredoxin oxidoreductase (SEQ_ID NO 53).

Figure 8:
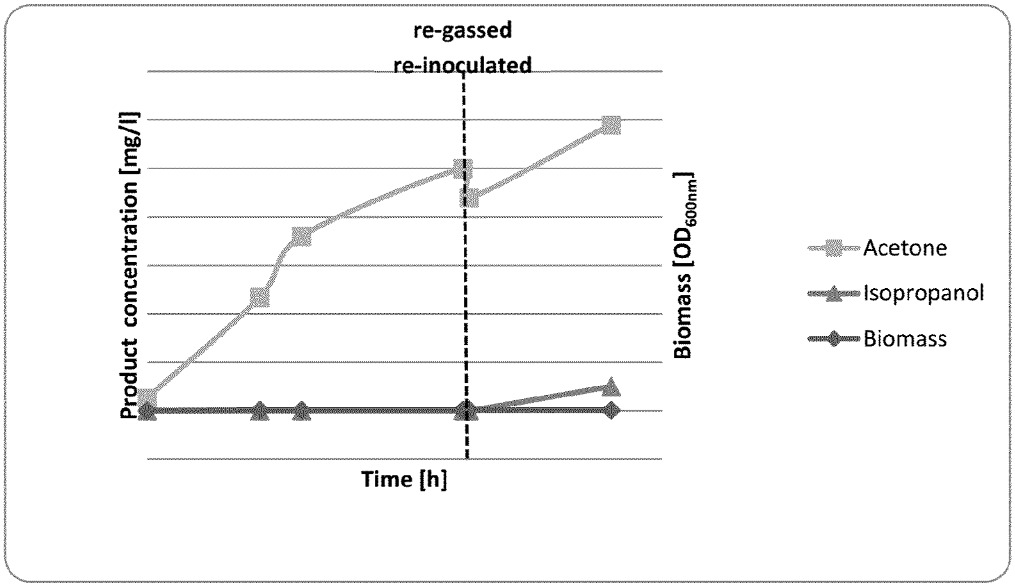
FIG. 8 shows the result of growth experiments with *C. autoethanogenum* DSM23693+pMTL85147-thlA-ctfAB-adc on steel mill gas.

Isopropanol Production from CO and $CO_2/H_2$ by *C. autoethanogenum* and *C. ljungdahlii* with Expression Plasmid Containing Clostridial Acetone Genes The 250 ml Schott bottle cultures of recombinant strains of *C. autoethanogenum* DSM23693 and *C. ljungdahlii* DSM 13528 carrying acetone expression plasmid pMTL85147-thlA-ctfAB-adc were shown to produce acetone, but no isopropanol could be detected (FIG. 8+9). This might be due to the lack of reducing power at end of growth, due to the given static conditions in Schott bottles, where CO gets depleted from the headspace and is not constantly fed like in a fed-batch or continuous fermentation process. Reducing equivalents such as NAD(P)H or ferredoxin gets generated from CO, but are also consumed for ethanol production, which already occurs during exponential and early stationary growth. At this point is the concentration of produced acetone, which is needed as precursor for isopropanol production, is still relatively low.

TABLE 15

Oligonucleotides for RT-PCR

| Target | Oligonucleotide Name | DNA Sequence (5' to 3') | SEQ_ID NO. |
|---|---|---|---|
| Guanylate kinase (gnk) | GnK-F | TCAGGACCTTCTGGAACTGG | 5 |
| | GnK-R | ACCTCCCCTTTTCTTGGAGA | 6 |
| Formate tetrahydrofolate ligase (FoT4L) | FoT4L-F | CAGGTTTCGGTGCTGACCTA | 7 |
| | FoT4L-F | AACTCCGCCGTTGTATTTCA | 8 |
| CO dehydrogenase (acsA) | acsA-F | ACAAGATGGGGTCGAAACAGTTTGG | 9 |
| | acsA-R | TGGCACTGGACTTACTCTACATGGG | 10 |
| Formyl-THF synthase (fhs) | fhs-F | TATTTCCGAAGATGATATTGAATTGTATGG | 11 |
| | fhs-R | TCCAGCAGGTGTTGGGTTTATAGC | 12 |
| Formimido-THF cyclodeaminase (fchA) | fchA-F | AGCTGCAACTCCTGGTGGAGGC | 13 |
| | fchA-R | GCCTTTTACCTTTTCGTCATACTGTGC | 14 |
| Methylene-THF dehydrogenase formyl-THF cyclohydrolase (folD) | folD-F | GCTTACATTAGTAAGAGTTGGAGCAAACG | 15 |
| | folD-R | ACTTGTCCTGTGATATATCTGCTGGTAGC | 16 |
| alcohol dehydrogenase (adh) | Adh-F | GGTCCTTATGATGCGATTGTACATCC | 17 |
| | Adh-R | GCTATTTCACCTACAGCTTCATGGCC | 18 |

The result of the qRT-PCR study showed, that the gene for the novel alcohol dehydrogenase is expressed over the whole growth on a relatively constant level and only ceases at end of growth (FIG. 2). Compared to over 200 genes chosen from every part of the metabolism, the alcohol dehydrogenase gene belongs to the top 50 expressed genes. The highest gene expression of all genes analyzed showed the genes of the Wood-Ljungdahl operon, with an mRNA level of more than Therefore, both cultures were re-gassed with 30 psi fresh steel-mill gas after 48 h of growth and also re-inoculated. While biomass didn't increase much further, some of the produced acetone got converted into isopropanol within 24 hours (Table 16).

TABLE 16

Conversion of acetone to isopropanol by cultures of *C. autoethanogenum* DSM23693 and *C. ljungdahlii* DSM 13528

| Organism | Acetone [mg/l] After 48 h | Acetone [mg/l] After 72 hours | Isopropanol [mg/l] After 48 h | Isopropanol [mg/l] After 72 hours |
|---|---|---|---|---|
| *C. autoethanogenum* + pMTL85147-thlA-ctfAB-adc | 220 | 295 | 0 | 25 |
| *C. ljungdahlii* + pMTL85147-thlA-ctfAB-adc | 171 | 175 | 0 | 5 |

In a fermentation system with constant supply of CO, sufficient reducing power is present for continuous production of isopropanol from CO or $CO/H_2$ and both acetone and isopropanol were produced in a respective fermentation run with C. autoethanogenum DSM23693 carrying acetone expression plasmid pMTL85147-thlA-ctfAB-adc.

Cloning of Novel Alcohol Dehydrogenase

The novel alcohol dehydrogenase was cloned into the acetone expression plasmid and put under control of the Wood-Ljungdahl promoter for gene over-expression and test of functionality in *E. coli.*

Figure 41:
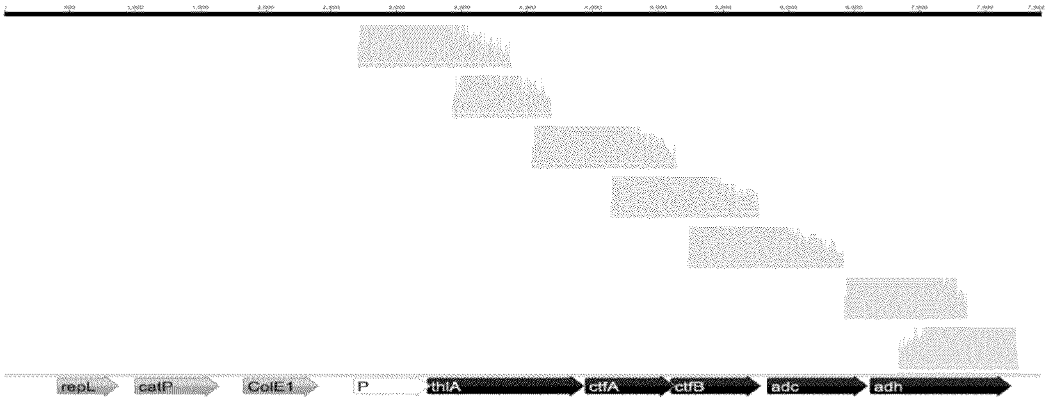
FIG. 41 shows the sequencing results of expression plasmid containing novel alcohol dehydrogenase pMTL85147-thlA-ctfA-ctfB-adc-adh.
Figure 43:
FIG. 43 shows expression plasmid containing novel alcohol dehydrogenase pMTL85147-thlA-ctfA-ctfB-adc-adh.

Alcohol dehydrogenase was amplified from isolated C. autoethanogenum DSM10061 chromosomal DNA using oligonucleotides SecAdh-SalI-F (SEQ_ID NO 54: TATTTGTCGACTTAGGAGGTTCTATTATGAAAGG) and SecAdh-XhoI-R (SEQ_ID NO 55: AAAACTCGAGACATTTTTTTAATGCGACAG). The 1129 bp PCR fragment was cloned into plasmid pMTL85147-thlA-ctfAB-adc using SalI and XhoI and *E. coli* XL-1 Blue MRF' Kan. The resulting plasmid pMTL85147-thlA-ctfA-ctfB-adc-adh (SEQ_ID NO 48; FIG. 43) was completely sequenced using oligonucleotides given in Table 9 and results confirmed that the isopropanol biosynthesis genes and promoter region were free of mutations (FIG. 41).

Production of Isopropanol with Novel Alcohol Dehydrogenase from *C. autoethanogenum* in *E. coli*

To further test the functionality of the novel alcohol dehydrogenase from C. autoethanogenum, growth experiments were carried out using *E. coli* XL-1 Blue MRF' Kan expressing only the acetone biosynthesis genes (carrying plasmid pMTL 85147-thlA-ctfA-ctfB-adc) and expressing the acetone biosynthesis genes plus the novel alcohol dehydrogenase (carrying plasmid pMTL85147-thlA-ctfA-ctfB-adc-adh) in 100 ml SD-8 minimal media with chloramphenicol (FIG. 42).

While no isopropanol could be detected with the strain carrying the acetone plasmid, an average maximum of 32.7 mg/L isopropanol was measured with the strain additionally expressing the novel alcohol dehydrogenase from *C. autoethanogenum.*

Identification of Genes from *Lactococcus lactis* and *Saccharomyces cerevisiae* that Confer Novel Activity Towards Acetone or Isopropanol in *C. autoethanogenum*

In addition to the Clostridial acetone and isopropanol pathway, two enzymes an Alpha-ketoisovalerate decarboxylase (KivD) from *Lactococcus lactis* and an Alcohol dehydrogenase (Adh2) from *Saccharomyces cerevisiae* (Table 18) were identified that confer activity towards acetone and isopropanol production in *C. autoethanogenum*. Those two enzymes haven't been reported to be involved in acetone or isopropanol production or have catalytic functions on any of the precursors in the Clostridial acetone and isopropanol pathway. Heterologous expression of these proteins in *E. coli* (Atsumi et al., 2008. Non-fermentative pathways for synthesis of branched-chain higher alcohols as biofuels. Nature, 451: 86-90) or other organisms like *Corynebacterium glutamicum* (Blombach et al., 2011. *Corynebacterium glutamicum* tailored for efficient Isobutanol production. *Appl. Environ. Microbiol.* 77: 3300-10) or *Clostridium cellulolyticum* (Higashide W., et al. 2011. Metabolic Engineering of *Clostridium* cellulolyticum for Production of Isobutanol from Cellulose. *Appl. Environ. Microbiol.* 77: 2727-33) led to production of branched-chain higher alcohols like isobutanol, 1-butanol, 2-methyl-1-butanol, 3-methyl-1-butanol and 2-phenylethanol from amino acid precursors, but neither acetone nor isobutanol was reported. Expression of codon-optimized Alpha-ketoisovalerate decarboxylase (KivD) from *Lactococcus lactis* alone or a combination of codon optimized Alpha-ketoisovalerate decarboxylase (KivD) from *Lactococcus lactis* and an Alcohol dehydrogenase (Adh2) from *Saccharomyces cerevisiae* in *C. autoethanogenum* however, led suprisingly to production of acetone and isopropanol.

TABLE 18

Sequences from *Lactococcus lactis* and *Saccharomyces cerevisiae* that confer novel activity towards acetone or isopropanol in *C. autoethanogenum*

| Description | nucleic acid | amino acid |
|---|---|---|
| | *L. lactis* | |
| Alpha-ketoisovalerate decarboxylase (KivD) | SEQ_ID No. 72 AJ746364 | SEQ_ID No. 73; YP_003353820.1 |
| | *S. cerevisiae* | |
| Alcohol dehydrogenase (Adh2) | SEQ_ID No. 74 NC_001145.2, GeneID: 855349 | SEQ_ID No. 75; AAA34408.1 |

Construction of Expression Plasmid with Alpha-Ketoisovalerate Decarboxylase (Kivd) from *Lactococcus lactis* and Alcohol Dehydrogenase (Adh2) from *Saccharomyces cerevisiae*

The Alpha-ketoisovalerate decarboxylase (decarboxylase; KivD) from *L. lactis*, and Alcohol dehydrogenase (Adh2) from *S. cerevisiae* (Table 18) were codon-optimised by ATG: Biosynthetics GmbH (Merzhausen, Germany) and flanked by NdeI and KpnI restriction sites for further sub-cloning. The Phosphiotransacetylase/Acetate kinase operon promoter of *C. autoethanogenum* was used for expression of target genes. All DNA sequences used are given in Table 19.

TABLE 19

Sequences used for expression plasmid with Alpha-ketoisovalerate decarboxylase (KivD) from *Lactococcus lactis* and Alcohol dehydrogenase (Adh2) from *Saccharomyces cerevisiae*

| Description | Source | SEQ_ID NO. |
|---|---|---|
| Alpha-ketoisovalerate decarboxylase (KivD) and Alcohol dehydrogenase (Adh2) | Codon optimized | 76-78 |

TABLE 19-continued

| Sequences used for expression plasmid with Alpha-ketoisovalerate decarboxylase (KivD) from *Lactococcus lactis* and Alcohol dehydrogenase (Adh2) from *Saccharomyces cerevisiae* | | |
|---|---|---|
| Description | Source | SEQ_ID NO. |
| Phosphotransacetylase/ Acetate kinase operon promoter region | *Clostridium autoethanogenum* DSM10061 | 79 |

The promoter region of the phosphotransacetylase-acetate kinase operon ($P_{pta-ack}$) was amplified using primers Ppta-ack-NotI-F (Seq. ID. No. 80: GAGCGGCCGCAATATGATATTTATGTCC) and Ppta-ack-NdeI-R (Seq. ID. No. 81: TTCCATATGTTTCATGTTCATTTCCTCC) and cloned into the *E. coli-Clostridium* shuttle vector pMTL 85141 (FJ797651.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] using NotI and NdeI restriction sites and strain XL1-Blue MRF' Kan.

The antibiotic resistance gene in the created plasmid pMTL85145 was subsequently replaced with an erythromycin resistance gene from pMTL 82254 (FJ797646.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] using FseI and PmeI restriction sites and strain XL1-Blue MRF' Kan.

Figure 63:
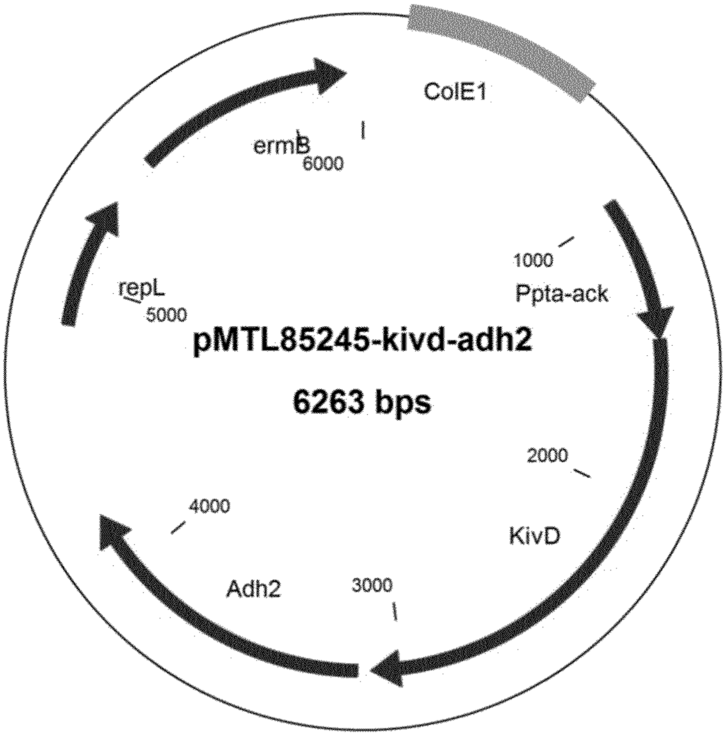
FIG. 63 shows acetone expression plasmid pMTL85245-kivd-adh2

The created plasmid pMTL85245 (Seq. ID. No. 80) and the 2746 bp codon-optimised product of the decarboxylase and alcohol dehydrogenase (Adh2) gene cluster were both cut with NdeI and KpnI. A ligation was transformed into *E. coli* XL1-Blue MRF' Kan resulting in plasmid pMTL85245-kivd-adh2 (Seq. ID. No. 83; FIG. 63). The insert of the resulting plasmid pMTL85245-kivd-adh was completely sequenced using oligonucleotides given in Table 20 and results confirmed that genes and promoter region were free of mutations.

Figure 64:
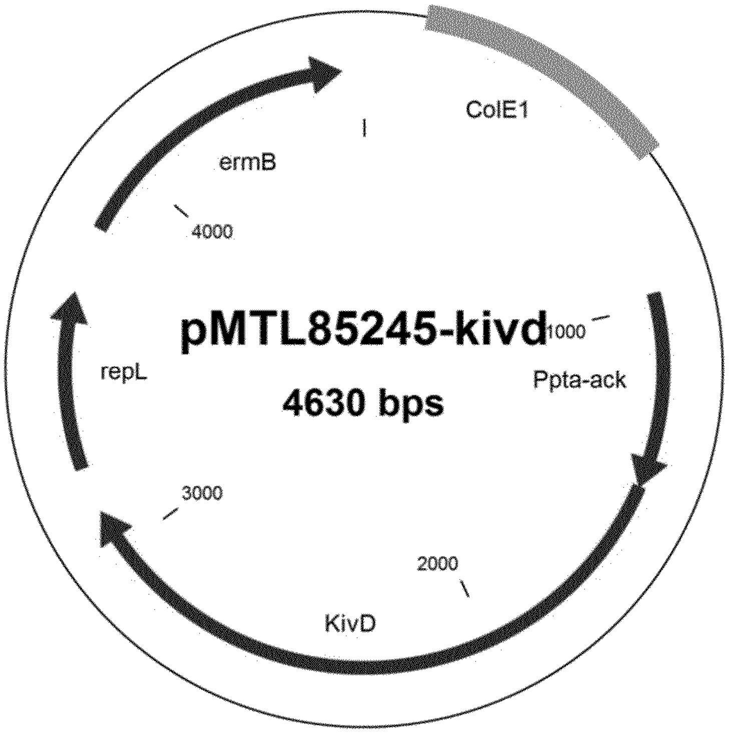
FIG. 64 shows acetone expression plasmid pMTL85245-kivd

The kivD gene alone was amplified using primer pair M13 Reverse (Seq. ID. 57: CAGGAAACAGCTATGAC) and Adh seqR1 (Seq. ID. 85; Table 16). The 2635 bp PCR fragment of KivD was cloned into the *E. coli-Clostridium* shuttle vector pMTL 85245 using NdeI and EcoRI restriction sites and strain *E. coli* XL1-Blue MRF' Kan, creating plasmid pMTL85245-kivd (Seq. ID No. 84; FIG. 64). The insert of the resulting plasmid pMTL85245-kivd was completely sequenced using oligonucleotides given in Table 20 and results confirmed that the acetone biosynthesis gene was free of mutations.

TABLE 20

| Oligonucleotides used for sequencing | | |
|---|---|---|
| Adh_seqR1 | TCAGTTCCCTGTGGAATGTGTGC | Seq. ID. No. 85 |
| Kivd_seqR2 | TCAGTAGCACCGAAAGATTCAG | Seq. ID. No. 86 |
| Kivd_seqR3 | AGTGCCTCATCTACTGAACTC | Seq. ID. No. 87 |
| -ori_F | ATTAGTTTAAACACGCCAGCAACGCGGCCTTTTTAC | Seq. ID. No. 88 |
| ctfAB_seqR1 | TCCTATTCCAAGGTTTACGAGTTGGTC | Seq. ID. No. 89 |
| ctfAB_seqR2 | ACCCCCAACCATAATTGTCATGCCATC | Seq. ID. No. 90 |
| ctfAB_seqR3 | TGCAAGAGCAAACTCATCTTGTTCTTC | Seq. ID. No. 91 |
| P-thl-ctfAB_R2 | AGGGTGCGGCCGCGATTCATATATCCATAATCTTTAAGTTATC | Seq. ID. No. 92 |

Figure 65:
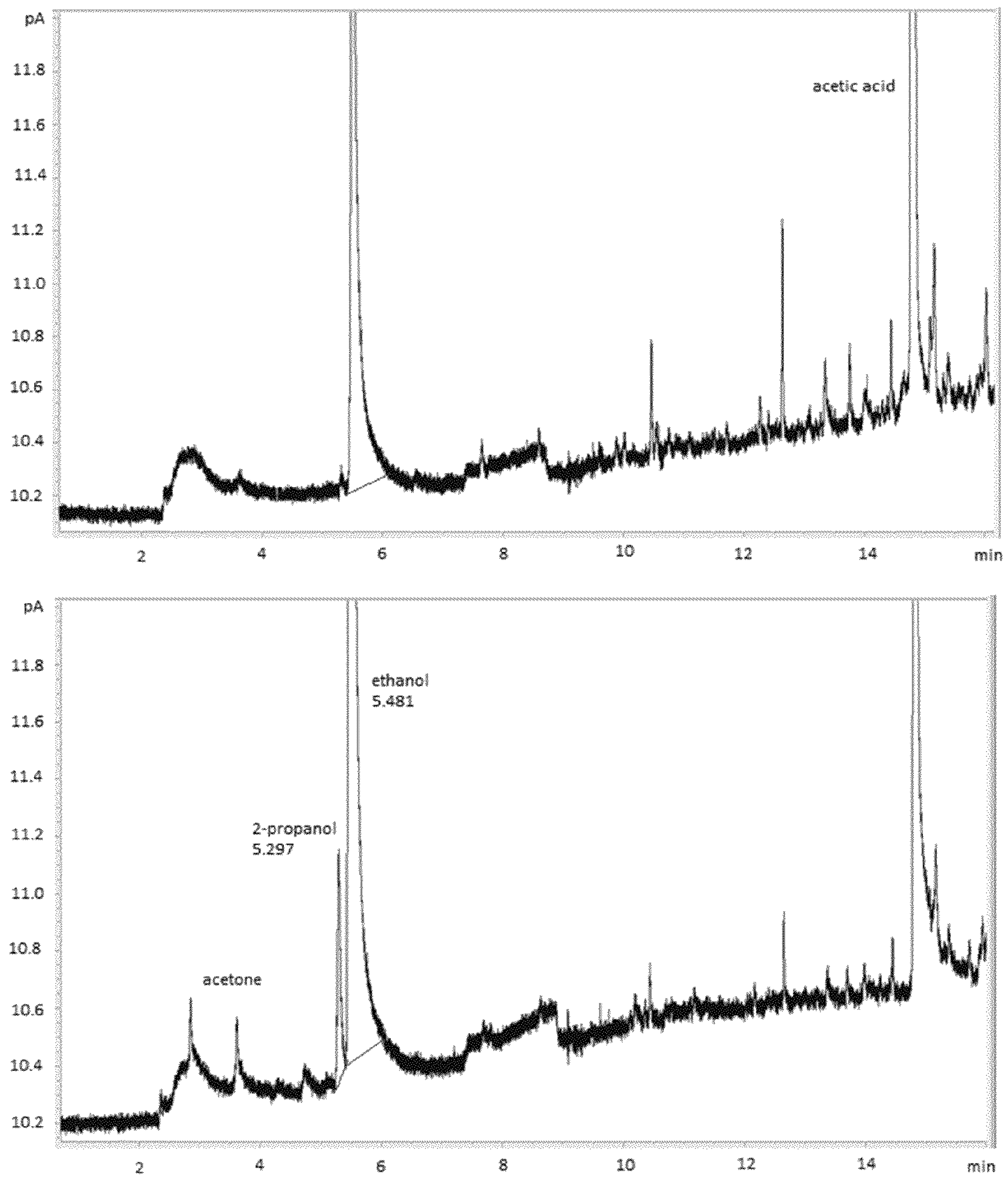
FIG. 65 shows the GC result confirming acetone and isopropanol production with *C. autoethanogenum* DSM23693 as a control strain (top) and *C. autoethanogenum* DSM23693+pMTL85245-kivd-adh2 (bottom) from CO-containing steel mill gas.
Figure 66:
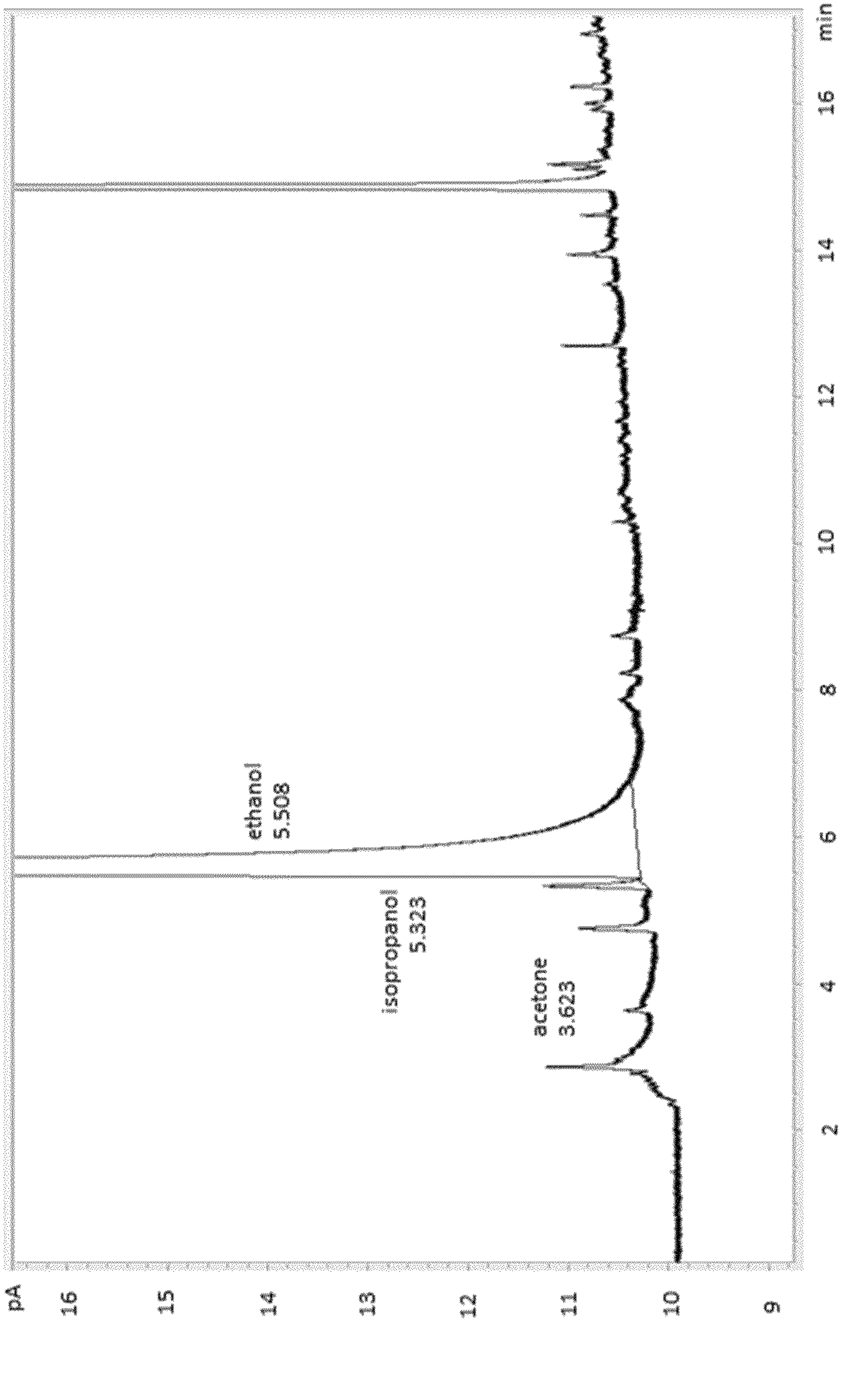
FIG. 66 shows the GC result confirming acetone and isopropanol production with *C. autoethanogenum* DSM23693+pMTL85245-kivd from CO-containing steel mill gas.

Expression of Codon-Optimized Genes for Alpha-Ketoisovalerate Decarboxylase (Kivd) from *Lactococcus lactis* and Alcohol Dehydrogenase (Adh2) from *Saccharomyces cerevisiae* in *C. autoethanogenum* for Production of Acetone and Isopropanol Constructed expression plasmids pMTL85245-kivd-adh2 and pMTL85245-kivd were transformed into *E. coli* strain JW3350-2 and prepared for transformation in *C. autoethanogenum* DSM23693, which was performed as described above. While in *E. coli* harbouring the two plasmids, neither acetone nor isopropanol could be detected (but higher branched-chain alcohols such as isobutanol as described in the literature), in *C. autoethanogenum*, both acetone and isopropanol could be detected. In serum bottle experiments, highest isopropanol concentrations from CO-containing steel mill gas were 0.050-0.064 g/L for both expression plasmids (FIGS. 65 and 66).

Production of Acetone and Isopropanol with a Combination of Clostridial Pathway Genes and Alpha-Ketoisovalerate Decarboxylase (KivD) from *Lactococcus lactis* and Alcohol Dehydrogenase (Adh2) from *Saccharomyces cerevisiae*

Without wanting to be bound by any particular theory, the inventors believe that the codon-optimized alpha-ketoacid decarboxylase Kivd from *Lactococcus lactis* has activity converting acetoacetate to acetone, as the Clostridial acetoacetate decarboxylase, while the codon-optimized alcohol dehydrogenase Adh2 from *Saccharomyces cerevisiae* have activity converting acetone to isopropanol as the novel primary:secondary alcohol dehydrogenase identified or the primary:secondary alcohol dehydrogease from *Clostridium beijkerickii*. To test this hypothesis several combinations of Clostridial acetone/isopropanol pathway genes and the alpha-ketoacid decarboxylase Kivd from *Lactococcus lactis* and alcohol dehydrogenase Adh2 from *Saccharomyces cerevisiae* have been created and tested within *E. coli* and *C. autoethanogenum* demonstrating production of acetone and isopropanol.

Construction of Expression Plasmids with Different Gene Combinations

Based on the constructed expression plasmids pMTL85147-thlA-ctfA-ctfB-adc, pMTL85245-kivd-adh2 and pMTL85245-kivd, new combinations were constructed.

Figure 67:
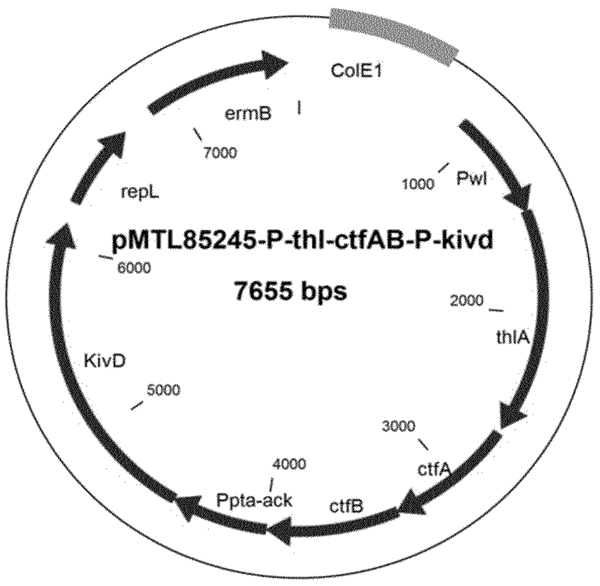
FIG. 67 shows acetone expression plasmid pMTL85147-thlA-ctfA-ctfB-adc-P-kivd

A 3122 bp $P_{WL}$-thlA-ctfAB fragment was amplified from plasmid pMTL85147-thlA-ctfA-ctfB-adc using oligonucleotides P-thl-ctfAB_F2 (Seq. ID. No. 93: ATCTTCTGCAGGGCCGCAGATAGTCATAATAGTTCCAG) and P-thl-ctfAB_R2 (Seq. ID. No. 94: AGGGTGCGGCCGCGATTCATATATCCATAATCTTTAAGTTATC). The amplified fragment was cloned into plasmid pMTL 85245-kivd using PstI and NotI restriction sites and strain *E. coli* XL1-Blue MRF' Kan, creating plasmid pMTL85245-$P_{WL}$-thlA-ctfAB-kivd (Seq. ID. No. 95; FIG. 67). The insert of the resulting plasmid pMTL85245-$P_{WL}$-thlA-ctfAB-kivd was completely sequenced using oligonucleotides given in Table 9 and 20 and confirmed that the plasmid was free of mutations.

Figure 68:
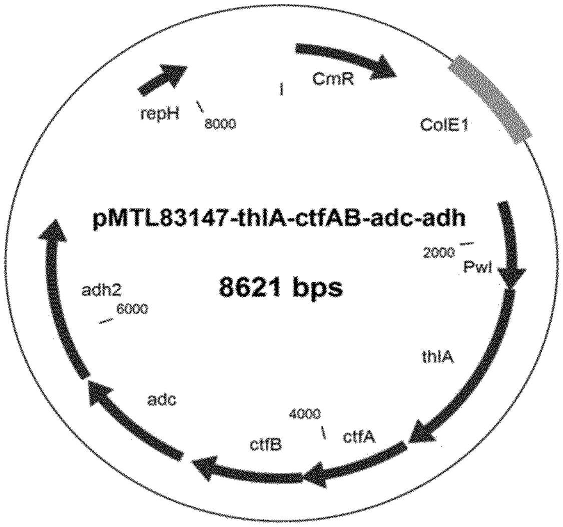
FIG. 68 shows acetone expression plasmid pMTL83147-thlA-ctfA-ctfB-adc-adh
Figure 69:
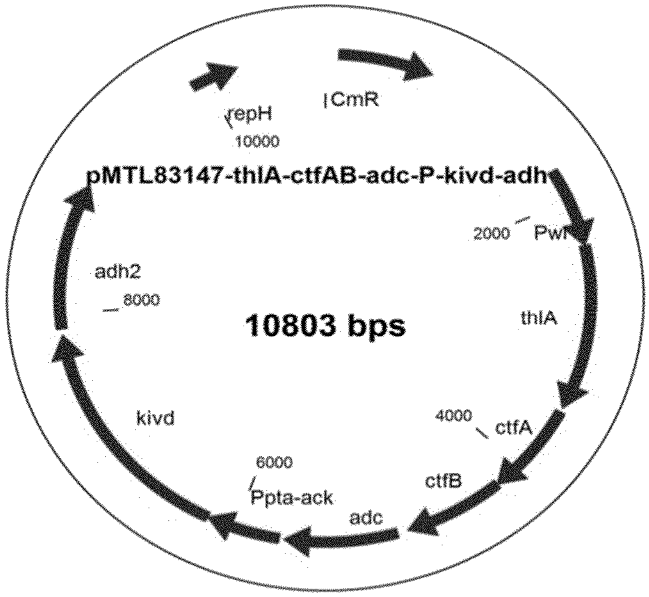
FIG. 69 shows acetone expression plasmid pMTL83147-thlA-ctfA-ctfB-adc-P-kivd-adh

The Adh2 gene was amplified from plasmid pMTL85245-kivd-adh2 using primer pair adh_F (Seq. ID. No. 96: ACGTTGGATCCAGGAGGAACAAAGATGAGTATACC) and P-kivd-adh_R (Seq. ID. No. 97: AGCGTCCATGGCCTTATTTACTTGTATCTACAACATATC). The 1084 bp PCR fragment was cloned into the plasmid pMTL85147-thlA-ctfAB-adc using BamHI and NcoI restriction sites and strain *E. coli* XL1-Blue MRF' Kan, creating plasmid pMTL85147-thlA-ctfAB-adc-adh2 (Seq. ID. No. 98; FIG. 68). The created plasmid pMTL85147-thlA-ctfAB-adc-adh2 and a 1625 bp fragment of the repL gene from pMTL83151 (FJ797647.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] were both cut with FseI and AscI. A ligation was performed resulting in plasmid pMTL83147-thlA-ctfAB-adc-adh2. The insert of the resulting plasmid pMTL83147-thlA-ctfAB-adc-adh2 was completely sequenced using oligonucleotides given in Table 9 and 20 and results confirmed that the fragment was mutation free. Oligonucleotides P-kivd-adh_F (Seq. ID. No. 99: ATATTGGATCCACAGCTATGACCGCGGCCGCAATATG) and P-kivd-adh_R (Seq. ID. No. 100: AGCGTCCATGGCCTTATTTACTTGTATCTACAACATATC) were used to amplify a 3266 bp PCR fragment of $P_{pta\text{-}ack}$-kivd-$adh^2$ from plasmid pMTL85245-kivd-adh2, which was then cloned into the plasmid pMTL85147-thlA-ctfAB-adc using BamHI and NcoI restriction sites and strain *E. coli* XL1-Blue MRF' Kan, creating plasmid pMTL83147-thlA-ctfAB-adc-$P_{pta\text{-}ack}$-kivd-adh2 (Seq. ID. 101; FIG. 69). The created plasmid pMTL83147-thlA-ctfAB-adc-$P_{pta\text{-}ack}$-kivd-$adh^2$ and a 1625 bp fragment of the repL gene from pMTL83151 (FJ797647.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] were both cut with FseI and AscI. A ligation was performed resulting in plasmid pMTL83147-thlA-ctfAB-adc-$P_{pta\text{-}ack}$-kivd-$adh^2$. The insert of the resulting plasmid pMTL83147-thlA-ctfAB-adc-$P_{pta\text{-}ack}$-kivd-$adh^2$ was completely sequenced using oligonucleotides given in Table 9 and results confirmed that the plasmid was free of mutations.

Production of Acetone and Isopropanol in *C. autoethanogenum* Using Different Gene Combinations Methylation of the newly constructed expression plasmids pMTL85147-thlA-ctfA-ctfB-adc, pMTL83147-thlA-ctfAB-adc-adh2 and pMTL83147-thlA-ctfAB-adc-$P_{pta\text{-}ack}$-kivd-$adh^2$ were performed in vivo in *E. coli* using a synthesized hybrid Type II methyltransferase gene (SEQ_ID NO 35) designed from methyltransferase genes from *C. autoethanogenum, C. ragsdalei* and *C. ljungdahlii* and transformed into *C. autoethanogenum* DSM23693 as described above.

Figure 73:
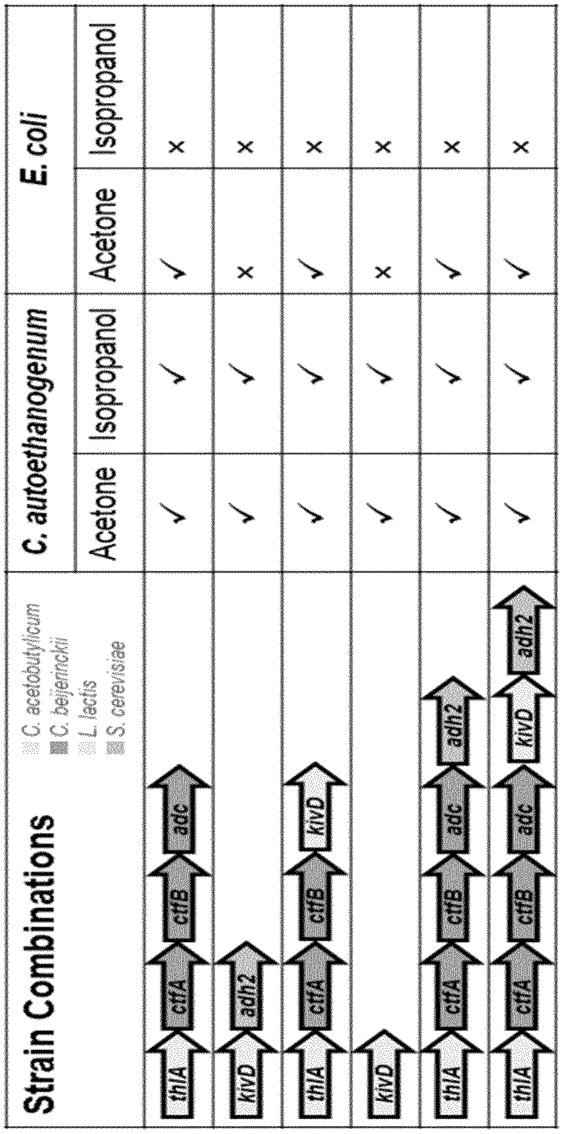
FIG. 73 shows tested gene combinations of Clostridial pathway genes and codon-optimized Alpha-ketoacid decarboxylase Kivd from *L lactis* and Alcohol dehydrogenase Adh2 from *S. cerevisiae* heterologously expressed in *E. coli* and *C. autoethanogenum.*

All plasmid construct were tested in *E. coli* and *C. autoethanogenum* DSM23693 using serum bottle experiments with sugar (*E. coli*) or CO-containing steel mill gas (*C. autoethanogenum*) as sole substrate. With all combinations tested, acetone and isopropanol production was measured when expressed heterologously in *C. autoethanogenum*, while in *E. coli* acetone production only occurred with few combinations and an alcohol dehydrogenase gene was needed for isopropanol production (Table 21). The results presented show that both, in *E. coli* as well as *C. autoethanogenum*, the codon-optimized Alpha-ketoacid decarboxylase Kivd from *Lactococcus lactis* is able to replace the Clostridial acetoacetate decarboxylase and catalyse the conversion of acetoacetate to acetone (FIG. 4). In *C. autoethanogenum*, acetone and isopropanol production even occurred with expressing the decarboxylase as only heterologous gene, indicating CoA-transferase activity. FIG. 4 illustrates the proposed pathway and Table 21 of acetone and isopropanol formation from CO and FIG. 73 gives an overview of combinations of Clostridial pathway genes and codon-optimized genes for Alpha-ketoacid decarboxylase Kivd from *L lactis* and Alcohol dehydrogenase Adh2 from *S. cerevisiae* tested in *E. coli* and *C. autoethanogenum.*

Figure 70:
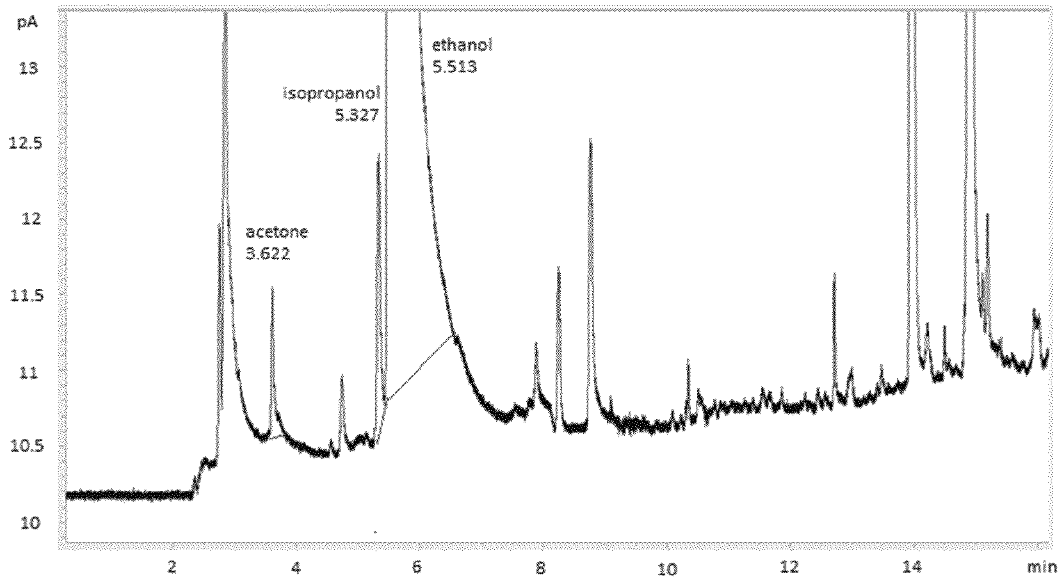
FIG. 70 shows the GC result confirming acetone and isopropanol production with *C. autoethanogenum* DSM23693 (top) and *C. autoethanogenum* DSM23693+pMTL85245-Pwl-thlA-ctfAB-kivd from CO-containing steel mill gas.
Figure 71:
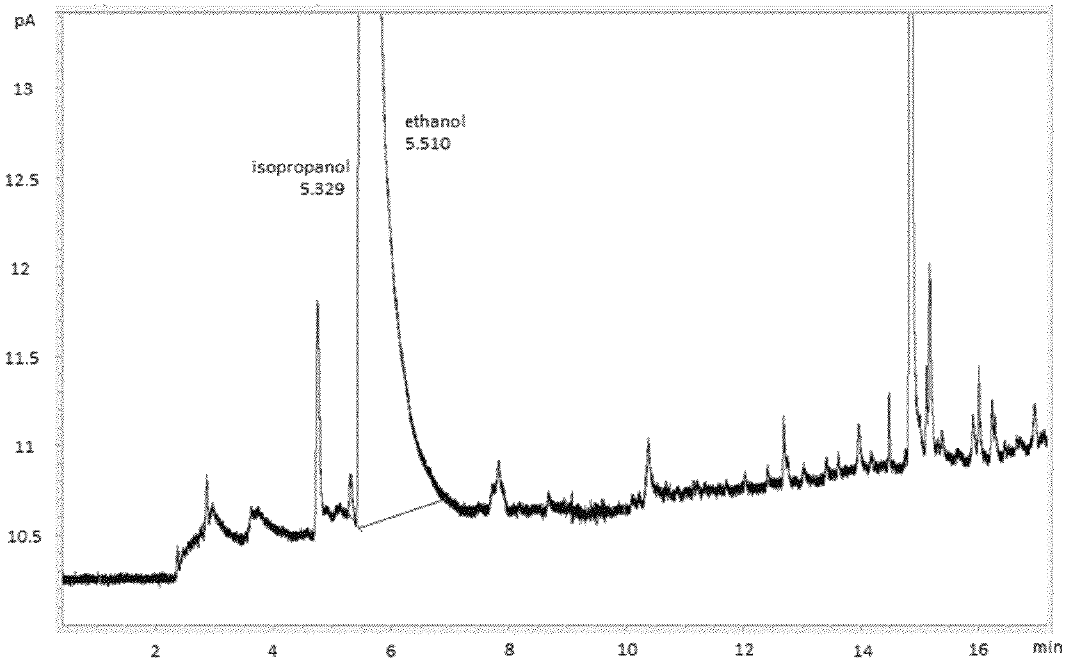
FIG. 71 shows the GC result confirming acetone and isopropanol production with *C. autoethanogenum* DSM23693+pMTL83147-thlA-ctfAB-adc-adh2 from CO-containing steel mill gas.
Figure 72:
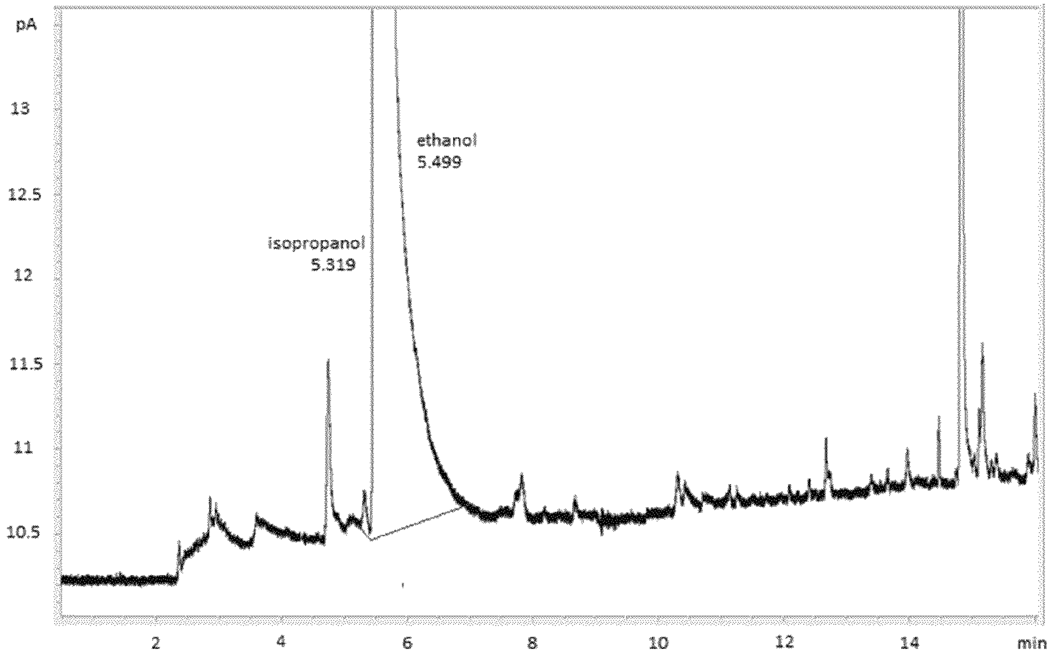
FIG. 72 shows the GC result confirming acetone and isopropanol production with *C. autoethanogenum* DSM23693+pMTL83147-thlA-ctfAB-adc-P-kivd-adh2 from CO-containing steel mill gas.

Production of acetone and isopropanol with *C. autoethanogenum* DSM23693 and plasmids pMTL85245-$P_{WL}$-thlA-ctfAB-kivd, pMTL83147-thlA-ctfAB-adc-adh2 and pMTL83147-thlA-ctfAB-adc-$P_{pta\text{-}ack}$-kivd-adh2 from CO-containing steel mill gas is shown in FIGS. 70, 71, and 72 respectively.

TABLE 21

Acetone and isopropanol produced from various combinations of genes

| | Organism | Substrate | Acetone (g/L) | Isopropanol (g/L) |
|---|---|---|---|---|
| Clostridia genes | | | | |
| pMTL85147-thlA-ctfAB-adc | *E. coli* | Sugar | 0.200 | N/A |
| | *C. autoethanogenum* | CO | 0.300 | 0.025 |
| | *C. ljungdahlii* | CO | 0.180 | 0.005 |

TABLE 21-continued

| Acetone and isopropanol produced from various combinations of genes | | | | |
|---|---|---|---|---|
| | Organism | Substrate | Acetone (g/L) | Isopropanol (g/L) |
| pMTL85147-thlA-ctfAB-adc-sadh (*C. beijerinckii*) | *E. coli* | Sugar | 0.080 | 0.070 |
| pMTL85147-thlA-ctfAB-adc-sadh (*C. autoethanogenum*) | *E. coli* | Sugar | 0.060 | 0.080 |
| Novel genes | | | | |
| pMTL85245-kivd-adh2 | *E. coli* | Sugar | N/A | N/A |
| | *C. autoethanogenum* | CO | Detected by GC qualitatively | 0.050 |
| pMTL85245-kivd | *E. coli* | Sugar | N/A | N/A |
| | *C. autoethanogenum* | CO | Detected by GC qualitatively | 0.064 |
| Combination of Clostridia and novel genes | | | | |
| pMTL85147-thlA-ctfAB-adc-kivd | *E. coli* | Sugar | Detected by GC qualitatively | N/A |
| | *C. autoethanogenum* | CO | Detected by GC qualitatively | 0.091 |
| pMTL83147-thlA-ctfAB-adc-adh2 | *E. coli* | Sugar | 0.040 | N/A |
| | *C. autoethanogenum* | CO | Detected by GC qualitatively | 0.648 |
| pMTL83147-thlA-ctfAB-adc-P-kivd-adh2 | *E. coli* | Sugar | 0.076 | N/A |
| | *C. autoethanogenum* | CO | Detected by GC qualitatively | 0.043 |

Tolerance to Acetone and Isopropanol and Detoxification of Acetate in Acetogens

Figure 12:
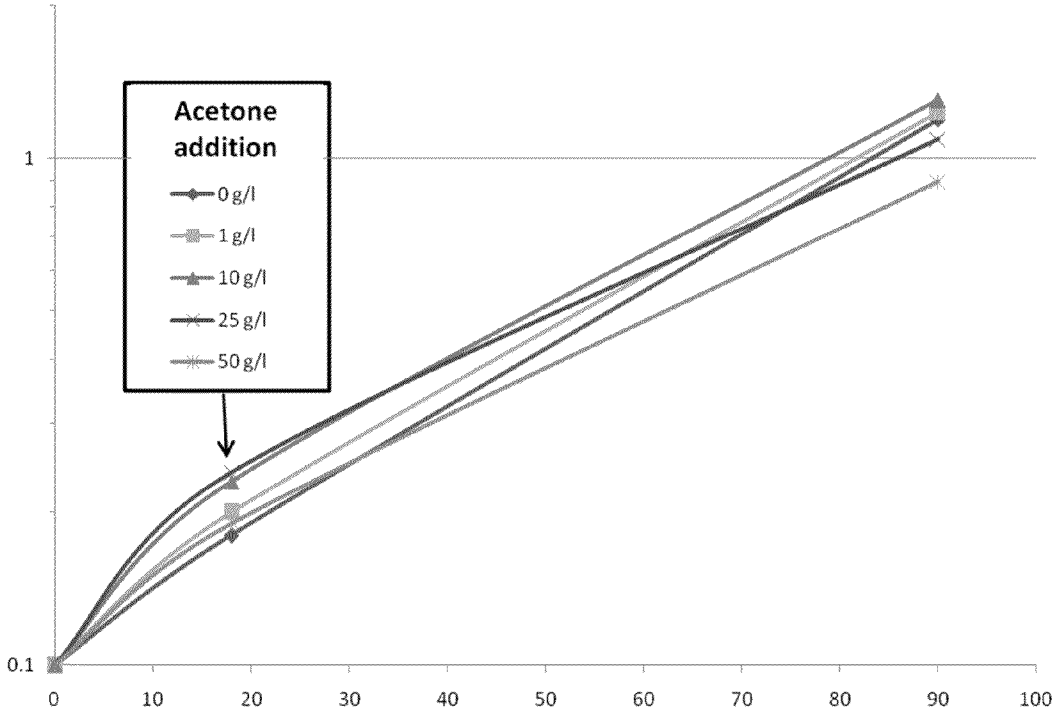
FIG. 12 shows the toxicity of acetone on cultures of *C. autoethanogenum* DSM23693.
Figure 13:
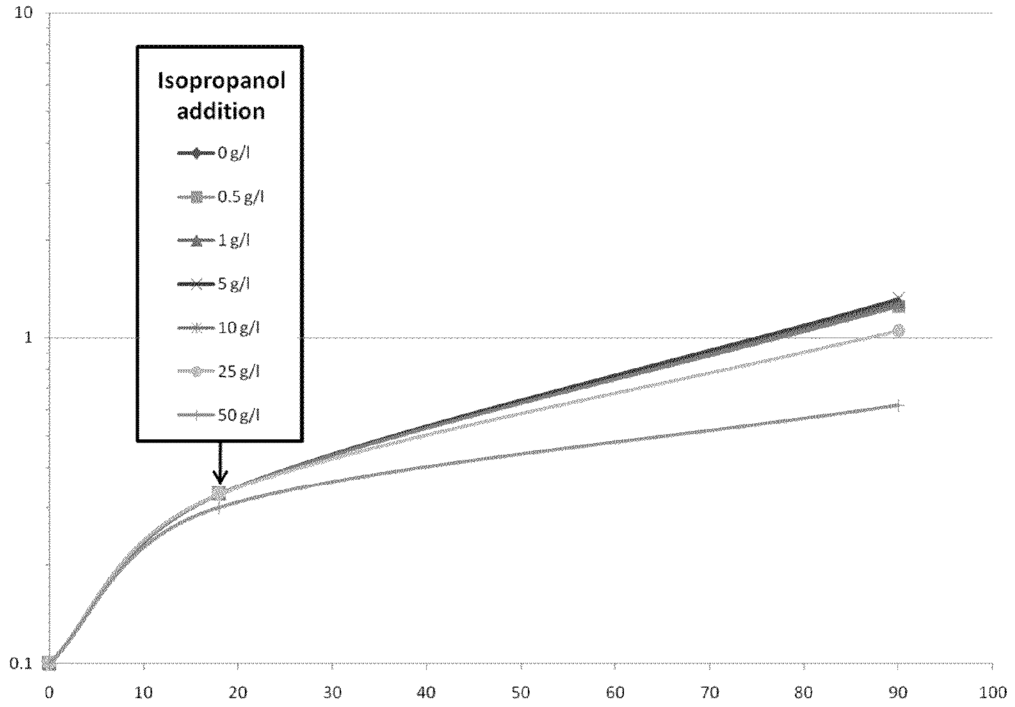
FIG. 13 shows the toxicity of isopropanol on cultures of *C. autoethanogenum* DSM23693.

Several metabolites such as alcohols (ethanol and butanol) or acids (acetic acid and butyric acid) are known to be toxic for bacteria in high concentrations and thus limit their biotechnological production [Alsaker K V, Parades C, Papoutsakis E T: Metabolite stress and tolerance in the production of biofuels and chemicals—systems analysis of butanol, butyrate, and Acetate Stresses in the Anaerobe *Clostridium acetobutylicum*. Biotechnol Bioeng, 2009, 105: 1131-1147]. To see if acetone and isopropanol have a toxic effect on cultures, growth experiments were carried out in 50 ml PETC media (Table 2) in serum bottles, adding different concentrations of acetone (FIG. 12) and isopropanol (FIG. 13) to growing cultures of *Clostridium autoethanogenum* DSM23693. Cell growth was visible in presence of concentrations as high as 5% acetone or isopropanol (with only slight inhibition of growth rate).

A high concentration of free or undissociated acetic acid on the other hand is known to be detrimental for most anaerobic bacteria (including acetogenic bacteria) due to the deleterious effect on the membrane gradient [Warnecke T, Gill R T: Organic acid toxicity, tolerance, and production in *Escherichia coli* biorefining applications. Microb Cell Fact, 2005, 4: 25; Köpke M, Dürre P: Biochemical production of biobutanol, in Luque R, Campelo J, Clark J H (Eds.): Handbook of biofuel production—Processes and technologies, Woodhead Publishing, Camebridge, 2010: 221-257]. Acetogenic bacteria however, need to produce acetic acid to gain ATP from substrate level phosphorylation [Drake H L, Küsel K, Matthies C: Acetogenic Prokaryotes. In Dworkin M, Falkow S, Rosenberg E, Schleifer K H, Stackebrandt E (eds.): The Prokaryotes, 3rd Edition, Volume 2, Springer, New York, 2006: 354-420] and thus all known acetogenic species produce acetic acid [Drake H L, Küsel K, Matthies C: Acetogenic Prokaryotes. In Dworkin M, Falkow S, Rosenberg E, Schleifer K H, Stackebrandt E (eds.): The Prokaryotes, 3rd Edition, Volume 2, Springer, New York, 2006: 354-420]. Conversion of acetic acid to other products such as ethanol via aldehyde ferredoxin oxidoreductase (AOR) or back to acetyl-CoA via phosphotransacetylase/acetate kinase (Pta/Ack) or AMP-dependent acetyl-CoA synthase (Acs) is unfavourable, since it requires energy in the form of reduced ferredoxin or ATP [Wolfe A J: The acetate switch. Microbiol Mol Biol Rev, 2005, 69: 12-50]. This invention presents a novel mode of acetic acid detoxification in acetogenic bacteria, which is free of energy requirement. Acetic acid can get recycled back to acetyl-CoA via a Acetoacetyl-CoA:Acetate/Butyrate Coenzyme A transferase system consisting of Acetyl-Coenzyme A acetyltransferase, Acetoacetyl-CoA:Acetate/Butyrate Coenzyme A transferase A, Acetoacetyl-CoA:Acetate/Butyrate Coenzyme A transferase B. This reaction drives the conversion of Acetoacetyl-CoA to Acetoacetate, which can then get decarboxylated to acetone and reduced to isopropanol (FIG. 4).

Isopropanol Production from Steel Mill Gas Comprising CO by *C. autoethanogenum* Carrying the vectorpMTL83147 thl-ctfAB-adc-adh2.

Experiment A

Figure 79:
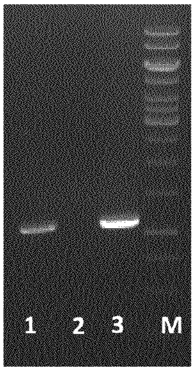
FIG. 79 shows a PCR check to confirm the presence of the plasmid on day 1 of the run depicted in FIG. 75 to FIG. 77.
Figure 80:
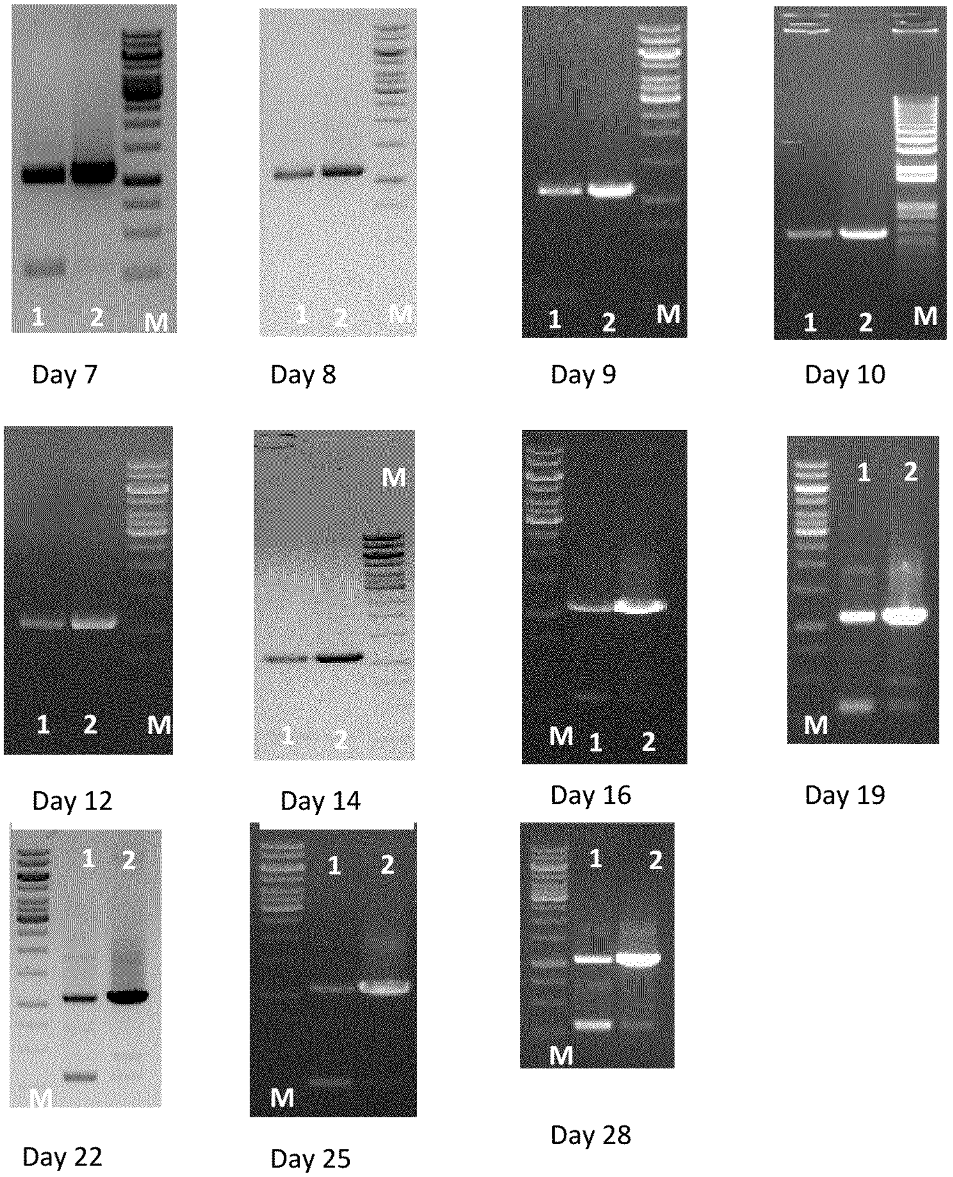
FIG. 80 shows PCR checks to confirm the presence of the plasmid throughout the remainder of the fermentation depicted in FIGS. 75 to 77.

*Clostridium autoethanogenum* DSM23693 carrying the vector pMTL83147 thl-ctfAB-adc-adh2 was grown at 37° C.

under mill gas (50% CO, 18% $CO_2$, 2% $H_2$, and 30% $N_2$) was continuously fed into the bioreactor. The gas flow was initially set at 80 ml/min, increasing to 200 ml/min over the course of the experiment, while the agitation was increased from 250 rpm to 750 rpm. $Na_2S$ was dosed into the bioreactor at 0.20 ml/hr, increasing to 0.4 ml/hr. The bioreactor was switched to a continuous mode at a rate of 1.0 ml/min (Dilution rate 0.96 $d^{-1}$) once the OD600 reached 0.17. The presence of the plasmid was checked regularly through PCR using plasmid specific M13 reverse primer and CtfAB sequencing primer to give a 1129 bp product and found to be present throughout the fermentation (FIGS. 79 and 80). The PCR gel of FIG. 79 shows the reactor sample at lane 1, the wild-type negative control at lane 2, the plasmid positive control at lane 3, and a 1 kBp marker labelled M. FIG. 80 depicts PCR checks throughout the remainder of the fermentation run with the reactor sample at lane 1, the plasmid positive control at lane 2 and a 1 kBp marker (M). This is a surprising result, as episomal plasmids are known to be not suitable and segregational instable in Clostridia species (US20110269201A1), and long continuous fermentation runs haven't be demonstrated with a *Clostridium* harbouring an introduced plasmid. Replication origin pCB102 for example has been shown to have a segregational stability of only 76% in ABE fermentation model organism *Clostridium acetobuylicum* or other Clostridia such as pathogen *Clostridium difficile*.

TABLE 22

Primers used to check for plasmid presence

| Primer name | Sequence |
|---|---|
| M13R | ATCAGGAAACAGCTATGAC |
| ctfAB_seqR3 | TGCAAGAGCAAACTCATCTTGTTCTTC |

Analytical Methods

Metabolites concentrations were measured using Agilent 1100 Series HPLC system equipped with a RID operated at 35° C. (Refractive Index Detector) and an Alltech IOA-2000 Organic acid column (150×6.5 mm, particle size 5 μm) kept at 60° C. The presence of Acetone and Isopropanol was also measured using Agilent 6890N headspace GC equipped with a Supelco PDMS 100 1 cm fiber, an Alltech EC-1000 (30 m×0.25 mm×0.25 μm) column, and a flame ionization detector (FID). The composition of the gas inflows and outflows was measured using a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Sampling of metabolites was performed daily. Gas analysis was automated and measured hourly.

Results

Figure 75:
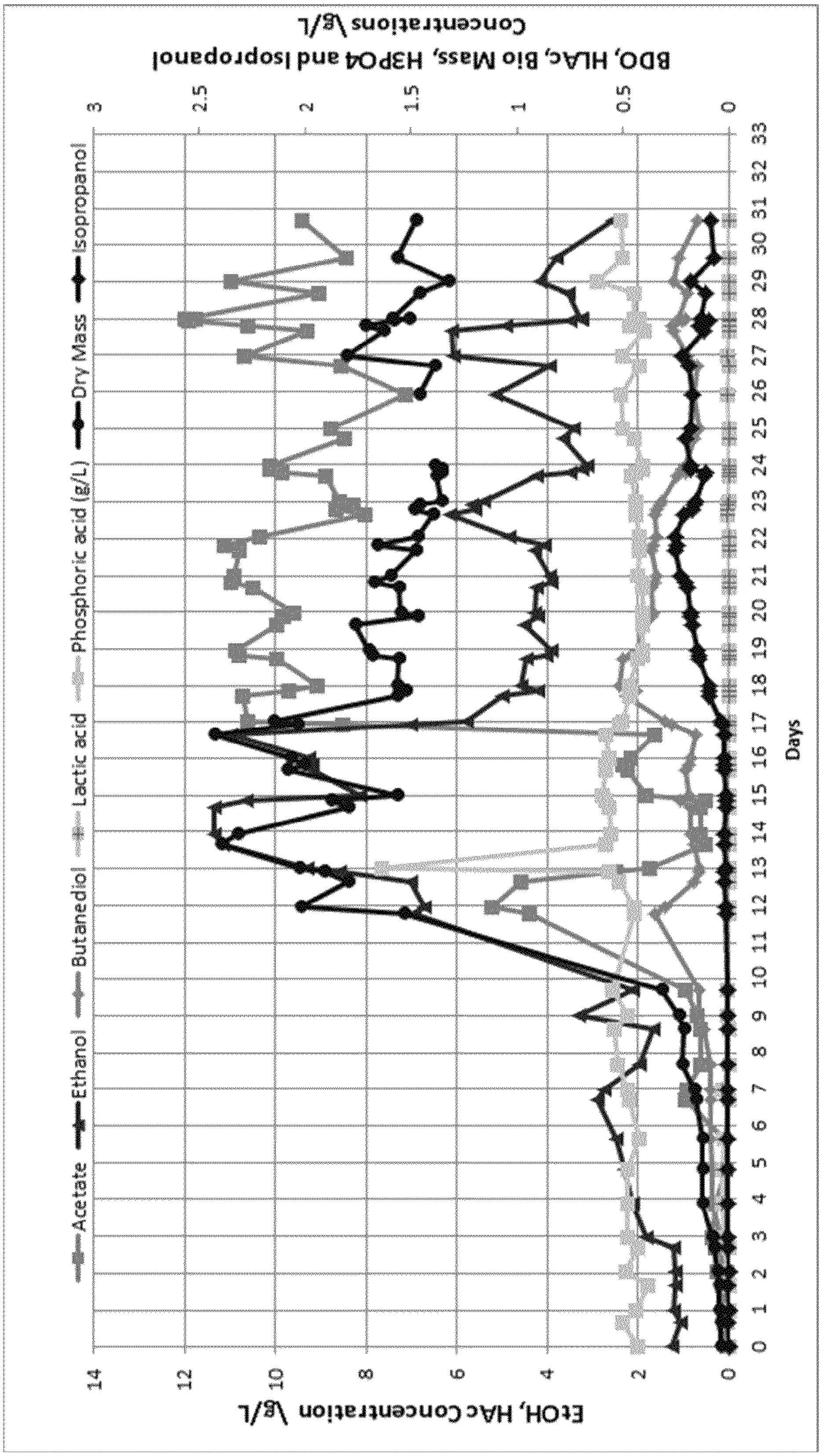
FIG. 75 shows metabolite concentrations from a stable continuous culture of *C. autoethanogenum* DSM23693 carrying the vector pMTL83147 thl-ctfAB-adc-adh2 over a 31 day period.
Figure 76:
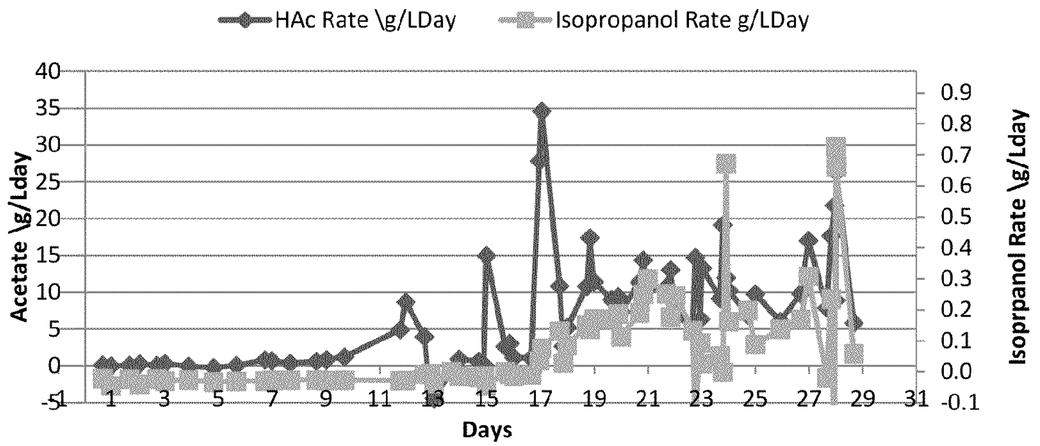
FIG. 76 shows acetate and Isopropanol productivity rates of a stable continuous culture of *C. autoethanogenum* DSM23693 carrying the vector pMTL83147 thl-ctfAB-adc-adh2 over a 31 day period.
Figure 77:
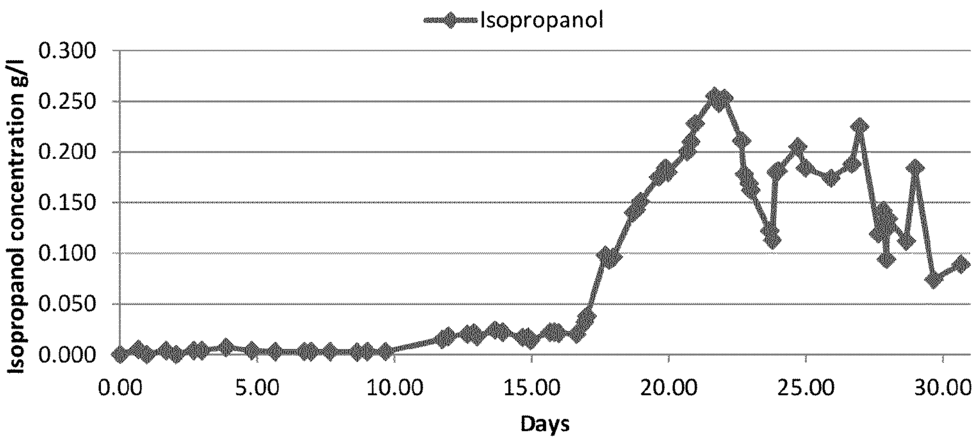
FIG. 77 shows the Isopropanol concentration from a stable continuous culture of *C. autoethanogenum* DSM23693 carrying the vector pMTL83147 thl-ctfAB-adc-adh2 over a 31 day period.
Figure 81:
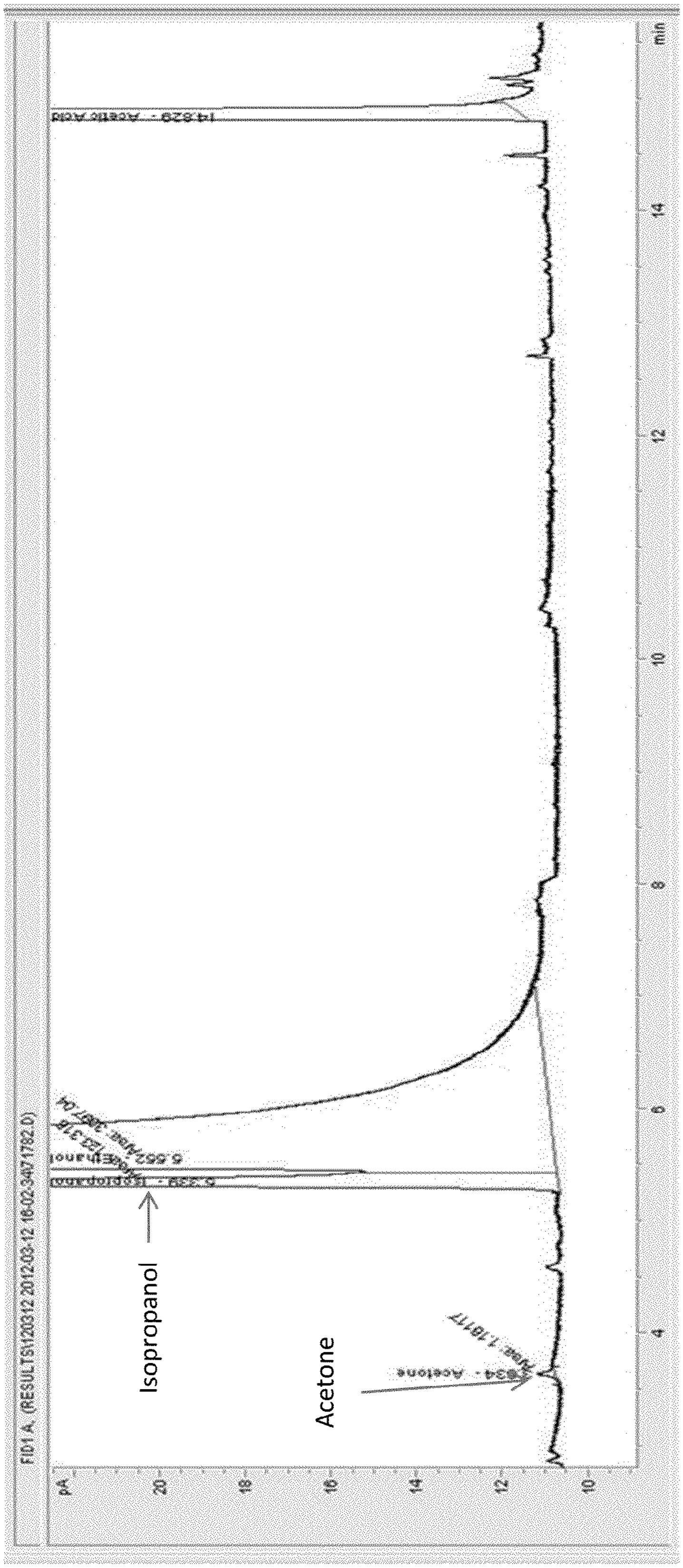
FIG. 81 is a GC analysis showing the presence of acetone and isopropanol in the fermentation broth of the continuous culture of FIGS. 75 to 77.

The growth and metabolite profile of *Clostridium autoethanogenum* DSM23693 carrying the vector pMTL83147 thl-ctfAB-adc-adh2 in a continuous fermentation over 31 days is shown in FIG. 75. The fermentation ran as a batch fermentation from inoculation to day 6. At day 7 the fermentation was switched to continuous fermentation. The increase in acetate concentration coupled with a decrease in ethanol concentration during continuous fermentation seems to have triggered a significant increase in isopropanol production. FIG. 76 highlights this result where the isopropanol production rate follows a similar trend to the acetate production rate and demonstrates an Isopropanol production rate of 0.7 g per litre per day. FIG. 77 shows the Isopropanol concentration over the 31 day period, with the concentration reaching a level of 0.250 g per litre. A GC sample was taken during the run, at day 19. FIG. 81 shows the GC results for the sample showing the production of both acetone and Isopropanol during the fermentation. The acetone peak was relatively small in comparison with the Isopropanol peak, demonstrating the conversion of acetone through to Isopropanol while there is acetone in the system.

Experiment B

Fermentations with *C. autoethanogenum* DSM23693 carrying the vector pMTL83147 thl-ctfAB-adc-adh2 were carried out in 1.5 L bioreactors at 37° C. and CO-containing steel mill gas. The fermenter was fed with corex gas (40% CO, 15% H2, 15% CO2, 30% N2) as sole energy and carbon source as described below. A defined medium was used containing per litre: MgCl, $CaCl_2$ (0.5 mM), KCl (3 mM), $H_3PO_4$ (5 mM), Fe (100 μM), Ni, Zn (5 μM), Mn, B, W, Mo, Se (2 μM) was prepared for culture growth. The media was transferred into the bioreactor and autoclaved at 121° C. for 45 minutes. After autoclaving, the medium was supplemented with Thiamine, Pantothenate (0.05 mg), Biotin (0.02 mg) and reduced with 3 mM Cysteine-HCl. To achieve anaerobic conditions the reactor vessel was sparged with nitrogen through a 0.2 μm filter.

Prior to inoculation, the gas was switched to CO-containing steel mill gas, feeding continuously to the reactor. The gas flow was initially set at 100 ml/min, increasing to 350 ml/min during mid exponential phase, while the agitation was increased from 600 rpm to 850 rpm. A solution of 0.5M of $Na_2S$ was dosed into the bioreactor at 0.25 ml/hr. Once the OD600 reached 0.5 the bioreactor was switched to a continuous mode at a rate of 1.0 ml/min (Dilution rate 0.96 $d^{-1}$). At the same time, cells were concentrated up in the fermenter by using a polysulfon membrane filtration system with 0.1 μm pore size (GE healthcare hallow fibre membrane). The rate of permeate withdrawing was the same as the medium feeding rate. For the microbes, it was a batch culture. Media samples were taken to measure the biomass and metabolites and a headspace analysis of the in- and outflowing gas was performed on regular basis.

Analytical Methods

Metabolites concentrations were measured using Agilent 1100 Series HPLC system equipped with a RID operated at 35° C. (Refractive Index Detector) and an Alltech IOA-2000 Organic acid column (150×6.5 mm, particle size 5 μm) kept at 60° C. The presence of Acetone and Isopropanol was also measured using Agilent 6890N headspace GC equipped with a Supelco PDMS 100 1 cm fiber, an Alltech EC-1000 (30 m×0.25 mm×0.25 μm) column, and a flame ionization detector (FID). The composition of the gas inflows and outflows was measured using a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Sampling of metabolites was performed daily. Gas analysis was automated and measured hourly.

Results

Figure 78:
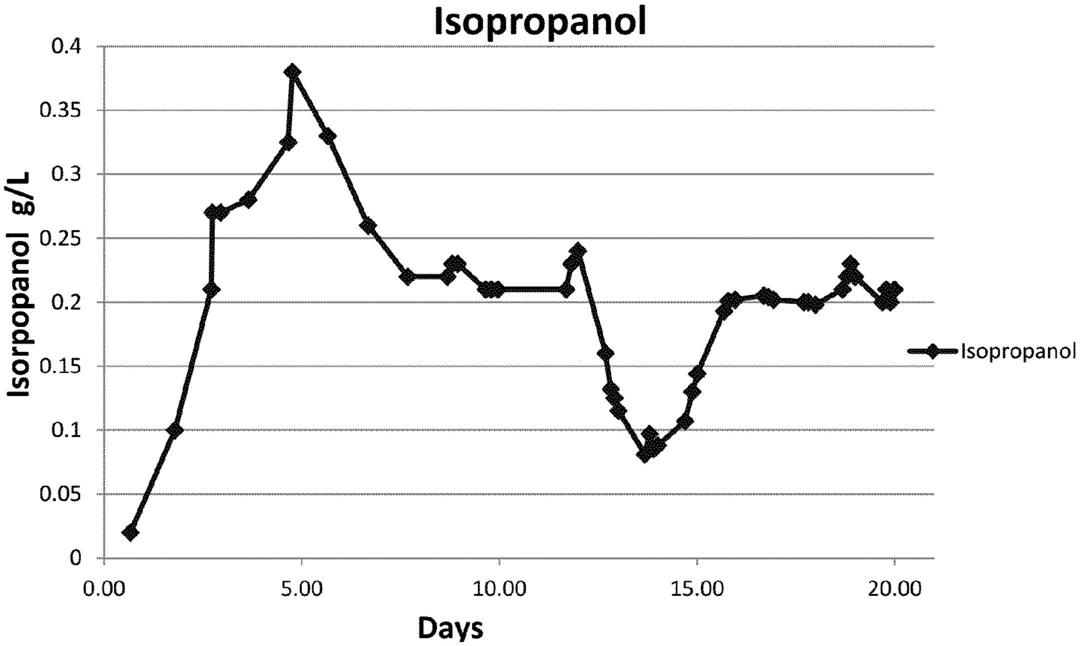
FIG. 78 shows the Isopropanol concentration from another stable continuous culture of *C. autoethanogenum* DSM23693 carrying the vector pMTL83147 thl-ctfAB-adc-adh2 over a 14 day period.

The growth and metabolite profile of *Clostridium autoethanogenum* DSM23693 carrying the vector pMTL83147 thl-ctfAB-adc-adh2 in a continuous fermentation over 21 days is shown in FIG. 78. The culture showed continuous production of Isopropanol, reaching an isopropanol concentration of 0.37 g per Litre.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method for producing a product comprising culturing a recombinant microorganism comprising an exogenous thiolase, an exogenous CoA transferase, and an exogenous decarboxylase in the presence of a gaseous substrate sornprisina one or more of CO, CO2, and H2 to produce isopropanol, wherein the recombinant microorganism is derived from a parental microorganism selected from the group consisting of *Clostridium autoethanogenurn Clostridium lfungdahlii*, and *Clostridium ragsdalei,* the exogenous thiolase is acetyl-CoA acetyltransferase (EC 2.3.1.9), the exogenous CoA transferase is acetoacetyl-Cokacetate CoA transferase (EC 2.8.3.9), and the exogenous decarboxylase is acetoacetate decarboxylase (EC 4.1.1.4) or alpha-ketolsovalerate decarboxylase (EC 4.1.1.74).

2. The method of claim 1, wherein the thiolase is *Clostridium acetobutylicum* ThlA comprising SEQ ID NO: 42.

3. The method of claim 1, wherein the acetoacetyl-CoA: acetate CoA transferase is *Clostridium beijerinckii* CtfA comprising SEQ ID NO: 43 and *Clostridium beijerinckii* CtfB comprising SEQ ID NO: 44.

4. The method of claim 1, wherein the acetoacetate decarboxylase is *Clostridium beijerinckii* Adc comprising SEQ ID NO: 45.

5. The method of claim 1, wherein the alpha-ketoisovalerate decarboxylase is *Lactococcus lactis* KivD comprising SEQ ID NO: 73.

6. The method of claim 1, wherein the recombinant microorganism further comprises an endogenous or exogenous alcohol dehydrogenase.

7. The method of claim 6, wherein the endogenous or exogenous alcohol dehydrogenase is alcohol dehydrogenase (Adh) (EC 1.1.1.2) or alcohol dehydrogenase (Adh2)(EC 1.1.1.1).

8. The method of claim 1, wherein the recombinant microorganism is a carboxydotrophic and acetogenic bacterium.

9. The method of claim 1, wherein the parental microorganism does not produce acetone or isopropanol.

10. The method of claim 1, wherein the parental microorganism is *Clostridium autoethanogenum* or *Clostridium ljungdahlii.*

11. The method of claim 10, wherein the parental microorganism is *Clostridium autoethanogenum* DSM23693 or *Clostridium ljungdahlii* DSM13528.

12. The method of claim 1, wherein the product is isopropanol.

13. The method of claim 1, wherein the gaseous substrate comprises 20-70% CO.

14. The method of claim 1, wherein the gaseous substrate is derived from an industrial process selected from the group consisting of ferrous metal products manufacturing, non-ferrous products manufacturing, petroleum refining, coal gasification, biomass gasification, electric power production, carbon black production, and coke manufacturing.

* * * * *

SEQUENCE LISTING

```
<160> NUMBER OF SEQ ID NOS: 101

<210> SEQ ID NO 1
<211> LENGTH: 351
<212> TYPE: PRT
<213> ORGANISM: Clostridium autoethanogenum

<400> SEQUENCE: 1

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285
```

```
Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350


<210> SEQ ID NO 2
<211> LENGTH: 1056
<212> TYPE: DNA
<213> ORGANISM: Clostridium autoethanogenum

<400> SEQUENCE: 2

atgaaaggtt ttgcaatgtt aggtattaac aaattaggat ggattgaaaa gaaaaaccca     60

gtgccaggtc cttatgatgc gattgtacat cctctagctg tatccccatg tacatcagat    120

atacatacgg tttttgaagg agcacttggt aatagggaaa atatgatttt aggccatgaa    180

gctgtaggtg aaatagccga agttggcagc gaagttaaag attttaaagt tggcgataga    240

gttatcgtac catgcacaac acctgactgg agatctttag aagtccaagc tggttttcag    300

cagcattcaa acggtatgct tgcaggatgg aagttttcca attttaaaga cggtgtattt    360

gcagattact ttcatgtaaa cgatgcagat atgaatcttg ccatactccc agatgaaata    420

cctttagaaa gtgcagttat gatgacagac atgatgacta ctggttttca tggagcagaa    480

cttgcagaca taaaaatggg ctccagcgtt gtagtaattg gtataggagc tgttggatta    540

atgggaatag ccggttccaa acttcgagga gcaggcagaa ttatcggtgt tggaagcaga    600

cctgtttgtg ttgaaacagc taaattttat ggagcaactg atattgtaaa ttataaaaat    660

ggtgatatag ttgaacaaat catggactta actcatggta aaggtgtaga ccgtgtaatc    720

atggcaggcg gtggtgctga aacactagca caagcagtaa ctatggttaa acctggcggc    780

gtaatttcta acatcaacta ccatggaagc ggtgatactt taccaatacc tcgtgttcaa    840

tggggctgcg gcatggctca caaaactata agaggaggat tatgccccgg cggacgtctt    900

agaatggaaa tgctaagaga tcttgttcta tataaacgtg ttgatttgag taaacttgtt    960

actcatgtat ttgatggtgc agaaaatatt gaaaaggccc ttttgcttat gaaaaataag   1020

ccaaaagatt taattaaatc agtagttaca ttctaa                             1056


<210> SEQ ID NO 3
<211> LENGTH: 1056
<212> TYPE: DNA
<213> ORGANISM: Clostridium ljungdahlii

<400> SEQUENCE: 3

atgaaaggtt ttgcaatgtt aggtattaac aaattaggat ggattgaaaa gaaaaaccca     60

gtgccaggtc cttatgatgc gattgtacat cctctagctg tatccccatg tacatcagat    120

atacatacgg tttttgaagg agcacttggt aatagggaaa atatgatttt aggccatgaa    180

gctgtaggtg aaatagccga agttggcagc gaagttaaag attttaaagt tggcgataga    240

gttatcgtac catgcacaac acctgactgg agatctttag aagtccaagc tggttttcag    300

cagcattcaa acggtatgct tgcaggatgg aagttttcca attttaaaga tggtgtattt    360

gcagattact ttcatgtaaa cgatgcagat atgaatcttg ccatactccc agatgaaata    420
```

cctttagaaa gtgcagttat gatgacagac atgatgacta ctggttttca tggagcagaa 480
cttgcagaca taaaaatggg ctccagcgtt gtagtaattg gtataggagc tgttggatta 540
atgggaatag ccggttccaa acttcgagga gcaggcagaa ttatcggtgt tggaagcaga 600
cctgtttgtg ttgaaacagc taaattttat ggagcaactg atattgtaaa ttataaaaat 660
ggtgatatag ttgaacaaat catggactta actcatggta aaggtgtaga ccgtgtaatc 720
atggcaggcg gtggtgctga aacactagca caagcagtaa ctatggttaa acctggcggc 780
gtaatttcta acatcaacta ccatggaagc ggtgatactt taccaatacc tcgtgttcaa 840
tggggctgcg gcatggctca caaaactata agaggaggat tatgccccgg cggacgtctt 900
agaatggaaa tgctaagaga tcttgttcta tataaacgtg ttgatttgag taaacttgtt 960
actcatgtat ttgatggtgc agaaaatatt gaaaaggccc ttttgcttat gaaaaataag 1020
ccaaaagatt taattaaatc agtagttaca ttctaa 1056

<210> SEQ ID NO 4
<211> LENGTH: 1056
<212> TYPE: DNA
<213> ORGANISM: Clostridium ragsdalei

<400> SEQUENCE: 4
atgaaaggtt ttgcaatgtt aggtattaac aagttaggat ggattgaaaa gaaaaaccca 60
gtaccaggtc cttatgatgc gattgtacat cctctagctg tatccccatg tacatcagat 120
atacatacgg tttttgaagg agcacttggt aatagggaaa atatgatttt aggtcacgaa 180
gctgtaggtg aaatagctga agttggcagt gaagttaaag attttaaagt tggcgataga 240
gttatcgtac catgcacaac acctgactgg agatccttag aagtccaagc tggttttcaa 300
cagcattcaa acggtatgct tgcaggatgg aagttttcca attttaaaga cggtgtattt 360
gcagattact ttcatgtaaa cgatgcagat atgaatcttg caatacttcc agatgaaata 420
cctttagaaa gtgcagttat gatgacagac atgatgacta ctggttttca tggggcagaa 480
cttgctgaca taaaaatggg ttccagtgtt gtcgtaattg gtataggagc tgttggatta 540
atgggaatag ccggttccaa acttcgagga gcaggtagaa ttatcggtgt tggaagcaga 600
cccgtttgtg ttgaaacagc taaattttat ggagcaactg atattgtaaa ttataaaaat 660
ggtgatatag ttgaacaaat aatggactta actcatggta aaggtgtaga ccgtgtaatc 720
atggcaggcg gtggtgctga aacactagca caagcagtaa ctatggttaa acctggcggc 780
gtaatttcta acatcaacta ccatggaagc ggtgatactt tgccaatacc tcgtgttcaa 840
tggggctgcg gcatggctca caaaactata agaggagggt tatgtcccgg cggacgtctt 900
agaatggaaa tgctaagaga ccttgttcta tataaacgtg ttgatttgag caaacttgtt 960
actcatgtat ttgatggtgc agaaaatatt gaaaaggccc ttttgcttat gaaaaataag 1020
ccaaaagatt taattaaatc agtagttaca ttctaa 1056

<210> SEQ ID NO 5
<211> LENGTH: 20
<212> TYPE: DNA
<213> ORGANISM: Artificial sequence
<220> FEATURE:
<223> OTHER INFORMATION: synthetic primer

<400> SEQUENCE: 5
tcaggacctt ctggaactgg 20

-continued

<210> SEQ ID NO 6
<211> LENGTH: 20
<212> TYPE: DNA
<213> ORGANISM: Artificial sequence
<220> FEATURE:
<223> OTHER INFORMATION: synthetic primer

<400> SEQUENCE: 6
acctcccctt ttcttggaga 20

<210> SEQ ID NO 7
<211> LENGTH: 20
<212> TYPE: DNA
<213> ORGANISM: Artificial sequence
<220> FEATURE:
<223> OTHER INFORMATION: synthetic primer

<400> SEQUENCE: 7
caggtttcgg tgctgaccta 20

<210> SEQ ID NO 8
<211> LENGTH: 20
<212> TYPE: DNA
<213> ORGANISM: Artificial sequence
<220> FEATURE:
<223> OTHER INFORMATION: synthetic primer

<400> SEQUENCE: 8
aactccgccg ttgtatttca 20

<210> SEQ ID NO 9
<211> LENGTH: 25
<212> TYPE: DNA
<213> ORGANISM: Artificial sequence
<220> FEATURE:
<223> OTHER INFORMATION: synthetic primer

<400> SEQUENCE: 9
acaagatggg gtcgaaacag tttgg 25

<210> SEQ ID NO 10
<211> LENGTH: 25
<212> TYPE: DNA
<213> ORGANISM: Artificial sequence
<220> FEATURE:
<223> OTHER INFORMATION: synthetic primer

<400> SEQUENCE: 10
tggcactgga cttactctac atggg 25

<210> SEQ ID NO 11
<211> LENGTH: 30
<212> TYPE: DNA
<213> ORGANISM: Artificial sequence
<220> FEATURE:
<223> OTHER INFORMATION: synthetic primer

<400> SEQUENCE: 11
tatttccgaa gatgatattg aattgtatgg 30

<210> SEQ ID NO 12
<211> LENGTH: 24
<212> TYPE: DNA
<213> ORGANISM: Artificial sequence
<220> FEATURE:
<223> OTHER INFORMATION: synthetic primer

<400> SEQUENCE: 12
tccagcaggt gttgggttta tagc 24

<210> SEQ ID NO 13
<211> LENGTH: 22
<212> TYPE: DNA
<213> ORGANISM: Artificial sequence
<220> FEATURE:
<223> OTHER INFORMATION: synthetic primer

<400> SEQUENCE: 13
agctgcaact cctggtggag gc 22

<210> SEQ ID NO 14
<211> LENGTH: 27
<212> TYPE: DNA
<213> ORGANISM: Artificial sequence
<220> FEATURE:
<223> OTHER INFORMATION: synthetic primer

<400> SEQUENCE: 14
gccttttacc ttttcgtcat actgtgc 27

<210> SEQ ID NO 15
<211> LENGTH: 29
<212> TYPE: DNA
<213> ORGANISM: Artificial sequence
<220> FEATURE:
<223> OTHER INFORMATION: synthetic primer

<400> SEQUENCE: 15
gcttacatta gtaagagttg gagcaaacg 29

<210> SEQ ID NO 16
<211> LENGTH: 29
<212> TYPE: DNA
<213> ORGANISM: Artificial sequence
<220> FEATURE:
<223> OTHER INFORMATION: synthetic primer

<400> SEQUENCE: 16
acttgtcctg tgatatatct gctggtagc 29

<210> SEQ ID NO 17
<211> LENGTH: 26
<212> TYPE: DNA
<213> ORGANISM: Artificial sequence
<220> FEATURE:
<223> OTHER INFORMATION: synthetic primer

<400> SEQUENCE: 17
ggtccttatg atgcgattgt acatcc 26

<210> SEQ ID NO 18
<211> LENGTH: 26
<212> TYPE: DNA
<213> ORGANISM: Artificial sequence
<220> FEATURE:
<223> OTHER INFORMATION: synthetic primer

<400> SEQUENCE: 18
gctatttcac ctacagcttc atggcc 26

<210> SEQ ID NO 19
<211> LENGTH: 654

<212> TYPE: DNA
<213> ORGANISM: Clostridium beijerinckii

<400> SEQUENCE: 19
atgaataaat tagtaaaatt aacagattta aagcgcattt tcaaagatgg catgacaatt 60
atggttgggg gtttttttaga ttgtggaact cctgaaaata ttatagatat gctagttgat 120
ttaaatataa aaaatctgac tattataagc aatgatacag cttttcctaa taaaggaata 180
ggaaaactta ttgtaaatgg tcaagtttct aaagtaattg cttcacatat tggaactaat 240
cctgaaactg gaaaaaaaat gagctctgga gaacttaaag ttgagctttc cccacaagga 300
acactgattg aaagaattcg tgcagctgga tctggactcg gaggtgtatt aactccaact 360
ggacttggaa ctatcgttga agaaggtaag aaaaaagtta ctatcgatgg caaagaatat 420
ctattagaac ttcctttatc tgctgatgtt tcattaataa aaggtagcat tgtagatgaa 480
tttggaaata ccttctatag ggctgctact aaaaatttca atccatatat ggcaatggct 540 gcaaaaaacag ttatagttga agcagaaaat ttagttaaat gtgaagattt aaaaagagat 600
gccataatga ctcctggcgt attagtagat tatatcgtta aggaggcggc ttaa 654

<210> SEQ ID NO 20
<211> LENGTH: 666
<212> TYPE: DNA
<213> ORGANISM: Clostridium beijerinckii

<400> SEQUENCE: 20
ttgattgtag ataaagtttt agcaaaagag ataattgcca aaagagttgc aaaagaacta 60
aaaaaagacc aactcgtaaa ccttggaata ggacttccaa ctttagtagc aaattatgta 120
ccaaaagaaa tgaacattac ttttgaatca gaaaatggca tggttggtat ggcacaaatg 180
gcatcatcag gtgaaaatga cccagatata ataaatgctg gcggggaata tgtaacatta 240
ttacctcaag gttcattttt tgatagttca atgtctttcg cactaatacg aggaggacat 300
gttgatgttg ctgttcttgg tgctctagaa gttgatgaaa aaggtaattt agctaactgg 360
attgttccaa ataaaattgt cccaggtatg ggtggcgcta tggatttagc aataggcgca 420
aaaaaaataa tagtggcaat gcaacataca ggaaaaagta aacctaaaat cgttaaaaaa 480
tgtactctcc cacttactgc taaggctcaa gtggatttaa ttgtcacaga actttgtgta 540
attgatgtaa caaatgacgg cttactttta aaagaaattc ataaagatac aactattgat 600
gaaattaaat ttttaacaga tgcagattta attattccag ataacttaaa gattatggat 660
atatga 666

<210> SEQ ID NO 21
<211> LENGTH: 741
<212> TYPE: DNA
<213> ORGANISM: Clostridium beijerinckii

<400> SEQUENCE: 21
atgttagaaa gtgaagtatc taaacaaatt acaactccac ttgctgctcc agcgtttcct 60
agaggaccat ataggtttca caatagagaa tatctaaaca ttatttatcg aactgattta 120
gatgctcttc gaaaaatagt accagagcca cttgaattag atagagcata tgttagattt 180
gaaatgatgg ctatgcctga tacaaccgga ctaggctcat atacagaatg tggtcaagct 240
attccagtaa aatataatgg tgttaagggt gactacttgc atatgatgta tctagataat 300
gaacctgcta ttgctgttgg aagagaaagt agcgcttatc caaaaaagct tggctatcca 360

-continued

```
aagctatttg ttgattcaga tactttagtt gggacactta aatatggtac attaccagta    420

gctactgcaa caatgggata taagcacgag cctctagatc ttaaagaagc ctatgctcaa    480

attgcaagac ccaattttat gctaaaaatc attcaaggtt acgatggtaa gccaagaatt    540

tgtgaactaa tatgtgcaga aaatactgat ataactattc acggtgcttg gactggaagt    600

gcacgtctac aattatttag ccatgcacta gctcctcttg ctgatttacc tgtattagag    660

attgtatcag catctcatat cctcacagat ttaactcttg gaacacctaa ggttgtacat    720

gattatcttt cagtaaaata a                                              741
```

<210> SEQ ID NO 22
<211> LENGTH: 558
<212> TYPE: DNA
<213> ORGANISM: Clostridium autoethanogenum

<400> SEQUENCE: 22

```
agatagtcat aatagttcca gaatagttca atttagaaat tagactaaac ttcaaaatgt     60

ttgttaaata tataccaaac tagtatagat attttttaaa tactggactt aaacagtagt    120

aatttgccta aaaaattttt tcaatttttt ttaaaaaatc cttttcaagt tgtacattgt    180

tatggtaata tgtaattgaa gaagttatgt agtaatattg taaacgtttc ttgatttttt    240

tacatccatg tagtgcttaa aaaaccaaaa tatgtcacat gcaattgtat atttcaaata    300

acaatattta ttttctcgtt aaattcacaa ataatttatt aataatatca ataaccaaga    360

ttatacttaa atggatgttt attttttaac acttttatag taaatatatt tattttatgt    420

agtaaaaagg ttataattat aattgtattt attacaatta attaaaataa aaaatagggt    480

tttaggtaaa attaagttat tttaagaagt aattacaata aaaattgaag ttatttcttt    540

aaggagggaa ttattaaa                                                  558
```

<210> SEQ ID NO 23
<211> LENGTH: 26
<212> TYPE: DNA
<213> ORGANISM: Artificial sequence
<220> FEATURE:
<223> OTHER INFORMATION: synthetic primer

<400> SEQUENCE: 23

```
gttcatatga aagaagttgt aatagc                                          26
```

<210> SEQ ID NO 24
<211> LENGTH: 25
<212> TYPE: DNA
<213> ORGANISM: Artificial sequence
<220> FEATURE:
<223> OTHER INFORMATION: synthetic primer

<400> SEQUENCE: 24

```
caagaattcc tagcactttt ctagc                                           25
```

<210> SEQ ID NO 25
<211> LENGTH: 26
<212> TYPE: DNA
<213> ORGANISM: Artificial sequence
<220> FEATURE:
<223> OTHER INFORMATION: synthetic primer

<400> SEQUENCE: 25

```
ctaggtacca gggagatatt aaaatg                                          26
```

<210> SEQ ID NO 26
<211> LENGTH: 26
<212> TYPE: DNA
<213> ORGANISM: Artificial sequence
<220> FEATURE:
<223> OTHER INFORMATION: synthetic primer

<400> SEQUENCE: 26
cgtggatcct ctatattgct tttatt 26

<210> SEQ ID NO 27
<211> LENGTH: 29
<212> TYPE: DNA
<213> ORGANISM: Artificial sequence
<220> FEATURE:
<223> OTHER INFORMATION: synthetic primer

<400> SEQUENCE: 27
aagcggccgc agatagtcat aatagttcc 29

<210> SEQ ID NO 28
<211> LENGTH: 29
<212> TYPE: DNA
<213> ORGANISM: Artificial sequence
<220> FEATURE:
<223> OTHER INFORMATION: synthetic primer

<400> SEQUENCE: 28
ttccatatga ataattccct ccttaaagc 29

<210> SEQ ID NO 29
<211> LENGTH: 20
<212> TYPE: DNA
<213> ORGANISM: Artificial sequence
<220> FEATURE:
<223> OTHER INFORMATION: synthetic primer

<400> SEQUENCE: 29
cagaggatgt taatgaagtc 20

<210> SEQ ID NO 30
<211> LENGTH: 18
<212> TYPE: DNA
<213> ORGANISM: Artificial sequence
<220> FEATURE:
<223> OTHER INFORMATION: synthetic primer

<400> SEQUENCE: 30
ctgtgcagca gtacttgt 18

<210> SEQ ID NO 31
<211> LENGTH: 15
<212> TYPE: DNA
<213> ORGANISM: Artificial sequence
<220> FEATURE:
<223> OTHER INFORMATION: synthetic primer

<400> SEQUENCE: 31
gcaatgatac agctt 15

<210> SEQ ID NO 32
<211> LENGTH: 19
<212> TYPE: DNA
<213> ORGANISM: Artificial sequence
<220> FEATURE:
<223> OTHER INFORMATION: synthetic primer

<400> SEQUENCE: 32
aaccttggaa taggacttc 19

<210> SEQ ID NO 33
<211> LENGTH: 20
<212> TYPE: DNA
<213> ORGANISM: Artificial sequence
<220> FEATURE:
<223> OTHER INFORMATION: synthetic primer

<400> SEQUENCE: 33
tgtgaactaa tatgtgcaga 20

<210> SEQ ID NO 34
<211> LENGTH: 601
<212> TYPE: PRT
<213> ORGANISM: Artificial sequence
<220> FEATURE:
<223> OTHER INFORMATION: synthetic protein

<400> SEQUENCE: 34

```
Met Phe Pro Cys Asn Ala Tyr Ile Glu Tyr Gly Asp Lys Asn Met Asn
1               5                   10                  15

Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Tyr Lys Gln Lys
        35                  40                  45

Ser Asn Met Lys Lys Glu Ile Ser Phe Ser Glu Glu Tyr Tyr Lys Gln
    50                  55                  60

Lys Ile Met Asn Gly Lys Asn Gly Val Val Tyr Thr Pro Pro Glu Met
65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140

Ser Tyr His Ile Val Arg Asn Asn Leu Phe Gly Phe Asp Ile Asp Glu
145                 150                 155                 160

Thr Ala Ile Lys Val Leu Lys Ile Asp Leu Phe Leu Ile Ser Asn Gln
                165                 170                 175

Phe Ser Glu Lys Asn Phe Gln Val Lys Asp Phe Leu Val Glu Asn Ile
            180                 185                 190

Asp Arg Lys Tyr Asp Val Phe Ile Gly Asn Pro Pro Tyr Ile Gly His
        195                 200                 205

Lys Ser Val Asp Ser Ser Tyr Ser Tyr Val Leu Arg Lys Ile Tyr Gly
    210                 215                 220

Ser Ile Tyr Arg Asp Lys Gly Asp Ile Ser Tyr Cys Phe Phe Gln Lys
225                 230                 235                 240

Ser Leu Lys Cys Leu Lys Glu Gly Gly Lys Leu Val Phe Val Thr Ser
                245                 250                 255

Arg Tyr Phe Cys Glu Ser Cys Ser Gly Lys Glu Leu Arg Lys Phe Leu
            260                 265                 270

Ile Glu Asn Thr Ser Ile Tyr Lys Ile Ile Asp Phe Tyr Gly Ile Arg
        275                 280                 285
```

```
Pro Phe Lys Arg Val Gly Ile Asp Pro Met Ile Ile Phe Leu Val Arg
    290                 295                 300

Thr Lys Asn Trp Asn Asn Asn Ile Glu Ile Ile Arg Pro Asn Lys Ile
305                 310                 315                 320

Glu Lys Asn Glu Lys Asn Lys Phe Leu Asp Ser Leu Phe Leu Asp Lys
                325                 330                 335

Ser Glu Lys Cys Lys Lys Phe Ser Ile Ser Gln Lys Ser Ile Asn Asn
            340                 345                 350

Asp Gly Trp Val Phe Val Asp Glu Val Glu Lys Asn Ile Ile Asp Lys
        355                 360                 365

Ile Lys Glu Lys Ser Lys Phe Ile Leu Lys Asp Ile Cys His Ser Cys
    370                 375                 380

Gln Gly Ile Ile Thr Gly Cys Asp Arg Ala Phe Ile Val Asp Arg Asp
385                 390                 395                 400

Ile Ile Asn Ser Arg Lys Ile Glu Leu Arg Leu Ile Lys Pro Trp Ile
                405                 410                 415

Lys Ser Ser His Ile Arg Lys Asn Glu Val Ile Lys Gly Glu Lys Phe
            420                 425                 430

Ile Ile Tyr Ser Asn Leu Ile Glu Asn Glu Thr Glu Cys Pro Asn Ala
        435                 440                 445

Ile Lys Tyr Ile Glu Gln Tyr Lys Lys Arg Leu Met Glu Arg Arg Glu
    450                 455                 460

Cys Lys Lys Gly Thr Arg Lys Trp Tyr Glu Leu Gln Trp Gly Arg Lys
465                 470                 475                 480

Pro Glu Ile Phe Glu Glu Lys Lys Ile Val Phe Pro Tyr Lys Ser Cys
                485                 490                 495

Asp Asn Arg Phe Ala Leu Asp Lys Gly Ser Tyr Phe Ser Ala Asp Ile
            500                 505                 510

Tyr Ser Leu Val Leu Lys Lys Asn Val Pro Phe Thr Tyr Glu Ile Leu
        515                 520                 525

Leu Asn Ile Leu Asn Ser Pro Leu Tyr Glu Phe Tyr Phe Lys Thr Phe
    530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
                565                 570                 575

Glu Lys Lys Leu Tyr Asp Phe Phe Gly Leu Thr Asp Lys Glu Ile Glu
            580                 585                 590

Ile Val Glu Lys Ile Lys Asp Asn Cys
        595                 600
```

<210> SEQ ID NO 35
<211> LENGTH: 1806
<212> TYPE: DNA
<213> ORGANISM: Artificial sequence
<220> FEATURE:
<223> OTHER INFORMATION: synthetic gene

<400> SEQUENCE: 35

```
atgtttccgt gcaatgccta tatcgaatat ggtgataaaa atatgaacag ctttatcgaa     60

gatgtggaac agatctacaa cttcattaaa aagaacattg atgtggaaga aaagatgcat    120

ttcattgaaa cctataaaca gaaaagcaac atgaagaaag agattagctt tagcgaagaa    180

tactataaac agaagattat gaacggcaaa aatggcgttg tgtacacccc gccggaaatg    240
```

-continued

```
gcggccttta tggttaaaaa tctgatcaac gttaacgatg ttattggcaa tccgtttatt    300

aaaatcattg acccgagctg cggtagcggc aatctgattt gcaaatgttt tctgtatctg    360

aatcgcatct ttattaagaa cattgaggtg attaacagca aaaataacct gaatctgaaa    420

ctggaagaca tcagctacca catcgttcgc aacaatctgt ttggcttcga tattgacgaa    480

accgcgatca aagtgctgaa aattgatctg tttctgatca gcaaccaatt tagcgagaaa    540

aatttccagg ttaaagactt tctggtggaa aatattgatc gcaaatatga cgtgttcatt    600

ggtaatccgc cgtatatcgg tcacaaaagc gtggacagca gctacagcta cgtgctgcgc    660

aaaatctacg gcagcatcta ccgcgacaaa ggcgatatca gctattgttt ctttcagaag    720

agcctgaaat gtctgaagga aggtggcaaa ctggtgtttg tgaccagccg ctacttctgc    780

gagagctgca gcggtaaaga actgcgtaaa ttcctgatcg aaaacacgag catttacaag    840

atcattgatt tttacggcat ccgcccgttc aaacgcgtgg gtatcgatcc gatgattatt    900

tttctggttc gtacgaagaa ctggaacaat aacattgaaa ttattcgccc gaacaagatt    960

gaaaagaacg aaaagaacaa attcctggat agcctgttcc tggacaaaag cgaaaagtgt   1020

aaaaagttta gcattagcca gaaaagcatt aataacgatg gctgggtttt cgtggacgaa   1080

gtggagaaaa acattatcga caaaatcaaa gagaaaagca agttcattct gaaagatatt   1140

tgccatagct gtcaaggcat tatcaccggt tgtgatcgcg cctttattgt ggaccgtgat   1200

atcatcaata gccgtaagat cgaactgcgt ctgattaaac cgtggattaa aagcagccat   1260

atccgtaaga atgaagttat taagggcgaa aaattcatca tctatagcaa cctgattgag   1320

aatgaaaccg agtgtccgaa tgcgattaaa tatatcgaac agtacaagaa acgtctgatg   1380

gagcgccgcg aatgcaaaaa gggcacgcgt aagtggtatg aactgcaatg gggccgtaaa   1440

ccggaaatct tcgaagaaaa gaaaattgtt ttcccgtata aaagctgtga caatcgtttt   1500

gcactggata agggtagcta ttttagcgca gacatttata gcctggttct gaagaaaaat   1560

gtgccgttca cctatgagat cctgctgaat atcctgaata gcccgctgta cgagttttac   1620

tttaagacct tcgcgaaaaa gctgggcgag aatctgtacg agtactatcc gaacaacctg   1680

atgaagctgt gcatcccgag catcgatttc ggcggtgaga acaatattga gaaaaagctg   1740

tatgatttct ttggtctgac ggataaagaa attgagattg tggagaagat caaagataac   1800

tgctaa                                                                1806
```

<210> SEQ ID NO 36
<211> LENGTH: 37
<212> TYPE: DNA
<213> ORGANISM: Artificial sequence
<220> FEATURE:
<223> OTHER INFORMATION: synthetic primer

<400> SEQUENCE: 36

```
ccgaattcgt cgacaacaga gtttgatcct ggctcag                              37
```

<210> SEQ ID NO 37
<211> LENGTH: 37
<212> TYPE: DNA
<213> ORGANISM: Artificial sequence
<220> FEATURE:
<223> OTHER INFORMATION: synthetic primer

<400> SEQUENCE: 37

```
cccgggatcc aagcttacgg ctaccttgtt acgactt                              37
```

-continued

<210> SEQ ID NO 38
<211> LENGTH: 351
<212> TYPE: PRT
<213> ORGANISM: Clostridium beijerinckii

<400> SEQUENCE: 38

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
            340                 345                 350
```

<210> SEQ ID NO 39
<211> LENGTH: 1056
<212> TYPE: DNA
<213> ORGANISM: Clostridium beijerinckii

<400> SEQUENCE: 39

```
atgaaaggtt ttgcaatgct aggtattaat aagttaggat ggatcgaaaa agaaaggcca     60
gttgcgggtt catatgatgc tattgtacgc ccattagcag tatctccgtg tacatcagat    120
atacatactg tttttgaggg agctcttgga gataggaaga atatgatttt agggcatgaa    180
gctgtaggtg aagttgttga agtaggaagt gaagtgaagg attttaaacc tggtgacaga    240
gttatagttc cttgtacaac tccagattgg agatctttgg aagttcaagc tggttttcaa    300
cagcactcaa acggtatgct cgcaggatgg aaattttcaa atttcaagga tggagttttt    360
ggtgaatatt ttcatgtaaa tgatgcggat atgaatcttg cgattctacc taaagacatg    420
ccattagaaa atgctgttat gataacagat atgatgacta ctggatttca tggagcagaa    480
cttgcagata ttcaaatggg ttcaagtgtt gtggtaattg gcattggagc tgttggctta    540
atgggaatag caggtgctaa attacgtgga gcaggtagaa taattggagt ggggagcagg    600
ccgatttgtg ttgaggctgc aaaattttat ggagcaacag atattctaaa ttataaaaat    660
ggtcatatag ttgatcaagt tatgaaatta acgaatggaa aaggcgttga ccgcgtaatt    720
atggcaggcg gtggttctga aacattatcc caagcagtat ctatggttaa accaggagga    780
ataatttcta atataaatta tcatggaagt ggagatgctt tactaatacc acgtgtagaa    840
tggggatgtg gaatggctca caagactata aaaggaggtc tttgtcctgg gggacgtttg    900
agagcagaaa tgttaagaga tatggtagta tataatcgtg ttgatctaag taaattagtt    960
acacatgtat atcatggatt tgatcacata gaagaagcac tgttattaat gaaagacaag   1020
ccaaaagact taattaaagc agtagttata ttataa                             1056
```

<210> SEQ ID NO 40
<211> LENGTH: 352
<212> TYPE: PRT
<213> ORGANISM: Thermoanaerobacter brockii

<400> SEQUENCE: 40

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175
```

-continued

```
Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350
```

<210> SEQ ID NO 41
<211> LENGTH: 1056
<212> TYPE: DNA
<213> ORGANISM: Thermoanaerobacter brockii

<400> SEQUENCE: 41

```
atgaaaggtt ttgcaatgct aggtattaat aagttaggat ggatcgaaaa agaaaggcca      60

gttgcgggtt catatgatgc tattgtacgc ccattagcag tatctccgtg tacatcagat     120

atacatactg tttttgaggg agctcttgga gataggaaga atatgatttt agggcatgaa     180

gctgtaggtg aagttgttga agtaggaagt gaagtgaagg attttaaacc tggtgacaga     240

gttatagttc cttgtacaac tccagattgg agatctttgg aagttcaagc tggttttcaa     300

cagcactcaa acggtatgct cgcaggatgg aaattttcaa atttcaagga tggagttttt     360

ggtgaatatt ttcatgtaaa tgatgcggat atgaatcttg cgattctacc taaagacatg     420

ccattagaaa atgctgttat gataacagat atgatgacta ctggatttca tggagcagaa     480

cttgcagata ttcaaatggg ttcaagtgtt gtggtaattg gcattggagc tgttggctta     540

atgggaatag caggtgctaa attacgtgga gcaggtagaa taattggagt ggggagcagg     600

ccgatttgtg ttgaggctgc aaaattttat ggagcaacag atattctaaa ttataaaaat     660

ggtcatatag ttgatcaagt tatgaaatta acgaatggaa aaggcgttga ccgcgtaatt     720

atggcaggcg gtggttctga aacattatcc caagcagtat ctatggttaa accaggagga     780

ataatttcta atataaatta tcatggaagt ggagatgctt tactaatacc acgtgtagaa     840

tggggatgtg gaatggctca caagactata aaaggaggtc tttgtcctgg gggacgtttg     900

agagcagaaa tgttaagaga tatggtagta tataatcgtg ttgatctaag taaattagtt     960

acacatgtat atcatggatt tgatcacata gaagaagcac tgttattaat gaaagacaag    1020

ccaaaagact taattaaagc agtagttata ttataa                              1056
```

<210> SEQ ID NO 42

<211> LENGTH: 392
<212> TYPE: PRT
<213> ORGANISM: Clostridium acetobutylicum

<400> SEQUENCE: 42

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
```

385 390

<210> SEQ ID NO 43
<211> LENGTH: 217
<212> TYPE: PRT
<213> ORGANISM: Clostridium beijerinckii

<400> SEQUENCE: 43

Met Asn Lys Leu Val Lys Leu Thr Asp Leu Lys Arg Ile Phe Lys Asp
1 5 10 15

Gly Met Thr Ile Met Val Gly Gly Phe Leu Asp Cys Gly Thr Pro Glu
20 25 30

Asn Ile Ile Asp Met Leu Val Asp Leu Asn Ile Lys Asn Leu Thr Ile
35 40 45

Ile Ser Asn Asp Thr Ala Phe Pro Asn Lys Gly Ile Gly Lys Leu Ile
50 55 60

Val Asn Gly Gln Val Ser Lys Val Ile Ala Ser His Ile Gly Thr Asn
65 70 75 80

Pro Glu Thr Gly Lys Lys Met Ser Ser Gly Glu Leu Lys Val Glu Leu
85 90 95

Ser Pro Gln Gly Thr Leu Ile Glu Arg Ile Arg Ala Ala Gly Ser Gly
100 105 110

Leu Gly Gly Val Leu Thr Pro Thr Gly Leu Gly Thr Ile Val Glu Glu
115 120 125

Gly Lys Lys Lys Val Thr Ile Asp Gly Lys Glu Tyr Leu Leu Glu Leu
130 135 140

Pro Leu Ser Ala Asp Val Ser Leu Ile Lys Gly Ser Ile Val Asp Glu
145 150 155 160

Phe Gly Asn Thr Phe Tyr Arg Ala Ala Thr Lys Asn Phe Asn Pro Tyr
165 170 175

Met Ala Met Ala Ala Lys Thr Val Ile Val Glu Ala Glu Asn Leu Val
180 185 190

Lys Cys Glu Asp Leu Lys Arg Asp Ala Ile Met Thr Pro Gly Val Leu
195 200 205

Val Asp Tyr Ile Val Lys Glu Ala Ala
210 215

<210> SEQ ID NO 44
<211> LENGTH: 221
<212> TYPE: PRT
<213> ORGANISM: Clostridium beijerinckii

<400> SEQUENCE: 44

Leu Ile Val Asp Lys Val Leu Ala Lys Glu Ile Ile Ala Lys Arg Val
1 5 10 15

Ala Lys Glu Leu Lys Lys Asp Gln Leu Val Asn Leu Gly Ile Gly Leu
20 25 30

Pro Thr Leu Val Ala Asn Tyr Val Pro Lys Glu Met Asn Ile Thr Phe
35 40 45

Glu Ser Glu Asn Gly Met Val Gly Met Ala Gln Met Ala Ser Ser Gly
50 55 60

Glu Asn Asp Pro Asp Ile Ile Asn Ala Gly Gly Glu Tyr Val Thr Leu
65 70 75 80

Leu Pro Gln Gly Ser Phe Phe Asp Ser Ser Met Ser Phe Ala Leu Ile
85 90 95

Arg Gly Gly His Val Asp Val Ala Val Leu Gly Ala Leu Glu Val Asp

```
            100                 105                 110

Glu Lys Gly Asn Leu Ala Asn Trp Ile Val Pro Asn Lys Ile Val Pro
        115                 120                 125

Gly Met Gly Gly Ala Met Asp Leu Ala Ile Gly Ala Lys Lys Ile Ile
    130                 135                 140

Val Ala Met Gln His Thr Gly Lys Ser Lys Pro Lys Ile Val Lys Lys
145                 150                 155                 160

Cys Thr Leu Pro Leu Thr Ala Lys Ala Gln Val Asp Leu Ile Val Thr
                165                 170                 175

Glu Leu Cys Val Ile Asp Val Thr Asn Asp Gly Leu Leu Leu Lys Glu
            180                 185                 190

Ile His Lys Asp Thr Thr Ile Asp Glu Ile Lys Phe Leu Thr Asp Ala
        195                 200                 205

Asp Leu Ile Ile Pro Asp Asn Leu Lys Ile Met Asp Ile
    210                 215                 220


<210> SEQ ID NO 45
<211> LENGTH: 246
<212> TYPE: PRT
<213> ORGANISM: Clostridium beijerinckii

<400> SEQUENCE: 45

Met Leu Glu Ser Glu Val Ser Lys Gln Ile Thr Thr Pro Leu Ala Ala
1               5                   10                  15

Pro Ala Phe Pro Arg Gly Pro Tyr Arg Phe His Asn Arg Glu Tyr Leu
            20                  25                  30

Asn Ile Ile Tyr Arg Thr Asp Leu Asp Ala Leu Arg Lys Ile Val Pro
        35                  40                  45

Glu Pro Leu Glu Leu Asp Arg Ala Tyr Val Arg Phe Glu Met Met Ala
    50                  55                  60

Met Pro Asp Thr Thr Gly Leu Gly Ser Tyr Thr Glu Cys Gly Gln Ala
65                  70                  75                  80

Ile Pro Val Lys Tyr Asn Gly Val Lys Gly Asp Tyr Leu His Met Met
                85                  90                  95

Tyr Leu Asp Asn Glu Pro Ala Ile Ala Val Gly Arg Glu Ser Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Lys Tyr Gly Thr Leu Pro Val Ala Thr Ala Thr
    130                 135                 140

Met Gly Tyr Lys His Glu Pro Leu Asp Leu Lys Glu Ala Tyr Ala Gln
145                 150                 155                 160

Ile Ala Arg Pro Asn Phe Met Leu Lys Ile Ile Gln Gly Tyr Asp Gly
                165                 170                 175

Lys Pro Arg Ile Cys Glu Leu Ile Cys Ala Glu Asn Thr Asp Ile Thr
            180                 185                 190

Ile His Gly Ala Trp Thr Gly Ser Ala Arg Leu Gln Leu Phe Ser His
        195                 200                 205

Ala Leu Ala Pro Leu Ala Asp Leu Pro Val Leu Glu Ile Val Ser Ala
    210                 215                 220

Ser His Ile Leu Thr Asp Leu Thr Leu Gly Thr Pro Lys Val Val His
225                 230                 235                 240

Asp Tyr Leu Ser Val Lys
                245
```

<210> SEQ ID NO 46
<211> LENGTH: 6832
<212> TYPE: DNA
<213> ORGANISM: Artificial sequence
<220> FEATURE:
<223> OTHER INFORMATION: synthetic plasmid

<400> SEQUENCE: 46
tgaaagaaag atatggaaca gtctataaag gctctcagag gctcatagac gaagaaagtg 60
gagaagtcat agaggtagac aagttatacc gtaaacaaac gtctggtaac ttcgtaaagg 120
catatatagt gcaattaata agtatgttag atatgattgg cggaaaaaaa cttaaaatcg 180
ttaactatat cctagataat gtccacttaa gtaacaatac aatgatagct acaacaagag 240
aaatagcaaa agctacagga acaagtctac aaacagtaat aacaacactt aaaatcttag 300
aagaaggaaa tattataaaa agaaaaactg gagtattaat gttaaaccct gaactactaa 360
tgagaggcga cgaccaaaaa caaaaatacc tcttactcga atttgggaac tttgagcaag 420
aggcaaatga aatagattga cctcccaata acaccacgta gttattggga ggtcaatcta 480
tgaaatgcga ttaagggccg gccagtgggc aagttgaaaa attcacaaaa atgtggtata 540
atatctttgt tcattagagc gataaacttg aatttgagag ggaacttaga tggtatttga 600
aaaaattgat aaaaatagtt ggaacagaaa agagtatttt gaccactact ttgcaagtgt 660
accttgtacc tacagcatga ccgttaaagt ggatatcaca caaataaagg aaaagggaat 720
gaaactatat cctgcaatgc tttattatat tgcaatgatt gtaaaccgcc attcagagtt 780
taggacggca atcaatcaag atggtgaatt ggggatatat gatgagatga taccaagcta 840
tacaatattt cacaatgata ctgaaacatt ttccagcctt tggactgagt gtaagtctga 900
ctttaaatca tttttagcag attatgaaag tgatacgcaa cggtatggaa acaatcatag 960
aatggaagga aagccaaatg ctccggaaaa catttttaat gtatctatga taccgtggtc 1020
aaccttcgat ggctttaatc tgaatttgca gaaaggatat gattatttga ttcctatttt 1080
tactatgggg aaatattata aagaagataa caaaattata cttcctttgg caattcaagt 1140
tcatcacgca gtatgtgacg gatttcacat ttgccgtttt gtaaacgaat tgcaggaatt 1200
gataaatagt taacttcagg tttgtctgta actaaaaaca agtatttaag caaaaacatc 1260
gtagaaatac ggtgtttttt gttaccctaa gtttaaactc ctttttgata atctcatgac 1320
caaaatccct taacgtgagt tttcgttcca ctgagcgtca gaccccgtag aaaagatcaa 1380
aggatcttct tgagatcctt tttttctgcg cgtaatctgc tgcttgcaaa caaaaaaacc 1440
accgctacca gcggtggttt gtttgccgga tcaagagcta ccaactcttt ttccgaaggt 1500
aactggcttc agcagagcgc agataccaaa tactgttctt ctagtgtagc cgtagttagg 1560
ccaccacttc aagaactctg tagcaccgcc tacatacctc gctctgctaa tcctgttacc 1620
agtggctgct gccagtggcg ataagtcgtg tcttaccggg ttggactcaa gacgatagtt 1680
accggataag gcgcagcggt cgggctgaac ggggggttcg tgcacacagc ccagcttgga 1740
gcgaacgacc tacaccgaac tgagatacct acagcgtgag ctatgagaaa gcgccacgct 1800
tcccgaaggg agaaaggcgg acaggtatcc ggtaagcggc agggtcggaa caggagagcg 1860
cacgagggag cttccagggg gaaacgcctg gtatctttat agtcctgtcg ggtttcgcca 1920
cctctgactt gagcgtcgat ttttgtgatg ctcgtcaggg gggcggagcc tatggaaaaa 1980
cgccagcaac gcggcctttt tacggttcct ggccttttgc tggccttttg ctcacatgtt 2040
ctttcctgcg ttatcccctg attctgtgga taaccgtatt accgcctttg agtgagctga 2100

```
taccgctcgc cgcagccgaa cgaccgagcg cagcgagtca gtgagcgagg aagcggaaga   2160
gcgcccaata cgcagggccc cctgcaggat aaaaaaattg tagataaatt ttataaaata   2220
gttttatcta caattttttt atcaggaaac agctatgacc gcggccgcag atagtcataa   2280
tagttccaga atagttcaat ttagaaatta gactaaactt caaaatgttt gttaaatata   2340
taccaaacta gtatagatat tttttaaata ctggacttaa acagtagtaa tttgcctaaa   2400
aaattttttc aatttttttt aaaaaatcct tttcaagttg tacattgtta tggtaatatg   2460
taattgaaga agttatgtag taatattgta aacgtttctt gatttttttta catccatgta   2520
gtgcttaaaa aaccaaaata tgtcacatgc aattgtatat ttcaaataac aatatttatt   2580
ttctcgttaa attcacaaat aatttattaa taatatcaat aaccaagatt atacttaaat   2640
ggatgtttat tttttaacac ttttatagta aatatattta ttttatgtag taaaaaggtt   2700
ataattataa ttgtatttat tacaattaat taaaataaaa aatagggttt taggtaaaat   2760
taagttattt taagaagtaa ttacaataaa aattgaagtt atttctttaa ggagggaatt   2820
attcatatga aagaagttgt aatagctagt gcagtaagaa cagcgattgg atcttatgga   2880
aagtctctta aggatgtacc agcagtagat ttaggagcta cagctataaa ggaagcagtt   2940
aaaaaagcag gaataaaacc agaggatgtt aatgaagtca ttttaggaaa tgttcttcaa   3000
gcaggtttag gacagaatcc agcaagacag gcatctttta aagcaggatt accagttgaa   3060
attccagcta tgactattaa taaggtttgt ggttcaggac ttagaacagt tagcttagca   3120
gcacaaatta taaaagcagg agatgctgac gtaataatag caggtggtat ggaaaatatg   3180
tctagagctc cttacttagc gaataacgct agatggggat atagaatggg aaacgctaaa   3240
tttgttgatg aaatgatcac tgacggattg tgggatgcat ttaatgatta ccacatggga   3300
ataacagcag aaaacatagc tgagagatgg aacatttcaa gagaagaaca agatgagttt   3360
gctcttgcat cacaaaaaaa agctgaagaa gctataaaat caggtcaatt taaagatgaa   3420
atagttcctg tagtaattaa aggcagaaag ggagaaactg tagttgatac agatgagcac   3480
cctagatttg gatcaactat agaaggactt gcaaaattaa aacctgcctt caaaaaagat   3540
ggaacagtta cagctggtaa tgcatcagga ttaaatgact gtgcagcagt acttgtaatc   3600
atgagtgcag aaaaagctaa agagcttgga gtaaaaccac ttgctaagat agtttcttat   3660
ggttcagcag gagttgaccc agcaataatg ggatatggac ctttctatgc aacaaaagca   3720
gctattgaaa aagcaggttg gacagttgat gaattagatt taatagaatc aaatgaagct   3780
tttgcagctc aaagtttagc agtagcaaaa gatttaaaat ttgatatgaa taaagtaaat   3840
gtaaatggag gagctattgc ccttggtcat ccaattggag catcaggtgc aagaatactc   3900
gttactcttg tacacgcaat gcaaaaaaga gatgcaaaaa aaggcttagc aactttatgt   3960
ataggtggcg gacaaggaac agcaatattg ctagaaaagt gctaggaatt cgagctcggt   4020
accagggaga tattaaaatg aataaattag taaaattaac agatttaaag cgcattttca   4080
aagatggcat gacaattatg gttgggggtt ttttagattg tggaactcct gaaaatatta   4140
tagatatgct agttgattta aatataaaaa atctgactat tataagcaat gatacagctt   4200
ttcctaataa aggaatagga aaacttattg taaatggtca agtttctaaa gtaattgctt   4260
cacatattgg aactaatcct gaaactggaa aaaaaatgag ctctggagaa cttaaagttg   4320
agctttcccc acaaggaaca ctgattgaaa gaattcgtgc agctggatct ggactcggag   4380
gtgtattaac tccaactgga cttggaacta tcgttgaaga aggtaagaaa aaagttacta   4440
```

-continued

```
tcgatggcaa agaatatcta ttagaacttc ctttatctgc tgatgtttca ttaataaaag   4500
gtagcattgt agatgaattt ggaaatacct tctatagggc tgctactaaa aatttcaatc   4560
catatatggc aatggctgca aaaacagtta tagttgaagc agaaaattta gttaaatgtg   4620
aagatttaaa aagagatgcc ataatgactc ctggcgtatt agtagattat atcgttaagg   4680
aggcggctta attgattgta gataaagttt tagcaaaaga gataattgcc aaaagagttg   4740
caaaagaact aaaaaaagac caactcgtaa accttggaat aggacttcca actttagtag   4800
caaattatgt accaaaagaa atgaacatta cttttgaatc agaaaatggc atggttggta   4860
tggcacaaat ggcatcatca ggtgaaaatg acccagatat aataaatgct ggcggggaat   4920
atgtaacatt attacctcaa ggttcatttt ttgatagttc aatgtctttc gcactaatac   4980
gaggaggaca tgttgatgtt gctgttcttg gtgctctaga agttgatgaa aaaggtaatt   5040
tagctaactg gattgttcca aataaaattg tcccaggtat gggtggcgct atggatttag   5100
caataggcgc aaaaaaaata atagtggcaa tgcaacatac aggaaaaagt aaacctaaaa   5160
tcgttaaaaa atgtactctc ccacttactg ctaaggctca agtggattta attgtcacag   5220
aactttgtgt aattgatgta acaaatgacg gcttactttt aaaagaaatt cataaagata   5280
caactattga tgaaattaaa tttttaacag atgcagattt aattattcca gataacttaa   5340
agattatgga tatatgaatc attctatttt aaatatataa ctttaaaaat cttatgtatt   5400
aaaaactaag aaaagaggtt gattgtttta tgttagaaag tgaagtatct aaacaaatta   5460
caactccact tgctgctcca gcgtttccta gaggaccata taggtttcac aatagagaat   5520
atctaaacat tatttatcga actgatttag atgctcttcg aaaaatagta ccagagccac   5580
ttgaattaga tagagcatat gttagatttg aaatgatggc tatgcctgat acaaccggac   5640
taggctcata tacagaatgt ggtcaagcta ttccagtaaa atataatggt gttaagggtg   5700
actacttgca tatgatgtat ctagataatg aacctgctat tgctgttgga agagaaagta   5760
gcgcttatcc aaaaaagctt ggctatccaa agctatttgt tgattcagat actttagttg   5820
ggacacttaa atatggtaca ttaccagtag ctactgcaac aatgggatat aagcacgagc   5880
ctctagatct taaagaagcc tatgctcaaa ttgcaagacc caattttatg ctaaaaatca   5940
ttcaaggtta cgatggtaag ccaagaattt gtgaactaat atgtgcagaa aatactgata   6000
taactattca cggtgcttgg actggaagtg cacgtctaca attatttagc catgcactag   6060
ctcctcttgc tgatttacct gtattagaga ttgtatcagc atctcatatc ctcacagatt   6120
taactcttgg aacacctaag gttgtacatg attatctttc agtaaaataa aagcaatata   6180
gaggatcctc tagagtcgac gtcacgcgtc catggagatc tcgaggcctg cagacatgca   6240
agcttggcac tggccgtcgt tttacaacgt cgtgactggg aaaaccctgg cgttacccaa   6300
cttaatcgcc ttgcagcaca tccccctttc gccagctggc gtaatagcga agaggcccgc   6360
accgatcgcc cttcccaaca gttgcgcagc ctgaatggcg aatggcgcta gcataaaaat   6420
aagaagcctg catttgcagg cttcttattt ttatggcgcg ccgcattcac ttcttttcta   6480
tataaatatg agcgaagcga ataagcgtcg gaaaagcagc aaaaagtttc ctttttgctg   6540
ttggagcatg ggggttcagg gggtgcagta tctgacgtca atgccgagcg aaagcgagcc   6600
gaagggtagc atttacgtta gataaccccc tgatatgctc cgacgcttta tatagaaaag   6660
aagattcaac taggtaaaat cttaatatag gttgagatga taaggtttat aaggaatttg   6720
tttgttctaa tttttcactc attttgttct aatttctttt aacaaatgtt cttttttttt   6780
tagaacagtt atgatatagt tagaatagtt taaaataagg agtgagaaaa ag           6832
```

<210> SEQ ID NO 47
<211> LENGTH: 2133
<212> TYPE: DNA
<213> ORGANISM: Clostridium beijerinckii

<400> SEQUENCE: 47
atgaataaat tagtaaaatt aacagattta aagcgcattt tcaaagatgg catgacaatt 60
atggttgggg gtttttaga ttgtggaact cctgaaaata ttatagatat gctagttgat 120
ttaaatataa aaaatctgac tattataagc aatgatacag cttttcctaa taaaggaata 180
ggaaaactta ttgtaaatgg tcaagtttct aaagtaattg cttcacatat tggaactaat 240
cctgaaactg gaaaaaaaat gagctctgga gaacttaaag ttgagctttc cccacaagga 300
acactgattg aaagaattcg tgcagctgga tctggactcg gaggtgtatt aactccaact 360
ggacttggaa ctatcgttga agaaggtaag aaaaaagtta ctatcgatgg caaagaatat 420
ctattagaac ttcctttatc tgctgatgtt tcattaataa aaggtagcat tgtagatgaa 480
tttggaaata ccttctatag ggctgctact aaaaatttca atccatatat ggcaatggct 540
gcaaaaacag ttatagttga agcagaaaat ttagttaaat gtgaagattt aaaaagagat 600
gccataatga ctcctggcgt attagtagat tatatcgtta aggaggcggc ttaattgatt 660
gtagataaag ttttagcaaa agagataatt gccaaaagag ttgcaaaaga actaaaaaaa 720
gaccaactcg taaaccttgg aataggactt ccaactttag tagcaaatta tgtaccaaaa 780
gaaatgaaca ttacttttga atcagaaaat ggcatggttg gtatggcaca aatggcatca 840
tcaggtgaaa atgacccaga tataataaat gctggcgggg aatatgtaac attattacct 900
caaggttcat tttttgatag ttcaatgtct ttcgcactaa tacgaggagg acatgttgat 960
gttgctgttc ttggtgctct agaagttgat gaaaaaggta atttagctaa ctggattgtt 1020
ccaaataaaa ttgtcccagg tatgggtggc gctatggatt tagcaatagg cgcaaaaaaa 1080
ataatagtgg caatgcaaca tacaggaaaa agtaaaccta aaatcgttaa aaaatgtact 1140
ctcccactta ctgctaaggc tcaagtggat ttaattgtca cagaactttg tgtaattgat 1200
gtaacaaatg acggcttact tttaaaagaa attcataaag atacaactat tgatgaaatt 1260
aaatttttaa cagatgcaga tttaattatt ccagataact taaagattat ggatatatga 1320
atcattctat tttaaatata taactttaaa aatcttatgt attaaaaact aagaaaagag 1380
gttgattgtt ttatgttaga aagtgaagta tctaaacaaa ttacaactcc acttgctgct 1440
ccagcgtttc ctagaggacc atataggttt cacaatagag aatatctaaa cattatttat 1500
cgaactgatt tagatgctct tcgaaaaata gtaccagagc cacttgaatt agatagagca 1560
tatgttagat ttgaaatgat ggctatgcct gatacaaccg gactaggctc atatacagaa 1620
tgtggtcaag ctattccagt aaaatataat ggtgttaagg gtgactactt gcatatgatg 1680
tatctagata atgaacctgc tattgctgtt ggaagagaaa gtagcgctta tccaaaaaag 1740
cttggctatc caaagctatt tgttgattca gatactttag ttgggacact taaatatggt 1800
acattaccag tagctactgc aacaatggga tataagcacg agcctctaga tcttaaagaa 1860
gcctatgctc aaattgcaag acccaatttt atgctaaaaa tcattcaagg ttacgatggt 1920
aagccaagaa tttgtgaact aatatgtgca gaaaatactg atataactat tcacggtgct 1980
tggactggaa gtgcacgtct acaattattt agccatgcac tagctcctct tgctgattta 2040
cctgtattag agattgtatc agcatctcat atcctcacag atttaactct tggaacacct 2100

-continued aaggttgtac atgattatct ttcagtaaaa taa 2133

<210> SEQ ID NO 48
<211> LENGTH: 7922
<212> TYPE: DNA
<213> ORGANISM: Artificial sequence
<220> FEATURE:
<223> OTHER INFORMATION: synthetic plasmid

<400> SEQUENCE: 48
atgaaagaaa gatatggaac agtctataaa ggctctcaga ggctcataga cgaagaaagt 60
ggagaagtca tagaggtaga caagttatac cgtaaacaaa cgtctggtaa cttcgtaaag 120
gcatatatag tgcaattaat aagtatgtta gatatgattg gcggaaaaaa acttaaaatc 180
gttaactata tcctagataa tgtccactta agtaacaata caatgatagc tacaacaaga 240
gaaatagcaa aagctacagg aacaagtcta caaacagtaa taacaacact taaaatctta 300
gaagaaggaa atattataaa aagaaaaact ggagtattaa tgttaaaccc tgaactacta 360
atgagaggcg acgaccaaaa acaaaaatac ctcttactcg aatttgggaa ctttgagcaa 420
gaggcaaatg aaatagattg acctcccaat aacaccacgt agttattggg aggtcaatct 480
atgaaatgcg attaagggcc ggccagtggg caagttgaaa aattcacaaa aatgtggtat 540
aatatctttg ttcattagag cgataaactt gaatttgaga gggaacttag atggtatttg 600
aaaaaattga taaaaatagt tggaacagaa aagagtattt tgaccactac tttgcaagtg 660
taccttgtac ctacagcatg accgttaaag tggatatcac acaaataaag gaaaagggaa 720
tgaaactata tcctgcaatg ctttattata ttgcaatgat tgtaaaccgc cattcagagt 780
ttaggacggc aatcaatcaa gatggtgaat tggggatata tgatgagatg ataccaagct 840
atacaatatt tcacaatgat actgaaacat tttccagcct ttggactgag tgtaagtctg 900
actttaaatc atttttagca gattatgaaa gtgatacgca acggtatgga aacaatcata 960
gaatggaagg aaagccaaat gctccggaaa acatttttaa tgtatctatg ataccgtggt 1020
caaccttcga tggctttaat ctgaatttgc agaaaggata tgattatttg attcctattt 1080
ttactatggg gaaatattat aaagaagata acaaaattat acttcctttg gcaattcaag 1140
ttcatcacgc agtatgtgac ggatttcaca tttgccgttt tgtaaacgaa ttgcaggaat 1200
tgataaatag ttaacttcag gtttgtctgt aactaaaaac aagtatttaa gcaaaaacat 1260
cgtagaaata cggtgttttt tgttacccta agtttaaact cctttttgat aatctcatga 1320
ccaaaatccc ttaacgtgag ttttcgttcc actgagcgtc agaccccgta gaaaagatca 1380
aaggatcttc ttgagatcct ttttttctgc gcgtaatctg ctgcttgcaa acaaaaaaac 1440
caccgctacc agcggtggtt tgtttgccgg atcaagagct accaactctt tttccgaagg 1500
taactggctt cagcagagcg cagataccaa atactgttct tctagtgtag ccgtagttag 1560
gccaccactt caagaactct gtagcaccgc ctacatacct cgctctgcta atcctgttac 1620
cagtggctgc tgccagtggc gataagtcgt gtcttaccgg gttggactca agacgatagt 1680
taccggataa ggcgcagcgg tcgggctgaa cggggggttc gtgcacacag cccagcttgg 1740
agcgaacgac ctacaccgaa ctgagatacc tacagcgtga gctatgagaa agcgccacgc 1800
ttcccgaagg gagaaaggcg gacaggtatc cggtaagcgg cagggtcgga acaggagagc 1860
gcacgaggga gcttccaggg ggaaacgcct ggtatcttta tagtcctgtc gggtttcgcc 1920
acctctgact tgagcgtcga tttttgtgat gctcgtcagg ggggcggagc ctatggaaaa 1980
acgccagcaa cgcggccttt ttacggttcc tggccttttg ctggcctttt gctcacatgt 2040

-continued

```
tctttcctgc gttatcccct gattctgtgg ataaccgtat taccgccttt gagtgagctg   2100
ataccgctcg ccgcagccga acgaccgagc gcagcgagtc agtgagcgag gaagcggaag   2160
agcgcccaat acgcagggcc ccctgcagga taaaaaaatt gtagataaat tttataaaat   2220
agttttatct acaatttttt tatcaggaaa cagctatgac cgcggccgca gatagtcata   2280
atagttccag aatagttcaa tttagaaatt agactaaact tcaaaatgtt tgttaaatat   2340
ataccaaact agtatagata tttttaaat actggactta aacagtagta atttgcctaa   2400
aaaatttttt caattttttt taaaaaatcc ttttcaagtt gtacattgtt atggtaatat   2460
gtaattgaag aagttatgta gtaatattgt aaacgtttct tgattttttt acatccatgt   2520
agtgcttaaa aaaccaaaat atgtcacatg caattgtata tttcaaataa caatatttat   2580
tttctcgtta aattcacaaa taatttatta ataatatcaa taaccaagat tatacttaaa   2640
tggatgttta ttttttaaca cttttatagt aaatatattt attttatgta gtaaaaaggt   2700
tataattata attgtattta ttacaattaa ttaaaataaa aaatagggtt ttaggtaaaa   2760
ttaagttatt ttaagaagta attacaataa aaattgaagt tatttcttta aggagggaat   2820
tattcatatg aaagaagttg taatagctag tgcagtaaga acagcgattg gatcttatgg   2880
aaagtctctt aaggatgtac cagcagtaga tttaggagct acagctataa aggaagcagt   2940
taaaaaagca ggaataaaac cagaggatgt taatgaagtc attttaggaa atgttcttca   3000
agcaggttta ggacagaatc cagcaagaca ggcatctttt aaagcaggat taccagttga   3060
aattccagct atgactatta ataaggtttg tggttcagga cttagaacag ttagcttagc   3120
agcacaaatt ataaaagcag gagatgctga cgtaataata gcaggtggta tggaaaatat   3180
gtctagagct ccttacttag cgaataacgc tagatgggga tatagaatgg gaaacgctaa   3240
atttgttgat gaaatgatca ctgacggatt gtgggatgca tttaatgatt accacatggg   3300
aataacagca gaaaacatag ctgagagatg gaacatttca agagaagaac aagatgagtt   3360
tgctcttgca tcacaaaaaa aagctgaaga agctataaaa tcaggtcaat ttaaagatga   3420
aatagttcct gtagtaatta aaggcagaaa gggagaaact gtagttgata cagatgagca   3480
ccctagattt ggatcaacta tagaaggact tgcaaaatta aaacctgcct tcaaaaaaga   3540
tggaacagtt acagctggta atgcatcagg attaaatgac tgtgcagcag tacttgtaat   3600
catgagtgca gaaaaagcta aagagcttgg agtaaaacca cttgctaaga tagtttctta   3660
tggttcagca ggagttgacc cagcaataat gggatatgga cctttctatg caacaaaagc   3720
agctattgaa aaagcaggtt ggacagttga tgaattagat ttaatagaat caaatgaagc   3780
ttttgcagct caaagtttag cagtagcaaa agatttaaaa tttgatatga ataaagtaaa   3840
tgtaaatgga ggagctattg cccttggtca tccaattgga gcatcaggtg caagaatact   3900
cgttactctt gtacacgcaa tgcaaaaaag agatgcaaaa aaaggcttag caactttatg   3960
tataggtggc ggacaaggaa cagcaatatt gctagaaaag tgctaggaat tcgagctcgg   4020
taccagggag atattaaaat gaataaatta gtaaaattaa cagatttaaa gcgcattttc   4080
aaagatggca tgacaattat ggttgggggt tttttagatt gtggaactcc tgaaaatatt   4140
atagatatgc tagttgattt aaatataaaa aatctgacta ttataagcaa tgatacagct   4200
tttcctaata aaggaatagg aaaacttatt gtaaatggtc aagtttctaa agtaattgct   4260
tcacatattg gaactaatcc tgaaactgga aaaaaaatga gctctggaga acttaaagtt   4320
gagctttccc cacaaggaac actgattgaa agaattcgtg cagctggatc tggactcgga   4380
```

```
ggtgtattaa ctccaactgg acttggaact atcgttgaag aaggtaagaa aaaagttact   4440
atcgatggca aagaatatct attagaactt cctttatctg ctgatgtttc attaataaaa   4500
ggtagcattg tagatgaatt tggaaatacc ttctataggg ctgctactaa aaatttcaat   4560
ccatatatgg caatggctgc aaaaacagtt atagttgaag cagaaaattt agttaaatgt   4620
gaagatttaa aaagagatgc cataatgact cctggcgtat tagtagatta tatcgttaag   4680
gaggcggctt aattgattgt agataaagtt ttagcaaaag agataattgc caaaagagtt   4740
gcaaaagaac taaaaaaaga ccaactcgta aaccttggaa taggacttcc aactttagta   4800
gcaaattatg taccaaaaga aatgaacatt actttgaat cagaaaatgg catggttggt   4860
atggcacaaa tggcatcatc aggtgaaaat gacccagata taataaatgc tggcggggaa   4920
tatgtaacat tattacctca aggttcattt tttgatagtt caatgtcttt cgcactaata   4980
cgaggaggac atgttgatgt tgctgttctt ggtgctctag aagttgatga aaaaggtaat   5040
ttagctaact ggattgttcc aaataaaatt gtcccaggta tgggtggcgc tatggattta   5100
gcaataggcg caaaaaaaat aatagtggca atgcaacata caggaaaaag taaacctaaa   5160
atcgttaaaa aatgtactct cccacttact gctaaggctc aagtggattt aattgtcaca   5220
gaactttgtg taattgatgt aacaaatgac ggcttacttt taaaagaaat tcataaagat   5280
acaactattg atgaaattaa atttttaaca gatgcagatt taattattcc agataactta   5340
aagattatgg atatatgaat cattctattt taaatatata actttaaaaa tcttatgtat   5400
taaaaactaa gaaaagaggt tgattgtttt atgttagaaa gtgaagtatc taaacaaatt   5460
acaactccac ttgctgctcc agcgtttcct agaggaccat ataggtttca caatagagaa   5520
tatctaaaca ttatttatcg aactgattta gatgctcttc gaaaaatagt accagagcca   5580
cttgaattag atagagcata tgttagattt gaaatgatgg ctatgcctga tacaaccgga   5640
ctaggctcat atacagaatg tggtcaagct attccagtaa aatataatgg tgttaagggt   5700
gactacttgc atatgatgta tctagataat gaacctgcta ttgctgttgg aagagaaagt   5760
agcgcttatc caaaaaagct tggctatcca aagctatttg ttgattcaga tactttagtt   5820
gggacactta aatatggtac attaccagta gctactgcaa caatgggata taagcacgag   5880
cctctagatc ttaaagaagc ctatgctcaa attgcaagac ccaattttat gctaaaaatc   5940
attcaaggtt acgatggtaa gccaagaatt tgtgaactaa tatgtgcaga aaatactgat   6000
ataactattc acggtgcttg gactggaagt gcacgtctac aattatttag ccatgcacta   6060
gctcctcttg ctgatttacc tgtattagag attgtatcag catctcatat cctcacagat   6120
ttaactcttg gaacacctaa ggttgtacat gattatcttt cagtaaaata aaagcaatat   6180
agaggatcct ctagagtcga cttaggaggt tctattatga aaggttttgc aatgttaggt   6240
attaacaaat taggatggat tgaaaagaaa aacccagtgc caggtcctta tgatgcgatt   6300
gtacatcctc tagctgtatc cccatgtaca tcagatatac atacggtttt tgaaggagca   6360
cttggtaata gggaaaatat gattttaggc catgaagctg taggtgaaat agccgaagtt   6420
ggcagcgaag ttaaagattt taaagttggc gatagagtta tcgtaccatg cacaacacct   6480
gactggagat ctttagaagt ccaagctggt tttcagcagc attcaaacgg tatgcttgca   6540
ggatggaagt tttccaattt taaagatggt gtatttgcag attactttca tgtaaacgat   6600
gcagatatga atcttgccat actcccagat gaaatacctt tagaaagtgc agttatgatg   6660
acagacatga tgactactgg ttttcatgga gcagaacttg cagacataaa aatgggctcc   6720
agcgttgtag taattggtat aggagctgtt ggattaatgg gaatagccgg ttccaaactt   6780
```

-continued

```
cgaggagcag gcagaattat cggtgttgga agcagacctg tttgtgttga aacagctaaa   6840

ttttatggag caactgatat tgtaaattat aaaaatggtg atatagttga acaaatcatg   6900

gacttaactc atggtaaagg tgtagaccgt gtaatcatgg caggcggtgg tgctgaaaca   6960

ctagcacaag cagtaactat ggttaaacct ggcggcgtaa tttctaacat caactaccat   7020

ggaagcggtg atactttacc aatacctcgt gttcaatggg gctgcggcat ggctcacaaa   7080

actataagag gaggattatg ccccggcgga cgtcttagaa tggaaatgct aagagatctt   7140

gttctatata aacgtgttga tttgagtaaa cttgttactc atgtatttga tggtgcagaa   7200

aatattgaaa aggccctttt gcttatgaaa aataagccaa aagatttaat taaatcagta   7260

gttacattct aaaaattcat ataaaaaaac tgtcgcatta aaaaaatgtc tcgaggcctg   7320

cagacatgca agcttggcac tggccgtcgt tttacaacgt cgtgactggg aaaaccctgg   7380

cgttacccaa cttaatcgcc ttgcagcaca tccccctttc gccagctggc gtaatagcga   7440

agaggcccgc accgatcgcc cttcccaaca gttgcgcagc ctgaatggcg aatggcgcta   7500

gcataaaaat aagaagcctg catttgcagg cttcttattt ttatggcgcg ccgcattcac   7560

ttcttttcta tataaatatg agcgaagcga ataagcgtcg gaaaagcagc aaaaagtttc   7620

ctttttgctg ttggagcatg ggggttcagg gggtgcagta tctgacgtca atgccgagcg   7680

aaagcgagcc gaagggtagc atttacgtta gataaccccc tgatatgctc cgacgcttta   7740

tatagaaaag aagattcaac taggtaaaat cttaatatag gttgagatga taaggtttat   7800

aaggaatttg tttgttctaa tttttcactc attttgttct aatttctttt aacaaatgtt   7860

cttttttttt tagaacagtt atgatatagt tagaatagtt taaaataagg agtgagaaaa   7920

ag                                                                  7922
```

<210> SEQ ID NO 49
<211> LENGTH: 4709
<212> TYPE: DNA
<213> ORGANISM: Artificial sequence
<220> FEATURE:
<223> OTHER INFORMATION: synthetic plasmid

<400> SEQUENCE: 49

```
gtttgccacc tgacgtctaa gaaaaggaat attcagcaat ttgcccgtgc cgaagaaagg     60

cccacccgtg aaggtgagcc agtgagttga ttgctacgta attagttagt tagcccttag    120

tgactcgtaa tacgactcac tatagggctc gaggcggccg cgcaacgcaa ttaatgtgag    180

ttagctcact cattaggcac cccaggcttt acactttatg cttccggctc gtatgttgtg    240

tggaattgtg agcggataac aatttcacac aggaaacaca tatgtttccg tgcaatgcct    300

atatcgaata tggtgataaa aatatgaaca gctttatcga agatgtggaa cagatctaca    360

acttcattaa aaagaacatt gatgtggaag aaaagatgca tttcattgaa acctataaac    420

agaaaagcaa catgaagaaa gagattagct ttagcgaaga atactataaa cagaagatta    480

tgaacggcaa aaatggcgtt gtgtacaccc cgccggaaat ggcggccttt atggttaaaa    540

atctgatcaa cgttaacgat gttattggca atccgtttat taaaatcatt gacccgagct    600

gcggtagcgg caatctgatt tgcaaatgtt ttctgtatct gaatcgcatc tttattaaga    660

acattgaggt gattaacagc aaaaataacc tgaatctgaa actggaagac atcagctacc    720

acatcgttcg caacaatctg tttggcttcg atattgacga aaccgcgatc aaagtgctga    780

aaattgatct gtttctgatc agcaaccaat ttagcgagaa aaatttccag gttaaagact    840
```

-continued

```
ttctggtgga aaatattgat cgcaaatatg acgtgttcat tggtaatccg ccgtatatcg    900
gtcacaaaag cgtggacagc agctacagct acgtgctgcg caaaatctac ggcagcatct    960
accgcgacaa aggcgatatc agctattgtt tctttcagaa gagcctgaaa tgtctgaagg   1020
aaggtggcaa actggtgttt gtgaccagcc gctacttctg cgagagctgc agcggtaaag   1080
aactgcgtaa attcctgatc gaaaacacga gcatttacaa gatcattgat ttttacggca   1140
tccgcccgtt caaacgcgtg ggtatcgatc cgatgattat ttttctggtt cgtacgaaga   1200
actggaacaa taacattgaa attattcgcc cgaacaagat tgaaaagaac gaaaagaaca   1260
aattcctgga tagcctgttc ctggacaaaa gcgaaaagtg taaaaagttt agcattagcc   1320
agaaaagcat taataacgat ggctgggttt tcgtggacga agtggagaaa aacattatcg   1380
acaaaatcaa agagaaaagc aagttcattc tgaaagatat ttgccatagc tgtcaaggca   1440
ttatcaccgg ttgtgatcgc gcctttattg tggaccgtga tatcatcaat agccgtaaga   1500
tcgaactgcg tctgattaaa ccgtggatta aaagcagcca tatccgtaag aatgaagtta   1560
ttaagggcga aaaattcatc atctatagca acctgattga gaatgaaacc gagtgtccga   1620
atgcgattaa atatatcgaa cagtacaaga aacgtctgat ggagcgccgc gaatgcaaaa   1680
agggcacgcg taagtggtat gaactgcaat ggggccgtaa accggaaatc ttcgaagaaa   1740
agaaaattgt tttcccgtat aaaagctgtg acaatcgttt tgcactggat aagggtagct   1800
attttagcgc agacatttat agcctggttc tgaagaaaaa tgtgccgttc acctatgaga   1860
tcctgctgaa tatcctgaat agcccgctgt acgagtttta ctttaagacc ttcgcgaaaa   1920
agctgggcga gaatctgtac gagtactatc cgaacaacct gatgaagctg tgcatcccga   1980
gcatcgattt cggcggtgag aacaatattg agaaaaagct gtatgatttc tttggtctga   2040
cggataaaga aattgagatt gtggagaaga tcaaagataa ctgctaagaa ttcgatatca   2100
cccgggaact agtctgcagc cctttagtga gggttaattg gagtcactaa gggttagtta   2160
gttagattag cagaaagtca aaagcctccg accggaggct tttgactaaa acttcccttg   2220
gggttatcat tggggctcac tcaaaggcgg taatcagata aaaaaaatcc ttagctttcg   2280
ctaaggatga tttctgctag agatggaata gactggatgg aggcggataa agttgcagga   2340
ccacttctgc gctcggccct tccggctggc tggtttattg ctgataaatc tggagccggt   2400
gagcgtgggt ctcgcggtat cattgcagca ctggggccag atggtaagcc ctcccgtatc   2460
gtagttatct acacgacggg gagtcaggca actatggatg aacgaaatag acagatcgct   2520
gagataggtg cctcactgat taagcattgg taactgtcag accaagttta ctcatatata   2580
ctttagattg atttaaaact tcatttttaa tttaaaagga tctaggtgaa gatccttttt   2640
gataatctca tgaccaaaat cccttaacgt gagttttcgt tccactgagc gtcagacccc   2700
ttaataagat gatcttcttg agatcgtttt ggtctgcgcg taatctcttg ctctgaaaac   2760
gaaaaaaccg ccttgcaggg cggtttttcg aaggttctct gagctaccaa ctctttgaac   2820
cgaggtaact ggcttggagg agcgcagtca ccaaaacttg tcctttcagt ttagccttaa   2880
ccggcgcatg acttcaagac taactcctct aaatcaatta ccagtggctg ctgccagtgg   2940
tgcttttgca tgtctttccg ggttggactc aagacgatag ttaccggata aggcgcagcg   3000
gtcggactga acggggggtt cgtgcataca gtccagcttg gagcgaactg cctacccgga   3060
actgagtgtc aggcgtggaa tgagacaaac gcggccataa cagcggaatg acaccggtaa   3120
accgaaaggc aggaacagga gagcgcacga gggagccgcc aggggaaacg cctggtatct   3180
ttatagtcct gtcgggtttc gccaccactg atttgagcgt cagatttcgt gatgcttgtc   3240
```

-continued agggggggcgg agcctatgga aaaacggctt tgccgcggcc ctctcacttc cctgttaagt 3300
atcttcctgg catcttccag gaaatctccg ccccgttcgt aagccatttc cgctcgccgc 3360
agtcgaacga ccgagcgtag cgagtcagtg agcgaggaag cggaatatat cctgtatcac 3420
atattctgct gacgcaccgg tgcagccttt tttctcctgc cacatgaagc acttcactga 3480
caccctcatc agtgccaaca tagtaagcca gtatacactc cgctagcgct gaggtctgcc 3540
tcgtgaagaa ggtgttgctg actcatacca ggcctgaatc gccccatcat ccagccagaa 3600
agtgagggag ccacggttga tgagagcttt gttgtaggtg gaccagttgg tgattttgaa 3660
cttttgcttt gccacggaac ggtctgcgtt gtcgggaaga tgcgtgatct gatccttcaa 3720
ctcagcaaaa gttcgattta ttcaacaaag ccacgttgtg tctcaaaatc tctgatgtta 3780
cattgcacaa gataaaaata tatcatcatg aacaataaaa ctgtctgctt acataaacag 3840
taatacaagg ggtgtttact agaggttgat cgggcacgta agaggttcca actttcacca 3900
taatgaaata agatcactac cgggcgtatt ttttgagtta tcgagatttt caggagctaa 3960
ggaagctaaa atggagaaaa aaatcacggg atataccacc gttgatatat cccaatggca 4020
tcgtaaagaa cattttgagg catttcagtc agttgctcaa tgtacctata accagaccgt 4080
tcagctggat attacggcct ttttaaagac cgtaaagaaa aataagcaca agttttatcc 4140
ggcctttatt cacattcttg cccgcctgat gaacgctcac ccggagtttc gtatggccat 4200
gaaagacggt gagctggtga tctgggatag tgttcaccct tgttacaccg ttttccatga 4260
gcaaactgaa acgttttcgt ccctctggag tgaataccac gacgatttcc ggcagtttct 4320
ccacatatat tcgcaagatg tggcgtgtta cggtgaaaac ctggcctatt tccctaaagg 4380
gtttattgag aatatgtttt ttgtctcagc caatccctgg gtgagtttca ccagttttga 4440
tttaaacgtg gccaatatgg acaacttctt cgcccccgtt ttcacgatgg gcaaatatta 4500
tacgcaaggc gacaaggtgc tgatgccgct ggcgatccag gttcatcatg ccgtttgtga 4560
tggcttccat gtcggccgca tgcttaatga attacaacag tactgtgatg agtggcaggg 4620
cggggcgtaa taatactagc tccggcaaaa aaacgggcaa ggtgtcacca ccctgccctt 4680
tttctttaaa accgaaaaga ttacttcgc 4709

<210> SEQ ID NO 50
<211> LENGTH: 128
<212> TYPE: DNA
<213> ORGANISM: Escherichia coli

<400> SEQUENCE: 50
gcggccgcgc aacgcaatta atgtgagtta gctcactcat taggcacccc aggctttaca 60
ctttatgctt ccggctcgta tgttgtgtgg aattgtgagc ggataacaat ttcacacagg 120
aaacacat 128

<210> SEQ ID NO 51
<211> LENGTH: 560
<212> TYPE: DNA
<213> ORGANISM: Clostridium autoethanogenum

<400> SEQUENCE: 51
ttataagaaa tcctaaggaa tatgatgtaa tgagtaaagc tataaatcct tatggagatg 60
gcaaggcagc ttatagaata acagaagcta ttttacaata ttttgattta gcaaaaggta 120
catatagtga gtttaaatca aattaaaaag ttataatttt caattttcat tctttttaaa 180

-continued

```
ggagattagc atacatttta tcataattat acagacaata tagtaatata tgatgttaaa    240

atatcaatat atggttaaaa atctgtatat tttttcccat tttaattatt tgtactataa    300

tattacactg agtgtattgt atatttaaaa aatatttggt acaattagtt agttaaataa    360

attctaaatt gtaaattatc agaatcctta ttaaggaaat acatagattt aaggagaaat    420

cataaaaagg tgtaatataa actggctaaa attgagcaaa aattgagcaa ttaagacttt    480

ttgattgtat ctttttatat atttaaggta tataatctta tttatattgg gggaacttga    540

tgaataaaca tattctagac                                                560


<210> SEQ ID NO 52
<211> LENGTH: 297
<212> TYPE: DNA
<213> ORGANISM: Clostridium autoethanogenum

<400> SEQUENCE: 52

taattttttg tgtcaataat ttttgttata ttattttaat taaatttttc acatgtataa     60

ttaaaagtaa gatagatatt ctaatgtact tacttaggta gaaaaacatg tatacaaaat    120

taaaaaacta ttataacaca tagtatcaat attgaaggta atactgttca atatcgatac    180

agataaaaaa atatataata cagaagaaaa aattataaat ttgtggtata atataaagta    240

tagtaattta agtttaaacc tcgtgaaaac gctaacaaat aataggaggt gtattat       297


<210> SEQ ID NO 53
<211> LENGTH: 599
<212> TYPE: DNA
<213> ORGANISM: Clostridium autoethanogenum

<400> SEQUENCE: 53

atagtataac tttaaaaaac tgtcttaaaa agttgttata taaaaaaatgt tgacaattaa     60

acagctattt agtgcaaaac aaccataaaa atttaaaaaa taccataaat tacttgaaaa    120

atagttgata ataatgtaga gttataaaca aaggtgaaaa gcattacttg tattcttttt    180

tatatattat tataaattaa aatgaagctg tattagaaaa aatacacacc tgtaatataa    240

aattttaaat taatttttaa ttttttcaaa atgtatttta catgtttaga attttgatgt    300

atattaaaat agtagaatac ataagatact taatttaatt aaagatagtt aagtactttt    360

caatgtgctt ttttagatgt ttaatacaaa tctttaattg taaaagaaat gctgtactat    420

ttactgtact agtgacggga ttaaactgta ttaattataa ataaaaaata agtacagttg    480

tttaaaatta tattttgtat taaatctaat agtacgatgt aagttatttt atactattgc    540

tagtttaata aaaagattta attatatact tgaaaaggag aggaattttt atgcgtaaa     599


<210> SEQ ID NO 54
<211> LENGTH: 34
<212> TYPE: DNA
<213> ORGANISM: Clostridium autoethanogenum

<400> SEQUENCE: 54

tatttgtcga cttaggaggt tctattatga aagg                                 34


<210> SEQ ID NO 55
<211> LENGTH: 30
<212> TYPE: DNA
<213> ORGANISM: Clostridium autoethanogenum

<400> SEQUENCE: 55

aaaactcgag acattttttt aatgcgacag                                      30
```

<210> SEQ ID NO 56
<211> LENGTH: 560
<212> TYPE: DNA
<213> ORGANISM: Clostridium ljungdahlii

<400> SEQUENCE: 56
agatagtcat aatagttcca gaatagttta atttagcatt tggattaaat tcccatatgt 60
ttgttaaata tataccaaac tagtatagat atttttaaaa tactgtactt aaacagtagt 120
aatttacgta aaaaaatttt ttgatttttt taaaaaagtc cttttcaagt tgtacattat 180
tatggtaata tgtaattgaa gaagttgtgt agtaatattg taaacgtttc ttaatttatt 240
ttcatccatg tagtgcttaa aaaaccaaaa tatgtcacac gcaattgcat atttcaaaca 300
ataatattta ttttctcgtt aaattcacaa ataatttatt aataatatca ataaccaaga 360
ttatacttaa atggatgttt attttttaac atttttata gtaaatatat ttattttatg 420
tagtaaaaag gttataatta taattgtatt tattacaatt aattaaaata aaaaaatagg 480
gttttaggta aaattaagtt attttaagaa gtaattacaa caaaaattga agttatttct 540
ttaaggaggg aattattaaa 560

<210> SEQ ID NO 57
<211> LENGTH: 557
<212> TYPE: DNA
<213> ORGANISM: Clostridium ragsdalei

<400> SEQUENCE: 57
agatagtcat aatagttcca gaatagttta attttgaaat tggagtaaac ttccaaatgt 60
ttgttaaata tataccaaac tagtatagat attttttaaa tactagactt aaacagtaga 120
aatttgccta aaaaattttt tagtttttta aaaaaatcct tttcaagttg tacgttatta 180
tggtaatatg taattgaaga agttatgtaa taatattgta aacgtttctt aattttttta 240
catccatgta atgcttaaaa gaccaaaata tgtcacatgt aattgtatat ttcacataat 300
aatatttatt ttcttattaa attcacaaat aatttattaa taatatcaat aaccaagatt 360
atacttaaat ggatgtttat tttttaacat tttttatggt aaatatattt attttatgta 420
gtaaaaaggt tataattata attgtattta ttacaattaa ttaaaataaa aaatagggtt 480
ttaggtaaaa ttaagttatt ttaagaagta attacaacaa aaattgaagt tatttcttta 540
aggagggaat tattaaa 557

<210> SEQ ID NO 58
<211> LENGTH: 536
<212> TYPE: DNA
<213> ORGANISM: Clostridium ljungdahlii

<400> SEQUENCE: 58
ttataagaaa tcctaaggaa tatgatgtaa tgagtaaagc tataaatcct tatggagatg 60
gcaaggcagc ttatagaata acagaagcta ttttacaata ttttgattta gcaaaaggta 120
catatagtga gtttaaatca aattaaaaag ttataatttt caattttcat tctttttaaa 180
ggagattagc atacatttta tcataattat acagacaata tagtaatata tgatgttaaa 240
atatcaatat atggttaaaa atctgtatat tttttcccat tttaattatt tgtactataa 300
tattacactg agtgtattgt atatttaaaa aatatttggt acaattagtt agttaaataa 360
attctaaatt gtaaattatc agaatcctta ttaaggaaat acatagattt aaggagaaat 420

-continued

```
cataaaaagg tgtaatataa actggctaaa attgagcaaa aattgagcaa ttaagacttt    480

ttgattgtat ctttttatat atttaaggta tataatctta tttatattgg gggaac        536


<210> SEQ ID NO 59
<211> LENGTH: 549
<212> TYPE: DNA
<213> ORGANISM: Clostridium ragsdalei

<400> SEQUENCE: 59

ttataagaaa tcctaaggaa tatgatgtaa tgagtaaagc tataaatcct tatggagatg     60

gcaaggcagc ttatagaata acagaagcta ttttacaata ttttgattta gcaaaaggta    120

catatagtga gtttaaatca aattaaaaag ttataatttt gaattttcat tctttttaaa    180

ggagattagc atacatttta tcataattat acagacaata tagtaatata tgatgttaaa    240

atatcaatat atggttaaaa aactgtatat tttttcccat tttaattatt tgtactataa    300

tattacactg agtgtattgt atatttaaaa aatatttggt acaattagtt agttaaataa    360

attctaaatt ataaattatc agaaacctta ttaaggaaat acatagattt agggagaaat    420

aataaaaagg tgtaatataa actggctaaa gttgagtaat taagactttt aggttgtatc    480

tttttatata tttaaggtat ataatcttag ttatataggg ggaacttgat gaataaacat    540

attctagac                                                            549


<210> SEQ ID NO 60
<211> LENGTH: 298
<212> TYPE: DNA
<213> ORGANISM: Clostridium ljungdahlii

<400> SEQUENCE: 60

taattttttg tgtcaataat ttttgttata ttattttaat taaatttttc acatgtataa     60

ttaaaagtaa gatagatatt ctaatgtact tacttaggta gaaaaacatg tatacaaaat    120

taaaaaacta ttataacaca tagtatcaat attgaaggta atactgttca atatcgatac    180

agataaaaaa aatatataat acagaagaaa aaattataaa tttgtggtat aatataaagt    240

atagtaattt aagtttaaac ctcgtgaaaa cgctaacaaa taataggagg tgtattat      298


<210> SEQ ID NO 61
<211> LENGTH: 300
<212> TYPE: DNA
<213> ORGANISM: Clostridium ragsdalei

<400> SEQUENCE: 61

taattttttta tatcaataat ttttattata ttattttaat taaatttttc acatgtataa     60

ttaaaagtaa gatagagata gttaggatat tttagtgcat ttatttagat aaaaaaatatg    120

tatacaagat tagaaaaaaa ttataacaca taatagttgc attgaaggta atactgttca    180

atatcgatac agataaaaaa atttataata cagaagaaaa aaatataaat ttgtggtata    240

atataaaata taataattta gatttacacc ccgtgaaaac gctaacaaat aaatagggag    300


<210> SEQ ID NO 62
<211> LENGTH: 590
<212> TYPE: DNA
<213> ORGANISM: Clostridium ljungdahlii

<400> SEQUENCE: 62

atagtataac tttaaaaaac tgtcttaaaa agttgttata taaaaaatgt tgacaattaa     60

acagctattt agtgcaaaac aaccataaaa atttaaaaaa taccataaat tacttgaaaa    120
```

-continued

```
atagttgata ataatgtaga gttataaaca aaggtgaaaa gcattacttg tattcttttt    180

tatatattat tataaattaa aatgaagctg tattagaaaa aatacacacc tgtaatataa    240

aattttaaat taatttttaa ttttttcaaa atgtatttta catgtttaga attttgatgt    300

atattaaaat agtagaatac ataagatact taatttaatt aaagatagtt aagtactttt    360

caatgtgctt ttttagatgt ttaatacaaa tctttaattg taaaagaaat gctgtactat    420

ttactgtact agtgacggga ttaaactgta ttaattataa ataaaaaata agtacagttg    480

tttaaaatta tattttgtat taaatctaat agtacgatgt aagttatttt atactattgc    540

tagtttaata aaaagattta attatatact tgaaaaggag aggaattttt               590
```

<210> SEQ ID NO 63
<211> LENGTH: 600
<212> TYPE: DNA
<213> ORGANISM: Clostridium ragsdalei

<400> SEQUENCE: 63

```
atagaataac ttaaaaaaac tgtcttaaaa agctgttata taaaaaaatg ttaacaatta     60

aacagctatt tagtgcaaaa caaccataaa aatttaaaaa ataccataaa ttacttgaaa    120

aatagtagag aataatgtag agttataaac gaaggtgaaa agcattactt gtattccttt    180

ttacagacta ttataaatta agataaagct gtattaggaa aaatgcacac ctgtaatata    240

aggttttaaa ttaattttta attttcccaa aatgtatttt acatgtttag aattttgatg    300

tatattaaaa tagtagaata cataagatac ttaatttaat aaagatagtt aagtactttt    360

caatgtactt ttttagatat ttaatacaag tttttaattg taaaaaaatg ctgtgctatt    420

tactgtacta atggtagtac tatatctgta ttaattgtat gtaaaaagta agtatagtta    480

tttaagatta tgttttgtat taaatctaaa tagtacaatg taggttatgt tatactattg    540

ctagtttaat aaaaagattt aattatatac ttgaaaagga gaggaatttt tatgcgtaaa    600
```

<210> SEQ ID NO 64
<211> LENGTH: 25
<212> TYPE: DNA
<213> ORGANISM: Artificial sequence
<220> FEATURE:
<223> OTHER INFORMATION: synthetic primer

<400> SEQUENCE: 64

```
ttgatgaaat gatcactgac ggatt                                           25
```

<210> SEQ ID NO 65
<211> LENGTH: 25
<212> TYPE: DNA
<213> ORGANISM: Artificial sequence
<220> FEATURE:
<223> OTHER INFORMATION: synthetic primer

<400> SEQUENCE: 65

```
gaaatgttcc atctctcagc tatgt                                           25
```

<210> SEQ ID NO 66
<211> LENGTH: 25
<212> TYPE: DNA
<213> ORGANISM: Artificial sequence
<220> FEATURE:
<223> OTHER INFORMATION: synthetic primer

<400> SEQUENCE: 66
ctaatacgag gaggacatgt tgatg 25

<210> SEQ ID NO 67
<211> LENGTH: 25
<212> TYPE: DNA
<213> ORGANISM: Artificial sequence
<220> FEATURE:
<223> OTHER INFORMATION: synthetic primer

<400> SEQUENCE: 67
cacccatacc tgggacaatt ttatt 25

<210> SEQ ID NO 68
<211> LENGTH: 25
<212> TYPE: DNA
<213> ORGANISM: Artificial sequence
<220> FEATURE:
<223> OTHER INFORMATION: synthetic primer

<400> SEQUENCE: 68
gggctgctac taaaaatttc aatcc 25

<210> SEQ ID NO 69
<211> LENGTH: 25
<212> TYPE: DNA
<213> ORGANISM: Artificial sequence
<220> FEATURE:
<223> OTHER INFORMATION: synthetic primer

<400> SEQUENCE: 69
caggagtcat tatggcatct ctttt 25

<210> SEQ ID NO 70
<211> LENGTH: 25
<212> TYPE: DNA
<213> ORGANISM: Artificial sequence
<220> FEATURE:
<223> OTHER INFORMATION: synthetic primer

<400> SEQUENCE: 70
tagtaccaga gccacttgaa ttaga 25

<210> SEQ ID NO 71
<211> LENGTH: 25
<212> TYPE: DNA
<213> ORGANISM: Artificial sequence
<220> FEATURE:
<223> OTHER INFORMATION: synthetic primer

<400> SEQUENCE: 71
ggaatagctt gaccacattc tgtat 25

<210> SEQ ID NO 72
<211> LENGTH: 1647
<212> TYPE: DNA
<213> ORGANISM: Lactococcus lactis

<400> SEQUENCE: 72
atgtatacag taggagatta cctattagac cgattacacg agttaggaat tgaagaaatt 60
tttggagtcc ctggagacta taacttacaa tttttagatc aaattatttc ccacaaggat 120
atgaaatggg tcggaaatgc taatgaatta aatgcttcat atatggctga tggctatgct 180
cgtactaaaa aagctgccgc atttcttaca acctttggag taggtgaatt gagtgcagtt 240
aatggattag caggaagtta cgccgaaaat ttaccagtag tagaaatagt gggatcacct 300

```
acatcaaaag ttcaaaatga aggaaaattt gttcatcata cgctggctga cggtgatttt    360
aaacacttta tgaaaatgca cgaacctgtt acagcagctc gaactttact gacagcagaa    420
aatgcaaccg ttgaaattga ccgagtactt tctgcactat taaaagaaag aaaacctgtc    480
tatatcaact taccagttga tgttgctgct gcaaaagcag agaaaccctc actccctttg    540
aaaaaggaaa actcaacttc aaatacaagt gaccaagaaa ttttgaacaa aattcaagaa    600
agcttgaaaa atgccaaaaa accaatcgtg attacaggac atgaaataat tagttttggc    660
ttagaaaaaa cagtcactca atttatttca aagacaaaac tacctattac gacattaaac    720
tttggtaaaa gttcagttga tgaagccctc ccttcatttt taggaatcta taatggtaca    780
ctctcagagc ctaatcttaa agaattcgtg gaatcagccg acttcatctt gatgcttgga    840
gttaaactca cagactcttc aacaggagcc ttcactcatc atttaaatga aaataaaatg    900
atttcactga atatagatga aggaaaaata tttaacgaaa gaatccaaaa ttttgatttt    960
gaatccctca tctcctctct cttagaccta agcgaaatag aatacaaagg aaaatatatc   1020
gataaaaagc aagaagactt tgttccatca aatgcgcttt tatcacaaga ccgcctatgg   1080
caagcagttg aaaacctaac tcaaagcaat gaaacaatcg ttgctgaaca agggacatca   1140
ttctttggcg cttcatcaat ttttcttaaa tcaaagagtc attttattgg tcaaccctta   1200
tggggatcaa ttggatatac attcccagca gcattaggaa gccaaattgc agataaagaa   1260
agcagacacc ttttatttat tggtgatggt tcacttcaac ttacagtgca agaattagga   1320
ttagcaatca gagaaaaaat taatccaatt tgctttatta tcaataatga tggttataca   1380
gtcgaaagag aaattcatgg accaaatcaa agctacaatg atattccaat gtggaattac   1440
tcaaaattac cagaatcgtt tggagcaaca gaagatcgag tagtctcaaa aatcgttaga   1500
actgaaaatg aatttgtgtc tgtcatgaaa gaagctcaag cagatccaaa tagaatgtac   1560
tggattgagt taattttggc aaaagaaggt gcaccaaaag tactgaaaaa aatgggcaaa   1620
ctatttgctg aacaaaataa atcataa                                       1647
```

<210> SEQ ID NO 73
<211> LENGTH: 548
<212> TYPE: PRT
<213> ORGANISM: Lactococcus lactis

<400> SEQUENCE: 73

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125
```

-continued

```
Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
```

545

<210> SEQ ID NO 74
<211> LENGTH: 2094
<212> TYPE: DNA
<213> ORGANISM: Saccharomyces cerevisiae

<400> SEQUENCE: 74
atgtctattc cagaaactca aaaagccatt atcttctacg aatccaacgg caagttggag 60
cataaggata tcccagttcc aaagccaaag cccaacgaat tgttaatcaa cgtcaagtac 120
tctggtgtct gccacaccga tttgcacgct tggcatggtg actggccatt gccaactaag 180
ttaccattag ttggtggtca cgaaggtgcc ggtgtcgttg tcggcatggg tgaaaacgtt 240
aagggctgga agatcggtga ctacgccggt atcaaatggt tgaacggttc ttgtatggcc 300
tgtgaatact gtgaattggg taacgaatcc aactgtcctc acgctgactt gtctggttac 360
acccacgacg gttctttcca agaatacgct accgctgacg ctgttcaagc cgctcacatt 420
cctcaaggta ctgacttggc tgaagtcgcg ccaatcttgt gtgctggtat caccgtatac 480
aaggctttga agtctgccaa cttgagagca ggccactggg cggccatttc tggtgctgct 540
ggtggtctag gttctttggc tgttcaatat gctaaggcga tgggttacag agtcttaggt 600
attgatggtg gtccaggaaa ggaagaattg tttacctcgc tcggtggtga agtattcatc 660
gacttcacca aagagaagga cattgttagc gcagtcgtta aggctaccaa cggcggtgcc 720
cacggtatca tcaatgtttc cgtttccgaa gccgctatcg aagcttctac cagatactgt 780
agggcgaacg gtactgttgt cttggttggt ttgccagccg gtgcaaagtg ctcctctgat 840
gtcttcaacc acgttgtcaa gtctatctcc attgtcggct cttacgtggg gaacagagct 900
gataccagag aagccttaga tttctttgcc agaggtctag tcaagtctcc aataaaggta 960
gttggcttat ccagtttacc agaaatttac gaaaagatgg agaagggcca aattgctggt 1020
agatacgttg ttgacacttc taaataaatg tctattccag aaactcaaaa agccattatc 1080
ttctacgaat ccaacggcaa gttggagcat aaggatatcc cagttccaaa gccaaagccc 1140
aacgaattgt taatcaacgt caagtactct ggtgtctgcc acaccgattt gcacgcttgg 1200
catggtgact ggccattgcc aactaagtta ccattagttg gtggtcacga aggtgccggt 1260
gtcgttgtcg gcatgggtga aaacgttaag ggctggaaga tcggtgacta cgccggtatc 1320
aaatggttga acggttcttg tatggcctgt gaatactgtg aattgggtaa cgaatccaac 1380
tgtcctcacg ctgacttgtc tggttacacc cacgacggtt ctttccaaga atacgctacc 1440
gctgacgctg ttcaagccgc tcacattcct caaggtactg acttggctga agtcgcgcca 1500
atcttgtgtg ctggtatcac cgtatacaag gctttgaagt ctgccaactt gagagcaggc 1560
cactgggcgg ccatttctgg tgctgctggt ggtctaggtt ctttggctgt tcaatatgct 1620
aaggcgatgg gttacagagt cttaggtatt gatggtggtc caggaaagga agaattgttt 1680
acctcgctcg gtggtgaagt attcatcgac ttcaccaaag agaaggacat tgttagcgca 1740
gtcgttaagg ctaccaacgg cggtgcccac ggtatcatca atgtttccgt ttccgaagcc 1800
gctatcgaag cttctaccag atactgtagg gcgaacggta ctgttgtctt ggttggtttg 1860
ccagccggtg caaagtgctc ctctgatgtc ttcaaccacg ttgtcaagtc tatctccatt 1920
gtcggctctt acgtggggaa cagagctgat accagagaag ccttagattt ctttgccaga 1980
ggtctagtca agtctccaat aaaggtagtt ggcttatcca gtttaccaga aatttacgaa 2040
aagatggaga agggccaaat tgctggtaga tacgttgttg acacttctaa ataa 2094

<210> SEQ ID NO 75
<211> LENGTH: 348
<212> TYPE: PRT
<213> ORGANISM: Saccharomyces cerevisiae

<400> SEQUENCE: 75

```
Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
            340                 345
```

<210> SEQ ID NO 76
<211> LENGTH: 1650
<212> TYPE: DNA

-continued

<213> ORGANISM: Lactococcus lactis

<400> SEQUENCE: 76

```
catatgtata cagtaggaga ttacctatta gaccgattac acgagttagg aattgaagaa      60
atttttggag tccctggaga ctataactta caatttttag atcaaattat ttcccacaag     120
gatatgaaat gggtcggaaa tgctaatgaa ttaaatgctt catatatggc tgatggctat     180
gctcgtacta aaaaagctgc cgcatttctt acaacctttg gagtaggtga attgagtgca     240
gttaatggat tagcaggaag ttacgccgaa aatttaccag tagtagaaat agtgggatca     300
cctacatcaa aagttcaaaa tgaaggaaaa tttgttcatc atacgctggc tgacggtgat     360
tttaaacact ttatgaaaat gcacgaacct gttacagcag ctcgaacttt actgacagca     420
gaaaatgcaa ccgttgaaat tgaccgagta ctttctgcac tattaaaaga aagaaaacct     480
gtctatatca acttaccagt tgatgttgct gctgcaaaag cagagaaacc ctcactccct     540
ttgaaaaagg aaaactcaac ttcaaataca agtgaccaag aaattttgaa caaaattcaa     600
gaaagcttga aaaatgccaa aaaaccaatc gtgattacag gacatgaaat aattagtttt     660
ggcttagaaa aaacagtcac tcaatttatt tcaaagacaa aactacctat tacgacatta     720
aactttggta aaagttcagt tgatgaagcc ctcccttcat ttttaggaat ctataatggt     780
acactctcag agcctaatct taaagaattc gtggaatcag ccgacttcat cttgatgctt     840
ggagttaaac tcacagactc ttcaacagga gccttcactc atcatttaaa tgaaaataaa     900
atgatttcac tgaatataga tgaaggaaaa atatttaacg aaagaatcca aaattttgat     960
tttgaatccc tcatctcctc tctcttagac ctaagcgaaa tagaatacaa aggaaaatat    1020
atcgataaaa agcaagaaga ctttgttcca tcaaatgcgc ttttatcaca agaccgccta    1080
tggcaagcag ttgaaaacct aactcaaagc aatgaaacaa tcgttgctga acaagggaca    1140
tcattctttg gcgcttcatc aattttctta aaatcaaaga gtcattttat tggtcaaccc    1200
ttatggggat caattggata tacattccca gcagcattag gaagccaaat tgcagataaa    1260
gaaagcagac accttttatt tattggtgat ggttcacttc aacttacagt gcaagaatta    1320
ggattagcaa tcagagaaaa aattaatcca atttgcttta ttatcaataa tgatggttat    1380
acagtcgaaa gagaaattca tggaccaaat caaagctaca atgatattcc aatgtggaat    1440
tactcaaaat taccagaatc gtttggagca acagaagatc gagtagtctc aaaaatcgtt    1500
agaactgaaa atgaatttgt gtctgtcatg aaagaagctc aagcagatcc aaatagaatg    1560
tactggattg agttaatttt ggcaaaagaa ggtgcaccaa aagtactgaa aaaaatgggc    1620
aaactatttg ctgaacaaaa taaatcataa                                    1650
```

<210> SEQ ID NO 77
<211> LENGTH: 1047
<212> TYPE: DNA
<213> ORGANISM: Saccharomyces cerevisiae

<400> SEQUENCE: 77

```
atgtctattc cagaaactca aaaagccatt atcttctacg aatccaacgg caagttggag      60
cataaggata tcccagttcc aaagccaaag cccaacgaat tgttaatcaa cgtcaagtac     120
tctggtgtct gccacaccga tttgcacgct tggcatggtg actggccatt gccaactaag     180
ttaccattag ttggtggtca cgaaggtgcc ggtgtcgttg tcggcatggg tgaaaacgtt     240
aagggctgga agatcggtga ctacgccggt atcaaatggt tgaacggttc ttgtatggcc     300
tgtgaatact gtgaattggg taacgaatcc aactgtcctc acgctgactt gtctggttac     360
```

```
acccacgacg gttctttcca agaatacgct accgctgacg ctgttcaagc cgctcacatt    420
cctcaaggta ctgacttggc tgaagtcgcg ccaatcttgt gtgctggtat caccgtatac    480
aaggctttga agtctgccaa cttgagagca ggccactggg cggccatttc tggtgctgct    540
ggtggtctag gttctttggc tgttcaatat gctaaggcga tgggttacag agtcttaggt    600
attgatggtg gtccaggaaa ggaagaattg tttacctcgc tcggtggtga agtattcatc    660
gacttcacca aagagaagga cattgttagc gcagtcgtta aggctaccaa cggcggtgcc    720
cacggtatca tcaatgtttc cgtttccgaa gccgctatcg aagcttctac cagatactgt    780
agggcgaacg gtactgttgt cttggttggt ttgccagccg gtgcaaagtg ctcctctgat    840
gtcttcaacc acgttgtcaa gtctatctcc attgtcggct cttacgtggg gaacagagct    900
gataccagag aagccttaga tttctttgcc agaggtctag tcaagtctcc aataaaggta    960
gttggcttat ccagtttacc agaaatttac gaaaagatgg agaagggcca aattgctggt   1020
agatacgttg ttgacacttc taaataa                                       1047
```

<210> SEQ ID NO 78
<211> LENGTH: 2744
<212> TYPE: DNA
<213> ORGANISM: Artificial sequence
<220> FEATURE:
<223> OTHER INFORMATION: Synthetic operon

<400> SEQUENCE: 78

```
catatgtata cagtaggaga ttacctatta gaccgattac acgagttagg aattgaagaa      60
atttttggag tccctggaga ctataactta caatttttag atcaaattat ttcccacaag    120
gatatgaaat gggtcggaaa tgctaatgaa ttaaatgctt catatatggc tgatggctat    180
gctcgtacta aaaaagctgc cgcatttctt acaacctttg gagtaggtga attgagtgca    240
gttaatggat tagcaggaag ttacgccgaa aatttaccag tagtagaaat agtgggatca    300
cctacatcaa aagttcaaaa tgaaggaaaa tttgttcatc atacgctggc tgacggtgat    360
tttaaacact ttatgaaaat gcacgaacct gttacagcag ctcgaacttt actgacagca    420
gaaaatgcaa ccgttgaaat tgaccgagta ctttctgcac tattaaaaga aagaaaacct    480
gtctatatca acttaccagt tgatgttgct gctgcaaaag cagagaaacc ctcactccct    540
ttgaaaaagg aaaactcaac ttcaaataca agtgaccaag aaattttgaa caaaattcaa    600
gaaagcttga aaaatgccaa aaaaccaatc gtgattacag gacatgaaat aattagtttt    660
ggcttagaaa aaacagtcac tcaatttatt tcaaagacaa aactacctat tacgacatta    720
aactttggta aaagttcagt tgatgaagcc ctcccttcat ttttaggaat ctataatggt    780
acactctcag agcctaatct taaagaattc gtggaatcag ccgacttcat cttgatgctt    840
ggagttaaac tcacagactc ttcaacagga gccttcactc atcatttaaa tgaaaataaa    900
atgatttcac tgaatataga tgaaggaaaa atatttaacg aaagaatcca aaattttgat    960
tttgaatccc tcatctcctc tctcttagac ctaagcgaaa tagaatacaa aggaaaatat   1020
atcgataaaa agcaagaaga ctttgttcca tcaaatgcgc ttttatcaca agaccgccta   1080
tggcaagcag ttgaaaacct aactcaaagc aatgaaacaa tcgttgctga acaagggaca   1140
tcattctttg gcgcttcatc aattttctta aaatcaaaga gtcattttat tggtcaaccc   1200
ttatggggat caattggata tacattccca gcagcattag gaagccaaat tgcagataaa   1260
gaaagcagac accttttatt tattggtgat ggttcacttc aacttacagt gcaagaatta   1320
```

```
ggattagcaa tcagagaaaa aattaatcca atttgcttta ttatcaataa tgatggttat   1380

acagtcgaaa gagaaattca tggaccaaat caaagctaca atgatattcc aatgtggaat   1440

tactcaaaat taccagaatc gtttggagca acagaagatc gagtagtctc aaaaatcgtt   1500

agaactgaaa atgaatttgt gtctgtcatg aaagaagctc aagcagatcc aaatagaatg   1560

tactggattg agttaatttt ggcaaaagaa ggtgcaccaa aagtactgaa aaaaatgggc   1620

aaactatttg ctgaacaaaa taaatcataa gaattcaaaa aaaaaaaaaa aaaaaaaaaa   1680

aaaaaaaaaa aatgtctatt ccagaaactc aaaaagccat tatcttctac gaatccaacg   1740

gcaagttgga gcataaggat atcccagttc caaagccaaa gcccaacgaa ttgttaatca   1800

acgtcaagta ctctggtgtc tgccacaccg atttgcacgc ttggcatggt gactggccat   1860

tgccaactaa gttaccatta gttggtggtc acgaaggtgc cggtgtcgtt gtcggcatgg   1920

gtgaaaacgt taagggctgg aagatcggtg actacgccgg tatcaaatgg ttgaacggtt   1980

cttgtatggc ctgtgaatac tgtgaattgg gtaacgaatc caactgtcct cacgctgact   2040

tgtctggtta cacccacgac ggttctttcc aagaatacgc taccgctgac gctgttcaag   2100

ccgctcacat tcctcaaggt actgacttgg ctgaagtcgc gccaatcttg tgtgctggta   2160

tcaccgtata caaggctttg aagtctgcca acttgagagc aggccactgg gcggccattt   2220

ctggtgctgc tggtggtcta ggttctttgg ctgttcaata tgctaaggcg atgggttaca   2280

gagtcttagg tattgatggt ggtccaggaa aggaagaatt gtttacctcg ctcggtggtg   2340

aagtattcat cgacttcacc aaagagaagg acattgttag cgcagtcgtt aaggctacca   2400

acggcggtgc ccacggtatc atcaatgttt ccgtttccga agccgctatc gaagcttcta   2460

ccagatactg tagggcgaac ggtactgttg tcttggttgg tttgccagcc ggtgcaaagt   2520

gctcctctga tgtcttcaac cacgttgtca agtctatctc cattgtcggc tcttacgtgg   2580

ggaacagagc tgataccaga gaagccttag atttctttgc cagaggtcta gtcaagtctc   2640

caataaaggt agttggctta tccagtttac cagaaattta cgaaaagatg gagaagggcc   2700

aaattgctgg tagatacgtt gttgacactt ctaaataagg tacc                    2744
```

<210> SEQ ID NO 79
<211> LENGTH: 479
<212> TYPE: DNA
<213> ORGANISM: Clostridium autoethanogenum

<400> SEQUENCE: 79

```
aatatgatat ttatgtccat tgtgaaaggg attatattca actattattc cagttacgtt     60

catagaaatt ttcctttcta aaatatttta ttccatgtca agaactctgt ttatttcatt    120

aaagaactat aagtacaaag tataaggcat ttgaaaaaat aggctagtat attgattgat    180

tatttatttt aaaatgccta agtgaaatat atacatatta taacaataaa ataagtatta    240

gtgtaggatt tttaaataga gtatctattt tcagattaaa tttttgatta tttgatttac    300

attatataat attgagtaaa gtattgacta gcaaaatttt ttgatacttt aatttgtgaa    360

atttcttatc aaaagttata tttttgaata atttttattg aaaaatacaa ctaaaaagga    420

ttatagtata agtgtgtgta attttgtgtt aaatttaaag ggaggaaatg aacatgaaa     479
```

<210> SEQ ID NO 80
<211> LENGTH: 28
<212> TYPE: DNA
<213> ORGANISM: Artificial sequence
<220> FEATURE:
<223> OTHER INFORMATION: synthetic primer

<400> SEQUENCE: 80
gagcggccgc aatatgatat ttatgtcc 28

<210> SEQ ID NO 81
<211> LENGTH: 28
<212> TYPE: DNA
<213> ORGANISM: Artificial sequence
<220> FEATURE:
<223> OTHER INFORMATION: synthetic primer

<400> SEQUENCE: 81
ttccatatgt ttcatgttca tttcctcc 28

<210> SEQ ID NO 82
<211> LENGTH: 3552
<212> TYPE: DNA
<213> ORGANISM: Artificial sequence
<220> FEATURE:
<223> OTHER INFORMATION: synthetic plasmid

<400> SEQUENCE: 82
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc caggggggaaa cgcctggtat 600 ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggcccccctg caggataaaa 900 aaattgtaga taaattttat aaaatagttt tatctacaat ttttttatca ggaaacagct 960
atgaccgcgg ccgcaatatg atatttatgt ccattgtgaa agggattata ttcaactatt 1020
attccagtta cgttcataga aattttcctt tctaaaatat tttattccat gtcaagaact 1080
ctgtttattt cattaaagaa ctataagtac aaagtataag gcatttgaaa aaataggcta 1140
gtatattgat tgattattta ttttaaaatg cctaagtgaa atatatacat attataacaa 1200
taaaataagt attagtgtag gatttttaaa tagagtatct attttcagat taaatttttg 1260
attatttgat ttacattata taatattgag taaagtattg actagcaaaa ttttttgata 1320
ctttaatttg tgaaatttct tatcaaaagt tatatttttg aataattttt attgaaaaat 1380
acaactaaaa aggattatag tataagtgtg tgtaattttg tgttaaattt aaagggagga 1440
aatgaacatg aaacatatgg tgaccatgat tacgaattcg agctcggtac ccggggatcc 1500
tctagagtcg acgtcacgcg tccatggaga tctcgaggcc tgcagacatg caagcttggc 1560

-continued

```
actggccgtc gttttacaac gtcgtgactg ggaaaaccct ggcgttaccc aacttaatcg   1620

ccttgcagca catccccctt tcgccagctg gcgtaatagc gaagaggccc gcaccgatcg   1680

cccttcccaa cagttgcgca gcctgaatgg cgaatggcgc tagcataaaa ataagaagcc   1740

tgcatttgca ggcttcttat ttttatggcg cgccgcattc acttcttttc tatataaata   1800

tgagcgaagc gaataagcgt cggaaaagca gcaaaaagtt tcctttttgc tgttggagca   1860

tgggggttca gggggtgcag tatctgacgt caatgccgag cgaaagcgag ccgaagggta   1920

gcatttacgt tagataaccc cctgatatgc tccgacgctt tatatagaaa agaagattca   1980

actaggtaaa atcttaatat aggttgagat gataaggttt ataaggaatt tgtttgttct   2040

aatttttcac tcattttgtt ctaatttctt ttaacaaatg ttcttttttt tttagaacag   2100

ttatgatata gttagaatag tttaaaataa ggagtgagaa aaagatgaaa gaaagatatg   2160

gaacagtcta taaaggctct cagaggctca tagacgaaga aagtggagaa gtcatagagg   2220

tagacaagtt ataccgtaaa caaacgtctg gtaacttcgt aaaggcatat atagtgcaat   2280

taataagtat gttagatatg attggcggaa aaaaacttaa aatcgttaac tatatcctag   2340

ataatgtcca cttaagtaac aatacaatga tagctacaac aagagaaata gcaaaagcta   2400

caggaacaag tctacaaaca gtaataacaa cacttaaaat cttagaagaa ggaaatatta   2460

taaaaagaaa aactggagta ttaatgttaa accctgaact actaatgaga ggcgacgacc   2520

aaaaacaaaa atacctctta ctcgaatttg ggaactttga gcaagaggca aatgaaatag   2580

attgacctcc caataacacc acgtagttat tgggaggtca atctatgaaa tgcgattaag   2640

ggccggccga agcaaactta agagtgtgtt gatagtgcag tatcttaaaa ttttgtataa   2700

taggaattga agttaaatta gatgctaaaa atttgtaatt aagaaggagt gattacatga   2760

acaaaaatat aaaatattct caaaactttt taacgagtga aaaagtactc aaccaaataa   2820

taaaacaatt gaatttaaaa gaaaccgata ccgtttacga aattggaaca ggtaaagggc   2880

atttaacgac gaaactggct aaaataagta aacaggtaac gtctattgaa ttagacagtc   2940

atctattcaa cttatcgtca gaaaaattaa aactgaatac tcgtgtcact ttaattcacc   3000

aagatattct acagtttcaa ttccctaaca aacagaggta taaaattgtt gggagtattc   3060

cttaccattt aagcacacaa attattaaaa aagtggtttt tgaaagccat gcgtctgaca   3120

tctatctgat tgttgaagaa ggattctaca agcgtacctt ggatattcac cgaacactag   3180

ggttgctctt gcacactcaa gtctcgattc agcaattgct taagctgcca gcggaatgct   3240

ttcatcctaa accaaaagta aacagtgtct taataaaact tacccgccat accacagatg   3300

ttccagataa atattggaag ctatatacgt actttgtttc aaaatgggtc aatcgagaat   3360

atcgtcaact gtttactaaa aatcagtttc atcaagcaat gaaacacgcc aaagtaaaca   3420

atttaagtac cgttacttat gagcaagtat tgtctatttt taatagttat ctattattta   3480

acgggaggaa ataattctat gagtcgcttt tgtaaatttg gaaagttaca cgttactaaa   3540

gggaatgtgt tt                                                       3552
```

```
<210> SEQ ID NO 83
<211> LENGTH: 6263
<212> TYPE: DNA
<213> ORGANISM: Artificial sequence
<220> FEATURE:
<223> OTHER INFORMATION: synthetic plasmid

<400> SEQUENCE: 83

aaactccttt ttgataatct catgaccaaa atcccttaac gtgagttttc gttccactga     60
```

-continued

```
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat ttttttatca ggaaacagct    960
atgaccgcgg ccgcaatatg atatttatgt ccattgtgaa agggattata ttcaactatt   1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gatttttaaa tagagtatct attttcagat taaatttttg   1260
attatttgat ttacattata taatattgag taaagtattg actagcaaaa ttttttgata   1320
ctttaatttg tgaaatttct tatcaaaagt tatattttg aataattttt attgaaaaat   1380
acaactaaaa aggattatag tataagtgtg tgtaattttg tgttaaattt aaagggagga   1440
aatgaacatg aaacatatgt atacagttgg tgattattta cttgatagat tacatgaact   1500
tggaatagaa gaaattttg gtgtaccagg tgattacaat cttcaattct tagatcaaat   1560
aatatcacat aaggatatga aatgggttgg taatgctaat gaattaaatg catcatatat   1620
ggcagacgga tatgcaagaa ctaaaaaggc agcagcattt cttactacat ttggtgttgg   1680
tgaattaagt gcagtaaatg gattagctgg aagttacgca gaaaacttac cagttgttga   1740
aatagttgga tctcctacta gtaaagtaca aaatgaaggt aaatttgtac atcacactct   1800
tgcagatggt gattttaagc attttatgaa aatgcatgaa cctgttacag ctgcaagaac   1860
acttcttaca gctgaaaacg ctactgtaga aattgataga gttttatctg ctttacttaa   1920
agaaagaaag ccagtatata ttaaccttcc agtagatgta gcagcagcaa aagctgagaa   1980
accttcatta ccacttaaaa aggaaaattc aacatcaaat acatctgatc aagagatatt   2040
aaataaaatt caggaaagtc ttaaaaatgc aaagaaacct atagtaataa ctggacatga   2100
aataattagt tttggattag aaaagacagt tacacagttt ataagtaaaa ctaagcttcc   2160
aattacaact ttaaattttg gaaagagttc agtagatgag gcacttccat cattcttagg   2220
aatttataat ggaacattat ctgaacctaa tcttaaagaa tttgtagaga gtgctgattt   2280
tatattaatg ttaggtgtaa aacttactga tagtagtact ggtgcattta ctcatcatct   2340
taacgaaaat aagatgatat cattaaatat agacgaaggt aaaatattca atgaaagaat   2400
```

-continued

```
acagaacttt gattttgaat cacttatatc atcattactt gatttatcag agatagaata   2460
caaaggaaaa tatatagata aaaagcaaga agattttgtt ccatctaatg ctcttctttc   2520
tcaagataga ctttggcaag cagttgagaa tcttacacag tctaatgaaa ctatagttgc   2580
tgagcaagga acatcatttt tcggtgcatc aagtatattt ttaaaatcta aaagtcactt   2640
tattggacaa cctctttggg gttctattgg atatactttt ccagcagctt taggaagtca   2700
aatagctgat aaagaaagta gacatttatt atttattggt gacggttcac ttcagcttac   2760
agtacaagaa ttaggattag ctataagaga gaagataaat cctatttgtt tcataataaa   2820
caatgatgga tatactgtag aaagagaaat tcacggacca aatcagtcat ataatgatat   2880
tccaatgtgg aattattcaa agttacctga atctttcggt gctactgaag atagagtagt   2940
ttctaaaatt gttagaacag agaacgaatt tgtatctgtt atgaaagaag ctcaggctga   3000
ccctaataga atgtattgga ttgaattaat tttagcaaaa gaaggtgctc ctaaagtact   3060
taagaaaatg ggaaaattat ttgcagaaca aaataagtca taagaattcc cataataaag   3120
aaagaatttt aaataaagga ggaacaaaga tgagtatacc agaaacacaa aaagcaatta   3180
tattttatga gtcaaatgga aaattagagc ataaagatat acctgtacca aaaccaaaac   3240
caaacgaact tcttataaat gttaagtatt ctggtgtttg tcatactgat cttcatgcat   3300
ggcatggtga ttggcctctt ccaactaaat tacctcttgt aggtggtcat gaaggtgctg   3360
gtgtagttgt aggtatgggt gaaaatgtta aaggttggaa aataggtgat tatgctggaa   3420
ttaaatggct taatggatct tgtatggcat gcgagtattg tgaattagga aatgaaagta   3480
attgtccaca tgctgactta agtggttata ctcatgatgg atcttttcaa gaatatgcta   3540
ctgcagatgc agttcaggct gcacacattc cacagggaac tgatcttgct gaagtagctc   3600
ctatattatg cgctggaatt acagtataca aagcattaaa aagtgctaat cttagagcag   3660
gacactgggc agctataagt ggtgctgcag gtggtttagg atctttagca gttcaatatg   3720
ctaaagctat gggatataga gtattaggaa tagacggtgg tccaggaaaa gaagagttat   3780
ttacatcatt aggtggtgaa gtttttatag atttcacaaa ggaaaaagat attgtttcag   3840
ctgtagtaaa ggcaactaat ggtggtgcac acggaattat aaatgtttca gtatctgaag   3900
cagcaataga agcaagtact agatattgta gagcaaacgg aacagtagtt ttagttggac   3960
ttccagctgg tgcaaagtgt tcatctgacg tatttaacca tgtagtaaag agtatttcaa   4020
tagttggatc ttacgtaggt aatagagctg atacaagaga agctttagat ttctttgcaa   4080
gaggtttagt taagagtcct ataaaagtag taggactttc atcacttcct gaaatttatg   4140
aaaagatgga aaagggacaa atagctggta gatatgttgt agatacaagt aaataaggta   4200
cccggggatc ctctagagtc gacgtcacgc gtccatggag atctcgaggc ctgcagacat   4260
gcaagcttgg cactggccgt cgttttacaa cgtcgtgact gggaaaaccc tggcgttacc   4320
caacttaatc gccttgcagc acatccccct ttcgccagct ggcgtaatag cgaagaggcc   4380
cgcaccgatc gcccttccca acagttgcgc agcctgaatg gcgaatggcg ctagcataaa   4440
aataagaagc ctgcatttgc aggcttctta tttttatggc gcgccgcatt cacttctttt   4500
ctatataaat atgagcgaag cgaataagcg tcggaaaagc agcaaaaagt ttcctttttg   4560
ctgttggagc atgggggttc agggggtgca gtatctgacg tcaatgccga gcgaaagcga   4620
gccgaagggt agcatttacg ttagataacc ccctgatatg ctccgacgct ttatatagaa   4680
aagaagattc aactaggtaa aatcttaata taggttgaga tgataaggtt tataaggaat   4740
ttgtttgttc taatttttca ctcattttgt tctaatttct tttaacaaat gttctttttt   4800
```

ttttagaaca gttatgatat agttagaata gtttaaaata aggagtgaga aaaagatgaa 4860
agaaagatat ggaacagtct ataaaggctc tcagaggctc atagacgaag aaagtggaga 4920
agtcatagag gtagacaagt tataccgtaa acaaacgtct ggtaacttcg taaaggcata 4980
tatagtgcaa ttaataagta tgttagatat gattggcgga aaaaaactta aaatcgttaa 5040
ctatatccta gataatgtcc acttaagtaa caatacaatg atagctacaa caagagaaat 5100
agcaaaagct acaggaacaa gtctacaaac agtaataaca acacttaaaa tcttagaaga 5160
aggaaatatt ataaaaagaa aaactggagt attaatgtta aaccctgaac tactaatgag 5220
aggcgacgac caaaaacaaa aatacctctt actcgaattt gggaactttg agcaagaggc 5280
aaatgaaata gattgacctc ccaataacac cacgtagtta ttgggaggtc aatctatgaa 5340
atgcgattaa gggccggccg aagcaaactt aagagtgtgt tgatagtgca gtatcttaaa 5400
attttgtata ataggaattg aagttaaatt agatgctaaa aatttgtaat taagaaggag 5460
tgattacatg aacaaaaata taaaatattc tcaaaacttt ttaacgagtg aaaaagtact 5520
caaccaaata ataaaacaat tgaatttaaa agaaaccgat accgtttacg aaattggaac 5580
aggtaaaggg catttaacga cgaaactggc taaaataagt aaacaggtaa cgtctattga 5640
attagacagt catctattca acttatcgtc agaaaaatta aaactgaata ctcgtgtcac 5700
tttaattcac caagatattc tacagtttca attccctaac aaacagaggt ataaaattgt 5760
tgggagtatt ccttaccatt taagcacaca aattattaaa aaagtggttt ttgaaagcca 5820
tgcgtctgac atctatctga ttgttgaaga aggattctac aagcgtacct tggatattca 5880
ccgaacacta gggttgctct tgcacactca agtctcgatt cagcaattgc ttaagctgcc 5940
agcggaatgc tttcatccta aaccaaaagt aaacagtgtc ttaataaaac ttacccgcca 6000
taccacagat gttccagata aatattggaa gctatatacg tactttgttt caaaatgggt 6060
caatcgagaa tatcgtcaac tgtttactaa aaatcagttt catcaagcaa tgaaacacgc 6120
caaagtaaac aatttaagta ccgttactta tgagcaagta ttgtctattt ttaatagtta 6180
tctattattt aacgggagga aataattcta tgagtcgctt ttgtaaattt ggaaagttac 6240
acgttactaa agggaatgtg ttt 6263

<210> SEQ ID NO 84
<211> LENGTH: 4630
<212> TYPE: DNA
<213> ORGANISM: Artificial sequence
<220> FEATURE:
<223> OTHER INFORMATION: synthetic plasmid

<400> SEQUENCE: 84
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540

-continued

```
agcggcaggg tcggaacagg agagcgcacg agggagcttc cagggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat ttttttatca ggaaacagct    960
atgaccgcgg ccgcaatatg atatttatgt ccattgtgaa agggattata ttcaactatt   1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gatttttaaa tagagtatct attttcagat taaatttttg   1260
attatttgat ttacattata taatattgag taaagtattg actagcaaaa tttttttgata   1320
ctttaatttg tgaaatttct tatcaaaagt tatatttttg aataattttt attgaaaaat   1380
acaactaaaa aggattatag tataagtgtg tgtaattttg tgttaaattt aaagggagga   1440
aatgaacatg aaacatatgt atacagttgg tgattattta cttgatagat tacatgaact   1500
tggaatagaa gaaatttttg gtgtaccagg tgattacaat cttcaattct tagatcaaat   1560
aatatcacat aaggatatga aatgggttgg taatgctaat gaattaaatg catcatatat   1620
ggcagacgga tatgcaagaa ctaaaaaggc agcagcattt cttactacat ttggtgttgg   1680
tgaattaagt gcagtaaatg gattagctgg aagttacgca gaaaacttac cagttgttga   1740
aatagttgga tctcctacta gtaaagtaca aaatgaaggt aaatttgtac atcacactct   1800
tgcagatggt gattttaagc attttatgaa aatgcatgaa cctgttacag ctgcaagaac   1860
acttcttaca gctgaaaacg ctactgtaga aattgataga gttttatctg ctttacttaa   1920
agaaagaaag ccagtatata ttaaccttcc agtagatgta gcagcagcaa aagctgagaa   1980
accttcatta ccacttaaaa aggaaaattc aacatcaaat acatctgatc aagagatatt   2040
aaataaaatt caggaaagtc ttaaaaatgc aaagaaacct atagtaataa ctggacatga   2100
aataattagt tttggattag aaaagacagt tacacagttt ataagtaaaa ctaagcttcc   2160
aattacaact ttaaatttg gaaagagttc agtagatgag gcacttccat cattcttagg   2220
aatttataat ggaacattat ctgaacctaa tcttaaagaa tttgtagaga gtgctgattt   2280
tatattaatg ttaggtgtaa aacttactga tagtagtact ggtgcattta ctcatcatct   2340
taacgaaaat aagatgatat cattaaatat agacgaaggt aaaatattca atgaaagaat   2400
acagaacttt gattttgaat cacttatatc atcattactt gatttatcag agatagaata   2460
caaaggaaaa tatatagata aaaagcaaga agattttgtt ccatctaatg ctcttctttc   2520
tcaagataga ctttggcaag cagttgagaa tcttacacag tctaatgaaa ctatagttgc   2580
tgagcaagga acatcatttt tcggtgcatc aagtatattt ttaaaatcta aaagtcactt   2640
tattggacaa cctctttggg gttctattgg atatactttt ccagcagctt taggaagtca   2700
aatagctgat aaagaaagta gacatttatt atttattggt gacggttcac ttcagcttac   2760
agtacaagaa ttaggattag ctataagaga gaagataaat cctatttgtt tcataataaa   2820
caatgatgga tatactgtag aaagagaaat tcacggacca aatcagtcat ataatgatat   2880
tccaatgtgg aattattcaa agttacctga atctttcggt gctactgaag atagagtagt   2940
```

ttctaaaatt gttagaacag agaacgaatt tgtatctgtt atgaaagaag ctcaggctga 3000
ccctaataga atgtattgga ttgaattaat tttagcaaaa gaaggtgctc ctaaagtact 3060
taagaaaatg ggaaaattat ttgcagaaca aaataagtca taagaatttg tttgttctaa 3120
tttttcactc attttgttct aatttctttt aacaaatgtt cttttttttt tagaacagtt 3180
atgatatagt tagaatagtt taaaataagg agtgagaaaa agatgaaaga aagatatgga 3240
acagtctata aaggctctca gaggctcata gacgaagaaa gtggagaagt catagaggta 3300
gacaagttat accgtaaaca aacgtctggt aacttcgtaa aggcatatat agtgcaatta 3360
ataagtatgt tagatatgat tggcggaaaa aaacttaaaa tcgttaacta tatcctagat 3420
aatgtccact taagtaacaa tacaatgata gctacaacaa gagaaatagc aaaagctaca 3480
ggaacaagtc tacaaacagt aataacaaca cttaaaatct tagaagaagg aaatattata 3540
aaaagaaaaa ctggagtatt aatgttaaac cctgaactac taatgagagg cgacgaccaa 3600
aaacaaaaat acctcttact cgaatttggg aactttgagc aagaggcaaa tgaaatagat 3660
tgacctccca ataacaccac gtagttattg ggaggtcaat ctatgaaatg cgattaaggg 3720
ccggccgaag caaacttaag agtgtgttga tagtgcagta tcttaaaatt ttgtataata 3780
ggaattgaag ttaaattaga tgctaaaaat ttgtaattaa gaaggagtga ttacatgaac 3840
aaaaatataa aatattctca aaacttttta acgagtgaaa aagtactcaa ccaaataata 3900
aaacaattga atttaaaaga aaccgatacc gtttacgaaa ttggaacagg taaagggcat 3960
ttaacgacga aactggctaa aataagtaaa caggtaacgt ctattgaatt agacagtcat 4020
ctattcaact tatcgtcaga aaaattaaaa ctgaatactc gtgtcacttt aattcaccaa 4080
gatattctac agtttcaatt ccctaacaaa cagaggtata aaattgttgg gagtattcct 4140
taccatttaa gcacacaaat tattaaaaaa gtggtttttg aaagccatgc gtctgacatc 4200
tatctgattg ttgaagaagg attctacaag cgtaccttgg atattcaccg aacactaggg 4260
ttgctcttgc acactcaagt ctcgattcag caattgctta agctgccagc ggaatgcttt 4320
catcctaaac caaaagtaaa cagtgtctta ataaaactta cccgccatac cacagatgtt 4380
ccagataaat attggaagct atatacgtac tttgtttcaa aatgggtcaa tcgagaatat 4440
cgtcaactgt ttactaaaaa tcagtttcat caagcaatga aacacgccaa agtaaacaat 4500
ttaagtaccg ttacttatga gcaagtattg tctattttta atagttatct attatttaac 4560
gggaggaaat aattctatga gtcgcttttg taaatttgga aagttacacg ttactaaagg 4620
gaatgtgttt 4630

<210> SEQ ID NO 85
<211> LENGTH: 23
<212> TYPE: DNA
<213> ORGANISM: Artificial sequence
<220> FEATURE:
<223> OTHER INFORMATION: synthetic primer

<400> SEQUENCE: 85
tcagttccct gtggaatgtg tgc 23

<210> SEQ ID NO 86
<211> LENGTH: 22
<212> TYPE: DNA
<213> ORGANISM: Artificial sequence
<220> FEATURE:
<223> OTHER INFORMATION: synthetic primer

<400> SEQUENCE: 86
tcagtagcac cgaaagattc ag 22

<210> SEQ ID NO 87
<211> LENGTH: 21
<212> TYPE: DNA
<213> ORGANISM: Artificial sequence
<220> FEATURE:
<223> OTHER INFORMATION: synthetic primer

<400> SEQUENCE: 87
agtgcctcat ctactgaact c 21

<210> SEQ ID NO 88
<211> LENGTH: 36
<212> TYPE: DNA
<213> ORGANISM: Artificial sequence
<220> FEATURE:
<223> OTHER INFORMATION: synthetic primer

<400> SEQUENCE: 88
attagtttaa acacgccagc aacgcggcct ttttac 36

<210> SEQ ID NO 89
<211> LENGTH: 27
<212> TYPE: DNA
<213> ORGANISM: Artificial sequence
<220> FEATURE:
<223> OTHER INFORMATION: synthetic primer

<400> SEQUENCE: 89
tcctattcca aggtttacga gttggtc 27

<210> SEQ ID NO 90
<211> LENGTH: 27
<212> TYPE: DNA
<213> ORGANISM: Artificial sequence
<220> FEATURE:
<223> OTHER INFORMATION: synthetic primer

<400> SEQUENCE: 90
acccccaacc ataattgtca tgccatc 27

<210> SEQ ID NO 91
<211> LENGTH: 27
<212> TYPE: DNA
<213> ORGANISM: Artificial sequence
<220> FEATURE:
<223> OTHER INFORMATION: synthetic primer

<400> SEQUENCE: 91
tgcaagagca aactcatctt gttcttc 27

<210> SEQ ID NO 92
<211> LENGTH: 43
<212> TYPE: DNA
<213> ORGANISM: Artificial sequence
<220> FEATURE:
<223> OTHER INFORMATION: synthetic primer

<400> SEQUENCE: 92
agggtgcggc cgcgattcat atatccataa tctttaagtt atc 43

<210> SEQ ID NO 93
<211> LENGTH: 38

-continued

<212> TYPE: DNA
<213> ORGANISM: Artificial sequence
<220> FEATURE:
<223> OTHER INFORMATION: synthetic primer

<400> SEQUENCE: 93
atcttctgca gggccgcaga tagtcataat agttccag 38

<210> SEQ ID NO 94
<211> LENGTH: 43
<212> TYPE: DNA
<213> ORGANISM: Artificial sequence
<220> FEATURE:
<223> OTHER INFORMATION: synthetic primer

<400> SEQUENCE: 94
agggtgcggc cgcgattcat atatccataa tctttaagtt atc 43

<210> SEQ ID NO 95
<211> LENGTH: 7655
<212> TYPE: DNA
<213> ORGANISM: Artificial sequence
<220> FEATURE:
<223> OTHER INFORMATION: synthetic plasmid

<400> SEQUENCE: 95
aaactccttt ttgataatct catgaccaaa atcccttaac gtgagttttc gttccactga 60
gcgtcagacc ccgtagaaaa gatcaaagga tcttcttgag atcctttttt tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc caggggggaaa cgcctggtat 600 ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggccccctg cagggccgca 900
gatagtcata atagttccag aatagttcaa tttagaaatt agactaaact tcaaaatgtt 960
tgttaaatat ataccaaact agtatagata ttttttaaat actggactta aacagtagta 1020
atttgcctaa aaaatttttt caattttttt taaaaaatcc ttttcaagtt gtacattgtt 1080
atggtaatat gtaattgaag aagttatgta gtaatattgt aaacgtttct tgattttttt 1140
acatccatgt agtgcttaaa aaaccaaaat atgtcacatg caattgtata tttcaaataa 1200
caatatttat tttctcgtta aattcacaaa taatttatta ataatatcaa taaccaagat 1260
tatacttaaa tggatgttta ttttttaaca cttttatagt aaatatattt attttatgta 1320
gtaaaaaggt tataattata attgtattta ttacaattaa ttaaaataaa aaatagggtt 1380
ttaggtaaaa ttaagttatt ttaagaagta attacaataa aaattgaagt tatttcttta 1440

-continued

```
aggagggaat tattcatatg aaagaagttg taatagctag tgcagtaaga acagcgattg   1500
gatcttatgg aaagtctctt aaggatgtac cagcagtaga tttaggagct acagctataa   1560
aggaagcagt taaaaaagca ggaataaaac cagaggatgt taatgaagtc attttaggaa   1620
atgttcttca agcaggttta ggacagaatc cagcaagaca ggcatctttt aaagcaggat   1680
taccagttga aattccagct atgactatta ataaggtttg tggttcagga cttagaacag   1740
ttagcttagc agcacaaatt ataaaagcag gagatgctga cgtaataata gcaggtggta   1800
tggaaaatat gtctagagct ccttacttag cgaataacgc tagatgggga tatagaatgg   1860
gaaacgctaa atttgttgat gaaatgatca ctgacggatt gtgggatgca tttaatgatt   1920
accacatggg aataacagca gaaaacatag ctgagagatg gaacatttca agagaagaac   1980
aagatgagtt tgctcttgca tcacaaaaaa aagctgaaga agctataaaa tcaggtcaat   2040
ttaaagatga aatagttcct gtagtaatta aaggcagaaa gggagaaact gtagttgata   2100
cagatgagca ccctagattt ggatcaacta tagaaggact tgcaaaatta aaacctgcct   2160
tcaaaaaaga tggaacagtt acagctggta atgcatcagg attaaatgac tgtgcagcag   2220
tacttgtaat catgagtgca gaaaaagcta aagagcttgg agtaaaacca cttgctaaga   2280
tagtttctta tggttcagca ggagttgacc cagcaataat gggatatgga cctttctatg   2340
caacaaaagc agctattgaa aaagcaggtt ggacagttga tgaattagat ttaatagaat   2400
caaatgaagc ttttgcagct caaagtttag cagtagcaaa agatttaaaa tttgatatga   2460
ataaagtaaa tgtaaatgga ggagctattg cccttggtca tccaattgga gcatcaggtg   2520
caagaatact cgttactctt gtacacgcaa tgcaaaaaag agatgcaaaa aaaggcttag   2580
caactttatg tataggtggc ggacaaggaa cagcaatatt gctagaaaag tgctaggaat   2640
tcgagctcgg taccagggag atattaaaat gaataaatta gtaaaattaa cagatttaaa   2700
gcgcattttc aaagatggca tgacaattat ggttgggggt tttttagatt gtggaactcc   2760
tgaaaatatt atagatatgc tagttgattt aaatataaaa aatctgacta ttataagcaa   2820
tgatacagct tttcctaata aaggaatagg aaaacttatt gtaaatggtc aagtttctaa   2880
agtaattgct tcacatattg gaactaatcc tgaaactgga aaaaaaatga gctctggaga   2940
acttaaagtt gagctttccc cacaaggaac actgattgaa agaattcgtg cagctggatc   3000
tggactcgga ggtgtattaa ctccaactgg acttggaact atcgttgaag aaggtaagaa   3060
aaaagttact atcgatggca aagaatatct attagaactt cctttatctg ctgatgtttc   3120
attaataaaa ggtagcattg tagatgaatt tggaaatacc ttctataggg ctgctactaa   3180
aaatttcaat ccatatatgg caatggctgc aaaaaacagtt atagttgaag cagaaaattt   3240
agttaaatgt gaagatttaa aaagagatgc cataatgact cctggcgtat tagtagatta   3300
tatcgttaag gaggcggctt aattgattgt agataaagtt ttagcaaaag agataattgc   3360
caaaagagtt gcaaaagaac taaaaaaaga ccaactcgta aaccttggaa taggacttcc   3420
aactttagta gcaaattatg taccaaaaga aatgaacatt acttttgaat cagaaaatgg   3480
catggttggt atggcacaaa tggcatcatc aggtgaaaat gacccagata taataaatgc   3540
tggcggggaa tatgtaacat tattacctca aggttcattt tttgatagtt caatgtcttt   3600
cgcactaata cgaggaggac atgttgatgt tgctgttctt ggtgctctag aagttgatga   3660
aaaaggtaat ttagctaact ggattgttcc aaataaaatt gtcccaggta tgggtggcgc   3720
tatggattta gcaataggcg caaaaaaaat aatagtggca atgcaacata caggaaaaag   3780
taaacctaaa atcgttaaaa aatgtactct cccacttact gctaaggctc aagtggattt   3840
```

aattgtcaca gaactttgtg taattgatgt aacaaatgac ggcttacttt taaaagaaat 3900
tcataaagat acaactattg atgaaattaa atttttaaca gatgcagatt taattattcc 3960
agataactta aagattatgg atatatgaat cgcggccgca atatgatatt tatgtccatt 4020
gtgaaaggga ttatattcaa ctattattcc agttacgttc atagaaattt tcctttctaa 4080
aatattttat tccatgtcaa gaactctgtt tatttcatta aagaactata agtacaaagt 4140
ataaggcatt tgaaaaaata ggctagtata ttgattgatt atttatttta aaatgcctaa 4200
gtgaaatata tacatattat aacaataaaa taagtattag tgtaggattt ttaaatagag 4260
tatctatttt cagattaaat ttttgattat ttgatttaca ttatataata ttgagtaaag 4320
tattgactag caaaattttt tgatacttta atttgtgaaa tttcttatca aaagttatat 4380
ttttgaataa tttttattga aaaatacaac taaaaaggat tatagtataa gtgtgtgtaa 4440
ttttgtgtta aatttaaagg gaggaaatga acatgaaaca tatgtataca gttggtgatt 4500
atttacttga tagattacat gaacttggaa tagaagaaat ttttggtgta ccaggtgatt 4560
acaatcttca attcttagat caaataatat cacataagga tatgaaatgg gttggtaatg 4620
ctaatgaatt aaatgcatca tatatggcag acggatatgc aagaactaaa aaggcagcag 4680
catttcttac tacatttggt gttggtgaat taagtgcagt aaatggatta gctggaagtt 4740
acgcagaaaa cttaccagtt gttgaaatag ttggatctcc tactagtaaa gtacaaaatg 4800
aaggtaaatt tgtacatcac actcttgcag atggtgattt taagcatttt atgaaaatgc 4860
atgaacctgt tacagctgca agaacacttc ttacagctga aaacgctact gtagaaattg 4920
atagagtttt atctgcttta cttaaagaaa gaaagccagt atatattaac cttccagtag 4980
atgtagcagc agcaaaagct gagaaacctt cattaccact taaaaaggaa aattcaacat 5040
caaatacatc tgatcaagag atattaaata aaattcagga aagtcttaaa aatgcaaaga 5100
aacctatagt aataactgga catgaaataa ttagttttgg attagaaaag acagttacac 5160
agtttataag taaaactaag cttccaatta caactttaaa ttttggaaag agttcagtag 5220
atgaggcact tccatcattc ttaggaattt ataatggaac attatctgaa cctaatctta 5280
aagaatttgt agagagtgct gattttatat taatgttagg tgtaaaactt actgatagta 5340
gtactggtgc atttactcat catcttaacg aaaataagat gatatcatta aatatagacg 5400
aaggtaaaat attcaatgaa agaatacaga actttgattt tgaatcactt atatcatcat 5460
tacttgattt atcagagata gaatacaaag gaaaatatat agataaaaag caagaagatt 5520
ttgttccatc taatgctctt ctttctcaag atagactttg gcaagcagtt gagaatctta 5580
cacagtctaa tgaaactata gttgctgagc aaggaacatc atttttcggt gcatcaagta 5640
tatttttaaa atctaaaagt cactttattg gacaacctct ttggggttct attggatata 5700
cttttccagc agctttagga agtcaaatag ctgataaaga aagtagacat ttattattta 5760
ttggtgacgg ttcacttcag cttacagtac aagaattagg attagctata agagagaaga 5820
taaatcctat ttgtttcata ataaacaatg atggatatac tgtagaaaga gaaattcacg 5880
gaccaaatca gtcatataat gatattccaa tgtggaatta ttcaaagtta cctgaatctt 5940
tcggtgctac tgaagataga gtagtttcta aaattgttag aacagagaac gaatttgtat 6000
ctgttatgaa agaagctcag gctgacccta atagaatgta ttggattgaa ttaattttag 6060
caaaagaagg tgctcctaaa gtacttaaga aaatgggaaa attatttgca gaacaaaata 6120
agtcataaga atttgtttgt tctaattttt cactcatttt gttctaattt cttttaacaa 6180

-continued

```
atgttctttt ttttttagaa cagttatgat atagttagaa tagtttaaaa taaggagtga   6240

gaaaaagatg aaagaaagat atggaacagt ctataaaggc tctcagaggc tcatagacga   6300

agaaagtgga gaagtcatag aggtagacaa gttataccgt aaacaaacgt ctggtaactt   6360

cgtaaaggca tatatagtgc aattaataag tatgttagat atgattggcg gaaaaaaact   6420

taaaatcgtt aactatatcc tagataatgt ccacttaagt aacaatacaa tgatagctac   6480

aacaagagaa atagcaaaag ctacaggaac aagtctacaa acagtaataa caacacttaa   6540

aatcttagaa gaaggaaata ttataaaaag aaaaactgga gtattaatgt taaaccctga   6600

actactaatg agaggcgacg accaaaaaca aaaatacctc ttactcgaat ttgggaactt   6660

tgagcaagag gcaaatgaaa tagattgacc tcccaataac accacgtagt tattgggagg   6720

tcaatctatg aaatgcgatt aagggccggc cgaagcaaac ttaagagtgt gttgatagtg   6780

cagtatctta aaattttgta taataggaat tgaagttaaa ttagatgcta aaaatttgta   6840

attaagaagg agtgattaca tgaacaaaaa tataaaatat tctcaaaact ttttaacgag   6900

tgaaaaagta ctcaaccaaa taataaaaca attgaattta aaagaaaccg ataccgttta   6960

cgaaattgga acaggtaaag ggcatttaac gacgaaactg gctaaaataa gtaaacaggt   7020

aacgtctatt gaattagaca gtcatctatt caacttatcg tcagaaaaat taaaactgaa   7080

tactcgtgtc actttaattc accaagatat tctacagttt caattcccta acaaacagag   7140

gtataaaatt gttgggagta ttccttacca tttaagcaca caaattatta aaaaagtggt   7200

ttttgaaagc catgcgtctg acatctatct gattgttgaa gaaggattct acaagcgtac   7260

cttggatatt caccgaacac tagggttgct cttgcacact caagtctcga ttcagcaatt   7320

gcttaagctg ccagcggaat gctttcatcc taaaccaaaa gtaaacagtg tcttaataaa   7380

acttacccgc cataccacag atgttccaga taaatattgg aagctatata cgtactttgt   7440

ttcaaaatgg gtcaatcgag aatatcgtca actgtttact aaaaatcagt ttcatcaagc   7500

aatgaaacac gccaaagtaa acaatttaag taccgttact tatgagcaag tattgtctat   7560

ttttaatagt tatctattat ttaacgggag gaaataattc tatgagtcgc ttttgtaaat   7620

ttggaaagtt acacgttact aaagggaatg tgttt                              7655
```

<210> SEQ ID NO 96
<211> LENGTH: 35
<212> TYPE: DNA
<213> ORGANISM: Artificial sequence
<220> FEATURE:
<223> OTHER INFORMATION: synthetic primer

<400> SEQUENCE: 96

```
acgttggatc caggaggaac aaagatgagt atacc                                35
```

<210> SEQ ID NO 97
<211> LENGTH: 39
<212> TYPE: DNA
<213> ORGANISM: Artificial sequence
<220> FEATURE:
<223> OTHER INFORMATION: synthetic primer

<400> SEQUENCE: 97

```
agcgtccatg gccttattta cttgtatcta caacatatc                            39
```

<210> SEQ ID NO 98
<211> LENGTH: 8621
<212> TYPE: DNA
<213> ORGANISM: Artificial sequence -continued
<220> FEATURE:
<223> OTHER INFORMATION: synthetic plasmid

<400> SEQUENCE: 98
ccagtgggca agttgaaaaa ttcacaaaaa tgtggtataa tatctttgtt cattagagcg 60
ataaacttga atttgagagg gaacttagat ggtatttgaa aaaattgata aaaatagttg 120
gaacagaaaa gagtattttg accactactt tgcaagtgta ccttgtacct acagcatgac 180
cgttaaagtg gatatcacac aaataaagga aaagggaatg aaactatatc ctgcaatgct 240
ttattatatt gcaatgattg taaaccgcca ttcagagttt aggacggcaa tcaatcaaga 300
tggtgaattg ggatatatgg atgagatgat accaagctat acaatatttc acaatgatac 360
tgaaacattt tccagccttt ggactgagtg taagtctgac tttaaatcat ttttagcaga 420
ttatgaaagt gatacgcaac ggtatggaaa caatcataga atggaaggaa agccaaatgc 480
tccggaaaac atttttaatg tatctatgat accgtggtca accttcgatg gctttaatct 540
gaatttgcag aaaggatatg attatttgat tcctattttt actatgggga aatattataa 600
agaagataac aaaattatac ttcctttggc aattcaagtt catcacgcag tatgtgacgg 660
atttcacatt tgccgttttg taaacgaatt gcaggaattg ataaatagtt aacttcaggt 720
ttgtctgtaa ctaaaaacaa gtatttaagc aaaaacatcg tagaaatacg gtgtttttg 780 ttaccctaag tttaaactcc tttttgataa tctcatgacc aaaatccctt aacgtgagtt 840
ttcgttccac tgagcgtcag accccgtaga aaagatcaaa ggatcttctt gagatccttt 900
ttttctgcgc gtaatctgct gcttgcaaac aaaaaaacca ccgctaccag cggtggtttg 960
tttgccggat caagagctac caactctttt tccgaaggta actggcttca gcagagcgca 1020
gataccaaat actgttcttc tagtgtagcc gtagttaggc caccacttca agaactctgt 1080
agcaccgcct acatacctcg ctctgctaat cctgttacca gtggctgctg ccagtggcga 1140
taagtcgtgt cttaccgggt tggactcaag acgatagtta ccggataagg cgcagcggtc 1200
gggctgaacg gggggttcgt gcacacagcc cagcttggag cgaacgacct acaccgaact 1260
gagataccta cagcgtgagc tatgagaaag cgccacgctt cccgaaggga gaaaggcgga 1320
caggtatccg gtaagcggca gggtcggaac aggagagcgc acgagggagc ttccaggggg 1380
aaacgcctgg tatctttata gtcctgtcgg gtttcgccac ctctgacttg agcgtcgatt 1440
tttgtgatgc tcgtcagggg ggcggagcct atggaaaaac gccagcaacg cggccttttt 1500
acggttcctg gccttttgct ggccttttgc tcacatgttc tttcctgcgt tatcccctga 1560
ttctgtggat aaccgtatta ccgcctttga gtgagctgat accgctcgcc gcagccgaac 1620
gaccgagcgc agcgagtcag tgagcgagga agcggaagag cgcccaatac gcagggcccc 1680
ctgcaggata aaaaaattgt agataaattt tataaaatag ttttatctac aattttttta 1740
tcaggaaaca gctatgaccg cggccgcaga tagtcataat agttccagaa tagttcaatt 1800
tagaaattag actaaacttc aaaatgtttg ttaaatatat accaaactag tatagatatt 1860
ttttaaatac tggacttaaa cagtagtaat ttgcctaaaa aatttttca atttttttta 1920 aaaaatcctt ttcaagttgt acattgttat ggtaatatgt aattgaagaa gttatgtagt 1980
aatattgtaa acgtttcttg atttttttac atccatgtag tgcttaaaaa accaaaatat 2040
gtcacatgca attgtatatt tcaaataaca atatttattt tctcgttaaa ttcacaaata 2100
atttattaat aatatcaata accaagatta tacttaaatg gatgtttatt ttttaacact 2160
tttatagtaa atatatttat tttatgtagt aaaaaggtta taattataat tgtatttatt 2220

-continued

```
acaattaatt aaaataaaaa atagggtttt aggtaaaatt aagttatttt aagaagtaat   2280
tacaataaaa attgaagtta tttctttaag gagggaatta ttcatatgaa agaagttgta   2340
atagctagtg cagtaagaac agcgattgga tcttatggaa agtctcttaa ggatgtacca   2400
gcagtagatt taggagctac agctataaag gaagcagtta aaaaagcagg aataaaacca   2460
gaggatgtta atgaagtcat tttaggaaat gttcttcaag caggtttagg acagaatcca   2520
gcaagacagg catcttttaa agcaggatta ccagttgaaa ttccagctat gactattaat   2580
aaggtttgtg gttcaggact tagaacagtt agcttagcag cacaaattat aaaagcagga   2640
gatgctgacg taataatagc aggtggtatg gaaaatatgt ctagagctcc ttacttagcg   2700
aataacgcta gatggggata tagaatggga aacgctaaat ttgttgatga aatgatcact   2760
gacggattgt gggatgcatt taatgattac cacatgggaa taacagcaga aaacatagct   2820
gagagatgga acatttcaag agaagaacaa gatgagtttg ctcttgcatc acaaaaaaaa   2880
gctgaagaag ctataaaatc aggtcaattt aaagatgaaa tagttcctgt agtaattaaa   2940
ggcagaaagg gagaaactgt agttgataca gatgagcacc ctagatttgg atcaactata   3000
gaaggacttg caaaattaaa acctgccttc aaaaaagatg gaacagttac agctggtaat   3060
gcatcaggat taaatgactg tgcagcagta cttgtaatca tgagtgcaga aaaagctaaa   3120
gagcttggag taaaaccact tgctaagata gtttcttatg gttcagcagg agttgaccca   3180
gcaataatgg gatatggacc tttctatgca acaaaagcag ctattgaaaa agcaggttgg   3240
acagttgatg aattagattt aatagaatca aatgaagctt ttgcagctca aagtttagca   3300
gtagcaaaag atttaaaatt tgatatgaat aaagtaaatg taaatggagg agctattgcc   3360
cttggtcatc caattggagc atcaggtgca agaatactcg ttactcttgt acacgcaatg   3420
caaaaaagag atgcaaaaaa aggcttagca actttatgta taggtggcgg acaaggaaca   3480
gcaatattgc tagaaaagtg ctaggaattc gagctcggta ccagggagat attaaaatga   3540
ataaattagt aaaattaaca gatttaaagc gcattttcaa agatggcatg acaattatgg   3600
ttgggggttt tttagattgt ggaactcctg aaaatattat agatatgcta gttgatttaa   3660
atataaaaaa tctgactatt ataagcaatg atacagcttt tcctaataaa ggaataggaa   3720
aacttattgt aaatggtcaa gtttctaaag taattgcttc acatattgga actaatcctg   3780
aaactggaaa aaaaatgagc tctggagaac ttaaagttga gctttcccca caaggaacac   3840
tgattgaaag aattcgtgca gctggatctg gactcggagg tgtattaact ccaactggac   3900
ttggaactat cgttgaagaa ggtaagaaaa aagttactat cgatggcaaa gaatatctat   3960
tagaacttcc tttatctgct gatgtttcat taataaaagg tagcattgta gatgaatttg   4020
gaaatacctt ctatagggct gctactaaaa atttcaatcc atatatggca atggctgcaa   4080
aaacagttat agttgaagca gaaaatttag ttaaatgtga agatttaaaa agagatgcca   4140
taatgactcc tggcgtatta gtagattata tcgttaagga ggcggcttaa ttgattgtag   4200
ataaagtttt agcaaaagag ataattgcca aaagagttgc aaaagaacta aaaaaagacc   4260
aactcgtaaa ccttggaata ggacttccaa ctttagtagc aaattatgta ccaaaagaaa   4320
tgaacattac ttttgaatca gaaaatggca tggttggtat ggcacaaatg gcatcatcag   4380
gtgaaaatga cccagatata ataaatgctg gcggggaata tgtaacatta ttacctcaag   4440
gttcattttt tgatagttca atgtctttcg cactaatacg aggaggacat gttgatgttg   4500
ctgttcttgg tgctctagaa gttgatgaaa aaggtaattt agctaactgg attgttccaa   4560
ataaaattgt cccaggtatg ggtggcgcta tggatttagc aataggcgca aaaaaaataa   4620
```

-continued

```
tagtggcaat gcaacataca ggaaaaagta aacctaaaat cgttaaaaaa tgtactctcc   4680
cacttactgc taaggctcaa gtggatttaa ttgtcacaga actttgtgta attgatgtaa   4740
caaatgacgg cttactttta aaagaaattc ataaagatac aactattgat gaaattaaat   4800
ttttaacaga tgcagattta attattccag ataacttaaa gattatggat atatgaatca   4860
ttctatttta aatatataac tttaaaaatc ttatgtatta aaaactaaga aaagaggttg   4920
attgttttat gttagaaagt gaagtatcta aacaaattac aactccactt gctgctccag   4980
cgtttcctag aggaccatat aggtttcaca atagagaata tctaaacatt atttatcgaa   5040
ctgatttaga tgctcttcga aaaatagtac cagagccact tgaattagat agagcatatg   5100
ttagatttga aatgatggct atgcctgata caaccggact aggctcatat acagaatgtg   5160
gtcaagctat tccagtaaaa tataatggtg ttaagggtga ctacttgcat atgatgtatc   5220
tagataatga acctgctatt gctgttggaa gagaaagtag cgcttatcca aaaaagcttg   5280
gctatccaaa gctatttgtt gattcagata ctttagttgg gacacttaaa tatggtacat   5340
taccagtagc tactgcaaca atgggatata agcacgagcc tctagatctt aaagaagcct   5400
atgctcaaat tgcaagaccc aattttatgc taaaaatcat tcaaggttac gatggtaagc   5460
caagaatttg tgaactaata tgtgcagaaa atactgatat aactattcac ggtgcttgga   5520
ctggaagtgc acgtctacaa ttatttagcc atgcactagc tcctcttgct gatttacctg   5580
tattagagat tgtatcagca tctcatatcc tcacagattt aactcttgga acacctaagg   5640
ttgtacatga ttatctttca gtaaaataaa agcaatatag aggatccagg aggaacaaag   5700
atgagtatac cagaaacaca aaaagcaatt atattttatg agtcaaatgg aaaattagag   5760
cataaagata tacctgtacc aaaaccaaaa ccaaacgaac ttcttataaa tgttaagtat   5820
tctggtgttt gtcatactga tcttcatgca tggcatggtg attggcctct tccaactaaa   5880
ttacctcttg taggtggtca tgaaggtgct ggtgtagttg taggtatggg tgaaaatgtt   5940
aaaggttgga aaataggtga ttatgctgga attaaatggc ttaatggatc ttgtatggca   6000
tgcgagtatt gtgaattagg aaatgaaagt aattgtccac atgctgactt aagtggttat   6060
actcatgatg gatcttttca agaatatgct actgcagatg cagttcaggc tgcacacatt   6120
ccacagggaa ctgatcttgc tgaagtagct cctatattat gcgctggaat tacagtatac   6180
aaagcattaa aaagtgctaa tcttagagca ggacactggg cagctataag tggtgctgca   6240
ggtggtttag gatctttagc agttcaatat gctaaagcta tgggatatag agtattagga   6300
atagacggtg gtccaggaaa agaagagtta tttacatcat taggtggtga agtttttata   6360
gatttcacaa aggaaaaaga tattgtttca gctgtagtaa aggcaactaa tggtggtgca   6420
cacggaatta taaatgtttc agtatctgaa gcagcaatag aagcaagtac tagatattgt   6480
agagcaaacg gaacagtagt tttagttgga cttccagctg gtgcaaagtg ttcatctgac   6540
gtatttaacc atgtagtaaa gagtatttca atagttggat cttacgtagg taatagagct   6600
gatacaagag aagctttaga tttctttgca agaggtttag ttaagagtcc tataaaagta   6660
gtaggacttt catcacttcc tgaaatttat gaaaagatgg aaaagggaca aatagctggt   6720
agatatgttg tagatacaag taaataaggc catggagatc tcgaggcctg cagacatgca   6780
agcttggcac tggccgtcgt tttacaacgt cgtgactggg aaaaccctgg cgttacccaa   6840
cttaatcgcc ttgcagcaca tccccctttc gccagctggc gtaatagcga agaggcccgc   6900
accgatcgcc cttcccaaca gttgcgcagc ctgaatggcg aatggcgcta gcataaaaat   6960
```

```
aagaagcctg catttgcagg cttcttattt ttatggcgcg ccgccattat ttttttgaac   7020

aattgacaat tcatttctta ttttttatta agtgatagtc aaaaggcata acagtgctga   7080

atagaaagaa atttacagaa aagaaaatta tagaatttag tatgattaat tatactcatt   7140

tatgaatgtt taattgaata caaaaaaaaa tacttgttat gtattcaatt acgggttaaa   7200

atatagacaa gttgaaaaat ttaataaaaa aataagtcct cagctcttat atattaagct   7260

accaacttag tatataagcc aaaacttaaa tgtgctacca acacatcaag ccgttagaga   7320

actctatcta tagcaatatt tcaaatgtac cgacatacaa gagaaacatt aactatatat   7380

attcaattta tgagattatc ttaacagata taaatgtaaa ttgcaataag taagatttag   7440

aagtttatag cctttgtgta ttggaagcag tacgcaaagg ctttttttatt tgataaaaat   7500

tagaagtata tttatttttt cataattaat ttatgaaaat gaaagggggt gagcaaagtg   7560

acagaggaaa gcagtatctt atcaaataac aaggtattag caatatcatt attgacttta   7620

gcagtaaaca ttatgacttt tatagtgctt gtagctaagt agtacgaaag ggggagcttt   7680

aaaaagctcc ttggaataca tagaattcat aaattaattt atgaaaagaa gggcgtatat   7740

gaaaacttgt aaaaattgca aagagtttat taaagatact gaaatatgca aaatacattc   7800

gttgatgatt catgataaaa cagtagcaac ctattgcagt aaatacaatg agtcaagatg   7860

tttacataaa gggaaagtcc aatgtattaa ttgttcaaag atgaaccgat atggatggtg   7920

tgccataaaa atgagatgtt ttacagagga agaacagaaa aaagaacgta catgcattaa   7980

atattatgca aggagcttta aaaaagctca tgtaaagaag agtaaaaaga aaaaataatt   8040

tatttattaa tttaatattg agagtgccga cacagtatgc actaaaaaat atatctgtgg   8100

tgtagtgagc cgatacaaaa ggatagtcac tcgcattttc ataatacatc ttatgttatg   8160

attatgtgtc ggtgggactt cacgacgaaa acccacaata aaaaaagagt tcggggtagg   8220

gttaagcata gttgaggcaa ctaaacaatc aagctaggat atgcagtagc agaccgtaag   8280

gtcgttgttt aggtgtgttg taatacatac gctattaaga tgtaaaaata cggataccaa   8340

tgaagggaaa agtataattt ttggatgtag tttgtttgtt catctatggg caaactacgt   8400

ccaaagccgt ttccaaatct gctaaaaagt atatcctttc taaaatcaaa gtcaagtatg   8460

aaatcataaa taaagtttaa ttttgaagtt attatgatat tatgtttttc tattaaaata   8520

aattaagtat atagaatagt ttaataatag tatatactta atgtgataag tgtctgacag   8580

tgtcacagaa aggatgattg ttatggatta taagcggccg g                       8621
```

<210> SEQ ID NO 99
<211> LENGTH: 37
<212> TYPE: DNA
<213> ORGANISM: Artificial sequence
<220> FEATURE:
<223> OTHER INFORMATION: synthetic primer

<400> SEQUENCE: 99

```
atattggatc cacagctatg accgcggccg caatatg                             37
```

<210> SEQ ID NO 100
<211> LENGTH: 39
<212> TYPE: DNA
<213> ORGANISM: Artificial sequence
<220> FEATURE:
<223> OTHER INFORMATION: synthetic primer

<400> SEQUENCE: 100

```
agcgtccatg gccttattta cttgtatcta caacatatc                           39
```

<210> SEQ ID NO 101
<211> LENGTH: 10803
<212> TYPE: DNA
<213> ORGANISM: Artificial sequence
<220> FEATURE:
<223> OTHER INFORMATION: synthetic plasmid

<400> SEQUENCE: 101
ccagtgggca agttgaaaaa ttcacaaaaa tgtggtataa tatctttgtt cattagagcg 60
ataaacttga atttgagagg gaacttagat ggtatttgaa aaaattgata aaaatagttg 120
gaacagaaaa gagtattttg accactactt tgcaagtgta ccttgtacct acagcatgac 180
cgttaaagtg gatatcacac aaataaagga aaagggaatg aaactatatc ctgcaatgct 240
ttattatatt gcaatgattg taaaccgcca ttcagagttt aggacggcaa tcaatcaaga 300
tggtgaattg gggatatatg atgagatgat accaagctat acaatatttc acaatgatac 360
tgaaacattt tccagccttt ggactgagtg taagtctgac tttaaatcat ttttagcaga 420
ttatgaaagt gatacgcaac ggtatggaaa caatcataga atggaaggaa agccaaatgc 480
tccggaaaac atttttaatg tatctatgat accgtggtca accttcgatg gctttaatct 540
gaatttgcag aaaggatatg attatttgat tcctattttt actatgggga aatattataa 600
agaagataac aaaattatac ttcctttggc aattcaagtt catcacgcag tatgtgacgg 660
atttcacatt tgccgttttg taaacgaatt gcaggaattg ataaatagtt aacttcaggt 720
ttgtctgtaa ctaaaaacaa gtatttaagc aaaaacatcg tagaaatacg gtgttttttg 780
ttaccctaag tttaaactcc tttttgataa tctcatgacc aaaatccctt aacgtgagtt 840
ttcgttccac tgagcgtcag accccgtaga aaagatcaaa ggatcttctt gagatccttt 900
ttttctgcgc gtaatctgct gcttgcaaac aaaaaaacca ccgctaccag cggtggtttg 960
tttgccggat caagagctac caactctttt tccgaaggta actggcttca gcagagcgca 1020
gataccaaat actgttcttc tagtgtagcc gtagttaggc caccacttca agaactctgt 1080
agcaccgcct acatacctcg ctctgctaat cctgttacca gtggctgctg ccagtggcga 1140
taagtcgtgt cttaccgggt tggactcaag acgatagtta ccggataagg cgcagcggtc 1200
gggctgaacg gggggttcgt gcacacagcc cagcttggag cgaacgacct acaccgaact 1260
gagataccta cagcgtgagc tatgagaaag cgccacgctt cccgaaggga gaaaggcgga 1320
caggtatccg gtaagcggca gggtcggaac aggagagcgc acgagggagc ttccaggggg 1380
aaacgcctgg tatctttata gtcctgtcgg gtttcgccac ctctgacttg agcgtcgatt 1440
tttgtgatgc tcgtcagggg ggcggagcct atggaaaaac gccagcaacg cggccttttt 1500
acggttcctg gccttttgct ggccttttgc tcacatgttc tttcctgcgt tatcccctga 1560
ttctgtggat aaccgtatta ccgcctttga gtgagctgat accgctcgcc gcagccgaac 1620
gaccgagcgc agcgagtcag tgagcgagga agcggaagag cgcccaatac gcagggcccc 1680
ctgcaggata aaaaaattgt agataaattt tataaaatag ttttatctac aattttttta 1740
tcaggaaaca gctatgaccg cggccgcaga tagtcataat agttccagaa tagttcaatt 1800
tagaaattag actaaacttc aaaatgtttg ttaaatatat accaaactag tatagatatt 1860
ttttaaatac tggacttaaa cagtagtaat ttgcctaaaa aatttttca atttttttta 1920 aaaaatcctt ttcaagttgt acattgttat ggtaatatgt aattgaagaa gttatgtagt 1980
aatattgtaa acgtttcttg attttttac atccatgtag tgcttaaaaa accaaaatat 2040

-continued

```
gtcacatgca attgtatatt tcaaataaca atatttattt tctcgttaaa ttcacaaata   2100
atttattaat aatatcaata accaagatta tacttaaatg gatgtttatt ttttaacact   2160
tttatagtaa atatatttat tttatgtagt aaaaaggtta taattataat tgtatttatt   2220
acaattaatt aaaataaaaa atagggtttt aggtaaaatt aagttatttt aagaagtaat   2280
tacaataaaa attgaagtta tttctttaag gagggaatta ttcatatgaa agaagttgta   2340
atagctagtg cagtaagaac agcgattgga tcttatggaa agtctcttaa ggatgtacca   2400
gcagtagatt taggagctac agctataaag gaagcagtta aaaaagcagg aataaaacca   2460
gaggatgtta atgaagtcat tttaggaaat gttcttcaag caggtttagg acagaatcca   2520
gcaagacagg catcttttaa agcaggatta ccagttgaaa ttccagctat gactattaat   2580
aaggtttgtg gttcaggact tagaacagtt agcttagcag cacaaattat aaaagcagga   2640
gatgctgacg taataatagc aggtggtatg gaaaatatgt ctagagctcc ttacttagcg   2700
aataacgcta gatggggata tagaatggga aacgctaaat ttgttgatga aatgatcact   2760
gacggattgt gggatgcatt taatgattac cacatgggaa taacagcaga aaacatagct   2820
gagagatgga acatttcaag agaagaacaa gatgagtttg ctcttgcatc acaaaaaaaa   2880
gctgaagaag ctataaaatc aggtcaattt aaagatgaaa tagttcctgt agtaattaaa   2940
ggcagaaagg gagaaactgt agttgataca gatgagcacc ctagatttgg atcaactata   3000
gaaggacttg caaaattaaa acctgccttc aaaaaagatg gaacagttac agctggtaat   3060
gcatcaggat taaatgactg tgcagcagta cttgtaatca tgagtgcaga aaaagctaaa   3120
gagcttggag taaaaccact tgctaagata gtttcttatg gttcagcagg agttgaccca   3180
gcaataatgg gatatggacc tttctatgca acaaaagcag ctattgaaaa agcaggttgg   3240
acagttgatg aattagattt aatagaatca aatgaagctt ttgcagctca aagtttagca   3300
gtagcaaaag atttaaaatt tgatatgaat aaagtaaatg taaatggagg agctattgcc   3360
cttggtcatc caattggagc atcaggtgca agaatactcg ttactcttgt acacgcaatg   3420
caaaaaagag atgcaaaaaa aggcttagca actttatgta taggtggcgg acaaggaaca   3480
gcaatattgc tagaaaagtg ctaggaattc gagctcggta ccagggagat attaaaatga   3540
ataaattagt aaaattaaca gatttaaagc gcattttcaa agatggcatg acaattatgg   3600
ttgggggttt tttagattgt ggaactcctg aaaatattat agatatgcta gttgatttaa   3660
atataaaaaa tctgactatt ataagcaatg atacagcttt tcctaataaa ggaataggaa   3720
aacttattgt aaatggtcaa gtttctaaag taattgcttc acatattgga actaatcctg   3780
aaactggaaa aaaaatgagc tctggagaac ttaaagttga gctttcccca caaggaacac   3840
tgattgaaag aattcgtgca gctggatctg gactcggagg tgtattaact ccaactggac   3900
ttggaactat cgttgaagaa ggtaagaaaa aagttactat cgatggcaaa gaatatctat   3960
tagaacttcc tttatctgct gatgtttcat taataaaagg tagcattgta gatgaatttg   4020
gaaatacctt ctatagggct gctactaaaa atttcaatcc atatatggca atggctgcaa   4080
aaacagttat agttgaagca gaaaatttag ttaaatgtga agatttaaaa agagatgcca   4140
taatgactcc tggcgtatta gtagattata tcgttaagga ggcggcttaa ttgattgtag   4200
ataaagtttt agcaaaagag ataattgcca aaagagttgc aaaagaacta aaaaaagacc   4260
aactcgtaaa ccttggaata ggacttccaa ctttagtagc aaattatgta ccaaaagaaa   4320
tgaacattac ttttgaatca gaaaatggca tggttggtat ggcacaaatg gcatcatcag   4380
gtgaaaatga cccagatata ataaatgctg gcggggaata tgtaacatta ttacctcaag   4440
```

-continued

```
gttcattttt tgatagttca atgtctttcg cactaatacg aggaggacat gttgatgttg   4500
ctgttcttgg tgctctagaa gttgatgaaa aaggtaattt agctaactgg attgttccaa   4560
ataaaattgt cccaggtatg ggtggcgcta tggatttagc aataggcgca aaaaaaataa   4620
tagtggcaat gcaacataca ggaaaaagta aacctaaaat cgttaaaaaa tgtactctcc   4680
cacttactgc taaggctcaa gtggatttaa ttgtcacaga actttgtgta attgatgtaa   4740
caaatgacgg cttactttta aaagaaattc ataaagatac aactattgat gaaattaaat   4800
ttttaacaga tgcagattta attattccag ataacttaaa gattatggat atatgaatca   4860
ttctatttta aatatataac tttaaaaatc ttatgtatta aaaactaaga aaagaggttg   4920
attgttttat gttagaaagt gaagtatcta aacaaattac aactccactt gctgctccag   4980
cgtttcctag aggaccatat aggtttcaca atagagaata tctaaacatt atttatcgaa   5040
ctgatttaga tgctcttcga aaaatagtac cagagccact tgaattagat agagcatatg   5100
ttagatttga aatgatggct atgcctgata caaccggact aggctcatat acagaatgtg   5160
gtcaagctat tccagtaaaa tataatggtg ttaagggtga ctacttgcat atgatgtatc   5220
tagataatga acctgctatt gctgttggaa gagaaagtag cgcttatcca aaaaagcttg   5280
gctatccaaa gctatttgtt gattcagata ctttagttgg gacacttaaa tatggtacat   5340
taccagtagc tactgcaaca atgggatata agcacgagcc tctagatctt aaagaagcct   5400
atgctcaaat tgcaagaccc aattttatgc taaaaatcat tcaaggttac gatggtaagc   5460
caagaatttg tgaactaata tgtgcagaaa atactgatat aactattcac ggtgcttgga   5520
ctggaagtgc acgtctacaa ttatttagcc atgcactagc tcctcttgct gatttacctg   5580
tattagagat tgtatcagca tctcatatcc tcacagattt aactcttgga acacctaagg   5640
ttgtacatga ttatctttca gtaaaataaa agcaatatag aggatccaca gctatgaccg   5700
cggccgcaat atgatattta tgtccattgt gaaagggatt atattcaact attattccag   5760
ttacgttcat agaaatttc ctttctaaaa tattttattc catgtcaaga actctgttta    5820
tttcattaaa gaactataag tacaaagtat aaggcatttg aaaaaatagg ctagtatatt   5880
gattgattat ttattttaaa atgcctaagt gaaatatata catattataa caataaaata   5940
agtattagtg taggattttt aaatagagta tctattttca gattaaattt ttgattattt   6000
gatttacatt atataatatt gagtaaagta ttgactagca aaattttttg atactttaat   6060
ttgtgaaatt tcttatcaaa agttatattt ttgaataatt tttattgaaa aatacaacta   6120
aaaaggatta tagtataagt gtgtgtaatt ttgtgttaaa tttaaaggga ggaaatgaac   6180
atgaaacata tgtatacagt tggtgattat ttacttgata gattacatga acttggaata   6240
gaagaaattt ttggtgtacc aggtgattac aatcttcaat tcttagatca aataatatca   6300
cataaggata tgaaatgggt tggtaatgct aatgaattaa atgcatcata tatggcagac   6360
ggatatgcaa gaactaaaaa ggcagcagca tttcttacta catttggtgt tggtgaatta   6420
agtgcagtaa atggattagc tggaagttac gcagaaaact taccagttgt tgaaatagtt   6480
ggatctccta ctagtaaagt acaaaatgaa ggtaaatttg tacatcacac tcttgcagat   6540
ggtgatttta agcattttat gaaaatgcat gaacctgtta cagctgcaag aacacttctt   6600
acagctgaaa acgctactgt agaaattgat agagttttat ctgctttact taaagaaaga   6660
aagccagtat atattaacct tccagtagat gtagcagcag caaaagctga gaaaccttca   6720
ttaccactta aaaaggaaaa ttcaacatca aatacatctg atcaagagat attaaataaa   6780
```

-continued

```
attcaggaaa gtcttaaaaa tgcaaagaaa cctatagtaa taactggaca tgaaataatt   6840
agttttggat tagaaaagac agttacacag tttataagta aaactaagct tccaattaca   6900
actttaaatt ttggaaagag ttcagtagat gaggcacttc catcattctt aggaatttat   6960
aatggaacat tatctgaacc taatcttaaa gaatttgtag agagtgctga ttttatatta   7020
atgttaggtg taaaacttac tgatagtagt actggtgcat ttactcatca tcttaacgaa   7080
aataagatga tatcattaaa tatagacgaa ggtaaaatat tcaatgaaag aatacagaac   7140
tttgattttg aatcacttat atcatcatta cttgatttat cagagataga atacaaagga   7200
aaatatatag ataaaaagca agaagatttt gttccatcta atgctcttct ttctcaagat   7260
agactttggc aagcagttga gaatcttaca cagtctaatg aaactatagt tgctgagcaa   7320
ggaacatcat ttttcggtgc atcaagtata tttttaaaat ctaaaagtca ctttattgga   7380
caacctcttt ggggttctat tggatatact tttccagcag ctttaggaag tcaaatagct   7440
gataaagaaa gtagacattt attatttatt ggtgacggtt cacttcagct tacagtacaa   7500
gaattaggat tagctataag agagaagata aatcctattt gtttcataat aaacaatgat   7560
ggatatactg tagaaagaga aattcacgga ccaaatcagt catataatga tattccaatg   7620
tggaattatt caaagttacc tgaatctttc ggtgctactg aagatagagt agtttctaaa   7680
attgttagaa cagagaacga atttgtatct gttatgaaag aagctcaggc tgaccctaat   7740
agaatgtatt ggattgaatt aattttagca aaagaaggtg ctcctaaagt acttaagaaa   7800
atgggaaaat tatttgcaga acaaaataag tcataagaat tcccataata aagaaagaat   7860
tttaaataaa ggaggaacaa agatgagtat accagaaaca caaaaagcaa ttatatttta   7920
tgagtcaaat ggaaaattag agcataaaga tatacctgta ccaaaaccaa aaccaaacga   7980
acttcttata aatgttaagt attctggtgt ttgtcatact gatcttcatg catggcatgg   8040
tgattggcct cttccaacta aattacctct tgtaggtggt catgaaggtg ctggtgtagt   8100
tgtaggtatg ggtgaaaatg ttaaaggttg gaaaataggt gattatgctg gaattaaatg   8160
gcttaatgga tcttgtatgg catgcgagta ttgtgaatta ggaaatgaaa gtaattgtcc   8220
acatgctgac ttaagtggtt atactcatga tggatctttt caagaatatg ctactgcaga   8280
tgcagttcag gctgcacaca ttccacaggg aactgatctt gctgaagtag ctcctatatt   8340
atgcgctgga attacagtat acaaagcatt aaaaagtgct aatcttagag caggacactg   8400
ggcagctata agtggtgctg caggtggttt aggatcttta gcagttcaat atgctaaagc   8460
tatgggatat agagtattag gaatagacgg tggtccagga aaagaagagt tatttacatc   8520
attaggtggt gaagttttta tagatttcac aaaggaaaaa gatattgttt cagctgtagt   8580
aaaggcaact aatggtggtg cacacggaat tataaatgtt tcagtatctg aagcagcaat   8640
agaagcaagt actagatatt gtagagcaaa cggaacagta gttttagttg gacttccagc   8700
tggtgcaaag tgttcatctg acgtatttaa ccatgtagta aagagtattt caatagttgg   8760
atcttacgta ggtaatagag ctgatacaag agaagcttta gatttctttg caagaggttt   8820
agttaagagt cctataaaag tagtaggact ttcatcactt cctgaaattt atgaaaagat   8880
ggaaaaggga caaatagctg gtagatatgt tgtagataca agtaaataag gccatggaga   8940
tctcgaggcc tgcagacatg caagcttggc actggccgtc gttttacaac gtcgtgactg   9000
ggaaaaccct ggcgttaccc aacttaatcg ccttgcagca catccccctt tcgccagctg   9060
gcgtaatagc gaagaggccc gcaccgatcg cccttcccaa cagttgcgca gcctgaatgg   9120
cgaatggcgc tagcataaaa ataagaagcc tgcatttgca ggcttcttat ttttatggcg   9180
```

-continued

```
cgccgccatt attttttga acaattgaca attcatttct tattttttat taagtgatag    9240
tcaaaaggca taacagtgct gaatagaaag aaatttacag aaaagaaaat tatagaattt    9300
agtatgatta attatactca tttatgaatg tttaattgaa tacaaaaaaa aatacttgtt    9360
atgtattcaa ttacgggtta aaatatagac aagttgaaaa atttaataaa aaaataagtc    9420
ctcagctctt atatattaag ctaccaactt agtatataag ccaaaactta aatgtgctac    9480
caacacatca agccgttaga gaactctatc tatagcaata tttcaaatgt accgacatac    9540
aagagaaaca ttaactatat atattcaatt tatgagatta tcttaacaga tataaatgta    9600
aattgcaata agtaagattt agaagtttat agcctttgtg tattggaagc agtacgcaaa    9660
ggctttttta tttgataaaa attagaagta tatttatttt ttcataatta atttatgaaa    9720
atgaaagggg gtgagcaaag tgacagagga aagcagtatc ttatcaaata acaaggtatt    9780
agcaatatca ttattgactt tagcagtaaa cattatgact tttatagtgc ttgtagctaa    9840
gtagtacgaa agggggagct ttaaaaagct ccttggaata catagaattc ataaattaat    9900
ttatgaaaag aagggcgtat atgaaaactt gtaaaaattg caaagagttt attaaagata    9960
ctgaaatatg caaaatacat tcgttgatga ttcatgataa aacagtagca acctattgca   10020
gtaaatacaa tgagtcaaga tgtttacata aagggaaagt ccaatgtatt aattgttcaa   10080
agatgaaccg atatggatgg tgtgccataa aaatgagatg ttttacagag gaagaacaga   10140
aaaaagaacg tacatgcatt aaatattatg caaggagctt taaaaaagct catgtaaaga   10200
agagtaaaaa gaaaaaataa tttatttatt aatttaatat tgagagtgcc gacacagtat   10260
gcactaaaaa atatatctgt ggtgtagtga gccgatacaa aaggatagtc actcgcattt   10320
tcataataca tcttatgtta tgattatgtg tcggtgggac ttcacgacga aaacccacaa   10380
taaaaaaaga gttcggggta gggttaagca tagttgaggc aactaaacaa tcaagctagg   10440
atatgcagta gcagaccgta aggtcgttgt ttaggtgtgt tgtaatacat acgctattaa   10500
gatgtaaaaa tacggatacc aatgaaggga aaagtataat ttttggatgt agtttgtttg   10560
ttcatctatg ggcaaactac gtccaaagcc gtttccaaat ctgctaaaaa gtatatcctt   10620
tctaaaatca aagtcaagta tgaaatcata aataaagttt aattttgaag ttattatgat   10680
attatgtttt tctattaaaa taaattaagt atatagaata gtttaataat agtatatact   10740
taatgtgata agtgtctgac agtgtcacag aaaggatgat tgttatggat tataagcggc   10800
cgg                                                                 10803
```